United States Patent [19]
Vlasuk et al.

[11] Patent Number: 5,866,542
[45] Date of Patent: *Feb. 2, 1999

[54] NEMATODE-EXTRACTED ANTICOAGULANT PROTEIN

[75] Inventors: George Phillip Vlasuk, Carlsbad, Calif.; Patrick Eric Hugo Stanssens, St-Matens-Latem, Belgium; Joris Hilda Lieven Messens, Antwerp, Belgium; Marc Jozef Lauwereys, Haaltert, Belgium; Yves René n Laroche, Brussels, Belgium; Laurent Stéphane Jespers, Tervuren, Belgium; Yannick George Jozef Gansemans, Bredene, Belgium; Matthew Moyle, Escondido; Peter W. Bergum, San Diego, both of Calif.

[73] Assignee: Corvas International, Inc., San Diego, Calif.

[*] Notice: The term of this patent shall not extend beyond the expiration date of Pat. Nos. 5,863,894, 5,866,543 and 5,872,098.

[21] Appl. No.: 486,397

[22] Filed: Jun. 5, 1995

Related U.S. Application Data

[63] Continuation-in-part of Ser. No. 326,110, Oct. 18, 1994.

[51] Int. Cl.$^6$ .............................. A61K 38/57; C07K 14/81
[52] U.S. Cl. .............................. 514/12; 530/350; 530/324
[58] Field of Search .................................... 530/350, 324; 514/12

[56] References Cited

U.S. PATENT DOCUMENTS

| | | | |
|---|---|---|---|
| 4,458,066 | 7/1984 | Caruthers et al. | 536/27 |
| 4,683,293 | 7/1987 | Craig | 530/359 |
| 4,745,051 | 5/1988 | Smith et al. | 435/68 |
| 4,777,242 | 10/1988 | Nelles | 530/351 |
| 4,808,537 | 2/1989 | Stroman et al. | 435/6 |
| 4,812,405 | 3/1989 | Lair et al. | 435/255 |
| 4,818,700 | 4/1989 | Cregg et al. | 435/252.33 |
| 4,837,148 | 6/1989 | Cregg | 435/172.3 |
| 4,855,231 | 8/1989 | Stroman et al. | 435/68 |
| 4,857,467 | 8/1989 | Sreekrishna et al. | 435/255 |
| 4,879,231 | 11/1989 | Stroman et al. | 435/172.3 |
| 4,882,279 | 11/1989 | Cregg | 435/172.3 |
| 4,885,242 | 12/1989 | Cregg et al. | 435/68 |
| 4,895,800 | 1/1990 | Tschopp et al. | 435/69.3 |
| 5,002,876 | 3/1991 | Sreekrishma et al. | 435/69.5 |
| 5,004,688 | 4/1991 | Craig et al. | 435/69.3 |

(List continued on next page.)

FOREIGN PATENT DOCUMENTS

| | | |
|---|---|---|
| 0255771 | 2/1988 | European Pat. Off. . |
| 0419099 | 3/1991 | European Pat. Off. . |
| 0439442 | 7/1991 | European Pat. Off. . |
| 0454372 | 10/1991 | European Pat. Off. . |
| 88/09811 | 12/1988 | WIPO . |
| 91/02753 | 3/1991 | WIPO . |
| 94/25000 | 11/1994 | WIPO . |
| 95/12615 | 5/1995 | WIPO . |
| 96/04378 | 2/1996 | WIPO . |
| 96/12021 | 4/1996 | WIPO . |
| 96/04377 | 2/1997 | WIPO . |

OTHER PUBLICATIONS

Cappello, M. et al. (1993) "Ancylostoma factor Xa inhibitor: partial purification and its identification as a major hookworm–derived anticoagulant in vitro" J. Inf. Dis. 167:1474–1477, Jun. 1993.

Curtis, H. (1983) Biology, Fourth Edition. New York: Worth Publishers, Inc., pp. 500–501, 1983.

(List continued on next page.)

Primary Examiner—Kawai Lau
Attorney, Agent, or Firm—Lyon & Lyon LLP

[57] ABSTRACT

Proteins which are potent anticoagulants and have at least one NAP domain and are described. These proteins having anticoagulant activity can be isolated from natural sources such as nematodes, chemically synthesized or made by recombinant methods using various DNA expression systems.

50 Claims, 45 Drawing Sheets

U.S. PATENT DOCUMENTS

| | | |
|---|---|---|
| 5,023,236 | 6/1991 | Edgington et al. ............... 514/18 |
| 5,032,516 | 7/1991 | Cregg ............... 435/172.3 |
| 5,106,833 | 4/1992 | Broze et al. ............... 514/12 |
| 5,122,465 | 6/1992 | Cregg et al. ............... 435/172.3 |
| 5,135,868 | 8/1992 | Cregg ............... 435/255 |
| 5,166,329 | 11/1992 | Cregg ............... 536/27 |
| 5,189,019 | 2/1993 | Palladino et al. ............... 514/12 |
| 5,204,261 | 4/1993 | Prevatt et al. ............... 435/255 |
| 5,239,058 | 8/1993 | Vlasuk et al. ............... 530/524 |
| 5,239,059 | 8/1993 | Zasloff et al. ............... 530/325 |
| 5,268,273 | 12/1993 | Buckholz ............... 435/69.1 |
| 5,330,901 | 7/1994 | Prevatt et al. ............... 435/69.6 |
| 5,427,937 | 6/1995 | Cappello et al. ............... 435/212 |
| 5,525,477 | 6/1996 | Hassouna ............... 435/13 |
| 5,601,571 | 2/1997 | Lyle et al. ............... 424/1.41 |
| 5,605,671 | 2/1997 | Lyle et al. ............... 424/1.41 |

OTHER PUBLICATIONS

Aoki, Y., et al., "Effects of Recombinant Human Soluble Thrombomodulin (rhs–TM) in a Rat Model of Disseminated Intravascular Coagulation with Deceased Levels of Plasma Antithrombin" *Thrombosis and Hemostasis* 71(4):452–455 (1994).

Babin et al., "The Isoinhibitors of Chymotrypsin/Elastase from Ascaris lumbricoides: The Primary Structure" *Arch. of Biochem. and Biophy.* 232(1):143–161 (1984).

Beaucage et al., "Deoxynucleoside Phosphoramidites–A New Class of Key Intermediates for Deoxypolynucleotide Synthesis" *Tetrahedron Letters*, 22(20):1859–1862 (1981).

Bernard, et al., "The Serine Protease Inhibitor Family from *Ascaris Suum*: Chemical Determination of the Five Disulfide Bridges" *Arch. Biochem. Biophys.*, 303(2):367–376 (1993).

Bock, P.E. et al. "Isolation of Human Coagulation a–Factor $X_a$ by Soybean Trypsin Inhibitor Sepharose Chromatography and Its Active–Site Titration with Fluorescein Mono–p–guanidinobenzoate" *Archives of Biochem. Biophys.* 273(2):375–388 (1989).

Bolivar et al., "Construction and Characterization of New Cloning Vehicles" *Gene*, 2:95–113 (1977).

Broach, J. et al. "Transformation In Yeast: Development of a Hybrid Cloning Vector and Isolation of the CAN1 Gene" *Gene*, 8:121–133 (1978).

Brown, E. et al., "Chemical Synthesis and Cloning of a Tyrosine tRNA Gene" *Methods in Enzymology*, 68, 109–151 (1979).

Bullock et al., "XL1–Blue: A High Efficiency Plasmid Transforming recA Escherichia coli Strain with Beta–Galactosidase Selection"*Biotechniques* 5(4):376–379 (1987).

Cairns et al., "Antithrombotic Agents in Coronary Artery Disease" *Chest* 102:456S–481S (1992).

Crameri et al., "Display of Biologically Active Proteins on the Surface of Filamentous Phages: cDNA Cloning System for Selection of Functional Gene Products Linked to the Genetic Information Responsible for their Production" *Gene*, 137:69–75 (1993).

Cappello et al., "Ancylostoma Factor Xa Inhibitor: Partial Purification and Its Identification as a Major Hookworm–Derived Anticoagulant In Vitro" *J. Infect. Diseases*, 167:1474–1477 (1993).

Cappello et al., "*Ancylostoma caninum* anticoagulant peptide: A Hookworm–derived Inhibitor of Human Coagulation Factor Xa," *Proc. Natl. Acad. Sci. U.S.A.* 92:6152–6156 (1995).

Carroll et al., "The Anticoagulant Effects of the Hookworm, *Ancylostoma Ceylanicum*: Observations of Human and Dog Blood In Vitro and Infected Dogs In Vivo" *Thromb, Haemostat.* (Stuttgart), 51(2):222–227 (1984).

Carson,"Computerized Analysis of Enzyme Cascade Reactions Using Continuous Rate Data Obtained with an ELISA Reader" *Comput. Prog. Biomed* 19:151–157 (1985).

Clements et al., "Secretion of Human Epidermal Growth Factor from *Saccharomyces Cerevisiae* Using Synthetic Leader Sequences" *Gene* 106:267–272 (1991).

Cohen, Nonchromosomal Antibiotic Resistance in Bacteria: Genetic Transformation of *Escherichia coli* by R–Factor DNA *Proc. Natl. Acad. Sci. USA*, 69(8):2110–2114 (1972).

Crawford, et al., "Inhibition of Human Blood Clotting By Extracts of *Ascaris Suum*" *J. Parasitol.*, 68(6):1044–1047 (1982).

Curtis, *Biology Fourth ed.* N.Y. Worth Publishers, Inc. pp. 500–501 (1983).

Depicker et al., "Nopaline Synthase: Transcript Mapping and DNA Sequence" *J. Mol. Appl. Gen.*, 1(6):561–573 (1978).

Despreaux et al., "The dac A Gene of *Bacillus Stearothermophilus* Coding for D–Alanine Carboxypeptidase: Cloning Structure and Expression in *Escherichia Coli* and *Pichia Pastoris*" *Gene* 131:35–41 (1993).

Fiers, et al., "Complete Nucleotide Sequence of SV40 DNA" *Nature*, 273:113–120 (1978).

Fuster, V. The Pathogenesis i of Coronary Artery Disease and the Acute Coronary Syndromes *New Engl. J. Med.* 326(5):310–318 (1992).

Glaser–Wuttke. G., "Pore Forming Properties of the Adsorption protein of Filamentous Phage fd" *Biochem. Biophys. Acta*, 985:239–247 (1989).

Glover, "Gene Cloning: The Mechanics of DNA Manipulation" 1–20 (1984).

Goeddel et al., "Synthesis of Human Fibroblast Interferon by *E. Coli*" *Nucleic Acids Res.*, 8(18):4057–4074 (1980).

Gold et al., "Evidence for a Rebound Coagulation Phenomenon After Cessation of 4–hour Infusion of a Specific Thrombin Inhibitor in Patients with Unstable Angina Pectoris" *JACC* 21(5):1039–1047 (1993).

Grasberger et al., "High–Resolution Structure of *Ascaris Trypsin* Inhibitor in Solution: Direct Evidence for a pH–induced Conformational Transition in the Reactive Site" *Structure*, 2:669–678 (1994).

Hemker et al., "Feedback Mechanisms in Coagulation" *Hemostasis* 21:189–196 (1991).

Hirsh, J., "Heparin" *N. Engl. J. Med* 324(22):1565–1574 (1992).

Hitzeman et al., "Isolation and Charazterization of the Yeast 3–Phosphoglycerokinase Gene (PGK) by an Immunological Screening Technique"*J. Biol. Chem.*, 255(24):12073–12080 (1980).

Holland et al., "The Primary Structures of Two Yeast Enolase Genes" *J. Biol. Chem.*, 256(3):1385–1395 (1981).

Houghten, "General Method for the Rapid Solid–Phase Synthesis of Large Numbers of Peptides: Specificity of Antigen–Antibody Interaction at the level of Individual Amino Acids" *Proc. Natl. Acad. Sci..* 82:5131–5135 (1985).

Hsiao, C.L. et al.,. "High–Frequency Transformation of Yeast by Plasmids Containing the Cloned Yeast ARG4 Gene" *Proc. Natl. Acad. Sci.* USA 76(8):3829–3833 (1979).

Huang et al., "The Molecular Structure of the Complex of the Complex of *Ascaris Chymotrypsin/Elastase* Inhibitor with porcine Elastase" *Structure* 2:679–689 (1994).

Itakura et al., "Expression in *Escherichia Coli* of a Chemically Synthesized Gene for the Hormone Somatostatin" Science 198:1056–1063 (1977).

Kasten, B.L., "Specimen Collection", *Laboratory Test Handbook,* 2nd Edition, Lexi–Comp Inc., Cleveland pp. 16–17 (Edits. Jacobs, D.S. et al. 1990).

Kessler, C. "The Pharmacology of Aspirin, Heparin, Coumarin and Thrombolytic Agents" Chest 99:97S–112S (1991).

Kurz, K.D., et al., "Rat Model of Arterial Thrombosis Induced by Ferric Chloride" *Thromb. Res.* 60:269–280 (1990).

Lawson et al., "A Model for the Tissue Factor Pathway to Thrombin" *J. Biol. Chem.* 269(37):23357–23366 (1994).

Levine et al., "Hemorrhagic Complications of Anticoagulant Treatment" *Chest* 102:352S–363S (1992).

Lidon et al., "Initial Experience with Direct Antithrombin Hirulog, in Unstable Angina" *Circulation* 88(4):1495–1501 (1993).

Loeb et al., "The Presence of a Substance Inhibiting the Coagulation of the Blood in Ancylostoma" *Proc. Pathol. Soc.of Philadelphia,* 7(6):173–178 (1904).

Lucchesi et al., "Prevention of Thrombosis and Rethrombosis and Enhancement of the Thrombolytic Actions of Recombinant Tissue–Type Plasminogen Activator in the Canine Heart by DMP728, A Glycoprotein Iib/IIIa Antagonist" *Brit. J. Pharmacol.* 113:1333–1343 (1994).

Maniatis et al., "Molecular Cloning: A Laboratory Manual " *Cold Spring Harbor Press* pp. 254–255 (1982).

Mann et al., "Surface–Dependent Hemostasis" *Sem. Hematology* 29(3):213–226 (1992).

Mann et al., Blood 76(1):1–16 (1990).

Merrifield, "Solid Phase Peptide Synthesis.I. The Synthesis of a Tetrapeptide" *J. Amer. Chem. Soc.* 85:2149–2154 (1963).

Messing et al., "A System for Shotgun DNA Sequencing" *Nucleic Acids Res.* 9(2):309–321 (1981).

*Methods of Enzymology,* 65:499–560 (1980).

Mizushima et al., "pEF–BOS, A Powerful Mammalian Expression Vector" *Nucl. Acids Res.,* 18(17):5322 (1990).

Morrison et al.,"The Behavior and Significance of Slow–Binding Enzyme Inibitors" *C.T. Adv. Enzymol.* 61:201–301 (1988).

Maruyama et al., "Lambda foo: a λ phage vector for the expression of foreign proteins" *Proc. Nat'l. Acad. Sci., USA* 91:8273–8277 (1944).

Narang et al., "Improved Phosphotriester Method for the Synthesis of Gene Fragments" *Methods in Enzymol* 68:90–109 (1979).

Nawa et al., "The Glycosaminoglycan of Recombinant Human Soluble Thrombomodulin Affects Antithrombotic Activity in a Rat Model of Tissue Factor–Induced Disseminated Intravascular Coagulation" *Thrombosis and Hemostasis* 67(3):366–370 (1992).

Nutt et al., "The Amino Acid Sequence of Antistasin" *J. Biol. Chem,* 263(21):10162–10167 (1988).

Oklahoma Medical Research Foundation, "Thrombin–binding polypeptides as antithrombotic agent for artificial organs or other surfaces" *Chemical Abstracts* 113:18 abstract No. 158738 (1990).

"Principle and Applications for DNA Amplification" *PCR Technology* (1989) New York:Stockton Press (complete volume).

Pritchard D., "The Anti–haemostatic Strategies of the Human Hookworm *Necator Americanus*" *Thromb. Haemost.* 73(3):546–(1995).

"The Source for Discovery" *Protocols and Applications Guide 3rd ed.* Promega Corp. USA (1996) (complete volume).

Rappaport, S., "Initiation and Regulation of Tissue Factor–Dependent Blood Coagulation" *Arteriosclerosis and Thrombosis* 12(10):1111–1121 (1992).

Roberts et al., "Directed Evolution of a Potent Neutrophil Elastase Inhibitors Displayed on M13 Fusion Phage" *Proc. Nat'l. Acad. Sci., USA* 89:2429–2433 (1992).

Ruf et al., "Mutational Analysis of Receptor and Cofactor Function of Tissue Factor" *Methods in Enzymol. 222,* 209–224 (1993).

Salvensen et al., "Proteinase Inhibitors: a–Macroglobulins, Serpins and Kunins," *Hemostasis and Thrombosis Third ed.* 251–253 (1994) J.B. Lippincott Comp.

Sambrook et al., "Molecular Cloning, A Laboratory Manual", Second Edition, vol. 1 to 3, *Cold Spring Harbor Laboratory Press* (1989) pp. xi –xxxviii.

Sanger et al. "DNA Sequencing with Chain–Terminating Inhibitors" *Proc. Natl. Acad. Sci. USA.* 74(12):5463–5467 (1977).

Sharma et al., "Usefulness and Tolerability of Hirulog, a Direct Thrombin–Inhibitor, in Unstable Angina Pectoris" *Am. J. Cardiol.* 72:1357–1360 (1993).

Shaw et al., "A General Method for the Transfer of Cloned Genes to Plant Cells " *Gene,* 23:15–330 (1983).

Shimatake et al., "Purified λ Regulatory Protein cII Positively Activates Promoters for Lysogenic Development" *Nature,* 292:128–132 (1981).

Shulman et al., "Platelet Dynamics" *Hemostasis and Thrombosis: Basic Principles and Clinical Practice* 251–253 (1982) J.B. Lippincott Comp., Philadelphia.

Capello et al., "Ancylostoma caninum anticoagulant peptide: cloning by PCR and expression of soluble, active protein in *E. coli* ", *Molec. Biochem. Parasitol.* 80:113–117 (1996).

Smith et al., "Libraries of Peptide and Proteins Displayed on Filamentous Phage" *Methods of Enzomol. 217,* 228–257 (1993).

Soumillion et al., "Selection of β–lactamase on Filamentous Bacteriophage by Catalytic Activity" *J. Mol. Biol.* 237:415–422 (1994).

Spellman et al., "Anticoagulant Activity of Dog Hookworm" *Am. J. Physiol.* 220(4):922–927 (1971).

Stanssens et al., "Anticoagulant Repertoire of the Hookworm *Ancylostoma Caninum*" *Proc. Natl. Acad. Sci. U.S.A.* 93:2149–2154 (1996).

Taylor, "Identification of Protein Sequence Homology by Censenus Template Alignment" *J. Mol. Biol.* 188:233–258 (1986).

Tuszynski et al., "Isolation and Characterization of Antistatin" *J. Biol. Chem,* 262(20):9718–9723 (1987).

Van Solingen et al., "Fusion of Yeast Spheroplasts" *J. Bacter.* 130:946–947 (1977).

Van Lenten et al., "Studies on the Chemical and Enzymatic Modification of Glycoproteins" *J. Biol. Chem.* 246(6):1889–1894 (1971).

Vieira et al., "Production of Single–Stranded Plasmid DNA" *Methods in Enzymol. 153,* 3–11 (1987).

Vlasuk, et al., "Structural and Functional Characterization of Tick Anticoagulant Peptide (TAP): A Potent and Selective Inhibitor of Blood Coagulation Factor Xa" *Thromb. Haemostas.* 70(1):212–216 (1993).

Vrijsen et al., "Resolution of the Major Poliovirus Polypeptides into Doublets" *Virology,* 86:546–555 (1978).

Waxman et al., "Tick Anticoagulant Peptide (TAP) Is a Novel Inhibitor of Blood Coagulation Factor Xa" *Science* 248:593–596 (1990).

Weitz et al., "New Anticoagulant Strategies" *J. Lab. Clin. Med.* 122(4):364–373 (1993).

Zell et al., "DNA Mismatch—Repair in *Escherichia Coli* Counteracting the Hydrolytic Deamination of 5-Methyl-Cytosine Residues" *Embo J.,* 6(6):1809–1815 (1987).

Hotez and Pritchard, "Hookworm Infection", *Sci. Am.,* Jun. 1995, pp. 68–74.

Jespers et al., "Surface Expression and Ligand-Based Selection of cDNAs Fused to Fileamentous Phage Gene IV", *Bio/Technology* 13:378–382 (1995).

Jock Friedly, "New Anticoagulant Prompts Bad Blood Between Partners", *Science* 271:1800–1801 (1996).

May 10, 1996 letter from David Kabakoff *Science;* not published.

May 13, 1996 fax from Yale University to Corvas including letter (May 10, 1996) said to have been sent to *Science;* not published.

Jul. 16, 1996 e–mail from Science to Jean Ellis noting receipt of May 10, 1996 Kabakoff letter.

Sep. 17, 1996 e–mail from *Science* to Jean Ellis noting Science decision to not publish May 10, 1996 Kabakoff letter.

Sep. 26, 1996 letter from Randall Woods to *Science;* not published.

Apr. 21, 1995 letter from George Vlasuk to *Thrombosis and Heamostasis;* not published.

Fig. 1

```
          1                    10                    20                    30
          *                     *                     *                     *
G AATTCCGCTA CTACTCAACA ATG AAG ATG CTT TAC GCT ATC GCT
                       Met Lys Met Leu Tyr Ala Ile Ala 40                    50                    60                    70
      *                     *                     *                     *
ATA ATG TTT CTC CTG GTA TCA TTA TGC AGC GCA AGA ACA GTG
Ile Met Phe Leu Leu Val Ser Leu Cys Ser Ala Arg Thr Val 80              90                  100                 110                 120
      *               *                    *                   *                   *
AGG AAG GCA TAC CCG GAG TGT GGT GAG AAT GAA TGG CTC GAC
Arg Lys Ala Tyr Pro Glu Cys Gly Glu Asn Glu Trp Leu Asp 130                 140                 150                 160
                *                   *                   *                   *
GAC TGT GGA ACT CAG AAG CCA TGC GAG GCC AAG TGC AAT GAG
Asp Cys Gly Thr Gln Lys Pro Cys Glu Ala Lys Cys Asn Glu 170                 180                 190                 200
            *                   *                   *                   *
GAA CCC CCT GAG GAG GAA GAT CCG ATA TGC CGC TCA CGT GGT
Glu Pro Pro Glu Glu Glu Asp Pro Ile Cys Arg Ser Arg Gly 210                 220                 230                 240
            *                   *                   *                   *
TGT TTA TTA CCT CCT GCT TGC GTA TGC AAA GAC GGA TTC TAC
Cys Leu Leu Pro Pro Ala Cys Val Cys Lys Asp Gly Phe Tyr 250                 260                 270                 280
        *                   *                   *                   *
AGA GAC ACG GTG ATC GGC GAC TGT GTT AGG GAA GAA GAA TGC
Arg Asp Thr Val Ile Gly Asp Cys Val Arg Glu Glu Glu Cys 290             300                 310                 320                 330
        *               *                   *                   *                   *
GAC CAA CAT GAG ATT ATA CAT GTC TGA ACGAGAAAGC AACAATAACC
Asp Gln His Glu Ile Ile His Val 340         350         360         370         380
            *           *           *           *           *
      AAAGGTTCCA ACTCTCGCTC TGCAAAATCG CTAGTTGGAT GTCTCTTTTG 390         400         410         420         430
            *           *           *           *           *
      CGTCCGAATA GTTTTAGTTG ATGTTAAGTA AGAACTCCTG CTGGAGAGAA 440         450
            *           *
      TAAAGCTTTC CAACTCC poly(A)
```

Fig. 2

Lys Ala Tyr Pro Glu Cys Gly Glu Asn Glu Trp Leu Asp Asp
1               5                   10

Cys Gly Thr Gln Lys Pro Cys Glu Ala Lys Cys Asn Glu Glu
15              20                  25

Pro Pro Glu Glu Glu Asp Pro Ile Cys Arg Ser Arg Gly Cys
    30              35                  40

Leu Leu Pro Pro Ala Cys Val Cys Lys Asp Gly Phe Tyr Arg
        45              50                  55

Asp Thr Val Ile Gly Asp Cys Val Arg Glu Glu Glu Cys Asp
            60              65                  70

Gln His Glu Ile Ile His Val
            75

Fig. 3

```
         1              10             20             30
         *              *              *              *
G AATTCCGCTA CTACTCAACA ATG AAG ATG CTT TAC GCT ATC GCT
                       Met Lys Met Leu Tyr Ala Ile Ala 40             50             60             70
    *              *              *              *
ATA ATG TTT CTC CTG GTG TCA TTA TGC AGC ACA AGA ACA GTG
Ile Met Phe Leu Leu Val Ser Leu Cys Ser Thr Arg Thr Val 80             90            100            110            120
    *              *              *              *              *
AGG AAG GCA TAC CCG GAG TGT GGT GAG AAT GAA TGG CTC GAC
Arg Lys Ala Tyr Pro Glu Cys Gly Glu Asn Glu Trp Leu Asp 130            140            150            160
                *              *              *              *
GTC TGT GGA ACT AAG AAG CCA TGC GAG GCC AAG TGC AGT GAG
Val Cys Gly Thr Lys Lys Pro Cys Glu Ala Lys Cys Ser Glu 170            180            190            200
           *              *              *              *
GAA GAG GAG GAA GAT CCG ATA TGC CGA TCA TTT TCT TGT CCG
Glu Glu Glu Glu Asp Pro Ile Cys Arg Ser Phe Ser Cys Pro 210            220            230            240
          *              *              *              *
GGT CCC GCT GCT TGC GTA TGC GAA GAC GGA TTC TAC AGA GAC
Gly Pro Ala Ala Cys Val Cys Glu Asp Gly Phe Tyr Arg Asp 250            260            270            280
          *              *              *              *
ACG GTG ATC GGC GAC TGT GTT AAG GAA GAA GAA TGC GAC CAA
Thr Val Ile Gly Asp Cys Val Lys Glu Glu Glu Cys Asp Gln 290            300            310            320            330
          *              *              *              *              *
CAT GAG ATT ATT CAT GTC TGA ACGAGAGAGC AGTAATAACC
His Glu Ile Ile His Val 340            350            360            370            380
               *              *              *              *              *
         AAAGGTTCCA ACTTTCGCTC TACAAAATCG CTAGTTGGAT TTCTCCTTTG 390            400            410            420            430
               *              *              *              *              *
         CGTGCGAATA GTTTTAGTTG ATATTAAGTA AAACCTCCTG TTGAAGAGAA

440
               *
         TAAAGCTTTC CAACTTC poly(A)
```

Fig. 4

```
Lys Ala Tyr Pro Glu Cys Gly Glu Asn Glu Trp Leu Asp Val
1               5                       10

Cys Gly Thr Lys Lys Pro Cys Glu Ala Lys Cys Ser Glu Glu
15              20                      25

Glu Glu Glu Asp Pro Ile Cys Arg Ser Phe Ser Cys Pro Gly
    30                  35                  40

Pro Ala Ala Cys Val Cys Glu Asp Gly Phe Tyr Arg Asp Thr
    45                  50                      55

Val Ile Gly Asp Cys Val Lys Glu Glu Cys Asp Gln His
            60              65                  70

Glu Ile Ile His Val
                75
```

Fig. 5

```
Arg Thr Val Arg Lys Ala Tyr Pro Glu Cys Gly Glu Asn Glu
            1               5                       10

Trp Leu Asp Asp Cys Gly Thr Gln Lys Pro Cys Glu Ala Lys
            15                      20

Cys Asn Glu Glu Pro Pro Glu Glu Glu Asp Pro Ile Cys Arg
25              30                      35

Ser Arg Gly Cys Leu Leu Pro Pro Ala Cys Val Cys Lys Asp
    40                  45                  50

Gly Phe Tyr Arg Asp Thr Val Ile Gly Asp Cys Val Arg Glu
        55                  60                      65

Glu Glu Cys Asp Gln His Glu Ile Ile His Val
            70                      75
```

Fig. 6

Arg Thr Val Arg Lys Ala Tyr Pro Glu Cys Gly Glu Asn Glu
                  1               5                      10

Trp Leu Asp Val Cys Gly Thr Lys Lys Pro Cys Glu Ala Lys
              15                      20

Cys Ser Glu Glu Glu Glu Glu Asp Pro Ile Cys Arg Ser Phe
25              30                      35

Ser Cys Pro Gly Pro Ala Ala Cys Val Cys Glu Asp Gly Phe
    40              45                      50

Tyr Arg Asp Thr Val Ile Gly Asp Cys Val Lys Glu Glu Glu
        55                  60                      65

Cys Asp Gln His Glu Ile Ile His Val
            70              75

Fig. 7A-1

```
      1          10          20              30            40
      *           *           *               *             *
      GAATTCACTA TTATCCAACA ATG GCG GTG CTT TAT TCA GTA GCA
      EcoRI                 Met Ala Val Leu Tyr Ser Val Ala 50              60              70            80
            *               *               *             *
      ATA GCG TTA CTA CTG GTA TCA CAA TGC AGT GGG AAA CCG AAC
      Ile Ala Leu Leu Leu Val Ser Gln Cys Ser Gly Lys Pro Asn 90             100             110           120
            *               *               *             *
      AAT GTG ATG ACT AAC GCT TGT GGT CTT AAT GAA TAT TTC GCT
      Asn Val Met Thr Asn Ala Cys Gly Leu Asn Glu Tyr Phe Ala 130             140             150           160           170
       *               *               *             *             *
      GAG TGT GGC AAT ATG AAG GAA TGC GAG CAC AGA TGC AAT GAG
      Glu Cys Gly Asn Met Lys Glu Cys Glu His Arg Cys Asn Glu 180             190             200           210
                   *               *               *             *
      GAG GAA AAT GAG GAA AGG GAC GAG GAA AGA ATA ACG GCA TGC
      Glu Glu Asn Glu Glu Arg Asp Glu Glu Arg Ile Thr Ala Cys 220             230             240           250
                   *               *               *             *
      CTC ATC CGT GTG TGT TTC CGT CCT GGT GCT TGC GTA TGC AAA
      Leu Ile Arg Val Cys Phe Arg Pro Gly Ala Cys Val Cys Lys 260             270             280           290
                   *               *               *             *
      GAC GGA TTC TAT AGA AAC AGA ACA GGC AGC TGT GTG GAA GAA
      Asp Gly Phe Tyr Arg Asn Arg Thr Gly Ser Cys Val Glu Glu 300             310             320           330
                   *               *               *             *
      GAT GAC TGC GAG TAC GAG AAT ATG GAG TTC ATT ACT TTT GCA
      Asp Asp Cys Glu Tyr Glu Asn Met Glu Phe Ile Thr Phe Ala 340             350             360           370           380
       *               *               *             *             *
      CCA GAA GTA CCG ATA TGT GGT TCC AAC GAA AGG TAC TCC GAC
      Pro Glu Val Pro Ile Cys Gly Ser Asn Glu Arg Tyr Ser Asp 390             400             410           420
                   *               *               *             *
      TGC GGC AAT GAC AAA CAA TGC GAG CGC AAA TGC AAC GAG GAC
      Cys Gly Asn Asp Lys Gln Cys Glu Arg Lys Cys Asn Glu Asp 430             440             450           460
                   *               *               *             *
      GAT TAT GAG AAG GGA GAT GAG GCA TGC CGC TCA CAT GTT TGT
      Asp Tyr Glu Lys Gly Asp Glu Ala Cys Arg Ser His Val Cys
```

Fig. 7A-2

```
      470              480              490              500
       *                *                *                *
GAA  CGT  CCT  GGT  GCC  TGT  GTA  TGC  GAA  GAC  GGG  TTC  TAC  AGA
Glu  Arg  Pro  Gly  Ala  Cys  Val  Cys  Glu  Asp  Gly  Phe  Tyr  Arg 510              520              530              540
       *                *                *                *
AAC  AAA  AAA  GGT  AGC  TGT  GTG  GAA  AGC  GAT  GAC  TGC  GAA  TAC
Asn  Lys  Lys  Gly  Ser  Cys  Val  Glu  Ser  Asp  Asp  Cys  Glu  Tyr 550              560              570              580              590
       *                *                *                *                *
GAT  AAT  ATG  GAT  TTC  ATC  ACT  TTT  GCA  CCA  GAA  ACC  TCA  CGA
Asp  Asn  Met  Asp  Phe  Ile  Thr  Phe  Ala  Pro  Glu  Thr  Ser  Arg 600         610         620         630         640
            *           *           *           *           *
TAA  CCAAAGATGC  TACCTCTCGT  ACGCAACTCC  GCTGATTGAGGTTGATTC 650         660         670         680         690
            *           *           *           *           *
ACTCCCTTGCATCTCAACATTTTTTTTGTGATGCTGTGCATCTGAGCTTAACCTG 700         710
       *           *
ATAAAGCCTATGGTG  poly(A)
```

Fig. 7B

```
  1           10              20              30              40
  *            *               *               *               *
GAATTCCGC ATG CGG ACG CTC TAC CTC ATT TCT ATC TGG TTG
EcoRI     Met Arg Thr Leu Tyr Leu Ile Ser Ile Trp Leu 50              60              70              80
       *               *               *               *
TTC CTC ATC TCG CAA TGT AAT GGA AAA GCA TTC CCG AAA TGT
Phe Leu Ile Ser Gln Cys Asn Gly Lys Ala Phe Pro Lys Cys 90             100             110             120
       *               *               *               *
GAC GTC AAT GAA AGA TTC GAG GTG TGT GGC AAT CTG AAG GAG
Asp Val Asn Glu Arg Phe Glu Val Cys Gly Asn Leu Lys Glu 130             140             150             160
       *               *               *               *
TGC GAG CTC AAG TGC GAT GAG GAC CCT AAG ATA TGC TCT CGT
Cys Glu Leu Lys Cys Asp Glu Asp Pro Lys Ile Cys Ser Arg 170             180             190             200             210
       *               *               *               *               *
GCA TGT ATT CGT CCC CCT GCT TGC GTA TGC GAT GAC GGA TTC
Ala Cys Ile Arg Pro Pro Ala Cys Val Cys Asp Asp Gly Phe 220             230             240             250
               *               *               *               *
TAC AGA GAC AAA TAT GGC TTC TGT GTT GAA GAA GAC GAA TGT
Tyr Arg Asp Lys Tyr Gly Phe Cys Val Glu Glu Asp Glu Cys 260             270             280             290
       *               *               *               *
AAC GAT ATG GAG ATT ATT ACT TTT CCA CCA GAA ACC AAA TGA
Asn Asp Met Glu Ile Ile Thr Phe Pro Pro Glu Thr Lys 300             310             320             330             340
       *               *               *               *               *
TGACCGAAGC TTCCACCTTT CTATACATAT CTTCACTGCTTGACAGGCTTCT 350             360             370             380             390             400
       *               *               *               *               *               *
CGACAATTTAGAAGTTCTGCTTGACTTTGTCTATTTGAAATTGTTCACACTAATG 410             420
           *               *
GGGGAAGTAAAGCATTTTCACGAC poly(A)
```

Fig. 7C

```
  1           10          20                30              40
  *           *           *                 *               *
GAATTCCGCT ACATTTTCAA CA ATG TCG ACG CTT TAT GTT ATC
EcoRI                     Met Ser Thr Leu Tyr Val Ile 50            60             70              80
       *             *              *               *
GCA ATA TGT TTG CTG CTT GTT TCG CAA TGC AAT GGA AGA ACG
Ala Ile Cys Leu Leu Leu Val Ser Gln Cys Asn Gly Arg Thr 90           100            110             120
       *             *              *               *
GTG AAG AAG TGT GGC AAG AAT GAA AGA TAC GAC GAC TGT GGC
Val Lys Lys Cys Gly Lys Asn Glu Arg Tyr Asp Asp Cys Gly 130           140            150             160
 *             *              *               *
AAT GCA AAG GAC TGC GAG ACC AAG TGC GGT GAA GAG GAA AAG
Asn Ala Lys Asp Cys Glu Thr Lys Cys Gly Glu Glu Glu Lys 170           180            190             200             210
 *             *              *               *               *
GTG TGC CGT TCG CGT GAG TGT ACT AGT CCT GGT GCC TGC GTA
Val Cys Arg Ser Arg Glu Cys Thr Ser Pro Gly Ala Cys Val 220            230             240             250
               *              *               *               *
    TGC GAA CAA GGA TTC TAC AGA GAT CCG GCT GGC GAC TGT GTC
    Cys Glu Gln Gly Phe Tyr Arg Asp Pro Ala Gly Asp Cys Val 260            270             280             290
               *              *               *               *
    ACT GAT GAA GAA TGT GAT GAA TGG AAC AAT ATG GAG ATC ATT
    Thr Asp Glu Glu Cys Asp Glu Trp Asn Asn Met Glu Ile Ile 300           310            320             330             340
         *             *              *               *               *
    ACT ATG CCA AAA CAG TAG TGCGAAGTTC CCTTCTTTCT CCAAATCTG
    Thr Met Pro Lys Gln 350           360            370             380             390
               *             *              *               *               *
           C TCCGTGCTCAATTATCACACACCTCCACTAGTTAAGATTGACTGACTCTCTTG 400           410            420             430             440             450
         *             *              *               *               *               *
    CATTGTAGTATTTTCGCTTGACTCTGTGCATTTAAGCATGAGATACTACTAGGGA 460           470
               *             *
    GAATAAAAATTACTAACTAC poly(A)
```

Fig. 7D

```
  1                    10                   20                   30                   40
  *                    *                    *                    *                    *
GAATTCCGG  AAA  TGT  CCT  ACC  GAT  GAA  TGG  TTC  GAT  TGG  TGT
EcoRI      Lys  Cys  Pro  Thr  Asp  Glu  Trp  Phe  Asp  Trp  Cys 50                   60                   70                   80
          *                    *                    *                    *
GGA  ACT  TAC  AAG  CAT  TGC  GAA  CTC  AAG  TGC  GAT  AGG  GAG  CTA
Gly  Thr  Tyr  Lys  His  Cys  Glu  Leu  Lys  Cys  Asp  Arg  Glu  Leu 90                  100                  110                  120
          *                    *                    *                    *
ACT  GAG  AAA  GAA  GAG  CAG  GCA  TGT  CTC  TCA  CGT  GTT  TGT  GAG
Thr  Glu  Lys  Glu  Glu  Gln  Ala  Cys  Leu  Ser  Arg  Val  Cys  Glu 130                  140                  150                  160
          *                    *                    *                    *
AAG  TCC  GCT  TGC  GTA  TGC  AAT  GAC  GGA  TTA  TAC  AGA  GAC  AAG
Lys  Ser  Ala  Cys  Val  Cys  Asn  Asp  Gly  Leu  Tyr  Arg  Asp  Lys 170                  180                  190                  200                  210
  *                    *                    *                    *                    *
TTT  GGC  AAC  TGT  GTT  GAA  AAA  GAC  GAA  TGC  AAC  GAT  ATG  GAG
Phe  Gly  Asn  Cys  Val  Glu  Lys  Asp  Glu  Cys  Asn  Asp  Met  Glu 220                  230                  240                  250
               *                    *                    *                    *
ATT  ATT  ACT  TTT  GCA  CCA  GAA  ACC  AAA  TAA  TGGCCTAAGG  TTCC
Ile  Ile  Thr  Phe  Ala  Pro  Glu  Thr  Lys 260                  270                  280                  290                  300
          *                    *                    *                    *                    *
AAACCT  TGCTACACAC  CGTCAGTGCTTTACTGTTTCCTCTACGTGTTAGTAGT 310                  320                  330                  340                  350                  360
  *                    *                    *                    *                    *                    *
TTTGCTTGACTCTGTGTATTTAAGCATTGTCTACTAATGGGCAAAGTAAAGCATT 370                  380                  390
          *                    *                    *
GTAAGGACATAATAATGAGTAAACCTTCTGATTT  poly(A)
```

Fig. 7E-1

```
1           10          20               30              40
*           *           *                *               *
GAATTCCGGG  CGGCAGAAAG  ATG CGA ATG CTC TAC CTT GTT CCT
EcoRI                   Met Arg Met Leu Tyr Leu Val Pro 50              60              70              80
        *               *               *               *
ATC TGG TTG CTG CTC ATT TCG CTA TGC AGT GGA AAA GCT GCG
Ile Trp Leu Leu Leu Ile Ser Leu Cys Ser Gly Lys Ala Ala 90              100             110             120
        *               *               *               *
AAG AAA TGT GGT CTC AAT GAA AGG CTG GAC TGT GGC AAT CTG
Lys Lys Cys Gly Leu Asn Glu Arg Leu Asp Cys Gly Asn Leu 130             140             150         160             170
    *               *               *           *               *
AAG CAA TGC GAG CCC AAG TGC AGC GAC TTG GAA AGT GAG GAG
Lys Gln Cys Glu Pro Lys Cys Ser Asp Leu Glu Ser Glu Glu 180             190             200             210
            *               *               *               *
TAT GAG GAG GAA GAT GAG TCG AAA TGT CGA TCA CGT GAA TGT
Tyr Glu Glu Glu Asp Glu Ser Lys Cys Arg Ser Arg Glu Cys 220             230             240             250
        *               *               *               *
TCT CGT CGT GTT TGT GTA TGC GAT GAA GGA TTC TAC AGA AAC
Ser Arg Arg Val Cys Val Cys Asp Glu Gly Phe Tyr Arg Asn 260             270             280             290
        *               *               *               *
AAG AAG GGC AAG TGT GTT GCA AAA GAT GTT TGC GAG GAC GAC
Lys Lys Gly Lys Cys Val Ala Lys Asp Val Cys Glu Asp Asp 300             310             320             330
        *               *               *               *
AAT ATG GAG ATT ATC ACT TTT CCA CCA GAA GAC GAA TGT GGT
Asn Met Glu Ile Ile Thr Phe Pro Pro Glu Asp Glu Cys Gly 340             350             360             370         380
    *               *               *               *           *
CCC GAT GAA TGG TTC GAC TAC TGT GGA AAT TAT AAG AAG TGC
Pro Asp Glu Trp Phe Asp Tyr Cys Gly Asn Tyr Lys Lys Cys 390             400             410             420
            *               *               *               *
GAA CGC AAG TGC AGT GAG GAG ACA AGT GAG AAA AAT GAG GAG
Glu Arg Lys Cys Ser Glu Glu Thr Ser Glu Lys Asn Glu Glu 430             440             450             460
            *               *               *               *
GCA TGC CTC TCT CGT GCT TGT ACT GGT CGT GCT TGC GTA TGC
Ala Cys Leu Ser Arg Ala Cys Thr Gly Arg Ala Cys Val Cys
```

*Fig. 7E-2*

```
          470              480              490              500
           *                *                *                *
AAA GAC GGA TTG TAC AGA GAC GAC TTT GGC AAC TGT GTT CCA
Lys Asp Gly Leu Tyr Arg Asp Asp Phe Gly Asn Cys Val Pro 510              520              530              540
           *                *                *                *
CAT GAC GAA TGC AAC GAT ATG GAG ATC ATC ACT TTT CCA CCG
His Asp Glu Cys Asn Asp Met Glu Ile Ile Thr Phe Pro Pro 550              560              570              580              590
           *                *                *                *                *
GAA ACC AAA CAT TGA CCAGAGGCTC CAACTCTCGC TACACAACGT CA
Glu Thr Lys His 600              610              620              630              640              650
           *                *                *                *                *                *
GGGCTAGAAT GGCCCCTCTG CGAGTTAGTA GTTTTGCTTG ACTCTGCTTA TTTGA 660              670              680
           *                *                *
GCACTTTCTA TTGATGGCGA AAATAAAGCA TTTAAAAC poly(A)
```

Fig. 7F

```
    1          10         20         30         40
    *          *          *          *          *
GAATTCCGCG CACCTGAGAG GTGAGCTACG CAAGTCTTCG CTGGTACA
EcoRI 50         60         70         80         90
 *          *          *          *          *
ATG ATC CGA AAG CTC GTT CTG CTG ACT GCT ATC GTC ACG GTG
Met Ile Arg Lys Leu Val Leu Leu Thr Ala Ile Val Thr Val 100        110        120        130
            *          *          *          *
GTG CTA AGT GCG AAG ACC TGT GGA CCA AAC GAG GAG TAC ACT
Val Leu Ser Ala Lys Thr Cys Gly Pro Asn Glu Glu Tyr Thr 140        150        160        170
       *          *          *          *
GAA TGC GGG ACG CCA TGC GAG CCG AAG TGC AAT GAA CCG ATG
Glu Cys Gly Thr Pro Cys Glu Pro Lys Cys Asn Glu Pro Met 180        190        200        210
       *          *          *          *
CCA GAC ATC TGT ACT CTG AAC TGC ATC GTG AAC GTG TGT CAG
Pro Asp Ile Cys Thr Leu Asn Cys Ile Val Asn Val Cys Gln 220        230        240        250
       *          *          *          *
TGC AAA CCC GGC TTC AAG CGC GGA CCG AAA GGA TGC GTC GCC
Cys Lys Pro Gly Phe Lys Arg Gly Pro Lys Gly Cys Val Ala 260        270        280        290        300
       *          *          *          *          *
CCC GGA CCA GGC TGT AAA TAG TTCTCCACCT GCCCTTTCGT TGGAA
Pro Gly Pro Gly Cys Lys 310        320        330        340
          *          *          *          *
CAAAT GGCTGTCTTTTTACATTCTGAATCAATAAAGCCGAACGGT poly(A)
```

Fig. 8A

```
  1          10          20          30          40
  *           *           *           *           *
  AAGCTTTGCT AACATACTGC GTAATAAGGA GTCTTAATC ATG CCA GTT
  HindIII                                      Met Pro Val 50          60          70          80          90
  *           *           *           *           *
  CTT TTG GGT ATT CCG TTA TTA TTG CGT TTC CTC GGT TTC CTT
  Leu Leu Gly Ile Pro Leu Leu Leu Arg Phe Leu Gly Phe Leu 100         110         120         130
               *           *           *           *
  CTG GTA ACT TTG TTC GGC TAT CTG CTT ACT TTC CTT AAA AAG
  Leu Val Thr Leu Phe Gly Tyr Leu Leu Thr Phe Leu Lys Lys 140         150         160         170
               *           *           *           *
  GGC TTC GGT AAG ATA GCT ATT GCT ATT TCA TTG TTT CTT GCT
  Gly Phe Gly Lys Ile Ala Ile Ala Ile Ser Leu Phe Leu Ala 180         190         200         210
               *           *           *           *
  CTT ATT ATT GGG CTT AAC TCA ATT CTT GTG GGT TAT CTC TCT
  Leu Ile Ile Gly Leu Asn Ser Ile Leu Val Gly Tyr Leu Ser 220         230         240         250
               *           *           *           *
  GAT ATT AGC GCA CAA TTA CCC TCT GAT TTT GTT CAG GGC GTT
  Asp Ile Ser Ala Gln Leu Pro Ser Asp Phe Val Gln Gly Val 260         270         280         290         300
   *           *           *           *           *
  CAG TTA ATT CTC CCG TCT AAT GCG CTT CCC TGT TTT TAT GTT
  Gln Leu Ile Leu Pro Ser Asn Ala Leu Pro Cys Phe Tyr Val 310         320         330         340
               *           *           *           *
  ATT CTC TCT GTA AAG GCT GCT ATT TTC ATT TTT GAC GTT AAA
  Ile Leu Ser Val Lys Ala Ala Ile Phe Ile Phe Asp Val Lys 350         360         370         380
               *           *           *           *
  CAA AAA ATC GTT TCT TAT TTG GAT TGG GAT AAA GGT GGA GGC
  Gln Lys Ile Val Ser Tyr Leu Asp Trp Asp Lys Gly Gly Gly 390         400         410         420         430
               *           *           *           *           *
  TCA GGC GGA GGCCAAGTCGGCC ATCCCATATCAC GCGGCCGC GGATCC
  Ser Gly Gly     SfiI                   NotI     BamHI
```

Fig. 8B

```
1          10         20         30         40
*          *          *          *          *
AAGCTTTGCT AACATACTGC GTAATAAGGA GTCTTAATC  ATG CCA GTT
HindIII                                     Met Pro Val 50         60         70         80         90
*          *          *          *          *
CTT TTG GGT ATT CCG TTA TTA TTG CGT TTC CTC GGT TTC CTT
Leu Leu Gly Ile Pro Leu Leu Leu Arg Phe Leu Gly Phe Leu 100        110        120        130
           *          *          *          *
CTG GTA ACT TTG TTC GGC TAT CTG CTT ACT TTC CTT AAA AAG
Leu Val Thr Leu Phe Gly Tyr Leu Leu Thr Phe Leu Lys Lys 140        150        160        170
           *          *          *          *
GGC TTC GGT AAG ATA GCT ATT GCT ATT TCA TTG TTT CTT GCT
Gly Phe Gly Lys Ile Ala Ile Ala Ile Ser Leu Phe Leu Ala 180        190        200        210
           *          *          *          *
CTT ATT ATT GGG CTT AAC TCA ATT CTT GTG GGT TAT CTC TCT
Leu Ile Ile Gly Leu Asn Ser Ile Leu Val Gly Tyr Leu Ser 220        230        240        250
           *          *          *          *
GAT ATT AGC GCA CAA TTA CCC TCT GAT TTT GTT CAG GGC GTT
Asp Ile Ser Ala Gln Leu Pro Ser Asp Phe Val Gln Gly Val 260        270        280        290        300
           *          *          *          *          *
CAG TTA ATT CTC CCG TCT AAT GCG CTT CCC TGT TTT TAT GTT
Gln Leu Ile Leu Pro Ser Asn Ala Leu Pro Cys Phe Tyr Val 310        320        330        340
           *          *          *          *
ATT CTC TCT GTA AAG GCT GCT ATT TTC ATT TTT GAC GTT AAA
Ile Leu Ser Val Lys Ala Ala Ile Phe Ile Phe Asp Val Lys 350        360        370        380
           *          *          *          *
CAA AAA ATC GTT TCT TAT TTG GAT TGG GAT AAA GGT GGA GGC
Gln Lys Ile Val Ser Tyr Leu Asp Trp Asp Lys Gly Gly Gly 390        400        410        420        430
           *          *          *          *          *
TCA GGC GGA G GGCCAAGTCGGCC ATCCCATATCAC GCGGCCGC GGATCC
Ser Gly Gly     SfiI                     NotI     BamHI
```

Fig. 8C

```
  1          10         20         30         40
  *           *          *          *          *
AAGCTTTGCT AACATACTGC GTAATAAGGA GTCTTAATC ATG CCA GTT
HindIII                                    Met Pro Val 50         60         70         80         90
  *          *          *          *          *
CTT TTG GGT ATT CCG TTA TTA TTG CGT TTC CTC GGT TTC CTT
Leu Leu Gly Ile Pro Leu Leu Leu Arg Phe Leu Gly Phe Leu 100        110        120        130
            *          *          *          *
CTG GTA ACT TTG TTC GGC TAT CTG CTT ACT TTC CTT AAA AAG
Leu Val Thr Leu Phe Gly Tyr Leu Leu Thr Phe Leu Lys Lys 140        150        160        170
            *          *          *          *
GGC TTC GGT AAG ATA GCT ATT GCT ATT TCA TTG TTT CTT GCT
Gly Phe Gly Lys Ile Ala Ile Ala Ile Ser Leu Phe Leu Ala 180        190        200        210
            *          *          *          *
CTT ATT ATT GGG CTT AAC TCA ATT CTT GTG GGT TAT CTC TCT
Leu Ile Ile Gly Leu Asn Ser Ile Leu Val Gly Tyr Leu Ser 220        230        240        250
            *          *          *          *
GAT ATT AGC GCA CAA TTA CCC TCT GAT TTT GTT CAG GGC GTT
Asp Ile Ser Ala Gln Leu Pro Ser Asp Phe Val Gln Gly Val 260        270        280        290        300
            *          *          *          *          *
CAG TTA ATT CTC CCG TCT AAT GCG CTT CCC TGT TTT TAT GTT
Gln Leu Ile Leu Pro Ser Asn Ala Leu Pro Cys Phe Tyr Val 310        320        330        340
            *          *          *          *
ATT CTC TCT GTA AAG GCT GCT ATT TTC ATT TTT GAC GTT AAA
Ile Leu Ser Val Lys Ala Ala Ile Phe Ile Phe Asp Val Lys 350        360        370        380
            *          *          *          *
CAA AAA ATC GTT TCT TAT TTG GAT TGG GAT AAA GGT GGA GGC
Gln Lys Ile Val Ser Tyr Leu Asp Trp Asp Lys Gly Gly Gly 390        400        410        420        430
            *          *          *          *          *
TCA GGC GGA TC GGCCAAGTCGGCC ATCCCATATCAC GCGGCCGC GGATCC
Ser Gly Gly        SfiI                    NotI     BamHI
```

Fig. 9

```
1          10         20         30         40
*          *          *          *          *
GAATTCCGG  CTG GTW TCC TAC TGC AGT GGA AAA GCA ACG ATG
EcoRI      Leu Val Ser Tyr Cys Ser Gly Lys Ala Thr Met 50         60         70         80
       *          *          *          *
CAG TGT GGT GAG AAT GAA AAG TAC GAT TCG TGC GGT AGC AAG
Gln Cys Gly Glu Asn Glu Lys Tyr Asp Ser Cys Gly Ser Lys 90         100        110        120
       *          *          *          *
GAG TGC GAT AAG AAG TGC AAA TAT GAC GGA GTT GAG GAG GAA
Glu Cys Asp Lys Lys Cys Lys Tyr Asp Gly Val Glu Glu Glu 130        140        150        160
       *          *          *          *
GAC GAC GAG GAA CCT AAT GTG CCA TGC CTA GTA CGT GTG TGT
Asp Asp Glu Glu Pro Asn Val Pro Cys Leu Val Arg Val Cys 170        180        190        200        210
  *          *          *          *          *
CAT CAA GAT TGC GTA TGC GAA GAA GGA TTC TAT AGA AAC AAA
His Gln Asp Cys Val Cys Glu Glu Gly Phe Tyr Arg Asn Lys 220        230        240        250
       *          *          *          *
GAT GAC AAA TGT GTA TCA GCA GAA GAC TGC GAA CTT GAC AAT
Asp Asp Lys Cys Val Ser Ala Glu Asp Cys Glu Leu Asp Asn 260        270        280        290
       *          *          *          *
ATG GAC TTT ATA TAT CCC GGA ACT CGA AAC TGA ACGAAGGCTC
Met Asp Phe Ile Tyr Pro Gly Thr Arg Asn 300        310        320        330        340
   *          *          *          *          *
CATTCTTGCT GCACAAGATC GATTGTCTCTCCCCTGCATCTCAGTAGTTTTGC 350        360        370        380        390        400
   *          *          *          *          *          *
TACATTGTATATGGTAGCAAAAAATTAGCTTAGGGAGAATAAAATCTTTACCTAT 410        420        430
      *          *          *
ATTTAATCAATGAAGTATTCTCTTTCT poly(A)
```

Fig. 11A

| | | | | | | | | | | |
|---|---|---|---|---|---|---|---|---|---|---|
| NAP5 | Met | Lys | Met | Leu | Tyr | Ala | Ile | Ala | Ile | Met | Phe | Leu | Leu | Val |
| NAP6 | Met | Lys | Met | Leu | Tyr | Ala | Ile | Ala | Ile | Met | Phe | Leu | Leu | Val |
| NAPc2 | | | | | | | | | | | | Leu | Val |
| AceNAP5 | Met | Arg | Thr | Leu | Tyr | Leu | Ile | Ser | Ile | Trp | Leu | Phe | Leu | Ile |
| AceNAP7 | Met | Ser | Thr | Leu | Tyr | Val | Ile | Ala | Ile | Cys | Leu | Leu | Leu | Val |
| AceNAP4d1 | Met | Ala | Val | Leu | Tyr | Ser | Val | Ala | Ile | Ala | Leu | Leu | Leu | Val |
| AceNAP4d2 | | | | | | | | | | | | | |
| AduNAP4 | | | | | | | | | | | | | |
| AduNAP7d1 | Met | Arg | Met | Leu | Tyr | Leu | Val | Pro | Ile | Trp | Leu | Leu | Leu | Ile |
| AduNAP7d2 | | | | | | | | | | | | | |
| HpoNAP5 | Met | Ile | Arg | Lys | Leu | Val | Leu | Leu | Leu | Thr | Ala | Ile | Val | Thr |

Fig. 11B

| | | | | | | | | | | | | | | |
|---|---|---|---|---|---|---|---|---|---|---|---|---|---|---|
| NAP5      | Ser | Leu | Cys | Ser | Ala | Arg | Thr | Val | Arg | Lys | Ala | Tyr | Pro | Glu |
| NAP6      | Ser | Leu | Cys | Ser | Thr | Arg | Thr | Val | Arg | Lys | Ala | Tyr | Pro | Glu |
| NAPc2     | Ser | Tyr | Cys | Ser | Gly | --- | --- | --- | --- | Lys | Ala | Thr | Met | Gln |
| AceNAP5   | Ser | Gln | Cys | Asn | Gly | --- | --- | --- | --- | Lys | Ala | Phe | Pro | Lys |
| AceNAP7   | Ser | Gln | Cys | Asn | Gly | --- | --- | --- | --- | Arg | Thr | Val | Lys | Lys |
| AceNAP4d1 | Ser | Gln | Cys | Ser | Gly | Lys | Pro | Asn | Asn | Val | Met | Thr | Asn | Ala |
| AceNAP4d2 |     |     |     |     |     |     |     |     |     |     | Val | Pro | Ile |     |
| AduNAP4   |     |     |     |     |     |     |     |     |     |     |     |     | Lys |     |
| AduNAP7d1 | Ser | Leu | Cys | Ser | Gly | --- | --- | --- | --- | Lys | Ala | Ala | Lys | Lys |
| AduNAP7d2 |     |     |     |     |     |     |     |     |     |     |     |     | Asp | Glu |
| HpoNAP5   | Val | Val | Leu | Ser | Ala | --- | --- | --- | --- | --- | --- | --- | Lys | Thr |

Fig. 11C

| | 1 | | | | | | | | 2 | | | |
|---|---|---|---|---|---|---|---|---|---|---|---|---|
| NAP5 | Cys | Gly | Glu | Asn | Glu | Trp | Leu | Asp | Asp | Cys | Gly | Thr | Gln |
| NAP6 | Cys | Gly | Glu | Asn | Glu | Trp | Leu | Asp | Val | Cys | Gly | Thr | Lys |
| NAPc2 | Cys | Gly | Glu | Asn | Glu | Lys | Tyr | Asp | Ser | Cys | Gly | Ser | Lys |
| AceNAP5 | Cys | Asp | Val | Asn | Glu | Arg | Phe | Glu | Val | Cys | Gly | Asn | Leu |
| AceNAP7 | Cys | Gly | Lys | Asn | Glu | Arg | Tyr | Asp | Asp | Cys | Gly | Asn | Ala |
| AceNAP4d1 | Cys | Gly | Leu | Asn | Glu | Tyr | Phe | Ala | Glu | Cys | Gly | Asn | Met |
| AceNAP4d2 | Cys | Gly | Ser | Asn | Glu | Arg | Tyr | Ser | Asp | Cys | Gly | Asn | Asp |
| AduNAP4 | Cys | Pro | Thr | Asp | Glu | Trp | Phe | Asp | Trp | Cys | Gly | Thr | Tyr |
| AduNAP7d1 | Cys | Gly | Leu | Asn | Glu | Arg | Leu | Asp | --- | Cys | Gly | Asn | Leu |
| AduNAP7d2 | Cys | Gly | Pro | Asp | Glu | Trp | Phe | Asp | Tyr | Cys | Gly | Asn | Tyr |
| HpoNAP5 | Cys | Gly | Pro | Asn | Glu | Gly | Tyr | Thr | Glu | Cys | Gly | Thr | --- |

Fig. 11D

|  | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| NAP5 | Lys | Pro | Cys | Glu | Ala | Lys | Cys | --- | --- | --- | --- | Asn | Glu | Glu |
| NAP6 | Lys | Pro | Cys | Glu | Ala | Lys | Cys | --- | --- | --- | --- | Ser | Glu | Glu |
| NAPc2 | Glu | --- | --- | Cys | Asp | Lys | Cys | Lys | Tyr | Asp | Gly | Val | Glu | Glu |
| AceNAP5 | Lys | Glu | Cys | Glu | Leu | Lys | Cys | --- | --- | --- | --- | --- | --- | --- |
| AceNAP7 | Lys | Asp | Cys | Glu | Thr | Lys | Cys | --- | --- | --- | Gly | --- | --- | --- |
| AceNAP4d1 | Lys | Glu | Cys | Glu | His | Arg | Cys | Asn | Glu | Glu | Glu | Asn | Glu | Glu |
| AceNAP4d2 | Lys | Gln | Cys | Glu | Arg | Lys | Cys | Asn | Glu | Asp | Asp | Tyr | Glu | Lys |
| AduNAP4 | Lys | His | Cys | Glu | Leu | Lys | Cys | Asp | Arg | Glu | Leu | Thr | Glu | Lys |
| AduNAP7d1 | Lys | Gln | Cys | Glu | Pro | Lys | Cys | Ser | Asp | Leu | Glu | Ser | Glu | Glu |
| AduNAP7d2 | Lys | Lys | Cys | Glu | Arg | Lys | Cys | Ser | Glu | Thr | Glu | Ser | Glu | Lys |
| HpoNAP5 | --- | Pro | Cys | Glu | Pro | Lys | Cys | --- | --- | --- | --- | --- | --- | --- |

Fig. 11E

| | | | | | | | | | | 5 | | | |
|---|---|---|---|---|---|---|---|---|---|---|---|---|---|
| NAP5 | Pro | Pro | Glu | Glu | Asp | Pro | Ile | --- | --- | Cys | Arg | Ser | Arg |
| NAP6 | --- | --- | Glu | Glu | Asp | Pro | Ile | --- | --- | Cys | Arg | Ser | Phe |
| NAPc2 | --- | Glu | Asp | Asp | Glu | Pro | Asn | Val | Pro | Cys | Leu | Val | Arg |
| AceNAP5 | --- | --- | Asp | Glu | Asp | Pro | Lys | Ile | --- | Cys | --- | Ser | Arg |
| AceNAP7 | --- | --- | Glu | Glu | Glu | --- | Lys | --- | Val | Cys | Arg | Ser | Arg |
| AceNAP4d1 | Arg | --- | Asp | Glu | Glu | --- | Arg | Ile | Thr | Ala | Cys | Leu | Ile | Arg |
| AceNAP4d2 | Gly | --- | Asp | Glu | --- | --- | --- | --- | Ala | Cys | Arg | Ser | His |
| AduNAP4 | --- | --- | Glu | Glu | --- | --- | --- | --- | Ala | Cys | Leu | Ser | Arg |
| AduNAP7d1 | Tyr | --- | Glu | Glu | Asp | Glu | Ser | Lys | --- | Cys | Arg | Ser | Arg |
| AduNAP7d2 | Asn | --- | Glu | Glu | --- | --- | --- | --- | Ala | Cys | Leu | Ser | Arg |
| HpoNAP5 | --- | --- | Asn | Glu | Pro | Met | Pro | Asp | Ile | --- | Cys | --- | Thr | Leu |

Fig. 11F

|           | 6   |     |     |     |     | 7   |     | 8   |     |     |
|-----------|-----|-----|-----|-----|-----|-----|-----|-----|-----|-----|
| NAP5      | Gly | Cys | Leu | Leu | Pro | Pro | Ala | Cys | Val | Cys | Lys | Asp |
| NAP6      | Ser | Cys | Pro | Gly | Pro | Ala | Ala | Cys | Val | Cys | Glu | Asp |
| NAPc2     | Val | Cys | His | Gln | Asp | --- | --- | Cys | Val | Cys | Glu | Glu |
| AceNAP5   | Ala | Cys | Ile | Arg | Pro | Pro | Ala | Cys | Val | Cys | Asp | Asp |
| AceNAP7   | Glu | Cys | Thr | Ser | Pro | Gly | Ala | Cys | Val | Cys | Glu | Gln |
| AceNAP4d1 | Val | Cys | Phe | Arg | Pro | Gly | Ala | Cys | Val | Cys | Lys | Asp |
| AceNAP4d2 | Val | Cys | Glu | Arg | Pro | Gly | Ala | Cys | Val | Cys | Glu | Asp |
| AduNAP4   | Val | Cys | Glu | Lys | --- | Ser | Ala | Cys | Val | Cys | Asn | Asp |
| AduNAP7d1 | Glu | Cys | Ser | Arg | Arg | --- | Val | Cys | Val | Cys | Asp | Glu |
| AduNAP7d2 | Ala | Cys | Thr | Gly | Arg | --- | Ala | Cys | Val | Cys | Lys | Asp |
| HpoNAP5   | Asn | Cys | Ile | Val | Asn | --- | Val | Cys | Gln | Cys | Lys | Pro |

Fig. 11G

| | | | | | | | | | 9 | | | |
|---|---|---|---|---|---|---|---|---|---|---|---|---|
| NAP5 | Gly | Phe | Tyr | Arg | Asp | Thr | Val | Ile | Gly | Asp | Cys | Val | Arg | Glu |
| NAP6 | Gly | Phe | Tyr | Arg | Asp | Thr | Val | Ile | Gly | Asp | Cys | Val | Lys | Glu |
| NAPc2 | Gly | Phe | Tyr | Arg | Asn | Lys | --- | Asp | Asp | Lys | Cys | Val | Ser | Ala |
| AceNAP5 | Gly | Phe | Tyr | Arg | Asp | Lys | Tyr | --- | Gly | Phe | Cys | Val | Glu | Glu |
| AceNAP7 | Gly | Phe | Tyr | Arg | Asp | Pro | Ala | --- | Gly | Asp | Cys | Val | Thr | Asp |
| AceNAP4d1 | Gly | Phe | Tyr | Arg | Asn | Arg | Thr | --- | Gly | Ser | Cys | Val | Glu | Glu |
| AceNAP4d2 | Gly | Phe | Tyr | Arg | Asn | Lys | Lys | --- | Gly | Ser | Cys | Val | Glu | Ser |
| AduNAP4 | Gly | Leu | Tyr | Arg | Asp | Lys | Phe | --- | Gly | Asn | Cys | Val | Glu | Lys |
| AduNAP7d1 | Gly | Phe | Tyr | Arg | Asn | Lys | Lys | --- | Gly | Lys | Cys | Val | Ala | Lys |
| AduNAP7d2 | Gly | Leu | Tyr | Arg | Asp | Asp | Phe | --- | Gly | Asn | Cys | Val | Pro | His |
| HpoNAP5 | Gly | Phe | Lys | Arg | Gly | Pro | Lys | --- | Gly | --- | Cys | Val | Ala | Pro |

Fig. 11H

```
                                        10
NAP5        Glu Glu  -   -   -  Cys Asp Gln His  -   -   -   -  Glu Ile Ile His
NAP6        Glu Glu  -   -   -  Cys Asp Gln His  -   -   -   -  Glu Ile Ile His
NAPc2       Glu Asp  -   -   -  Cys Glu  -  Leu Asp Asn Met  -  Asp Phe Ile Tyr
AceNAP5     Asp Glu  -   -   -  Cys Asn Asp  -   -   -   -  Met Glu Ile Ile Thr
AceNAP7     Glu Glu  -   -   -  Cys Asp Glu Trp Asn Asn  -   -  Glu Ile Ile Thr
AceNAP4d1   Asp Asp  -   -   -  Cys Asp  -  Tyr Glu Asn Met  -  Glu Phe Ile Thr
AceNAP4d2   Asp Asp  -   -   -  Cys Glu  -  Tyr Asp Asn Met  -  Asp Phe Ile Thr
AduNAP4     Asp Glu  -   -   -  Cys Asn Asp  -   -   -   -  Met Glu Ile Ile Thr
AduNAP7d1   Asp Val  -   -   -  Cys Glu Asp  -  Asp Asn Met  -  Glu Ile Ile Thr
AduNAP7d2   Asp Glu  -   -   -  Cys Asn Asp  -   -   -   -  Met Glu Ile Ile Thr

HpoNAP5     Gly Pro Gly Cys Lys end
```

Fig. 11I

| | | | | | | | | | |
|---|---|---|---|---|---|---|---|---|---|
| NAP5 | Val | end | | | | | | | |
| NAP6 | Val | end | | | | | | | |
| NAPc2 | Pro | Gly | Thr | Arg | Asn | end | | | |
| AceNAP5 | Phe | Pro | Pro | Glu | Thr | Lys | end | | |
| AceNAP7 | Met | Pro | Lys | Gln | end | | | | |
| AceNAP4d1 | Phe | Ala | Pro | Glu | | | | | |
| AceNAP4d2 | Phe | Ala | Pro | Glu | Thr | Ser | Arg | end | |
| AduNAP4 | Phe | Ala | Pro | Glu | | | | | |
| AduNAP7d1 | Phe | Pro | Pro | Glu | Thr | Lys | end | | |
| AduNAP7d2 | Phe | Pro | Pro | Glu | Thr | Lys | His | end | |
| HpoNAP5 | | | | | | | | | |

```
<----5'AOX1------><--------PHO1 secretion signal (S)--
......TTATTCGAAACGATGTTCTCTCCAATTTTGTCCTTGGAAATTATTTTA ---------------------------><----Pro Sequence (P)---------
GCTACTTTGCAATCTGTCTTCGCCCAGCCAGTTATCTCCACTACCGTTGGTTCC ---------------------------><-Multi-Cloning Site (MCS)
GCTGCCGAGGGTTCTTTGGACAAGAGGCCTATCCGCGGAATTCAGATCTGAAT
                              StuI    SacIIEcoRI BglII ---------------------------><---3'T---->
GCGGCCGCTCGAGACTAGTGGATCCTTAGACA...
 NotI    XhoI SpeI BamHI
  EagI
```

(AcaNAP23)           Fig. 13A

```
           10         20         30         40
            *          *          *          *
GAATTCCGCG GAATTCCGCT TGCTACTACT CAACG ATG AAG ACG CTC
EcoRI                                  Met Lys Thr Leu 50         60         70         80
      *          *          *          *
TAT ATT GTC GCT ATA TGC TCG CTC CTC ATT TCG CTG TGT ACT
Tyr Ile Val Ala Ile Cys Ser Leu Leu Ile Ser Leu Cys Thr 90         100        110        120        130
  *          *          *          *          *
GGA AAA CCT TCG GAG AAA GAA TGT GGT CCC CAT GAA AGA CTC
Gly Lys Pro Ser Glu Lys Glu Cys Gly Pro His Glu Arg Leu
             140        150        160        170
              *          *          *          *
*** *** *** *** *** *** *** *** *** *** *** *** *** ***
Asp Cys Gly Asn Lys Lys Pro Cys Glu Arg Lys Cys Lys Ile
         180        190        200        210
          *          *          *          *
*** *** *** *** *** *** *** *** *** *** *** *** *** ***
Glu Thr Ser Glu Glu Glu Asp Asp Tyr Glu Glu Gly Thr Glu 220        230        240        250
         *          *          *          *
CGT TTT CGA TGC CTC TTA CGT GTG TGT GAT CAG CCT TAT GAA
Arg Phe Arg Cys Leu Leu Arg Val Cys Asp Gln Pro Tyr Glu 260        270        280        290
    *          *          *          *
TGC ATA TGC GAT GAT GGA TAC TAC AGA AAC AAG AAA GGC GAA
Cys Ile Cys Asp Asp Gly Tyr Tyr Arg Asn Lys Lys Gly Glu 300        310        320        330        340
  *          *          *          *          *
TGT GTG ACT GAT GAT GTA TGC CAG GAA GAC TTT ATG GAG TTT
Cys Val Thr Asp Asp Val Cys Gln Glu Asp Phe Met Glu Phe 350        360        370        380
        *          *          *          *
ATT ACT TTC GCA CCA TAA ACCCAATAAT GACCAATGAC TCCCATTCTT
Ile Thr Phe Ala Pro 390        400        410        420        430
 *          *          *          *          *
CGTGATCAGC GTCGGTGGTT GACAGTCTCC CCTACATCTT AGTAGTTTTG
440        450        460        470        480
 *          *          *          *          *
CTTGATAATG TATACATAAA CTGTACTTTC TGAGATAGAA TAAAGCTCTC

490
 *
AACTAC poly(A)
```

Fig. 13B (AcaNAP24)

```
          10           20              30          40
           *            *               *           *
   GAATTCCGCG GAATTCCGCA ACG ATG AAG ACG CTC TAT ATT ATC
   EcoRI                    Met Lys Thr Leu Tyr Ile Ile 50          60           70          80
        *           *            *           *
   GCT ATA TGC TCG CTC CTC ATT TCG TTG TGT ACT GGA AGA CCG
   Ala Ile Cys Ser Leu Leu Ile Ser Leu Cys Thr Gly Arg Pro 90         100          110         120
        *           *            *           *
   GAA AAA AAG TGC GGT CCC GGT GAA AGA CTC GCC TGT GGC AAT
   Glu Lys Lys Cys Gly Pro Gly Glu Arg Leu Ala Cys Gly Asn 130         140          150         160          170
    *           *            *           *            *
   AAG AAG CCA TGC GAG CGC AAG TGC AAA ATA GAG ACA AGT GAG
   Lys Lys Pro Cys Glu Arg Lys Cys Lys Ile Glu Thr Ser Glu 180          190         200          210
           *            *           *            *
   GAG GAG GAT GAC TAC CCA GAG GGA ACC GAA CGT TTT CGA TGC
   Glu Glu Asp Asp Tyr Pro Glu Gly Thr Glu Arg Phe Arg Cys 220          230         240          250
           *            *           *            *
   CTC TTA CGT GTG TGT GAT CAG CCT TAT GAA TGC ATA TGC GAT
   Leu Leu Arg Val Cys Asp Gln Pro Tyr Glu Cys Ile Cys Asp 260          270         280          290
           *            *           *            *
   GAT GGA TAC TAC AGA AAC AAG AAA GGC GAA TGT GTG ACT GAT
   Asp Gly Tyr Tyr Arg Asn Lys Lys Gly Glu Cys Val Thr Asp 300          310         320          330
           *            *           *            *
   GAT GTA TGC CAG GAA GAC TTT ATG GAG TTT ATT ACT TTC GCA
   Asp Val Cys Gln Glu Asp Phe Met Glu Phe Ile Thr Phe Ala 340         350          360         370          380
    *           *            *           *            *
   CCA TAA ACCCAATAAT GACCACTGGC TCCCATTCTT CGTGACCAGC
   Pro 390         400          410         420          430
        *           *            *           *            *
   GTCGGTGGTT GACAGTCTCC CCTGCATCTT AGTAGTTTTG CTTGATAATG 440         450          460         470
        *           *            *           *
   TATCCATAAA CAGTACTTTC TGAGATAGAA TAAAGCTCTC AACT poly(A)
```

Fig. 13C (AcaNAP25)

```
         10          20              30            40
          *           *               *             *
 GAATTCCGTA CTACTCAACG ATG AAG ACG CTC TAT ATT ATC GCT
 EcoRI                 Met Lys Thr Leu Tyr Ile Ile Ala 50          60          70          80
        *           *           *           *
 ATA TGC TCG CTG CTC TTT TCA CTG TGT ACT GGA AGA CCG GAA
 Ile Cys Ser Leu Leu Phe Ser Leu Cys Thr Gly Arg Pro Glu 90          100         110         120
        *           *           *           *
 AAA AAG TGC GGT CCC GGT GAA AGA CTC GAC TGT GCC AAC AAG
 Lys Lys Cys Gly Pro Gly Glu Arg Leu Asp Cys Ala Asn Lys 130         140         150         160         170
  *           *           *           *           *
 AAG CCA TGC GAG CCC AAG TGC AAA ATA GAG ACA AGT GAG GAG
 Lys Pro Cys Glu Pro Lys Cys Lys Ile Glu Thr Ser Glu Glu 180         190         200         210
            *           *           *           *
 GAG GAT GAC GAC GTA GAG GAT ACC GAT GTG AGA TGC CTC GTA
 Glu Asp Asp Asp Val Glu Asp Thr Asp Val Arg Cys Leu Val 220         230         240         250
        *           *           *           *
 CGT GTG TGT GAA CGT CCT CTT AAA TGC ATA TGC AAG GAT GGA
 Arg Val Cys Glu Arg Pro Leu Lys Cys Ile Cys Lys Asp Gly 260         270         280         290
        *           *           *           *
 TAC TAC AGA AAC AAG AAA GGC GAA TGT GTG ACT GAT GAT GTA
 Tyr Tyr Arg Asn Lys Lys Gly Glu Cys Val Thr Asp Asp Val 300         310         320         330
        *           *           *           *
 TGC CAG GAA GAC TTT ATG GAG TTT ATT ACT TTC GCA CCA TAA
 Cys Gln Glu Asp Phe Met Glu Phe Ile Thr Phe Ala Pro 340         350         360         370         380
  *           *           *           *           *
 ACCCAATAAT GACCACTGGC TCCCATTCTT CGTGATCAGC GTCGGTGGTT 390         400         410         420         430
  *           *           *           *           *
 GACAGTCTCC CCTGCATCTT AGTTGCTTTG CTTGATAATC TATACATAAA 440         450         460         470
  *           *           *           *
 CAGTACTTTC TGAGATAGAA TAAAGCTCTC AACT poly(A)
```

Fig. 13D (AcaNAP31)

```
         10          20          30          40          50
          *           *           *           *           *
GAATTCCGGA CTTACTAGTA CTCAGCGAAT CAAATACGAC TTACTACTAC
EcoRI
         60          70          80          90
          *           *           *           *
TCAACG ATG AAG ACG CTC TCT GCT ATC CCT ATA ATG CTG CTC
       Met Lys Thr Leu Ser Ala Ile Pro Ile Met Leu Leu 100         110         120         130
          *           *           *           *
CTG GTA TCG CAA TGC AGT GGA AAA TCA CTG TGG GAT CAG AAG
Leu Val Ser Gln Cys Ser Gly Lys Ser Leu Trp Asp Gln Lys 140         150         160         170
          *           *           *           *
TGT GGT GAG AAT GAA AGG CTC GAC TGT GGC AAT CAG AAG GAC
Cys Gly Glu Asn Glu Arg Leu Asp Cys Gly Asn Gln Lys Asp 180         190         200         210
          *           *           *           *
TGT GAG CGC AAG TGC GAT GAT AAA AGA AGT GAA GAA GAA ATT
Cys Glu Arg Lys Cys Asp Asp Lys Arg Ser Glu Glu Glu Ile 220        230         240         250         260
  *           *           *           *           *
ATG CAG GCA TGT CTC ACA CGT CAA TGT CTT CCT CCT GTT TGC
Met Gln Ala Cys Leu Thr Arg Gln Cys Leu Pro Pro Val Cys 270         280         290         300
          *           *           *           *
GTA TGT GAA GAT GGA TTC TAC AGA AAT GAC AAC GAC CAA TGT
Val Cys Glu Asp Gly Phe Tyr Arg Asn Asp Asn Asp Gln Cys 310         320         330         340
          *           *           *           *
GTT GAT GAA GAA GAA TGC AAT ATG GAG TTT ATT ACT TTC GCA
Val Asp Glu Glu Glu Cys Asn Met Glu Phe Ile Thr Phe Ala 350         360         370         380         390
          *           *           *           *           *
CCA TGA AGCAAATGAC AGCCGATGGT TTGGACTCTC GCTACAGATC
Pro 400         410         420         430         440
          *           *           *           *           *
ACAGCTTTAC TGTTTCCCTT GCATCATAGT AGTTTTGCTA GATAGTGTAT 450         460         470         480
          *           *           *           *
ATATTAGCAT GATTTTCTGA TAGGGAGAAT AAAGCTTTCC AATTTTC poly(A)
```

Fig. 13E (AcaNAP44)

```
         10          20              30              40
          *           *               *               *
GAATTCCGCG GAATTCCGCA ACG ATG AAG ACG CTC TAT ATT ATC
EcoRI                     Met Lys Thr Leu Tyr Ile Ile 50              60              70              80
      *               *               *               *
GCT ATA TGC TCG CTC CTC ATT TCG CTG TGT ACT GGA AGA CCG
Ala Ile Cys Ser Leu Leu Ile Ser Leu Cys Thr Gly Arg Pro 90             100             110             120
      *               *               *               *
GAA AAA AAG TGC GGT CCC GGT GAA AGA CTC GAC TGT GCC AAC
Glu Lys Lys Cys Gly Pro Gly Glu Arg Leu Asp Cys Ala Asn 130             140             150             160             170
  *               *               *               *               *
AAG AAG CCA TGC GAG CCC AAG TGC AAA ATA GAG ACA AGT GAG
Lys Lys Pro Cys Glu Pro Lys Cys Lys Ile Glu Thr Ser Glu 180             190             200             210
              *               *               *               *
GAG GAG GAT GAC GAC GTA GAG GAA ACC GAT GTG AGA TGC CTC
Glu Glu Asp Asp Asp Val Glu Glu Thr Asp Val Arg Cys Leu 220             230             240             250
          *               *               *               *
GTA CGT GTG TGT GAA CGG CCT CTT AAA TGC ATA TGC AAG GAT
Val Arg Val Cys Glu Arg Pro Leu Lys Cys Ile Cys Lys Asp 260             270             280             290
          *               *               *               *
GGA TAC TAC AGA AAC AAG AAA GGC GAA TGT GTG ACT GAT GAT
Gly Tyr Tyr Arg Asn Lys Lys Gly Glu Cys Val Thr Asp Asp 300             310             320             330
          *               *               *               *
GTA TGC CAG GAA GAC TTT ATG GAG TTT ATT ACT TTC GCA CCA
Val Cys Gln Glu Asp Phe Met Glu Phe Ile Thr Phe Ala Pro 340             350             360             370             380
  *               *               *               *               *
TAA ACCCAATAAT GACCACTGGC TCCCATTCTT CGTGATCAGC 390             400             410             420             430
          *               *               *               *               *
          GTCGGTGGTT GACAGTCTCC CCTGCATCTT AGTTGCTTTG CTTGATAATC 440             450             460             470
              *               *               *               *
          TATACATAAA CAGTACTTTC TGAGATAGAA TAAAGCTCTC AACTAC
poly(A)
```

Fig. 13F-1

(AcaNAP45)

```
              10             20             30             40
               *              *              *              *
     GAATTCCGGA AAA ATG CTG ATG CTC TAC CTT GTT CCT ATC TGG
     EcoRI         Met Leu Met Leu Tyr Leu Val Pro Ile Trp 50             60             70             80
            *              *              *              *
     TTG CTA CTC ATT TCG CAA TGC AGT GGA AAA TCC GCG AAG AAA
     Leu Leu Leu Ile Ser Gln Cys Ser Gly Lys Ser Ala Lys Lys 90            100            110            120
            *              *              *              *
     TGT GGT CTC AAT GAA AAA TTG GAC TGT GGC AAT CTG AAG GCA
     Cys Gly Leu Asn Glu Lys Leu Asp Cys Gly Asn Leu Lys Ala 130            140            150            160
            *              *              *              *
     TGC GAG AAA AAG TGC AGC GAC TTG GAC AAT GAG GAG GAT TAT
     Cys Glu Lys Lys Cys Ser Asp Leu Asp Asn Glu Glu Asp Tyr 170           180            190            200           210
  *             *              *              *             *
AAG GAG GAA GAT GAG TCG AAA TGC CGA TCA CGT GAA TGT AGT
Lys Glu Glu Asp Glu Ser Lys Cys Arg Ser Arg Glu Cys Ser 220            230            240            250
            *              *              *              *
     CGT CGT GTT TGT GTA TGC GAT GAA GGA TTC TAC AGA AAC AAG
     Arg Arg Val Cys Val Cys Asp Glu Gly Phe Tyr Arg Asn Lys 260            270            280            290
            *              *              *              *
     AAG GGC CAA TGT GTG ACA AGA GAT GAT TGC GAG TAT GAC AAT
     Lys Gly Gln Cys Val Thr Arg Asp Asp Cys Glu Tyr Asp Asn 300            310            320            330
            *              *              *              *
     ATG GAG ATT ATC ACT TTT CCA CCA GAA GAT AAA TGT GGT CCC
     Met Glu Ile Ile Thr Phe Pro Pro Glu Asp Lys Cys Gly Pro 340            350            360            370
            *              *              *              *
     GAT GAA TGG TTC GAC TGG TGT GGA ACT TAC AAG CAG TGT GAG
     Asp Glu Trp Phe Asp Trp Cys Gly Thr Tyr Lys Gln Cys Glu 380           390            400            410           420
  *             *              *              *             *
CGC AAG TGC AAT AAG GAG CTA AGT GAG AAA GAT GAA GAG GCA
Arg Lys Cys Asn Lys Glu Leu Ser Glu Lys Asp Glu Glu Ala
```

Fig. 13F-2

```
              430            440            450            460
               *              *              *              *
TGC CTC TCA CGT GCT TGT ACT GGT CGT GCT TGT GTT TGC AAC
Cys Leu Ser Arg Ala Cys Thr Gly Arg Ala Cys Val Cys Asn 470            480            490            500
               *              *              *              *
GAC GGA CTG TAC AGA GAC GAT TTT GGC AAT TGT GTT GAG AAA
Asp Gly Leu Tyr Arg Asp Asp Phe Gly Asn Cys Val Glu Lys 510            520            530            540
               *              *              *              *
GAC GAA TGT AAC GAT ATG GAG ATT ATC ACT TTT CCA CCG GAA
Asp Glu Cys Asn Asp Met Glu Ile Ile Thr Phe Pro Pro Glu 550           560           570           580
       *             *             *             *
ACC AAA CAC TGA CCAAAGGCTC TAACTCTCGC TACATAACGT
Thr Lys His 590           600           610           620           630
 *             *             *             *             *
CAGTGCTTGA ATTGCCCCTT TACGAGTTAG TAATTTTGAC TAACTCTGTG 640           650           660           670           680
 *             *             *             *             *
TAATTGAGCA TTGTCTACTG ATGGTGAAAA TGAAGTGTTC AATGTCT poly(A)
```

Fig. 13G-1

(AcaNAP47)

```
              10          20          30              40
              *           *           *               *
         GAATTCCGCG GAATTCCGGT TGGCGGCAGA AAA ATG CTG ATG CTC
         EcoRI                              Met Leu Met Leu 50          60          70          80
          *           *           *           *
     TAC CTT GTT CCT ATC TGG TTC CTG CTC ATT TCG CAA TGC AGT
     Tyr Leu Val Pro Ile Trp Phe Leu Leu Ile Ser Gln Cys Ser 90         100         110         120
          *           *           *           *
     GGA AAA TCC GCG AAG AAA TGT GGC CTC AAT GAA AAA TTG GAC
     Gly Lys Ser Ala Lys Lys Cys Gly Leu Asn Glu Lys Leu Asp 130         140         150         160         170
      *           *           *           *           *
     TGT GGC AAT CTG AAG GCA TGC GAG AAA AAG TGC AGC GAC TTG
     Cys Gly Asn Leu Lys Ala Cys Glu Lys Lys Cys Ser Asp Leu 180         190         200         210
              *           *           *           *
     GAC AAT GAG GAG GAT TAT GGG GAG GAA GAT GAG TCG AAA TGC
     Asp Asn Glu Glu Asp Tyr Gly Glu Glu Asp Glu Ser Lys Cys 220         230         240         250
              *           *           *           *
     CGA TCA CGT GAA TGT ATT GGT CGT GTT TGC GTA TGC GAT GAA
     Arg Ser Arg Glu Cys Ile Gly Arg Val Cys Val Cys Asp Glu 260         270         280         290
              *           *           *           *
     GGA TTC TAC AGA AAC AAG AAG GGC CAA TGT GTG ACA AGA GAC
     Gly Phe Tyr Arg Asn Lys Lys Gly Gln Cys Val Thr Arg Asp 300         310         320         330
              *           *           *           *
     GAT TGC GAG TAT GAC AAT ATG GAG ATT ATC ACT TTT CCA CCA
     Asp Cys Glu Tyr Asp Asn Met Glu Ile Ile Thr Phe Pro Pro 340         350         360         370         380
      *           *           *           *           *
     GAA GAT AAA TGT GGT CCC GAT GAA TGG TTC GAC TGG TGT GGA
     Glu Asp Lys Cys Gly Pro Asp Glu Trp Phe Asp Trp Cys Gly 390         400         410         420
              *           *           *           *
     ACT TAC AAG CAG TGT GAG CGC AAG TGC AGT GAG GAG CTA AGT
     Thr Tyr Lys Gln Cys Glu Arg Lys Cys Ser Glu Glu Leu Ser
```

Fig. 13G-2

```
        430              440              450              460
         *                *                *                *
GAG AAA AAT GAG GAG GCA TGC CTC TCA CGT GCT TGT ACT GGT
Glu Lys Asn Glu Glu Ala Cys Leu Ser Arg Ala Cys Thr Gly 470              480              490              500
         *                *                *                *
CGT GCT TGC GTT TGC AAC GAC GGA TTG TAT AGA GAC GAT TTT
Arg Ala Cys Val Cys Asn Asp Gly Leu Tyr Arg Asp Asp Phe 510              520              530              540
         *                *                *                *
GGC AAT TGT GTT GAG AAA GAC GAA TGT AAC GAT ATG GAG ATT
Gly Asn Cys Val Glu Lys Asp Glu Cys Asn Asp Met Glu Ile 550              560              570              580
    *                *                *                *
ATC ACT TTT CCA CCG GAA ACC AAA CAC TGA CCAAAGGCTC
Ile Thr Phe Pro Pro Glu Thr Lys His 590         600         610         620         630
    *           *           *           *           *
 TAGCTCTCGC TACATAACGT CAGTGCTTGA ATTGTCCCTT TACGTGTTAG 640         650         660         670         680
    *           *           *           *           *
 TAATTTTGAC TAACTCTGTG TATTTGAGCA TTGTCTACTA ATGGTGAAAA 690         700
    *           *
 TGAAGCTTTT CAATGACT poly(A)
```

Fig. 13H (AcaNAP48)

```
              10          20          30          40
               *           *           *           *
        GAATTCCGTA CGACCTACTA CTACTCAACG ATG AAG GCG CTC TAT
        EcoRI                           Met Lys Ala Leu Tyr 50          60          70          80
               *           *           *           *
        GTT ATC TCT ATA ACG TTG CTC CTG GTA TGG CAA TGC AGT GCA
        Val Ile Ser Ile Thr Leu Leu Leu Val Trp Gln Cys Ser Ala 90         100         110         120
               *           *           *           *
        AGA ACA GCG AGG AAA CCC CCA ACG TGT GGT GAA AAT GAA AGG
        Arg Thr Ala Arg Lys Pro Pro Thr Cys Gly Glu Asn Glu Arg 130         140         150         160         170
          *           *           *           *           *
        GTC GAA TGG TGT GGC AAG CAG TGC GAG ATC ACA TGT GAC GAC
        Val Glu Trp Cys Gly Lys Gln Cys Glu Ile Thr Cys Asp Asp 180         190         200         210
              *           *           *           *
        CCA GAT AAG ATA TGC CGC TCA CTC GCT TGT CCT GGT CCT CCT
        Pro Asp Lys Ile Cys Arg Ser Leu Ala Cys Pro Gly Pro Pro 220         230         240         250
              *           *           *           *
        GCT TGC GTA TGC GAC GAC GGA TAC TAC AGA GAC ACG AAC GTT
        Ala Cys Val Cys Asp Asp Gly Tyr Tyr Arg Asp Thr Asn Val 260         270         280         290
              *           *           *           *
        GGC TTG TGT GTA CAA TAT GAC GAA TGC AAC GAT ATG GAT ATT
        Gly Leu Cys Val Gln Tyr Asp Glu Cys Asn Asp Met Asp Ile 300         310         320         330         340
          *           *           *           *           *
        ATT ATG GTT TCA TAG GGTTGACTGA AGAATCGAAC AACCGGTGCA
        Ile Met Val Ser 350         360         370         380         390
              *           *           *           *           *
        CAACTTCTAT GCTTGACTAT CTCTCTTGCA TCATGCAAGT TTAGCTAGAT 400         410         420         430         440
              *           *           *           *           *
        AGTGTATATA TTAGCAAGAC CCCTTGGGGA GAATGAAGCT TCCCAACTAT 450         460         470         480         490
              *           *           *           *           *
        ATTAAATCAA TAACGTTTTC GCTTCATGTA CACGTGCTCA GCACATTCAT 500         510         520
              *           *           *
        ATCCACTCCT CACACTCCAT GAAAGCAGTG AAATGTT poly(A)
```

Fig. 14

```
         10              20              30              40
          *               *               *               *
GCC AAC TCT TCG AAC ATG ATT CGA GGC CTC GTT CTT CTT TCT CTC CTG
                    Met Ile Arg Gly Leu Val Leu Leu Ser Leu Leu>

50              60              70              80              90
  *               *               *               *               *
TTT TGC GTC ACT TTT GCA GCG AAG AGA GAT TGT CCA GCA AAT GAG GAA
Phe Cys Val Thr Phe Ala Ala Lys Arg Asp Cys Pro Ala Asn Glu Glu>

100             110             120             130             140
     *               *               *               *               *
TGG AGG GAA TGT GGC ACT CCA TGT GAA CCA AAA TGC AAT CAA CCG ATG
Trp Arg Glu Cys Gly Thr Pro Cys Glu Pro Lys Cys Asn Gln Pro Met>

150             160             170             180             190
         *               *               *               *               *
CCA GAT ATA TGT ACT ATG AAT TGT ATC GTC GAT GTG TGT CAA TGC AAG
Pro Asp Ile Cys Thr Met Asn Cys Ile Val Asp Val Cys Gln Cys Lys>

200             210             220             230             240
             *               *               *               *               *
GAG GGA TAC AAG CGT CAT GAA ACG AAG GGA TGC TTA AAG GAA GGA TCA
Glu Gly Tyr Lys Arg His Glu Thr Lys Gly Cys Leu Lys Glu Gly Ser>

250             260             270             280
                 *               *               *               *
GCT GAT TGT AAA TAA GTT ATC AGA ACG CTC GTT TTG TCT TAC ATT AGA
Ala Asp Cys Lys ***

290             300             310             320             330
 *               *               *               *               *
TGG GTG AGC TGA TGT ATC TGT CAG ATA AAC TCT TTC TTC TAA AAA AAA 340             350             360
     *               *               *
AAA AAA AAA AAA AAA AAA AAA AAA A
```

Fig. 16

|  | A1 | A2 | A3 | A4 | A5 | A6 | A7 | A8 | A9 | A10 |
|---|---|---|---|---|---|---|---|---|---|---|
| AcaNAP5 | KAYPECGE | NEWLDDC GTQKP | CEAKC | NEEPPE | EE DPIC RS | RGCL LPP | ACVCK D | GFYRD TV | IGDCVR E | EECDQ H EIIHV |
| AcaNAP6 | KAYPECGE | NEWLDVC GTKKP | CEAKC | SEEE | EE DPIC RS | FSCP GPA | ACVCE D | GFYRD TV | IGDCVK E | EECDQ H EIIHV |
| AcaNAP48 | RTARKPPTCGE | NERVEWC G | KQ CEITC | DDP | DKIC RS | LACP GPP | ACVCD D | GYYRD TN | VGLCVQ Y | DECND MDIIMVS |
| AcaNAP23 | KPSEKECGP | HERLD C GNKKP | CERKC | KIETSEEEDDYEEGTE | RFRC LL | RVCD QPY | ECICD D | GYYRN K | KGECVT D | DVCQE DFMEFITFAP |
| AcaNAP24 | RPEKKCGP | GERLA C GNKKP | CERKC | KIETSEEEDDYPEGTE | RFRC LL | RVCD QPY | ECICD D | GYYRN K | KGECVT D | DVCQE DFMEFITFAP |
| AcaNAP25 | RPEKKCGP | GERLD C ANKKP | CEPKC | KIETSEEEDDDVE DT | DVRC LV | RVCE RPL | KCICK D | GYYRN K | KGECVT D | DVCQE DFMEFITFAP |
| AcaNAP44 | RPEKKCGP | GERLD C ANKKP | CEPKC | KIETSEEEDDDVE ET | DVRC LV | RVCE RPL | KCICK D | GYYRN K | KGECVT D | DVCQE DFMEFITFAP |
| AcaNAP31,42,46 | NERLD C GNQKD | CERKC | DDKRSEE | EI | MQAC LT | RQCL PP | VCVCE D | GFYRN D | NDQCVD E | EECN MEFITFAP |
| AceNAP4-d1 | KSLWDQKCGE | NEYFAEC GNMKE | CEHRC | NEE ENEERDE | ER | ITAC LI | RVCF RPG | ACVCK D | GFYRN R | TGSCVE E DDCE YENMEFITFAPE→ |
| AceNAP4-d2 | KPNNVMTNACGL | VPICGS | NERYSDC GNDKQ | CERKC | NED DYEKG | DEAC RS | HVCE RPG | ACVCE D | GFYRN K | KGSCVE S DDCE YDNMDFITFAPETSR |
| AcaNAP45d1 | KSAKKCGL | NEKLD C GNLKA | CEKKC | DNEEDYKE | ED | ESKC RS | RECSR R | VCVCD E | GFYRN K | KGQCVT R DDCEY DNMEIITFPPE→ |
| AcaNAP47d1 | KSAKKCGL | NEKLD C GNLKA | CEKKC | DNEEDYGE | ED | ESKC RS | RECIG R | VCVCD E | GFYRN K | KGQCVT R DDCEY DNMEIITFPPE↑ |
| AduHAP7-d1 | KAAKKCGL | NERLD C GNLKQ | CEPKC | ESEEYEE | ED | ESKC RS | RECS R R | VCVCD E | GFYRN K | KGKCVA K DVCED DNMEIITFPPE↑ |
| AcaNAP45d2 | DKCGP | DEWFDWC GTYKQ | CERKC | LSEKD | | EEAC LS | RACTG R | ACVCN D | GLYRD D | FGNCVE K DECND MEIITFPPETKH |
| AcaNAP47d2 | DKCGP | DEWFDWC GTYKQ | CERKC | LSEKN | | EEAC LS | RACTG R | ACVCN D | GLYRD D | FGNCVE K DECND MEIITFPPETKH |
| AduNAP4 | KCPT | DEWFDWC GTYKH | CELKC | DRE LTEKE | | EQAC LS | RVCE K S | ACVCK D | GLYRD K | FGNCVE K DECND MEIITFAPEETK |
| AduNAP7-d2 | DECGP | DEWFDYC GNYKK | CERKC | SEE TSEKN | ED | EEAC LS | RACT G R | ACVCK D | GLYRD D | FGNCVP H DECND MEIITFPPETKH |
| AceNAP5 | KAFPKCDV | NERFEVC GNLKE | CELKC | D | ED | PKIC S | RACI RPP | ACVCD D | GFYRD K | YGFCVE E DECND MEIITFPPETK |
| AceNAP7 | RTVKKCGK | NERYDDC GNAKD | CETKC | G | EE | EKVC RS | RECT SPG | ACVCE Q | GFYRD P | AGDCVT D EECDE WNNMEIITMPKQ |
| AcaNAPc2 | KATMQCGE | NEKYDSC GSKE | CDKKC | KYDGVEEEDDE | EP | NVPC LV | RVCH Q | DCVCE E | GFYRN K | DDKCVS A EDCEL DNMDFIYPGTRN |
| HpoNAP5 | KTCGP | NEEYTEC GTP | CEPKC | NEPMPDI | | C TLN | CI VNV | CQCK P | GFKRGPKG | CVA PGPGC K |
| NamNAP | KRDCPA | NEEWREC GTP | CEPKC | NQPMPDI | | C TMN | CI VDV | CQCK E | GYKRHETKG | CLKEGSADC K |

NAP = nematode anticoagulant protein

- Aca = Ancyclostoma caninum
- Ace = Ancyclostoma ceylanium
- Adu = Ancyclostoma duodenale
- Hpo = Heligmosmoides polygyrus
- Asu = Ascaris suum
- Nam = Necator americanus

Fig. 17

Lys Pro Asn Asn Val Met Thr Asn Ala Cys Gly Leu Asn Glu
1                5                    10

Tyr Phe Ala Glu Cys Gly Asn Met Lys Glu Cys Glu His Arg
15              20                   25

Cys Asn Glu Glu Glu Asn Glu Glu Arg Asp Glu Glu Arg Ile
   30             35                40

Thr Ala Cys Leu Ile Arg Val Cys Phe Arg Pro Gly Ala Cys
        45          50              55

Val Cys Lys Asp Gly Phe Tyr Arg Asn Arg Thr Gly Ser Cys
        60              65                          70

Val Glu Glu Asp Asp Cys Glu Tyr Glu Asn Met Glu Phe Ile
            75              80

Thr Phe Ala Pro Glu Val Pro Ile Cys Gly Ser Asn Glu Arg
85              90              95

Tyr Ser Asp Cys Gly Asn Asp Lys Gln Cys Glu Arg Lys Cys
    100             105             110

Asn Glu Asp Asp Tyr Glu Lys Gly Asp Glu Ala Cys Arg Ser
        115             120             125

His Val Cys Glu Arg Pro Gly Ala Cys Val Cys Glu Asp Gly
        130             135             140

Phe Tyr Arg Asn Lys Lys Gly Ser Cys Val Glu Ser Asp Asp
            145             150

Cys Glu Tyr Asp Asn Met Asp Phe Ile Thr Phe Ala Pro Glu
155             160             165

Thr Ser Arg
    170

Fig. 18

Lys Ser Ala Lys Lys Cys Gly Leu Asn Glu Lys Leu Asp Cys
1              5                    10

Gly Asn Leu Lys Ala Cys Glu Lys Lys Cys Ser Asp Leu Asp
15                  20                   25

Asn Glu Glu Asp Tyr Lys Glu Asp Glu Ser Lys Cys Arg
    30              35                  40

Ser Arg Glu Cys Ser Arg Arg Val Cys Val Cys Asp Glu Gly
        45          50              55

Phe Tyr Arg Asn Lys Lys Gly Gln Cys Val Thr Arg Asp Asp
            60              65                      70

Cys Glu Tyr Asp Asn Met Glu Ile Ile Thr Phe Pro Pro Glu
                75                  80

Asp Lys Cys Gly Pro Asp Glu Trp Phe Asp Trp Cys Gly Thr
85              90                  95

Tyr Lys Gln Cys Glu Arg Lys Cys Asn Lys Glu Leu Ser Glu
    100             105                 110

Lys Asp Glu Glu Ala Cys Leu Ser Arg Ala Cys Thr Gly Arg
        115             120             125

Ala Cys Val Cys Asn Asp Gly Leu Tyr Arg Asp Asp Phe Gly
            130             135                 140

Asn Cys Val Glu Lys Asp Glu Cys Asn Asp Met Glu Ile Ile
                145             150

Thr Phe Pro Pro Glu Thr Lys His
155                 160

Fig. 19

Lys Ser Ala Lys Lys Cys Gly Leu Asn Glu Lys Leu Asp Cys
1              5                    10

Gly Asn Leu Lys Ala Cys Glu Lys Lys Cys Ser Asp Leu Asp
15                  20                  25

Asn Glu Glu Asp Tyr Gly Glu Glu Asp Glu Ser Lys Cys Arg
    30              35              40

Ser Arg Glu Cys Ile Gly Arg Val Cys Val Cys Asp Glu Gly
        45          50              55

Phe Tyr Arg Asn Lys Lys Gly Gln Cys Val Thr Arg Asp Asp
            60              65                      70

Cys Glu Tyr Asp Asn Met Glu Ile Ile Thr Phe Pro Pro Glu
                75                  80

Asp Lys Cys Gly Pro Asp Glu Trp Phe Asp Trp Cys Gly Thr
85              90                      95

Tyr Lys Gln Cys Glu Arg Lys Cys Ser Glu Glu Leu Ser Glu
    100             105                 110

Lys Asn Glu Glu Ala Cys Leu Ser Arg Ala Cys Thr Gly Arg
        115             120             125

Ala Cys Val Cys Asn Asp Gly Leu Tyr Arg Asp Asp Phe Gly
            130             135                 140

Asn Cys Val Glu Lys Asp Glu Cys Asn Asp Met Glu Ile Ile
                145             150

Thr Phe Pro Pro Glu Thr Lys His
155                 160

Fig. 20

Lys Ala Ala Lys Lys Cys Gly Leu Asn Glu Arg Leu Asp Cys
1              5                    10

Gly Asn Leu Lys Gln Cys Glu Pro Lys Cys Ser Asp Leu Glu
15                  20                  25

Ser Glu Glu Tyr Glu Glu Glu Asp Glu Ser Lys Cys Arg Ser
    30                  35                  40

Arg Glu Cys Ser Arg Arg Val Cys Val Cys Asp Glu Gly Phe
        45              50              55
Tyr Arg Asn Lys Lys Gly Lys Cys Val Ala Lys Asp Val Cys
                60              65                  70

Glu Asp Asp Asn Met Glu Ile Ile Thr Phe Pro Pro Glu Asp
                75                  80

Glu Cys Gly Pro Asp Glu Trp Phe Asp Tyr Cys Gly Asn Tyr
85                  90              95

Lys Lys Cys Glu Arg Lys Cys Ser Glu Glu Thr Ser Glu Lys
    100             105                 110

Asn Glu Glu Ala Cys Leu Ser Arg Ala Cys Thr Gly Arg Ala
        115             120             125

Cys Val Cys Lys Asp Gly Leu Tyr Arg Asp Asp Phe Gly Asn
            130             135             140

Cys Val Pro His Asp Glu Cys Asn Asp Met Glu Ile Ile Thr
                145             150

Phe Pro Pro Glu Thr Lys His
155             160

SEQUENCE LISTING ( 1 ) GENERAL INFORMATION:

( i i i ) NUMBER OF SEQUENCES: 357

( 2 ) INFORMATION FOR SEQ ID NO:1:

( i ) SEQUENCE CHARACTERISTICS:
        ( A ) LENGTH: 234 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AAGGCATACC  CGGAGTGTGG  TGAGAATGAA  TGGCTCGACG  ACTGTGGAAC  TCAGAAGCCA      60

TGCGAGGCCA  AGTGCAATGA  GGAACCCCCT  GAGGAGGAAG  ATCCGATATG  CCGCTCACGT     120

GGTTGTTTAT  TACCTCCTGC  TTGCGTATGC  AAAGACGGAT  TCTACAGAGA  CACGGTGATC     180

GGCGACTGTG  TTAGGGAAGA  AGAATGCGAC  CAACATGAGA  TTATACATGT  CTGA           234
```

( 2 ) INFORMATION FOR SEQ ID NO:2:

( i ) SEQUENCE CHARACTERISTICS:
        ( A ) LENGTH: 228 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
AAGGCATACC  CGGAGTGTGG  TGAGAATGAA  TGGCTCGACG  TCTGTGGAAC  TAAGAAGCCA      60

TGCGAGGCCA  AGTGCAGTGA  GGAAGAGGAG  GAAGATCCGA  TATGCCGATC  ATTTCTTGT     120

CCGGGTCCCG  CTGCTTGCGT  ATGCGAAGAC  GGATTCTACA  GAGACACGGT  GATCGGCGAC    180

TGTGTTAAGG  AAGAAGAATG  CGACCAACAT  GAGATTATAC  ATGTCTGA                   228
```

( 2 ) INFORMATION FOR SEQ ID NO:3:

( i ) SEQUENCE CHARACTERISTICS:
        ( A ) LENGTH: 461 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Ancyclostoma caninum ( i x ) FEATURE:

(A) NAME/KEY: Coding Sequence
(B) LOCATION: 22...321

(x i) SEQUENCE DESCRIPTION: SEQ ID NO:3:

| GAATTCCGCT | ACTACTCAAC | A | ATG<br>Met<br>1 | AAG<br>Lys | ATG<br>Met | CTT<br>Leu | TAC<br>Tyr<br>5 | GCT<br>Ala | ATC<br>Ile | GCT<br>Ala | ATA<br>Ile | ATG<br>Met<br>10 | 51 |
|---|---|---|---|---|---|---|---|---|---|---|---|---|---|
| TTT<br>Phe | CTC<br>Leu | CTG<br>Leu | GTA<br>Val | TCA<br>Ser<br>15 | TTA<br>Leu | TGC<br>Cys | AGC<br>Ser | GCA<br>Ala | AGA<br>Arg<br>20 | ACA<br>Thr | GTG<br>Val | AGG<br>Arg | AAG<br>Lys | GCA<br>Ala<br>25 | TAC<br>Tyr | 99 |
| CCG<br>Pro | GAG<br>Glu | TGT<br>Cys | GGT<br>Gly<br>30 | GAG<br>Glu | AAT<br>Asn | GAA<br>Glu | TGG<br>Trp | CTC<br>Leu<br>35 | GAC<br>Asp | GAC<br>Asp | TGT<br>Cys | GGA<br>Gly | ACT<br>Thr<br>40 | CAG<br>Gln | AAG<br>Lys | 147 |
| CCA<br>Pro | TGC<br>Cys | GAG<br>Glu<br>45 | GCC<br>Ala | AAG<br>Lys | TGC<br>Cys | AAT<br>Asn | GAG<br>Glu<br>50 | GAA<br>Glu | CCC<br>Pro | CCT<br>Pro | GAG<br>Glu | GAG<br>Glu<br>55 | GAA<br>Glu | GAT<br>Asp | CCG<br>Pro | 195 |
| ATA<br>Ile | TGC<br>Cys<br>60 | CGC<br>Arg | TCA<br>Ser | CGT<br>Arg | GGT<br>Gly | TGT<br>Cys<br>65 | TTA<br>Leu | TTA<br>Leu | CCT<br>Pro | CCT<br>Pro | GCT<br>Ala<br>70 | TGC<br>Cys | GTA<br>Val | TGC<br>Cys | AAA<br>Lys | 243 |
| GAC<br>Asp<br>75 | GGA<br>Gly | TTC<br>Phe | TAC<br>Tyr | AGA<br>Arg | GAC<br>Asp<br>80 | ACG<br>Thr | GTG<br>Val | ATC<br>Ile | GGC<br>Gly | GAC<br>Asp<br>85 | TGT<br>Cys | GTT<br>Val | AGG<br>Arg | GAA<br>Glu | GAA<br>Glu<br>90 | 291 |
| GAA<br>Glu | TGC<br>Cys | GAC<br>Asp | CAA<br>Gln | CAT<br>His<br>95 | GAG<br>Glu | ATT<br>Ile | ATA<br>Ile | CAT<br>His | GTC<br>Val<br>100 | T | GAACGAGAAA | GCAACAATAA | CC | | | 344 |

AAAGGTTCCA ACTCTCGCTC TGCAAAATCG CTAGTTGGAT GTCTCTTTTG CGTCCGAATA    404

GTTTTAGTTG ATGTTAAGTA AGAACTCCTG CTGGAGAGAA TAAAGCTTTC CAACTCC    461

(2) INFORMATION FOR SEQ ID NO:4:

(i) SEQUENCE CHARACTERISTICS:
        (A) LENGTH: 77 amino acids
        (B) TYPE: amino acid
        (D) TOPOLOGY: linear (i i) MOLECULE TYPE: peptide (v i) ORIGINAL SOURCE:
        (A) ORGANISM: Ancyclostoma caninum (x i) SEQUENCE DESCRIPTION: SEQ ID NO:4:

| Lys<br>1 | Ala | Tyr | Pro | Glu<br>5 | Cys | Gly | Glu | Asn | Glu<br>10 | Trp | Leu | Asp | Asp |
|---|---|---|---|---|---|---|---|---|---|---|---|---|---|
| Cys<br>15 | Gly | Thr | Gln | Lys | Pro<br>20 | Cys | Glu | Ala | Lys | Cys<br>25 | Asn | Glu | Glu |
| Pro | Pro<br>30 | Glu | Glu | Glu | Asp | Pro<br>35 | Ile | Cys | Arg | Ser | Arg<br>40 | Gly | Cys |
| Leu | Leu | Pro<br>45 | Pro | Ala | Cys | Val | Cys<br>50 | Lys | Asp | Gly | Phe | Tyr<br>55 | Arg |
| Asp | Thr | Val | Ile<br>60 | Gly | Asp | Cys | Val | Arg<br>65 | Glu | Glu | Glu | Cys | Asp<br>70 |
| Gln | His | Glu | Ile | Ile<br>75 | His | Val | | | | | | | |

(2) INFORMATION FOR SEQ ID NO:5:

(i) SEQUENCE CHARACTERISTICS:
        (A) LENGTH: 455 base pairs
        (B) TYPE: nucleic acid
        (C) STRANDEDNESS: single
        (D) TOPOLOGY: linear (v i) ORIGINAL SOURCE:

( A ) ORGANISM: Ancyclostoma caninum ( i x ) FEATURE:
    ( A ) NAME/KEY: Coding Sequence
    ( B ) LOCATION: 22...315

( x i ) SEQUENCE DESCRIPTION: SEQ ID NO:5:

```
GAATTCCGCT ACTACTCAAC A ATG AAG ATG CTT TAC GCT ATC GCT ATA ATG        51
                        Met Lys Met Leu Tyr Ala Ile Ala Ile Met
                         1           5                       10

TTT CTC CTG GTG TCA TTA TGC AGC ACA AGA ACA GTG AGG AAG GCA TAC        99
Phe Leu Leu Val Ser Leu Cys Ser Thr Arg Thr Val Arg Lys Ala Tyr
             15              20                      25

CCG GAG TGT GGT GAG AAT GAA TGG CTC GAC GTC TGT GGA ACT AAG AAG       147
Pro Glu Cys Gly Glu Asn Glu Trp Leu Asp Val Cys Gly Thr Lys Lys
             30              35                      40

CCA TGC GAG GCC AAG TGC AGT GAG GAA GAG GAG GAA GAT CCG ATA TGC       195
Pro Cys Glu Ala Lys Cys Ser Glu Glu Glu Glu Glu Asp Pro Ile Cys
             45              50                      55

CGA TCA TTT TCT TGT CCG GGT CCC GCT GCT TGC GTA TGC GAA GAC GGA       243
Arg Ser Phe Ser Cys Pro Gly Pro Ala Ala Cys Val Cys Glu Asp Gly
             60              65                      70

TTC TAC AGA GAC ACG GTG ATC GGC GAC TGT GTT AAG GAA GAA GAA TGC       291
Phe Tyr Arg Asp Thr Val Ile Gly Asp Cys Val Lys Glu Glu Glu Cys
 75                  80                      85                  90

GAC CAA CAT GAG ATT ATT CAT GTC TGAACGAGAG AGCAGTAATA ACCAAAGGTT C    346
Asp Gln His Glu Ile Ile His Val
                 95

CAACTTTCGC TCTACAAAAT CGCTAGTTGG ATTTCTCCTT TGCGTGCGAA TAGTTTTAGT     406

TGATATTAAG TAAAACCTCC TGTTGAAGAG AATAAAGCTT TCCAACTTC                 455
```

( 2 ) INFORMATION FOR SEQ ID NO:6:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:6:

```
Lys Ala Tyr Pro Glu Cys Gly Glu Asn Glu Trp Leu Asp Val Cys Gly
 1               5                  10                      15

Thr Lys Lys Pro Cys Glu Ala Lys Cys Ser Glu Glu Glu Glu Glu Asp
             20              25                      30

Pro Ile Cys Arg Ser Phe Ser Cys Pro Gly Pro Ala Ala Cys Val Cys
             35              40                      45

Glu Asp Gly Phe Tyr Arg Asp Thr Val Ile Gly Asp Cys Val Lys Glu
             50              55                      60

Glu Glu Cys Asp Gln His Glu Ile Ile His Val
 65                  70                  75
```

( 2 ) INFORMATION FOR SEQ ID NO:7:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( v i ) ORIGINAL SOURCE:
   ( A ) ORGANISM: Ancyclostoma caninum ( x i ) SEQUENCE DESCRIPTION: SEQ ID NO:7:

```
Arg Thr Val Arg Lys Ala Tyr Pro Glu Cys Gly Glu Asn Glu Trp Leu
1               5                   10                  15

Asp Asp Cys Gly Thr Gln Lys Pro Cys Glu Ala Lys Cys Asn Glu Glu
            20                  25                  30

Pro Pro Glu Glu Glu Asp Pro Ile Cys Arg Ser Arg Gly Cys Leu Leu
            35                  40                  45

Pro Pro Ala Cys Val Cys Lys Asp Gly Phe Tyr Arg Asp Thr Val Ile
        50              55                  60

Gly Asp Cys Val Arg Glu Glu Glu Cys Asp Gln His Glu Ile Ile His
65                  70                  75                  80

Val
```

( 2 ) INFORMATION FOR SEQ ID NO:8:

( i ) SEQUENCE CHARACTERISTICS:
       ( A ) LENGTH: 79 amino acids
       ( B ) TYPE: amino acid
       ( D ) TOPOLOGY: linear ( i i ) MOLECULE TYPE: peptide ( v i ) ORIGINAL SOURCE:
       ( A ) ORGANISM: Ancyclostoma caninum ( x i ) SEQUENCE DESCRIPTION: SEQ ID NO:8:

```
Arg Thr Val Arg Lys Ala Tyr Pro Glu Cys Gly Glu Asn Glu Trp Leu
1               5                   10                  15

Asp Val Cys Gly Thr Lys Lys Pro Cys Glu Ala Lys Cys Ser Glu Glu
            20                  25                  30

Glu Glu Glu Asp Pro Ile Cys Arg Ser Phe Ser Cys Pro Gly Pro Ala
            35                  40                  45

Ala Cys Val Cys Glu Asp Gly Phe Tyr Arg Asp Thr Val Ile Gly Asp
        50              55                  60

Cys Val Lys Glu Glu Glu Cys Asp Gln His Glu Ile Ile His Val
65                  70                  75
```

( 2 ) INFORMATION FOR SEQ ID NO:9:

( i ) SEQUENCE CHARACTERISTICS:
       ( A ) LENGTH: 711 base pairs
       ( B ) TYPE: nucleic acid
       ( C ) STRANDEDNESS: single
       ( D ) TOPOLOGY: linear ( v i ) ORIGINAL SOURCE:
       ( A ) ORGANISM: Ancyclostoma ceylanicum ( i x ) FEATURE:
       ( A ) NAME/KEY: Coding Sequence
       ( B ) LOCATION: 21...590

( x i ) SEQUENCE DESCRIPTION: SEQ ID NO:9:

```
GAATTCACTA TTATCCAACA ATG GCG GTG CTT TAT TCA GTA GCA ATA GCG        50
                     Met Ala Val Leu Tyr Ser Val Ala Ile Ala
                      1               5                   10

TTA CTA CTG GTA TCA CAA TGC AGT GGG AAA CCG AAC AAT GTG ATG ACT      98
Leu Leu Leu Val Ser Gln Cys Ser Gly Lys Pro Asn Asn Val Met Thr
                15                  20                  25

AAC GCT TGT GGT CTT AAT GAA TAT TTC GCT GAG TGT GGC AAT ATG AAG     146
Asn Ala Cys Gly Leu Asn Glu Tyr Phe Ala Glu Cys Gly Asn Met Lys
```

|  |  |  |  |  | 30 |  |  |  |  | 35 |  |  |  |  | 40 |  |  |
|---|---|---|---|---|---|---|---|---|---|---|---|---|---|---|---|---|---|

```
GAA  TGC  GAG  CAC  AGA  TGC  AAT  GAG  GAG  GAA  AAT  GAG  GAA  AGG  GAC  GAG      194
Glu  Cys  Glu  His  Arg  Cys  Asn  Glu  Glu  Glu  Asn  Glu  Glu  Arg  Asp  Glu
          45                           50                      55

GAA  AGA  ATA  ACG  GCA  TGC  CTC  ATC  CGT  GTG  TGT  TTC  CGT  CCT  GGT  GCT      242
Glu  Arg  Ile  Thr  Ala  Cys  Leu  Ile  Arg  Val  Cys  Phe  Arg  Pro  Gly  Ala
          60                           65                      70

TGC  GTA  TGC  AAA  GAC  GGA  TTC  TAT  AGA  AAC  AGA  ACA  GGC  AGC  TGT  GTG      290
Cys  Val  Cys  Lys  Asp  Gly  Phe  Tyr  Arg  Asn  Arg  Thr  Gly  Ser  Cys  Val
75                       80                      85                           90

GAA  GAA  GAT  GAC  TGC  GAG  TAC  GAG  AAT  ATG  GAG  TTC  ATT  ACT  TTT  GCA      338
Glu  Glu  Asp  Asp  Cys  Glu  Tyr  Glu  Asn  Met  Glu  Phe  Ile  Thr  Phe  Ala
                    95                          100                     105

CCA  GAA  GTA  CCG  ATA  TGT  GGT  TCC  AAC  GAA  AGG  TAC  TCC  GAC  TGC  GGC      386
Pro  Glu  Val  Pro  Ile  Cys  Gly  Ser  Asn  Glu  Arg  Tyr  Ser  Asp  Cys  Gly
               110                          115                     120

AAT  GAC  AAA  CAA  TGC  GAG  CGC  AAA  TGC  AAC  GAG  GAC  GAT  TAT  GAG  AAG      434
Asn  Asp  Lys  Gln  Cys  Glu  Arg  Lys  Cys  Asn  Glu  Asp  Asp  Tyr  Glu  Lys
          125                          130                     135

GGA  GAT  GAG  GCA  TGC  CGC  TCA  CAT  GTT  TGT  GAA  CGT  CCT  GGT  GCC  TGT      482
Gly  Asp  Glu  Ala  Cys  Arg  Ser  His  Val  Cys  Glu  Arg  Pro  Gly  Ala  Cys
140                      145                          150

GTA  TGC  GAA  GAC  GGG  TTC  TAC  AGA  AAC  AAA  AAA  GGT  AGC  TGT  GTG  GAA      530
Val  Cys  Glu  Asp  Gly  Phe  Tyr  Arg  Asn  Lys  Lys  Gly  Ser  Cys  Val  Glu
155                      160                          165                     170

AGC  GAT  GAC  TGC  GAA  TAC  GAT  AAT  ATG  GAT  TTC  ATC  ACT  TTT  GCA  CCA      578
Ser  Asp  Asp  Cys  Glu  Tyr  Asp  Asn  Met  Asp  Phe  Ile  Thr  Phe  Ala  Pro
                    175                         180                     185

GAA  ACC  TCA  CGA  TAACCAAGA  TGCTACCTCT  CGTACGCAAC  TCCGCTGATT  GAGGTT     636
Glu  Thr  Ser  Arg
               190

GATTCACTCC  CTTGCATCTC  AACATTTTTT  TTGTGATGCT  GTGCATCTGA  GCTTAACCTG            696

ATAAAGCCTA  TGGTG                                                                 711
```

( 2 ) INFORMATION FOR SEQ ID NO:10:

( i ) SEQUENCE CHARACTERISTICS:
        ( A ) LENGTH: 425 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Ancyclostoma ceylanicum ( i x ) FEATURE:
        ( A ) NAME/KEY: Coding Sequence
        ( B ) LOCATION: 10...291

( x i ) SEQUENCE DESCRIPTION: SEQ ID NO:10:

```
GAATTCCGC  ATG  CGG  ACG  CTC  TAC  CTC  ATT  TCT  ATC  TGG  TTG  TTC  CTC  ATC      51
           Met  Arg  Thr  Leu  Tyr  Leu  Ile  Ser  Ile  Trp  Leu  Phe  Leu  Ile
            1                 5                          10

TCG  CAA  TGT  AAT  GGA  AAA  GCA  TTC  CCG  AAA  TGT  GAC  GTC  AAT  GAA  AGA       99
Ser  Gln  Cys  Asn  Gly  Lys  Ala  Phe  Pro  Lys  Cys  Asp  Val  Asn  Glu  Arg
15                       20                      25                           30

TTC  GAG  GTG  TGT  GGC  AAT  CTG  AAG  GAG  TGC  GAG  CTC  AAG  TGC  GAT  GAG      147
Phe  Glu  Val  Cys  Gly  Asn  Leu  Lys  Glu  Cys  Glu  Leu  Lys  Cys  Asp  Glu
                    35                          40                      45

GAC  CCT  AAG  ATA  TGC  TCT  CGT  GCA  TGT  ATT  CGT  CCC  CCT  GCT  TGC  GTA      195
Asp  Pro  Lys  Ile  Cys  Ser  Arg  Ala  Cys  Ile  Arg  Pro  Pro  Ala  Cys  Val
               50                           55                      60
```

| TGC | GAT | GAC | GGA | TTC | TAC | AGA | GAC | AAA | TAT | GGC | TTC | TGT | GTT | GAA | GAA | 243 |
|---|---|---|---|---|---|---|---|---|---|---|---|---|---|---|---|---|
| Cys | Asp | Asp | Gly | Phe | Tyr | Arg | Asp | Lys | Tyr | Gly | Phe | Cys | Val | Glu | Glu | |
| | | 65 | | | | | 70 | | | | | 75 | | | | |

| GAC | GAA | TGT | AAC | GAT | ATG | GAG | ATT | ATT | ACT | TTT | CCA | CCA | GAA | ACC | AAA | TG | 293 |
|---|---|---|---|---|---|---|---|---|---|---|---|---|---|---|---|---|---|
| Asp | Glu | Cys | Asn | Asp | Met | Glu | Ile | Ile | Thr | Phe | Pro | Pro | Glu | Thr | Lys | | |
| | 80 | | | | | 85 | | | | | | 90 | | | | | |

| ATGACCGAAG | CTTCCACCTT | TCTATACATA | TCTTCACTGC | TTGACAGGCT | TCTCGACAAT | 353 |
|---|---|---|---|---|---|---|

| TTAGAAGTTC | TGCTTGACTT | TGTCTATTTG | AAATTGTTCA | CACTAATGGG | GGAAGTAAAG | 413 |
|---|---|---|---|---|---|---|

| CATTTTCACG | AC | | | | | 425 |
|---|---|---|---|---|---|---|

( 2 ) INFORMATION FOR SEQ ID NO:11:

( i ) SEQUENCE CHARACTERISTICS:
        ( A ) LENGTH: 471 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Ancyclostoma ceylanicum ( i x ) FEATURE:
        ( A ) NAME/KEY: Coding Sequence
        ( B ) LOCATION: 23...310

( x i ) SEQUENCE DESCRIPTION: SEQ ID NO:11:

| GAATTCCGCT | ACATTTTCAA | CA | ATG | TCG | ACG | CTT | TAT | GTT | ATC | GCA | ATA | TGT | 52 |
|---|---|---|---|---|---|---|---|---|---|---|---|---|---|
| | | | Met | Ser | Thr | Leu | Tyr | Val | Ile | Ala | Ile | Cys | |
| | | | 1 | | | | 5 | | | | | 10 | |

| TTG | CTG | CTT | GTT | TCG | CAA | TGC | AAT | GGA | AGA | ACG | GTG | AAG | AAG | TGT | GGC | 100 |
|---|---|---|---|---|---|---|---|---|---|---|---|---|---|---|---|---|
| Leu | Leu | Leu | Val | Ser | Gln | Cys | Asn | Gly | Arg | Thr | Val | Lys | Lys | Cys | Gly | |
| | | | | 15 | | | | | 20 | | | | | 25 | | |

| AAG | AAT | GAA | AGA | TAC | GAC | GAC | TGT | GGC | AAT | GCA | AAG | GAC | TGC | GAG | ACC | 148 |
|---|---|---|---|---|---|---|---|---|---|---|---|---|---|---|---|---|
| Lys | Asn | Glu | Arg | Tyr | Asp | Asp | Cys | Gly | Asn | Ala | Lys | Asp | Cys | Glu | Thr | |
| | | | 30 | | | | | 35 | | | | | 40 | | | |

| AAG | TGC | GGT | GAA | GAG | GAA | AAG | GTG | TGC | CGT | TCG | CGT | GAG | TGT | ACT | AGT | 196 |
|---|---|---|---|---|---|---|---|---|---|---|---|---|---|---|---|---|
| Lys | Cys | Gly | Glu | Glu | Glu | Lys | Val | Cys | Arg | Ser | Arg | Glu | Cys | Thr | Ser | |
| | | | 45 | | | | | 50 | | | | | 55 | | | |

| CCT | GGT | GCC | TGC | GTA | TGC | GAA | CAA | GGA | TTC | TAC | AGA | GAT | CCG | GCT | GGC | 244 |
|---|---|---|---|---|---|---|---|---|---|---|---|---|---|---|---|---|
| Pro | Gly | Ala | Cys | Val | Cys | Glu | Gln | Gly | Phe | Tyr | Arg | Asp | Pro | Ala | Gly | |
| | | | 60 | | | | | 65 | | | | | 70 | | | |

| GAC | TGT | GTC | ACT | GAT | GAA | GAA | TGT | GAT | GAA | TGG | AAC | AAT | ATG | GAG | ATC | 292 |
|---|---|---|---|---|---|---|---|---|---|---|---|---|---|---|---|---|
| Asp | Cys | Val | Thr | Asp | Glu | Glu | Cys | Asp | Glu | Trp | Asn | Asn | Met | Glu | Ile | |
| 75 | | | | | 80 | | | | | 85 | | | | | 90 | |

| ATT | ACT | ATG | CCA | AAA | CAG | TAGTGCGAAG | TTCCCTTCTT | TCTCCAAATC | TGCTCCGTG | 349 |
|---|---|---|---|---|---|---|---|---|---|---|
| Ile | Thr | Met | Pro | Lys | Gln | | | | | |
| | | | | 95 | | | | | | |

| CTCAATTATC | ACACACCTCC | ACTAGTTAAG | ATTGACTGAC | TCTCTTGCAT | TGTAGTATTT | 409 |
|---|---|---|---|---|---|---|

| TCGCTTGACT | CTGTGCATTT | AAGCATGAGA | TACTACTAGG | GAGAATAAAA | ATTACTAACT | 469 |
|---|---|---|---|---|---|---|

| AC | | | | | | 471 |
|---|---|---|---|---|---|---|

( 2 ) INFORMATION FOR SEQ ID NO:12:

( i ) SEQUENCE CHARACTERISTICS:
        ( A ) LENGTH: 396 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Ancyclostoma duodenale ( i x ) FEATURE:
        ( A ) NAME/KEY: Coding Sequence (B) LOCATION: 10...237

(xi) SEQUENCE DESCRIPTION: SEQ ID NO:12:

```
GAATTCCGG AAA TGT CCT ACC GAT GAA TGG TTC GAT TGG TGT GGA ACT TAC      51
          Lys Cys Pro Thr Asp Glu Trp Phe Asp Trp Cys Gly Thr Tyr
           1               5                       10

AAG CAT TGC GAA CTC AAG TGC GAT AGG GAG CTA ACT GAG AAA GAA GAG         99
Lys His Cys Glu Leu Lys Cys Asp Arg Glu Leu Thr Glu Lys Glu Glu
15               20                  25                      30

CAG GCA TGT CTC TCA CGT GTT TGT GAG AAG TCC GCT TGC GTA TGC AAT        147
Gln Ala Cys Leu Ser Arg Val Cys Glu Lys Ser Ala Cys Val Cys Asn
                35                  40                  45

GAC GGA TTA TAC AGA GAC AAG TTT GGC AAC TGT GTT GAA AAA GAC GAA        195
Asp Gly Leu Tyr Arg Asp Lys Phe Gly Asn Cys Val Glu Lys Asp Glu
            50                  55                  60

TGC AAC GAT ATG GAG ATT ATT ACT TTT GCA CCA GAA ACC AAA TAATGGCTA      247
Cys Asn Asp Met Glu Ile Ile Thr Phe Ala Pro Glu Thr Lys
            65                  70                  75

AGGTTCCAAA CCTTGCTACA CACCGTCAGT GCTTTACTGT TTCCTCTACG TGTTAGTAGT      307

TTTGCTTGAC TCTGTGTATT TAAGCATTGT CTACTAATGG GCAAAGTAAA GCATTGTAAG      367

GACATAATAA TGAGTAAACC TTCTGATTT                                        396
```

(2) INFORMATION FOR SEQ ID NO:13:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 21...560

(vi) ORIGINAL SOURCE:
        (A) ORGANISM: Ancyclostoma duodenale (xi) SEQUENCE DESCRIPTION: SEQ ID NO:13:

```
GAATTCCGGG CGGCAGAAAG ATG CGA ATG CTC TAC CTT GTT CCT ATC TGG          50
                     Met Arg Met Leu Tyr Leu Val Pro Ile Trp
                      1               5                   10

TTG CTG CTC ATT TCG CTA TGC AGT GGA AAA GCT GCG AAG AAA TGT GGT        98
Leu Leu Leu Ile Ser Leu Cys Ser Gly Lys Ala Ala Lys Lys Cys Gly
                15                  20                  25

CTC AAT GAA AGG CTG GAC TGT GGC AAT CTG AAG CAA TGC GAG CCC AAG       146
Leu Asn Glu Arg Leu Asp Cys Gly Asn Leu Lys Gln Cys Glu Pro Lys
            30                  35                  40

TGC AGC GAC TTG GAA AGT GAG GAG TAT GAG GAG GAA GAT GAG TCG AAA       194
Cys Ser Asp Leu Glu Ser Glu Glu Tyr Glu Glu Glu Asp Glu Ser Lys
            45                  50                  55

TGT CGA TCA CGT GAA TGT TCT CGT CGT GTT TGT GTA TGC GAT GAA GGA       242
Cys Arg Ser Arg Glu Cys Ser Arg Arg Val Cys Val Cys Asp Glu Gly
        60                  65                  70

TTC TAC AGA AAC AAG AAG GGC AAG TGT GTT GCA AAA GAT GTT TGC GAG       290
Phe Tyr Arg Asn Lys Lys Gly Lys Cys Val Ala Lys Asp Val Cys Glu
75                  80                  85                  90

GAC GAC AAT ATG GAG ATT ATC ACT TTT CCA CCA GAA GAC GAA TGT GGT       338
Asp Asp Asn Met Glu Ile Ile Thr Phe Pro Pro Glu Asp Glu Cys Gly
                95                  100                 105

CCC GAT GAA TGG TTC GAC TAC TGT GGA AAT TAT AAG AAG TGC GAA CGC       386
Pro Asp Glu Trp Phe Asp Tyr Cys Gly Asn Tyr Lys Lys Cys Glu Arg
            110                 115                 120
```

| | | | | | | | | | | | | | | | | |
|---|---|---|---|---|---|---|---|---|---|---|---|---|---|---|---|---|
| AAG | TGC | AGT | GAG | GAG | ACA | AGT | GAG | AAA | AAT | GAG | GAG | GCA | TGC | CTC | TCT | 434 |
| Lys | Cys | Ser | Glu | Glu | Thr | Ser | Glu | Lys | Asn | Glu | Glu | Ala | Cys | Leu | Ser | |
| | | 125 | | | | | 130 | | | | | 135 | | | | |
| CGT | GCT | TGT | ACT | GGT | CGT | GCT | TGC | GTA | TGC | AAA | GAC | GGA | TTG | TAC | AGA | 482 |
| Arg | Ala | Cys | Thr | Gly | Arg | Ala | Cys | Val | Cys | Lys | Asp | Gly | Leu | Tyr | Arg | |
| | 140 | | | | | 145 | | | | | 150 | | | | | |
| GAC | GAC | TTT | GGC | AAC | TGT | GTT | CCA | CAT | GAC | GAA | TGC | AAC | GAT | ATG | GAG | 530 |
| Asp | Asp | Phe | Gly | Asn | Cys | Val | Pro | His | Asp | Glu | Cys | Asn | Asp | Met | Glu | |
| 155 | | | | | 160 | | | | | 165 | | | | | 170 | |
| ATC | ATC | ACT | TTT | CCA | CCG | GAA | ACC | AAA | CAT | TGACCAGAGG | CTCCAACTCT | CGCT | | | | 584 |
| Ile | Ile | Thr | Phe | Pro | Pro | Glu | Thr | Lys | His | | | | | | | |
| | | | | 175 | | | | | 180 | | | | | | | |

ACACAACGTC AGGGCTAGAA TGGCCCCTCT GCGAGTTAGT AGTTTTGCTT GACTCTGCTT    644

ATTTGAGCAC TTTCTATTGA TGGCGAAAAT AAAGCATTTA AAAC                     688

( 2 ) INFORMATION FOR SEQ ID NO:14:

( i ) SEQUENCE CHARACTERISTICS:
        ( A ) LENGTH: 349 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Heligmosomoides polygyrus ( i x ) FEATURE:
        ( A ) NAME/KEY: Coding Sequence
        ( B ) LOCATION: 49...276

( x i ) SEQUENCE DESCRIPTION: SEQ ID NO:14:

| | | | | | | | | | | | | | | | | |
|---|---|---|---|---|---|---|---|---|---|---|---|---|---|---|---|---|
| GAATTCCGCG | CACCTGAGAG | GTGAGCTACG | CAAGTCTTCG | CTGGTACA | ATG | ATC | CGA | | | | | | | | | 57 |
| | | | | | Met | Ile | Arg | | | | | | | | | |
| | | | | | 1 | | | | | | | | | | | |
| AAG | CTC | GTT | CTG | CTG | ACT | GCT | ATC | GTC | ACG | GTG | GTG | CTA | AGT | GCG | AAG | 105 |
| Lys | Leu | Val | Leu | Leu | Thr | Ala | Ile | Val | Thr | Val | Val | Leu | Ser | Ala | Lys | |
| | 5 | | | | 10 | | | | | 15 | | | | | | |
| ACC | TGT | GGA | CCA | AAC | GAG | GAG | TAC | ACT | GAA | TGC | GGG | ACG | CCA | TGC | GAG | 153 |
| Thr | Cys | Gly | Pro | Asn | Glu | Glu | Tyr | Thr | Glu | Cys | Gly | Thr | Pro | Cys | Glu | |
| 20 | | | | | 25 | | | | | 30 | | | | | 35 | |
| CCG | AAG | TGC | AAT | GAA | CCG | ATG | CCA | GAC | ATC | TGT | ACT | CTG | AAC | TGC | ATC | 201 |
| Pro | Lys | Cys | Asn | Glu | Pro | Met | Pro | Asp | Ile | Cys | Thr | Leu | Asn | Cys | Ile | |
| | | | | 40 | | | | | 45 | | | | | 50 | | |
| GTG | AAC | GTG | TGT | CAG | TGC | AAA | CCC | GGC | TTC | AAG | CGC | GGA | CCG | AAA | GGA | 249 |
| Val | Asn | Val | Cys | Gln | Cys | Lys | Pro | Gly | Phe | Lys | Arg | Gly | Pro | Lys | Gly | |
| | | | 55 | | | | | 60 | | | | | 65 | | | |
| TGC | GTC | GCC | CCC | GGA | CCA | GGC | TGT | AAA | TAGTTCTCCA | CCTGCCCTTT | CGTTGGAA | | | | | 304 |
| Cys | Val | Ala | Pro | Gly | Pro | Gly | Cys | Lys | | | | | | | | |
| | | 70 | | | | | 75 | | | | | | | | | |

CAAATGGCTG TCTTTTTACA TTCTGAATCA ATAAAGCCGA ACGGT                    349

( 2 ) INFORMATION FOR SEQ ID NO:15:

( i ) SEQUENCE CHARACTERISTICS:
        ( A ) LENGTH: 432 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 40...393

( x i ) SEQUENCE DESCRIPTION: SEQ ID NO:15:

AAGCTTTGCT AACATACTGC GTAATAAGGA GTCTTAATC ATG CCA GTT CTT TTG      54

|  |  |  |  |  |  |  |  |  |  | Met | Pro | Val | Leu | Leu |  |
|---|---|---|---|---|---|---|---|---|---|---|---|---|---|---|---|
|  |  |  |  |  |  |  |  |  |  | 1 |  |  |  | 5 |  |

| GGT | ATT | CCG | TTA | TTA | TTG | CGT | TTC | CTC | GGT | TTC | CTT | CTG | GTA | ACT | TTG | 102 |
|---|---|---|---|---|---|---|---|---|---|---|---|---|---|---|---|---|
| Gly | Ile | Pro | Leu | Leu | Leu | Arg | Phe | Leu | Gly | Phe | Leu | Leu | Val | Thr | Leu |  |
|  |  |  | 10 |  |  |  |  | 15 |  |  |  |  | 20 |  |  |  |

| TTC | GGC | TAT | CTG | CTT | ACT | TTC | CTT | AAA | AAG | GGC | TTC | GGT | AAG | ATA | GCT | 150 |
|---|---|---|---|---|---|---|---|---|---|---|---|---|---|---|---|---|
| Phe | Gly | Tyr | Leu | Leu | Thr | Phe | Leu | Lys | Lys | Gly | Phe | Gly | Lys | Ile | Ala |  |
|  |  | 25 |  |  |  |  |  | 30 |  |  |  |  | 35 |  |  |  |

| ATT | GCT | ATT | TCA | TTG | TTT | CTT | GCT | CTT | ATT | ATT | GGG | CTT | AAC | TCA | ATT | 198 |
|---|---|---|---|---|---|---|---|---|---|---|---|---|---|---|---|---|
| Ile | Ala | Ile | Ser | Leu | Phe | Leu | Ala | Leu | Ile | Ile | Gly | Leu | Asn | Ser | Ile |  |
|  |  |  | 40 |  |  |  |  | 45 |  |  |  |  | 50 |  |  |  |

| CTT | GTG | GGT | TAT | CTC | TCT | GAT | ATT | AGC | GCA | CAA | TTA | CCC | TCT | GAT | TTT | 246 |
|---|---|---|---|---|---|---|---|---|---|---|---|---|---|---|---|---|
| Leu | Val | Gly | Tyr | Leu | Ser | Asp | Ile | Ser | Ala | Gln | Leu | Pro | Ser | Asp | Phe |  |
|  | 55 |  |  |  |  | 60 |  |  |  |  | 65 |  |  |  |  |  |

| GTT | CAG | GGC | GTT | CAG | TTA | ATT | CTC | CCG | TCT | AAT | GCG | CTT | CCC | TGT | TTT | 294 |
|---|---|---|---|---|---|---|---|---|---|---|---|---|---|---|---|---|
| Val | Gln | Gly | Val | Gln | Leu | Ile | Leu | Pro | Ser | Asn | Ala | Leu | Pro | Cys | Phe |  |
| 70 |  |  |  |  | 75 |  |  |  |  | 80 |  |  |  |  | 85 |  |

| TAT | GTT | ATT | CTC | TCT | GTA | AAG | GCT | GCT | ATT | TTC | ATT | TTT | GAC | GTT | AAA | 342 |
|---|---|---|---|---|---|---|---|---|---|---|---|---|---|---|---|---|
| Tyr | Val | Ile | Leu | Ser | Val | Lys | Ala | Ala | Ile | Phe | Ile | Phe | Asp | Val | Lys |  |
|  |  |  |  | 90 |  |  |  |  | 95 |  |  |  |  | 100 |  |  |

| CAA | AAA | ATC | GTT | TCT | TAT | TTG | GAT | TGG | GAT | AAA | GGT | GGA | GGC | TCA | GGC | 390 |
|---|---|---|---|---|---|---|---|---|---|---|---|---|---|---|---|---|
| Gln | Lys | Ile | Val | Ser | Tyr | Leu | Asp | Trp | Asp | Lys | Gly | Gly | Gly | Ser | Gly |  |
|  |  |  | 105 |  |  |  |  | 110 |  |  |  |  | 115 |  |  |  |

| GGA | GGCCAAGTCG | GCCATCCCAT | ATCACGCGG | CGCGGATCC |  |  | 432 |
|---|---|---|---|---|---|---|---|
| Gly |  |  |  |  |  |  |  |

(2) INFORMATION FOR SEQ ID NO:16:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 40...393

(xi) SEQUENCE DESCRIPTION: SEQ ID NO:16:

| AAGCTTTGCT | AACATACTGC | GTAATAAGGA | GTCTTAATC | ATG | CCA | GTT | CTT | TTG | 54 |
|---|---|---|---|---|---|---|---|---|---|
|  |  |  |  | Met | Pro | Val | Leu | Leu |  |
|  |  |  |  | 1 |  |  |  | 5 |  |

| GGT | ATT | CCG | TTA | TTA | TTG | CGT | TTC | CTC | GGT | TTC | CTT | CTG | GTA | ACT | TTG | 102 |
|---|---|---|---|---|---|---|---|---|---|---|---|---|---|---|---|---|
| Gly | Ile | Pro | Leu | Leu | Leu | Arg | Phe | Leu | Gly | Phe | Leu | Leu | Val | Thr | Leu |  |
|  |  |  | 10 |  |  |  |  | 15 |  |  |  |  | 20 |  |  |  |

| TTC | GGC | TAT | CTG | CTT | ACT | TTC | CTT | AAA | AAG | GGC | TTC | GGT | AAG | ATA | GCT | 150 |
|---|---|---|---|---|---|---|---|---|---|---|---|---|---|---|---|---|
| Phe | Gly | Tyr | Leu | Leu | Thr | Phe | Leu | Lys | Lys | Gly | Phe | Gly | Lys | Ile | Ala |  |
|  |  | 25 |  |  |  |  |  | 30 |  |  |  |  | 35 |  |  |  |

| ATT | GCT | ATT | TCA | TTG | TTT | CTT | GCT | CTT | ATT | ATT | GGG | CTT | AAC | TCA | ATT | 198 |
|---|---|---|---|---|---|---|---|---|---|---|---|---|---|---|---|---|
| Ile | Ala | Ile | Ser | Leu | Phe | Leu | Ala | Leu | Ile | Ile | Gly | Leu | Asn | Ser | Ile |  |
|  |  |  | 40 |  |  |  |  | 45 |  |  |  |  | 50 |  |  |  |

| CTT | GTG | GGT | TAT | CTC | TCT | GAT | ATT | AGC | GCA | CAA | TTA | CCC | TCT | GAT | TTT | 246 |
|---|---|---|---|---|---|---|---|---|---|---|---|---|---|---|---|---|
| Leu | Val | Gly | Tyr | Leu | Ser | Asp | Ile | Ser | Ala | Gln | Leu | Pro | Ser | Asp | Phe |  |
|  | 55 |  |  |  |  | 60 |  |  |  |  | 65 |  |  |  |  |  |

| GTT | CAG | GGC | GTT | CAG | TTA | ATT | CTC | CCG | TCT | AAT | GCG | CTT | CCC | TGT | TTT | 294 |
|---|---|---|---|---|---|---|---|---|---|---|---|---|---|---|---|---|
| Val | Gln | Gly | Val | Gln | Leu | Ile | Leu | Pro | Ser | Asn | Ala | Leu | Pro | Cys | Phe |  |
| 70 |  |  |  |  | 75 |  |  |  |  | 80 |  |  |  |  | 85 |  |

| TAT | GTT | ATT | CTC | TCT | GTA | AAG | GCT | GCT | ATT | TTC | ATT | TTT | GAC | GTT | AAA | 342 |
|---|---|---|---|---|---|---|---|---|---|---|---|---|---|---|---|---|
| Tyr | Val | Ile | Leu | Ser | Val | Lys | Ala | Ala | Ile | Phe | Ile | Phe | Asp | Val | Lys |  |
|  |  |  |  | 90 |  |  |  |  | 95 |  |  |  |  | 100 |  |  |

| CAA | AAA | ATC | GTT | TCT | TAT | TTG | GAT | TGG | GAT | AAA | GGT | GGA | GGC | TCA | GGC | 390 |
|---|---|---|---|---|---|---|---|---|---|---|---|---|---|---|---|---|
| Gln | Lys | Ile | Val | Ser | Tyr | Leu | Asp | Trp | Asp | Lys | Gly | Gly | Gly | Ser | Gly |  |
|  |  |  | 105 |  |  |  |  | 110 |  |  |  |  | 115 |  |  |  |

```
GGA   GGGCCAAGTC   GGCCATCCCA   TATCACGCGG   CCGCGGATCC                            433
Gly
```

( 2 ) INFORMATION FOR SEQ ID NO:17:

( i ) SEQUENCE CHARACTERISTICS:
        ( A ) LENGTH: 434 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 40...393

( x i ) SEQUENCE DESCRIPTION: SEQ ID NO:17:

```
AAGCTTTGCT   AACATACTGC   GTAATAAGGA   GTCTTAATC  ATG  CCA  GTT  CTT  TTG           54
                                                  Met  Pro  Val  Leu  Leu
                                                   1                    5

GGT  ATT  CCG  TTA  TTA  TTG  CGT  TTC  CTC  GGT  TTC  CTT  CTG  GTA  ACT  TTG    102
Gly  Ile  Pro  Leu  Leu  Leu  Arg  Phe  Leu  Gly  Phe  Leu  Leu  Val  Thr  Leu
                10                       15                          20

TTC  GGC  TAT  CTG  CTT  ACT  TTC  CTT  AAA  AAG  GGC  TTC  GGT  AAG  ATA  GCT    150
Phe  Gly  Tyr  Leu  Leu  Thr  Phe  Leu  Lys  Lys  Gly  Phe  Gly  Lys  Ile  Ala
               25                       30                     35

ATT  GCT  ATT  TCA  TTG  TTT  CTT  GCT  CTT  ATT  ATT  GGG  CTT  AAC  TCA  ATT    198
Ile  Ala  Ile  Ser  Leu  Phe  Leu  Ala  Leu  Ile  Ile  Gly  Leu  Asn  Ser  Ile
               40                       45                     50

CTT  GTG  GGT  TAT  CTC  TCT  GAT  ATT  AGC  GCA  CAA  TTA  CCC  TCT  GAT  TTT    246
Leu  Val  Gly  Tyr  Leu  Ser  Asp  Ile  Ser  Ala  Gln  Leu  Pro  Ser  Asp  Phe
     55                       60                       65

GTT  CAG  GGC  GTT  CAG  TTA  ATT  CTC  CCG  TCT  AAT  GCG  CTT  CCC  TGT  TTT    294
Val  Gln  Gly  Val  Gln  Leu  Ile  Leu  Pro  Ser  Asn  Ala  Leu  Pro  Cys  Phe
70                       75                       80                          85

TAT  GTT  ATT  CTC  TCT  GTA  AAG  GCT  GCT  ATT  TTC  ATT  TTT  GAC  GTT  AAA    342
Tyr  Val  Ile  Leu  Ser  Val  Lys  Ala  Ala  Ile  Phe  Ile  Phe  Asp  Val  Lys
                    90                       95                          100

CAA  AAA  ATC  GTT  TCT  TAT  TTG  GAT  TGG  GAT  AAA  GGT  GGA  GGC  TCA  GGC    390
Gln  Lys  Ile  Val  Ser  Tyr  Leu  Asp  Trp  Asp  Lys  Gly  Gly  Gly  Ser  Gly
               105                      110                      115

GGA   TCGGCCAAGT   CGGCCATCCC   ATATCACGCG   GCCGCGGATC   C                        434
Gly
```

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Gly   Gly   Gly   Ser   Gly   Gly
 1                       5
```

( 2 ) INFORMATION FOR SEQ ID NO:19:

( i ) SEQUENCE CHARACTERISTICS:
        ( A ) LENGTH: 430 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Ancyclostoma caninum ( i x ) FEATURE:
    ( A ) NAME/KEY: Coding Sequence
    ( B ) LOCATION: 10...282
    ( D ) OTHER INFORMATION: "W"stands for A or T ( x i ) SEQUENCE DESCRIPTION: SEQ ID NO:19:

```
GAATTCCGG CTG GTW TCC TAC TGC AGT GGA AAA GCA ACG ATG CAG TGT GGT        51
          Leu Val Ser Tyr Cys Ser Gly Lys Ala Thr Met Gln Cys Gly
           1           5                      10

GAG AAT GAA AAG TAC GAT TCG TGC GGT AGC AAG GAG TGC GAT AAG AAG          99
Glu Asn Glu Lys Tyr Asp Ser Cys Gly Ser Lys Glu Cys Asp Lys Lys
15                  20                  25                  30

TGC AAA TAT GAC GGA GTT GAG GAG GAA GAC GAC GAG GAA CCT AAT GTG         147
Cys Lys Tyr Asp Gly Val Glu Glu Glu Asp Asp Glu Glu Pro Asn Val
                35                  40                  45

CCA TGC CTA GTA CGT GTG TGT CAT CAA GAT TGC GTA TGC GAA GAA GGA         195
Pro Cys Leu Val Arg Val Cys His Gln Asp Cys Val Cys Glu Glu Gly
            50                  55                  60

TTC TAT AGA AAC AAA GAT GAC AAA TGT GTA TCA GCA GAA GAC TGC GAA         243
Phe Tyr Arg Asn Lys Asp Asp Lys Cys Val Ser Ala Glu Asp Cys Glu
                65                  70                  75

CTT GAC AAT ATG GAC TTT ATA TAT CCC GGA ACT CGA AAC TGAACGAAGG CTC      295
Leu Asp Asn Met Asp Phe Ile Tyr Pro Gly Thr Arg Asn
80                  85                  90

CATTCTTGCT GCACAAGATC GATTGTCTCT CCCCTGCATC TCAGTAGTTT TGCTACATTG        355

TATATGGTAG CAAAAAATTA GCTTAGGGAG AATAAAATCT TTACCTATAT TTAATCAATG        415

AAGTATTCTC TTTCT                                                         430
```

( 2 ) INFORMATION FOR SEQ ID NO:20:

( i ) SEQUENCE CHARACTERISTICS:
        ( A ) LENGTH: 100 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:20:

```
Met Lys Met Leu Tyr Ala Ile Ala Ile Met Phe Leu Leu Val Ser Leu
 1               5                  10                  15

Cys Ser Ala Arg Thr Val Arg Lys Ala Tyr Pro Glu Cys Gly Glu Asn
            20                  25                  30

Glu Trp Leu Asp Asp Cys Gly Thr Gln Lys Pro Cys Glu Ala Lys Cys
        35                  40                  45

Asn Glu Glu Pro Pro Glu Glu Glu Asp Pro Ile Cys Arg Ser Arg Gly
        50                  55                  60

Cys Leu Leu Pro Pro Ala Cys Val Cys Lys Asp Gly Phe Tyr Arg Asp
65                  70                  75                  80

Thr Val Ile Gly Asp Cys Val Arg Glu Glu Glu Cys Asp Gln His Glu
                85                  90                  95

Ile Ile His Val
        100
```

( 2 ) INFORMATION FOR SEQ ID NO:21:

( i ) SEQUENCE CHARACTERISTICS:
        ( A ) LENGTH: 98 amino acids
        ( B ) TYPE: amino acid (D) TOPOLOGY: linear (ii) MOLECULE TYPE: peptide (vi) ORIGINAL SOURCE:
(A) ORGANISM: Ancyclostoma caninum (xi) SEQUENCE DESCRIPTION: SEQ ID NO:21:

| Met | Lys | Met | Leu | Tyr | Ala | Ile | Ala | Ile | Met | Phe | Leu | Leu | Val | Ser | Leu |
|---|---|---|---|---|---|---|---|---|---|---|---|---|---|---|---|
| 1 | | | | 5 | | | | | 10 | | | | | 15 | |
| Cys | Ser | Thr | Arg | Thr | Val | Arg | Lys | Ala | Tyr | Pro | Glu | Cys | Gly | Glu | Asn |
| | | | 20 | | | | 25 | | | | | | 30 | | |
| Glu | Trp | Leu | Asp | Val | Cys | Gly | Thr | Lys | Lys | Pro | Cys | Glu | Ala | Lys | Cys |
| | | 35 | | | | | 40 | | | | | 45 | | | |
| Ser | Glu | Glu | Glu | Glu | Glu | Asp | Pro | Ile | Cys | Arg | Ser | Phe | Ser | Cys | Pro |
| | 50 | | | | | | 55 | | | | | 60 | | | |
| Gly | Pro | Ala | Ala | Cys | Val | Cys | Glu | Asp | Gly | Phe | Tyr | Arg | Asp | Thr | Val |
| 65 | | | | | 70 | | | | | 75 | | | | | 80 |
| Ile | Gly | Asp | Cys | Val | Lys | Glu | Glu | Glu | Cys | Asp | Gln | His | Glu | Ile | Ile |
| | | | | 85 | | | | | 90 | | | | | 95 | |
| His | Val | | | | | | | | | | | | | | |

(2) INFORMATION FOR SEQ ID NO:22:

(i) SEQUENCE CHARACTERISTICS:
(A) LENGTH: 94 amino acids
(B) TYPE: amino acid
(D) TOPOLOGY: linear (ii) MOLECULE TYPE: peptide (vi) ORIGINAL SOURCE:
(A) ORGANISM: Ancyclostoma ceylanicum (xi) SEQUENCE DESCRIPTION: SEQ ID NO:22:

| Met | Arg | Thr | Leu | Tyr | Leu | Ile | Ser | Ile | Trp | Leu | Phe | Leu | Ile | Ser | Gln |
|---|---|---|---|---|---|---|---|---|---|---|---|---|---|---|---|
| 1 | | | | 5 | | | | | 10 | | | | | 15 | |
| Cys | Asn | Gly | Lys | Ala | Phe | Pro | Lys | Cys | Asp | Val | Asn | Glu | Arg | Phe | Glu |
| | | | 20 | | | | | 25 | | | | | 30 | | |
| Val | Cys | Gly | Asn | Leu | Lys | Glu | Cys | Glu | Leu | Lys | Cys | Asp | Glu | Asp | Pro |
| | | 35 | | | | | 40 | | | | | 45 | | | |
| Lys | Ile | Cys | Ser | Arg | Ala | Cys | Ile | Arg | Pro | Pro | Ala | Cys | Val | Cys | Asp |
| | 50 | | | | | 55 | | | | | | 60 | | | |
| Asp | Gly | Phe | Tyr | Arg | Asp | Lys | Tyr | Gly | Phe | Cys | Val | Glu | Glu | Asp | Glu |
| 65 | | | | | 70 | | | | | 75 | | | | | 80 |
| Cys | Asn | Asp | Met | Glu | Ile | Ile | Thr | Phe | Pro | Pro | Glu | Thr | Lys | | |
| | | | | 85 | | | | | 90 | | | | | | |

(2) INFORMATION FOR SEQ ID NO:23:

(i) SEQUENCE CHARACTERISTICS:
(A) LENGTH: 96 amino acids
(B) TYPE: amino acid
(D) TOPOLOGY: linear (ii) MOLECULE TYPE: peptide (vi) ORIGINAL SOURCE:
(A) ORGANISM: Ancyclostoma ceylanicum (xi) SEQUENCE DESCRIPTION: SEQ ID NO:23:

| Met | Ser | Thr | Leu | Tyr | Val | Ile | Ala | Ile | Cys | Leu | Leu | Leu | Val | Ser | Gln |
|---|---|---|---|---|---|---|---|---|---|---|---|---|---|---|---|
| 1 | | | | 5 | | | | | 10 | | | | | 15 | |

| Cys | Asn | Gly | Arg<br>20 | Thr | Val | Lys | Lys | Cys<br>25 | Gly | Lys | Asn | Glu | Arg<br>30 | Tyr | Asp |
|---|---|---|---|---|---|---|---|---|---|---|---|---|---|---|---|
| Asp | Cys | Gly<br>35 | Asn | Ala | Lys | Asp | Cys<br>40 | Glu | Thr | Lys | Cys<br>45 | Gly | Glu | Glu | Glu |
| Lys | Val<br>50 | Cys | Arg | Ser | Arg<br>55 | Cys | Thr | Ser | Pro | Gly<br>60 | Ala | Cys | Val | Cys |
| Glu<br>65 | Gln | Gly | Phe | Tyr | Arg<br>70 | Asp | Pro | Ala | Gly | Asp<br>75 | Cys | Val | Thr | Asp | Glu<br>80 |
| Glu | Cys | Asp | Glu | Trp<br>85 | Asn | Asn | Met | Glu | Ile<br>90 | Ile | Thr | Met | Pro | Lys<br>95 | Gln |

( 2 ) INFORMATION FOR SEQ ID NO:24:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma ceylanicum ( x i ) SEQUENCE DESCRIPTION: SEQ ID NO:24:

| Met<br>1 | Ala | Val | Leu | Tyr<br>5 | Ser | Val | Ala | Ile | Ala<br>10 | Leu | Leu | Leu | Val | Ser<br>15 | Gln |
|---|---|---|---|---|---|---|---|---|---|---|---|---|---|---|---|
| Cys | Ser | Gly | Lys<br>20 | Pro | Asn | Asn | Val | Met<br>25 | Thr | Asn | Ala | Cys | Gly<br>30 | Leu | Asn |
| Glu | Tyr | Phe<br>35 | Ala | Glu | Cys | Gly | Asn<br>40 | Met | Lys | Glu | Cys<br>45 | Glu | His | Arg | Cys |
| Asn | Glu<br>50 | Glu | Glu | Asn | Glu | Glu<br>55 | Arg | Asp | Glu | Glu | Arg<br>60 | Ile | Thr | Ala | Cys |
| Leu<br>65 | Ile | Arg | Val | Cys | Phe<br>70 | Arg | Pro | Gly | Ala | Cys<br>75 | Val | Cys | Lys | Asp | Gly<br>80 |
| Phe | Tyr | Arg | Asn | Arg<br>85 | Thr | Gly | Ser | Cys | Val<br>90 | Glu | Glu | Asp | Asp | Cys<br>95 | Glu |
| Tyr | Glu | Asn | Met<br>100 | Glu | Phe | Ile | Thr | Phe<br>105 | Ala | Pro | Glu | | | | |

( 2 ) INFORMATION FOR SEQ ID NO:25:

( i ) SEQUENCE CHARACTERISTICS:
        ( A ) LENGTH: 82 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma ceylanicum ( x i ) SEQUENCE DESCRIPTION: SEQ ID NO:25:

| Val<br>1 | Pro | Ile | Cys | Gly<br>5 | Ser | Asn | Glu | Arg | Tyr<br>10 | Ser | Asp | Cys | Gly | Asn<br>15 | Asp |
|---|---|---|---|---|---|---|---|---|---|---|---|---|---|---|---|
| Lys | Gln | Cys | Glu<br>20 | Arg | Lys | Cys | Asn | Glu<br>25 | Asp | Asp | Tyr | Glu | Lys<br>30 | Gly | Asp |
| Glu | Ala | Cys<br>35 | Arg | Ser | His | Val | Cys<br>40 | Glu | Arg | Pro | Gly<br>45 | Ala | Cys | Val | Cys |
| Glu | Asp<br>50 | Gly | Phe | Tyr | Arg<br>55 | Asn | Lys | Lys | Gly | Ser<br>60 | Cys | Val | Glu | Ser | Asp |
| Asp<br>65 | Cys | Glu | Tyr | Asp | Asn<br>70 | Met | Asp | Phe | Ile | Thr<br>75 | Phe | Ala | Pro | Glu | Thr<br>80 |

Ser Arg ( 2 ) INFORMATION FOR SEQ ID NO:26:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma duodenale ( x i ) SEQUENCE DESCRIPTION: SEQ ID NO:26:

```
Lys Cys Pro Thr Asp Glu Trp Phe Asp Trp Cys Gly Thr Tyr Lys His
 1               5                  10                  15
Cys Glu Leu Lys Cys Asp Arg Glu Leu Thr Glu Glu Glu Gln Ala Cys
                20                  25                  30
Leu Ser Arg Val Cys Glu Lys Ser Ala Cys Val Cys Asn Asp Gly Leu
             35                  40                  45
Tyr Arg Asp Lys Phe Gly Asn Cys Val Glu Lys Asp Glu Cys Asn Asp
         50                  55                  60
Met Glu Ile Ile Thr Phe Ala Pro Glu Thr Lys
 65              70                  75
```

( 2 ) INFORMATION FOR SEQ ID NO:27:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma duodenale ( x i ) SEQUENCE DESCRIPTION: SEQ ID NO:27:

```
Met Arg Met Leu Tyr Leu Val Pro Ile Trp Leu Leu Leu Ile Ser Leu
 1               5                  10                  15
Cys Ser Gly Lys Ala Ala Lys Lys Cys Gly Leu Asn Glu Arg Leu Asp
                20                  25                  30
Cys Gly Asn Leu Lys Gln Cys Glu Pro Lys Cys Ser Asp Leu Glu Ser
             35                  40                  45
Glu Glu Tyr Glu Glu Glu Asp Glu Ser Lys Cys Arg Ser Arg Glu Cys
         50                  55                  60
Ser Arg Arg Val Cys Val Cys Asp Glu Gly Phe Tyr Arg Asn Lys Lys
 65              70                  75                  80
Gly Lys Cys Val Ala Lys Asp Val Cys Glu Asp Asp Asn Met Glu Ile
                 85                  90                  95
Ile Thr Phe Pro Pro Glu
            100
```

( 2 ) INFORMATION FOR SEQ ID NO:28:

( i ) SEQUENCE CHARACTERISTICS:
        ( A ) LENGTH: 78 amino acids
        ( B ) TYPE: amino acid
        ( D ) TOPOLOGY: linear ( i i ) MOLECULE TYPE: peptide ( v i ) ORIGINAL SOURCE:

(A) ORGANISM: Ancyclostoma duodenale (xi) SEQUENCE DESCRIPTION: SEQ ID NO:28:

| Asp | Glu | Cys | Gly | Pro | Asp | Glu | Trp | Phe | Asp | Tyr | Cys | Gly | Asn | Tyr | Lys |
|---|---|---|---|---|---|---|---|---|---|---|---|---|---|---|---|
| 1 | | | | 5 | | | | | 10 | | | | | 15 | |
| Lys | Cys | Glu | Arg | Lys | Cys | Ser | Glu | Glu | Thr | Ser | Glu | Lys | Asn | Glu | Glu |
| | | | 20 | | | | 25 | | | | | 30 | | | |
| Ala | Cys | Leu | Ser | Arg | Ala | Cys | Thr | Gly | Arg | Ala | Cys | Val | Cys | Lys | Asp |
| | | | 35 | | | | 40 | | | | | 45 | | | |
| Gly | Leu | Tyr | Arg | Asp | Asp | Phe | Gly | Asn | Cys | Val | Pro | His | Asp | Glu | Cys |
| | | | 50 | | | | 55 | | | | | 60 | | | |
| Asn | Asp | Met | Glu | Ile | Ile | Thr | Phe | Pro | Pro | Glu | Thr | Lys | His | | |
| 65 | | | | | 70 | | | | | 75 | | | | | |

(2) INFORMATION FOR SEQ ID NO:29:

(i) SEQUENCE CHARACTERISTICS:
 (A) LENGTH: 76 amino acids
 (B) TYPE: amino acid
 (D) TOPOLOGY: linear (ii) MOLECULE TYPE: peptide (vi) ORIGINAL SOURCE:
 (A) ORGANISM: Heligmosomoides polygyrus (xi) SEQUENCE DESCRIPTION: SEQ ID NO:29:

| Met | Ile | Arg | Lys | Leu | Val | Leu | Leu | Thr | Ala | Ile | Val | Thr | Val | Val | Leu |
|---|---|---|---|---|---|---|---|---|---|---|---|---|---|---|---|
| 1 | | | | 5 | | | | | 10 | | | | | 15 | |
| Ser | Ala | Lys | Thr | Cys | Gly | Pro | Asn | Glu | Glu | Tyr | Thr | Glu | Cys | Gly | Thr |
| | | | 20 | | | | 25 | | | | | 30 | | | |
| Pro | Cys | Glu | Pro | Lys | Cys | Asn | Glu | Pro | Met | Pro | Asp | Ile | Cys | Thr | Leu |
| | | | 35 | | | | 40 | | | | | 45 | | | |
| Asn | Cys | Ile | Val | Asn | Val | Cys | Gln | Cys | Lys | Pro | Gly | Phe | Lys | Arg | Gly |
| | | | 50 | | | | 55 | | | | | 60 | | | |
| Pro | Lys | Gly | Cys | Val | Ala | Pro | Gly | Pro | Gly | Cys | Lys | | | | |
| 65 | | | | | 70 | | | | | 75 | | | | | |

(2) INFORMATION FOR SEQ ID NO:30:

(i) SEQUENCE CHARACTERISTICS:
 (A) LENGTH: 187 base pairs
 (B) TYPE: nucleic acid
 (C) STRANDEDNESS: single
 (D) TOPOLOGY: linear (xi) SEQUENCE DESCRIPTION: SEQ ID NO:30:

```
TTATTCGAAA CGATGTTCTC TCCAATTTTG TCCTTGGAAA TTATTTTAGC TACTTTGCAA      60
TCTGTCTTCG CCCAGCCAGT TATCTCCACT ACCGTTGGTT CCGCTGCCGA GGGTTCTTTG     120
GACAAGAGGC CTATCCGCGG AATTCAGATC TGAATGCGGC CGCTCGAGAC TAGTGGATCC     180
TTAGACA                                                                187
```

(2) INFORMATION FOR SEQ ID NO:31:

(i) SEQUENCE CHARACTERISTICS:
 (A) LENGTH: 495 base pairs
 (B) TYPE: nucleic acid
 (C) STRANDEDNESS: single
 (D) TOPOLOGY: linear (vi) ORIGINAL SOURCE:
 (A) ORGANISM: Ancyclostoma caninum -continued ( i x ) FEATURE:
    ( A ) NAME/KEY: Coding Sequence
    ( B ) LOCATION: 36...356
    ( D ) OTHER INFORMATION: "N"stands for an unidentified base ( x i ) SEQUENCE DESCRIPTION: SEQ ID NO:31:

```
GAATTCCGCG GAATTCCGCT TGCTACTACT CAACG ATG AAG ACG CTC TAT ATT        53
                                       Met Lys Thr Leu Tyr Ile
                                        1               5

GTC GCT ATA TGC TCG CTC CTC ATT TCG CTG TGT ACT GGA AAA CCT TCG      101
Val Ala Ile Cys Ser Leu Leu Ile Ser Leu Cys Thr Gly Lys Pro Ser
            10                  15                  20

GAG AAA GAA TGT GGT CCC CAT GAA AGA CTC NNN NNN NNN NNN NNN NNN      149
Glu Lys Glu Cys Gly Pro His Glu Arg Leu Asp Cys Gly Asn Lys Lys
        25                  30                  35

NNN NNN NNN NNN NNN NNN NNN NNN NNN NNN NNN NNN NNN NNN NNN NNN      197
Pro Cys Glu Arg Lys Cys Lys Ile Glu Thr Ser Glu Glu Glu Asp Asp
    40                  45                  50

NNN NNN NNN NNN NNN NNN CGT TTT CGA TGC CTC TTA CGT GTG TGT GAT      245
Tyr Glu Glu Gly Thr Glu Arg Phe Arg Cys Leu Leu Arg Val Cys Asp
55                  60                  65                  70

CAG CCT TAT GAA TGC ATA TGC GAT GAT GGA TAC TAC AGA AAC AAG AAA      293
Gln Pro Tyr Glu Cys Ile Cys Asp Asp Gly Tyr Tyr Arg Asn Lys Lys
                75                  80                  85

GGC GAA TGT GTG ACT GAT GAT GTA TGC CAG GAA GAC TTT ATG GAG TTT      341
Gly Glu Cys Val Thr Asp Asp Val Cys Gln Glu Asp Phe Met Glu Phe
            90                  95                 100

ATT ACT TTC GCA CCA TAAACCCAAT AATGACCAAT GACTCCCATT CTTCGTGATC AG   398
Ile Thr Phe Ala Pro
            105

CGTCGGTGGT TGACAGTCTC CCCTACATCT TAGTAGTTTT GCTTGATAAT GTATACATAA    458

ACTGTACTTT CTGAGATAGA ATAAAGCTCT CAACTAC                             495
```

( 2 ) INFORMATION FOR SEQ ID NO:32:

( i ) SEQUENCE CHARACTERISTICS:
        ( A ) LENGTH: 478 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Ancyclostoma caninum ( i x ) FEATURE:
        ( A ) NAME/KEY: Coding Sequence
        ( B ) LOCATION: 24...341

( x i ) SEQUENCE DESCRIPTION: SEQ ID NO:32:

```
GAATTCCGCG GAATTCCGCA ACG ATG AAG ACG CTC TAT ATT ATC GCT ATA TGC    53
                         Met Lys Thr Leu Tyr Ile Ile Ala Ile Cys
                          1               5                  10

TCG CTC CTC ATT TCG TTG TGT ACT GGA AGA CCG GAA AAA AAG TGC GGT      101
Ser Leu Leu Ile Ser Leu Cys Thr Gly Arg Pro Glu Lys Lys Cys Gly
                15                  20                  25

CCC GGT GAA AGA CTC GCC TGT GGC AAT AAG AAG CCA TGC GAG CGC AAG      149
Pro Gly Glu Arg Leu Ala Cys Gly Asn Lys Lys Pro Cys Glu Arg Lys
        30                  35                  40

TGC AAA ATA GAG ACA AGT GAG GAG GAG GAT GAC TAC CCA GAG GGA ACC      197
Cys Lys Ile Glu Thr Ser Glu Glu Glu Asp Asp Tyr Pro Glu Gly Thr
    45                  50                  55

GAA CGT TTT CGA TGC CTC TTA CGT GTG TGT GAT CAG CCT TAT GAA TGC      245
Glu Arg Phe Arg Cys Leu Leu Arg Val Cys Asp Gln Pro Tyr Glu Cys
60                  65                  70
```

| | | | | | | | | | | | | | | |
|---|---|---|---|---|---|---|---|---|---|---|---|---|---|---|
| ATA | TGC | GAT | GAT | GGA | TAC | TAC | AGA | AAC | AAG | AAA | GGC | GAA | TGT | GTG | ACT | 293 |
| Ile | Cys | Asp | Asp | Gly | Tyr | Tyr | Arg | Asn | Lys | Lys | Gly | Glu | Cys | Val | Thr |
| 75  |     |     |     |     | 80  |     |     |     | 85  |     |     |     |     | 90  |     |

| GAT | GAT | GTA | TGC | CAG | GAA | GAC | TTT | ATG | GAG | TTT | ATT | ACT | TTC | GCA | CCA | 341 |
|---|---|---|---|---|---|---|---|---|---|---|---|---|---|---|---|---|
| Asp | Asp | Val | Cys | Gln | Glu | Asp | Phe | Met | Glu | Phe | Ile | Thr | Phe | Ala | Pro |
|     |     |     |     | 95  |     |     |     | 100 |     |     |     |     |     | 105 |     |

TAAACCCAAT AATGACCACT GGCTCCCATT CTTCGTGACC AGCGTCGGTG GTTGACAGTC  401

TCCCCTGCAT CTTAGTAGTT TTGCTTGATA ATGTATCCAT AAACAGTACT TTCTGAGATA  461

GAATAAAGCT CTCAACT  478

( 2 ) INFORMATION FOR SEQ ID NO:33:

( i ) SEQUENCE CHARACTERISTICS:
        ( A ) LENGTH: 472 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Ancyclostoma caninum ( i x ) FEATURE:
        ( A ) NAME/KEY: Coding Sequence
        ( B ) LOCATION: 21...335

( x i ) SEQUENCE DESCRIPTION: SEQ ID NO:33:

| GAATTCCGTA | CTACTCAACG | ATG | AAG | ACG | CTC | TAT | ATT | ATC | GCT | ATA | TGC | 50 |
|---|---|---|---|---|---|---|---|---|---|---|---|---|
|  |  | Met | Lys | Thr | Leu | Tyr | Ile | Ile | Ala | Ile | Cys |  |
|  |  | 1 |  |  | 5 |  |  |  |  |  | 10 |  |

| TCG | CTG | CTC | TTT | TCA | CTG | TGT | ACT | GGA | AGA | CCG | GAA | AAA | AAG | TGC | GGT | 98 |
|---|---|---|---|---|---|---|---|---|---|---|---|---|---|---|---|---|
| Ser | Leu | Leu | Phe | Ser | Leu | Cys | Thr | Gly | Arg | Pro | Glu | Lys | Lys | Cys | Gly |
|  |  |  |  | 15 |  |  |  |  | 20 |  |  |  |  | 25 |  |

| CCC | GGT | GAA | AGA | CTC | GAC | TGT | GCC | AAC | AAG | AAG | CCA | TGC | GAG | CCC | AAG | 146 |
|---|---|---|---|---|---|---|---|---|---|---|---|---|---|---|---|---|
| Pro | Gly | Glu | Arg | Leu | Asp | Cys | Ala | Asn | Lys | Lys | Pro | Cys | Glu | Pro | Lys |
|  |  |  | 30 |  |  |  |  | 35 |  |  |  |  | 40 |  |  |

| TGC | AAA | ATA | GAG | ACA | AGT | GAG | GAG | GAG | GAT | GAC | GAC | GTA | GAG | GAT | ACC | 194 |
|---|---|---|---|---|---|---|---|---|---|---|---|---|---|---|---|---|
| Cys | Lys | Ile | Glu | Thr | Ser | Glu | Glu | Glu | Asp | Asp | Asp | Val | Glu | Asp | Thr |
|  |  | 45 |  |  |  | 50 |  |  |  |  |  | 55 |  |  |  |

| GAT | GTG | AGA | TGC | CTC | GTA | CGT | GTG | TGT | GAA | CGT | CCT | CTT | AAA | TGC | ATA | 242 |
|---|---|---|---|---|---|---|---|---|---|---|---|---|---|---|---|---|
| Asp | Val | Arg | Cys | Leu | Val | Arg | Val | Cys | Glu | Arg | Pro | Leu | Lys | Cys | Ile |
|  |  | 60 |  |  |  | 65 |  |  |  |  | 70 |  |  |  |  |

| TGC | AAG | GAT | GGA | TAC | TAC | AGA | AAC | AAG | AAA | GGC | GAA | TGT | GTG | ACT | GAT | 290 |
|---|---|---|---|---|---|---|---|---|---|---|---|---|---|---|---|---|
| Cys | Lys | Asp | Gly | Tyr | Tyr | Arg | Asn | Lys | Lys | Gly | Glu | Cys | Val | Thr | Asp |
| 75 |  |  |  |  | 80 |  |  |  | 85 |  |  |  |  | 90 |  |  |

| GAT | GTA | TGC | CAG | GAA | GAC | TTT | ATG | GAG | TTT | ATT | ACT | TTC | GCA | CCA | TAAACC | 341 |
|---|---|---|---|---|---|---|---|---|---|---|---|---|---|---|---|---|
| Asp | Val | Cys | Gln | Glu | Asp | Phe | Met | Glu | Phe | Ile | Thr | Phe | Ala | Pro |  |
|  |  |  | 95 |  |  |  | 100 |  |  |  |  |  | 105 |  |  |

CAATAATGAC CACTGGCTCC CATTCTTCGT GATCAGCGTC GGTGGTTGAC AGTCTCCCCT  401

GCATCTTAGT TGCTTTGCTT GATAATCTAT ACATAAACAG TACTTTCTGA GATAGAATAA  461

AGCTCTCAAC T  472

( 2 ) INFORMATION FOR SEQ ID NO:34:

( i ) SEQUENCE CHARACTERISTICS:
        ( A ) LENGTH: 487 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Ancyclostoma caninum ( i x ) FEATURE:

( A ) NAME/KEY: Coding Sequence
        ( B ) LOCATION: 57...347

( x i ) SEQUENCE DESCRIPTION: SEQ ID NO:34:

```
GAATTCCGGA CTTACTAGTA CTCAGCGAAT CAAATACGAC TTACTACTAC TCAACG ATG         59
                                                                 Met
                                                                  1

AAG ACG CTC TCT GCT ATC CCT ATA ATG CTG CTC CTG GTA TCG CAA TGC          107
Lys Thr Leu Ser Ala Ile Pro Ile Met Leu Leu Leu Val Ser Gln Cys
             5                  10                  15

AGT GGA AAA TCA CTG TGG GAT CAG AAG TGT GGT GAG AAT GAA AGG CTC          155
Ser Gly Lys Ser Leu Trp Asp Gln Lys Cys Gly Glu Asn Glu Arg Leu
         20                  25                  30

GAC TGT GGC AAT CAG AAG GAC TGT GAG CGC AAG TGC GAT GAT AAA AGA          203
Asp Cys Gly Asn Gln Lys Asp Cys Glu Arg Lys Cys Asp Asp Lys Arg
     35                  40                  45

AGT GAA GAA GAA ATT ATG CAG GCA TGT CTC ACA CGT CAA TGT CTT CCT          251
Ser Glu Glu Glu Ile Met Gln Ala Cys Leu Thr Arg Gln Cys Leu Pro
 50                  55                  60                  65

CCT GTT TGC GTA TGT GAA GAT GGA TTC TAC AGA AAT GAC AAC GAC CAA          299
Pro Val Cys Val Cys Glu Asp Gly Phe Tyr Arg Asn Asp Asn Asp Gln
             70                  75                  80

TGT GTT GAT GAA GAA GAA TGC AAT ATG GAG TTT ATT ACT TTC GCA CCA TG       349
Cys Val Asp Glu Glu Glu Cys Asn Met Glu Phe Ile Thr Phe Ala Pro
         85                  90                  95

AAGCAAATGA CAGCCGATGG TTTGGACTCT CGCTACAGAT CACAGCTTTA CTGTTTCCCT        409

TGCATCATAG TAGTTTTGCT AGATAGTGTA TATATTAGCA TGATTTTCTG ATAGGGAGAA        469

TAAAGCTTTC CAATTTTC                                                     487
```

( 2 ) INFORMATION FOR SEQ ID NO:35:

( i ) SEQUENCE CHARACTERISTICS:
        ( A ) LENGTH: 477 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Ancyclostoma caninum ( i x ) FEATURE:
        ( A ) NAME/KEY: Coding Sequence
        ( B ) LOCATION: 24...338

( x i ) SEQUENCE DESCRIPTION: SEQ ID NO:35:

```
GAATTCCGCG GAATTCCGCA ACG ATG AAG ACG CTC TAT ATT ATC GCT ATA TGC         53
                         Met Lys Thr Leu Tyr Ile Ile Ala Ile Cys
                          1               5                  10

TCG CTC CTC ATT TCG CTG TGT ACT GGA AGA CCG GAA AAA AAG TGC GGT          101
Ser Leu Leu Ile Ser Leu Cys Thr Gly Arg Pro Glu Lys Lys Cys Gly
             15                  20                  25

CCC GGT GAA AGA CTC GAC TGT GCC AAC AAG AAG CCA TGC GAG CCC AAG          149
Pro Gly Glu Arg Leu Asp Cys Ala Asn Lys Lys Pro Cys Glu Pro Lys
         30                  35                  40

TGC AAA ATA GAG ACA AGT GAG GAG GAG GAT GAC GAC GTA GAG GAA ACC          197
Cys Lys Ile Glu Thr Ser Glu Glu Glu Asp Asp Asp Val Glu Glu Thr
     45                  50                  55

GAT GTG AGA TGC CTC GTA CGT GTG TGT GAA CGG CCT CTT AAA TGC ATA          245
Asp Val Arg Cys Leu Val Arg Val Cys Glu Arg Pro Leu Lys Cys Ile
 60                  65                  70

TGC AAG GAT GGA TAC TAC AGA AAC AAG AAA GGC GAA TGT GTG ACT GAT          293
Cys Lys Asp Gly Tyr Tyr Arg Asn Lys Lys Gly Glu Cys Val Thr Asp
 75                  80                  85                  90
```

```
GAT GTA TGC CAG GAA GAC TTT ATG GAG TTT ATT ACT TTC GCA CCA TAAACC      344
Asp Val Cys Gln Glu Asp Phe Met Glu Phe Ile Thr Phe Ala Pro
             95                  100                 105

CAATAATGAC CACTGGCTCC CATTCTTCGT GATCAGCGTC GGTGGTTGAC AGTCTCCCT         404

GCATCTTAGT TGCTTTGCTT GATAATCTAT ACATAAACAG TACTTTCTGA GATAGAATAA        464

AGCTCTCAAC TAC                                                          477
```

( 2 ) INFORMATION FOR SEQ ID NO:36:

( i ) SEQUENCE CHARACTERISTICS:
        ( A ) LENGTH: 686 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Ancyclostoma caninum ( i x ) FEATURE:
        ( A ) NAME/KEY: Coding Sequence
        ( B ) LOCATION: 14...556

( x i ) SEQUENCE DESCRIPTION: SEQ ID NO:36:

```
GAATTCCGGA AAA ATG CTG ATG CTC TAC CTT GTT CCT ATC TGG TTG CTA          49
            Met Leu Met Leu Tyr Leu Val Pro Ile Trp Leu Leu
             1           5                       10

CTC ATT TCG CAA TGC AGT GGA AAA TCC GCG AAG AAA TGT GGT CTC AAT          97
Leu Ile Ser Gln Cys Ser Gly Lys Ser Ala Lys Lys Cys Gly Leu Asn
         15              20                  25

GAA AAA TTG GAC TGT GGC AAT CTG AAG GCA TGC GAG AAA AAG TGC AGC         145
Glu Lys Leu Asp Cys Gly Asn Leu Lys Ala Cys Glu Lys Lys Cys Ser
    30              35                  40

GAC TTG GAC AAT GAG GAG GAT TAT AAG GAG GAA GAT GAG TCG AAA TGC         193
Asp Leu Asp Asn Glu Glu Asp Tyr Lys Glu Glu Asp Glu Ser Lys Cys
45              50                  55                  60

CGA TCA CGT GAA TGT AGT CGT CGT GTT TGT GTA TGC GAT GAA GGA TTC         241
Arg Ser Arg Glu Cys Ser Arg Arg Val Cys Val Cys Asp Glu Gly Phe
             65                  70                  75

TAC AGA AAC AAG AAG GGC CAA TGT GTG ACA AGA GAT GAT TGC GAG TAT         289
Tyr Arg Asn Lys Lys Gly Gln Cys Val Thr Arg Asp Asp Cys Glu Tyr
         80                  85                  90

GAC AAT ATG GAG ATT ATC ACT TTT CCA CCA GAA GAT AAA TGT GGT CCC         337
Asp Asn Met Glu Ile Ile Thr Phe Pro Pro Glu Asp Lys Cys Gly Pro
     95                  100                 105

GAT GAA TGG TTC GAC TGG TGT GGA ACT TAC AAG CAG TGT GAG CGC AAG         385
Asp Glu Trp Phe Asp Trp Cys Gly Thr Tyr Lys Gln Cys Glu Arg Lys
     110                 115                 120

TGC AAT AAG GAG CTA AGT GAG AAA GAT GAA GAG GCA TGC CTC TCA CGT         433
Cys Asn Lys Glu Leu Ser Glu Lys Asp Glu Glu Ala Cys Leu Ser Arg
125             130                 135                 140

GCT TGT ACT GGT CGT GCT TGT GTT TGC AAC GAC GGA CTG TAC AGA GAC         481
Ala Cys Thr Gly Arg Ala Cys Val Cys Asn Asp Gly Leu Tyr Arg Asp
             145                 150                 155

GAT TTT GGC AAT TGT GTT GAG AAA GAC GAA TGT AAC GAT ATG GAG ATT         529
Asp Phe Gly Asn Cys Val Glu Lys Asp Glu Cys Asn Asp Met Glu Ile
         160                 165                 170

ATC ACT TTT CCA CCG GAA ACC AAA CAC TGACCAAAGG CTCTAACTCT CGCTACAT      584
Ile Thr Phe Pro Pro Glu Thr Lys His
         175                 180

AACGTCAGTG CTTGAATTGC CCCTTTACGA GTTAGTAATT TTGACTAACT CTGTGTAATT       644

GAGCATTGTC TACTGATGGT GAAAATGAAG TGTTCAATGT CT                          686
```

( 2 ) INFORMATION FOR SEQ ID NO:37:

( i ) SEQUENCE CHARACTERISTICS:
        ( A ) LENGTH: 707 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Ancyclostoma caninum ( i x ) FEATURE:
        ( A ) NAME/KEY: Coding Sequence
        ( B ) LOCATION: 34...576

( x i ) SEQUENCE DESCRIPTION: SEQ ID NO:37:

```
GAATTCCGCG GAATTCCGGT TGGCGGCAGA AAA ATG CTG ATG CTC TAC CTT GTT       54
                                    Met Leu Met Leu Tyr Leu Val
                                     1           5

CCT ATC TGG TTC CTG CTC ATT TCG CAA TGC AGT GGA AAA TCC GCG AAG       102
Pro Ile Trp Phe Leu Leu Ile Ser Gln Cys Ser Gly Lys Ser Ala Lys
         10              15                      20

AAA TGT GGC CTC AAT GAA AAA TTG GAC TGT GGC AAT CTG AAG GCA TGC       150
Lys Cys Gly Leu Asn Glu Lys Leu Asp Cys Gly Asn Leu Lys Ala Cys
 25              30                      35

GAG AAA AAG TGC AGC GAC TTG GAC AAT GAG GAG GAT TAT GGG GAG GAA       198
Glu Lys Lys Cys Ser Asp Leu Asp Asn Glu Glu Asp Tyr Gly Glu Glu
 40              45                      50                      55

GAT GAG TCG AAA TGC CGA TCA CGT GAA TGT ATT GGT CGT GTT TGC GTA       246
Asp Glu Ser Lys Cys Arg Ser Arg Glu Cys Ile Gly Arg Val Cys Val
             60              65                      70

TGC GAT GAA GGA TTC TAC AGA AAC AAG AAG GGC CAA TGT GTG ACA AGA       294
Cys Asp Glu Gly Phe Tyr Arg Asn Lys Lys Gly Gln Cys Val Thr Arg
             75              80                      85

GAC GAT TGC GAG TAT GAC AAT ATG GAG ATT ATC ACT TTT CCA CCA GAA       342
Asp Asp Cys Glu Tyr Asp Asn Met Glu Ile Ile Thr Phe Pro Pro Glu
         90              95                     100

GAT AAA TGT GGT CCC GAT GAA TGG TTC GAC TGG TGT GGA ACT TAC AAG       390
Asp Lys Cys Gly Pro Asp Glu Trp Phe Asp Trp Cys Gly Thr Tyr Lys
105             110                     115

CAG TGT GAG CGC AAG TGC AGT GAG GAG CTA AGT GAG AAA AAT GAG GAG       438
Gln Cys Glu Arg Lys Cys Ser Glu Glu Leu Ser Glu Lys Asn Glu Glu
120             125                     130                     135

GCA TGC CTC TCA CGT GCT TGT ACT GGT CGT GCT TGC GTT TGC AAC GAC       486
Ala Cys Leu Ser Arg Ala Cys Thr Gly Arg Ala Cys Val Cys Asn Asp
            140             145                     150

GGA TTG TAT AGA GAC GAT TTT GGC AAT TGT GTT GAG AAA GAC GAA TGT       534
Gly Leu Tyr Arg Asp Asp Phe Gly Asn Cys Val Glu Lys Asp Glu Cys
            155             160                     165

AAC GAT ATG GAG ATT ATC ACT TTT CCA CCG GAA ACC AAA CAC TGACCAAAGG    586
Asn Asp Met Glu Ile Ile Thr Phe Pro Pro Glu Thr Lys His
            170             175                     180

CTCTAGCTCT CGCTACATAA CGTCAGTGCT TGAATTGTCC CTTTACGTGT TAGTAATTTT     646

GACTAACTCT GTGTATTTGA GCATTGTCTA CTAATGGTGA AAATGAAGCT TTTCAATGAC     706

T                                                                     707
```

( 2 ) INFORMATION FOR SEQ ID NO:38:

( i ) SEQUENCE CHARACTERISTICS:
        ( A ) LENGTH: 529 base pairs
        ( B ) TYPE: nucleic acid
        ( C ) STRANDEDNESS: single

```
        ( D ) TOPOLOGY: linear ( v i ) ORIGINAL SOURCE:
            ( A ) ORGANISM: Ancyclostoma caninum ( i x ) FEATURE:
            ( A ) NAME/KEY: Coding Sequence
            ( B ) LOCATION: 31...309

( x i ) SEQUENCE DESCRIPTION: SEQ ID NO:38:

GAATTCCGTA  CGACCTACTA  CTACTCAACG   ATG  AAG  GCG  CTC  TAT  GTT  ATC  TCT        54
                                     Met  Lys  Ala  Leu  Tyr  Val  Ile  Ser
                                      1                  5

ATA  ACG  TTG  CTC  CTG  GTA  TGG  CAA  TGC  AGT  GCA  AGA  ACA  GCG  AGG  AAA    102
Ile  Thr  Leu  Leu  Leu  Val  Trp  Gln  Cys  Ser  Ala  Arg  Thr  Ala  Arg  Lys
      10                  15                       20

CCC  CCA  ACG  TGT  GGT  GAA  AAT  GAA  AGG  GTC  GAA  TGG  TGT  GGC  AAG  CAG    150
Pro  Pro  Thr  Cys  Gly  Glu  Asn  Glu  Arg  Val  Glu  Trp  Cys  Gly  Lys  Gln
 25                       30                       35                       40

TGC  GAG  ATC  ACA  TGT  GAC  GAC  CCA  GAT  AAG  ATA  TGC  CGC  TCA  CTC  GCT    198
Cys  Glu  Ile  Thr  Cys  Asp  Asp  Pro  Asp  Lys  Ile  Cys  Arg  Ser  Leu  Ala
                45                       50                       55

TGT  CCT  GGT  CCT  CCT  GCT  TGC  GTA  TGC  GAC  GAC  GGA  TAC  TAC  AGA  GAC    246
Cys  Pro  Gly  Pro  Pro  Ala  Cys  Val  Cys  Asp  Asp  Gly  Tyr  Tyr  Arg  Asp
           60                       65                       70

ACG  AAC  GTT  GGC  TTG  TGT  GTA  CAA  TAT  GAC  GAA  TGC  AAC  GAT  ATG  GAT    294
Thr  Asn  Val  Gly  Leu  Cys  Val  Gln  Tyr  Asp  Glu  Cys  Asn  Asp  Met  Asp
      75                       80                       85

ATT  ATT  ATG  GTT  TCA  TAGGGTTGAC  TGAAGAATCG  AACAACCGGT  GCACAACTTC           349
Ile  Ile  Met  Val  Ser
      90

TATGCTTGAC  TATCTCTCTT  GCATCATGCA  AGTTTAGCTA  GATAGTGTAT  ATATTAGCAA            409

GACCCCTTGG  GGAGAATGAA  GCTTCCCAAC  TATATTAAAT  CAATAACGTT  TTCGCTTCAT            469

GTACACGTGC  TCAGCACATT  CATATCCACT  CCTCACACTC  CATGAAAGCA  GTGAAATGTT            529

( 2 ) INFORMATION FOR SEQ ID NO:39:

( i ) SEQUENCE CHARACTERISTICS:
                ( A ) LENGTH: 361 base pairs
                ( B ) TYPE: nucleic acid
                ( C ) STRANDEDNESS: single
                ( D ) TOPOLOGY: linear ( v i ) ORIGINAL SOURCE:
            ( A ) ORGANISM: Necator americanus ( i x ) FEATURE:
            ( A ) NAME/KEY: Coding Sequence
            ( B ) LOCATION: 16...252

( x i ) SEQUENCE DESCRIPTION: SEQ ID NO:39:

GCCAACTCTT  CGAAC  ATG  ATT  CGA  GGC  CTC  GTT  CTT  CTT  TCT  CTC  CTG  TTT     51
                  Met  Ile  Arg  Gly  Leu  Val  Leu  Leu  Ser  Leu  Leu  Phe
                   1                  5                            10

TGC  GTC  ACT  TTT  GCA  GCG  AAG  AGA  GAT  TGT  CCA  GCA  AAT  GAG  GAA  TGG    99
Cys  Val  Thr  Phe  Ala  Ala  Lys  Arg  Asp  Cys  Pro  Ala  Asn  Glu  Glu  Trp
                15                       20                       25

AGG  GAA  TGT  GGC  ACT  CCA  TGT  GAA  CCA  AAA  TGC  AAT  CAA  CCG  ATG  CCA    147
Arg  Glu  Cys  Gly  Thr  Pro  Cys  Glu  Pro  Lys  Cys  Asn  Gln  Pro  Met  Pro
      30                       35                       40

GAT  ATA  TGT  ACT  ATG  AAT  TGT  ATC  GTC  GAT  GTG  TGT  CAA  TGC  AAG  GAG    195
Asp  Ile  Cys  Thr  Met  Asn  Cys  Ile  Val  Asp  Val  Cys  Gln  Cys  Lys  Glu
 45                       50                       55                       60

GGA  TAC  AAG  CGT  CAT  GAA  ACG  AAG  GGA  TGC  TTA  AAG  GAA  GGA  TCA  GCT    243
```

```
Gly  Tyr  Lys  Arg  His  Glu  Thr  Lys  Gly  Cys  Leu  Lys  Glu  Gly  Ser  Ala
               65                       70                       75

GAT TGT AAA TAAGTTATCA GAACGCTCGT TTTGTCTTAC ATTAGATGGG TGAGCTGATG    302
Asp Cys Lys

TATCTGTCAG ATAAACTCTT TCTTCTAAAA AAAAAAAAAA AAAAAAAAAA AAAAAAAA      361
```

( 2 ) INFORMATION FOR SEQ ID NO:40:

( i ) SEQUENCE CHARACTERISTICS:
        ( A ) LENGTH: 77 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:40:

```
Lys  Ala  Tyr  Pro  Glu  Cys  Gly  Glu  Asn  Glu  Trp  Leu  Asp  Asp  Cys  Gly
 1                    5                       10                       15

Thr  Gln  Lys  Pro  Cys  Glu  Ala  Lys  Cys  Asn  Glu  Glu  Pro  Pro  Glu  Glu
               20                       25                       30

Glu  Asp  Pro  Ile  Cys  Arg  Ser  Arg  Gly  Cys  Leu  Leu  Pro  Pro  Ala  Cys
               35                       40                       45

Val  Cys  Lys  Asp  Gly  Phe  Tyr  Arg  Asp  Thr  Val  Ile  Gly  Asp  Cys  Val
      50                       55                       60

Arg  Glu  Glu  Glu  Cys  Asp  Gln  His  Glu  Ile  Ile  His  Val
 65                      70                       75
```

( 2 ) INFORMATION FOR SEQ ID NO:41:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:41:

```
Lys  Ala  Tyr  Pro  Glu  Cys  Gly  Glu  Asn  Glu  Trp  Leu  Asp  Val  Cys  Gly
 1                    5                       10                       15

Thr  Lys  Lys  Pro  Cys  Glu  Ala  Lys  Cys  Ser  Glu  Glu  Glu  Glu  Glu  Asp
               20                       25                       30

Pro  Ile  Cys  Arg  Ser  Phe  Ser  Cys  Pro  Gly  Pro  Ala  Ala  Cys  Val  Cys
               35                       40                       45

Glu  Asp  Gly  Phe  Tyr  Arg  Asp  Thr  Val  Ile  Gly  Asp  Cys  Val  Lys  Glu
      50                       55                       60

Glu  Glu  Cys  Asp  Gln  His  Glu  Ile  Ile  His  Val
 65                      70                       75
```

( 2 ) INFORMATION FOR SEQ ID NO:42:

( i ) SEQUENCE CHARACTERISTICS:
        ( A ) LENGTH: 74 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:42:

| Arg | Thr | Ala | Arg | Lys | Pro | Pro | Thr | Cys | Gly | Glu | Asn | Glu | Arg | Val | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Trp | Cys | Gly | Lys | Gln | Cys | Glu | Ile | Thr | Cys | Asp | Asp | Pro | Asp | Lys | Ile |
|     |     |     |     | 20  |     |     |     | 25  |     |     |     |     | 30  |     |     |

| Cys | Arg | Ser | Leu | Ala | Cys | Pro | Gly | Pro | Pro | Ala | Cys | Val | Cys | Asp | Asp |
|     |     | 35  |     |     |     |     | 40  |     |     |     |     | 45  |     |     |     |

| Gly | Tyr | Tyr | Arg | Asp | Thr | Asn | Val | Gly | Leu | Cys | Val | Gln | Tyr | Asp | Glu |
|     | 50  |     |     |     |     | 55  |     |     |     |     | 60  |     |     |     |     |

| Cys | Asn | Asp | Met | Asp | Ile | Ile | Met | Val | Ser |
| 65  |     |     |     |     | 70  |     |     |     |     |

( 2 ) INFORMATION FOR SEQ ID NO:43:

( i ) SEQUENCE CHARACTERISTICS:
        ( A ) LENGTH: 88 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:43:

| Lys | Pro | Ser | Glu | Lys | Glu | Cys | Gly | Pro | His | Glu | Arg | Leu | Asp | Cys | Gly |
| 1   |     |     |     | 5   |     |     |     |     | 10  |     |     |     |     | 15  |     |

| Asn | Lys | Lys | Pro | Cys | Glu | Arg | Lys | Cys | Lys | Ile | Glu | Thr | Ser | Glu | Glu |
|     |     |     |     | 20  |     |     |     | 25  |     |     |     |     | 30  |     |     |

| Glu | Asp | Asp | Tyr | Glu | Glu | Gly | Thr | Glu | Arg | Phe | Arg | Cys | Leu | Leu | Arg |
|     |     |     | 35  |     |     |     |     | 40  |     |     |     |     | 45  |     |     |

| Val | Cys | Asp | Gln | Pro | Tyr | Glu | Cys | Ile | Cys | Asp | Asp | Gly | Tyr | Tyr | Arg |
|     |     | 50  |     |     |     |     | 55  |     |     |     |     | 60  |     |     |     |

| Asn | Lys | Lys | Gly | Glu | Cys | Val | Thr | Asp | Asp | Val | Cys | Gln | Glu | Asp | Phe |
| 65  |     |     |     |     |     | 70  |     |     |     |     | 75  |     |     |     | 80  |

| Met | Glu | Phe | Ile | Thr | Phe | Ala | Pro |
|     |     |     |     | 85  |     |     |     |

( 2 ) INFORMATION FOR SEQ ID NO:44:

( i ) SEQUENCE CHARACTERISTICS:
        ( A ) LENGTH: 87 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:44:

| Arg | Pro | Glu | Lys | Lys | Cys | Gly | Pro | Gly | Glu | Arg | Leu | Ala | Cys | Gly | Asn |
| 1   |     |     |     | 5   |     |     |     |     | 10  |     |     |     |     | 15  |     |

| Lys | Lys | Pro | Cys | Glu | Arg | Lys | Cys | Lys | Ile | Glu | Thr | Ser | Glu | Glu | Glu |
|     |     |     | 20  |     |     |     | 25  |     |     |     |     | 30  |     |     |     |

| Asp | Asp | Tyr | Pro | Glu | Gly | Thr | Glu | Arg | Phe | Arg | Cys | Leu | Leu | Arg | Val |
|     |     | 35  |     |     |     |     | 40  |     |     |     |     | 45  |     |     |     |

| Cys | Asp | Gln | Pro | Tyr | Glu | Cys | Ile | Cys | Asp | Asp | Gly | Tyr | Tyr | Arg | Asn |
|     | 50  |     |     |     |     | 55  |     |     |     |     | 60  |     |     |     |     |

| Lys | Lys | Gly | Glu | Cys | Val | Thr | Asp | Asp | Val | Cys | Gln | Glu | Asp | Phe | Met |
| 65  |     |     |     |     | 70  |     |     |     |     | 75  |     |     |     |     | 80  |

Glu Phe Ile Thr Phe Ala Pro
                    85

( 2 ) INFORMATION FOR SEQ ID NO:45:

( i ) SEQUENCE CHARACTERISTICS:
        ( A ) LENGTH: 86 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:45:

Arg Pro Glu Lys Lys Cys Gly Pro Gly Glu Arg Leu Asp Cys Ala Asn
1               5                   10                  15

Lys Lys Pro Cys Glu Pro Lys Cys Lys Ile Glu Thr Ser Glu Glu Glu
            20              25                  30

Asp Asp Asp Val Glu Asp Thr Asp Val Arg Cys Leu Val Arg Val Cys
            35              40                  45

Glu Arg Pro Leu Lys Cys Ile Cys Lys Asp Gly Tyr Tyr Arg Asn Lys
    50              55                  60

Lys Gly Glu Cys Val Thr Asp Asp Val Cys Gln Glu Asp Phe Met Glu
65                  70              75                      80

Phe Ile Thr Phe Ala Pro
                85

( 2 ) INFORMATION FOR SEQ ID NO:46:

( i ) SEQUENCE CHARACTERISTICS:
        ( A ) LENGTH: 86 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:46:

Arg Pro Glu Lys Lys Cys Gly Pro Gly Glu Arg Leu Asp Cys Ala Asn
1               5                   10                  15

Lys Lys Pro Cys Glu Pro Lys Cys Lys Ile Glu Thr Ser Glu Glu Glu
            20              25                  30

Asp Asp Asp Val Glu Glu Thr Asp Val Arg Cys Leu Val Arg Val Cys
            35              40                  45

Glu Arg Pro Leu Lys Cys Ile Cys Lys Asp Gly Tyr Tyr Arg Asn Lys
    50              55                  60

Lys Gly Glu Cys Val Thr Asp Asp Val Cys Gln Glu Asp Phe Met Glu
65                  70              75                      80

Phe Ile Thr Phe Ala Pro
                85

( 2 ) INFORMATION FOR SEQ ID NO:47:

( i ) SEQUENCE CHARACTERISTICS:
        ( A ) LENGTH: 78 amino acids
        ( B ) TYPE: amino acid
        ( D ) TOPOLOGY: linear ( i i ) MOLECULE TYPE: peptide (v i) ORIGINAL SOURCE:
    (A) ORGANISM: Ancyclostoma caninum (x i) SEQUENCE DESCRIPTION: SEQ ID NO:47:

| Lys | Ser | Leu | Trp | Asp | Gln | Lys | Cys | Gly | Glu | Asn | Glu | Arg | Leu | Asp | Cys |
| 1 | | | | 5 | | | | | 10 | | | | | 15 | |

| Gly | Asn | Gln | Lys | Asp | Cys | Glu | Arg | Lys | Cys | Asp | Asp | Lys | Arg | Ser | Glu |
| | | | 20 | | | | 25 | | | | | 30 | | | |

| Glu | Glu | Ile | Met | Gln | Ala | Cys | Leu | Thr | Arg | Gln | Cys | Leu | Pro | Pro | Val |
| | | 35 | | | | | 40 | | | | | 45 | | | |

| Cys | Val | Cys | Glu | Asp | Gly | Phe | Tyr | Arg | Asn | Asp | Asn | Asp | Gln | Cys | Val |
| | 50 | | | | | 55 | | | | | 60 | | | | |

| Asp | Glu | Glu | Glu | Cys | Asn | Met | Glu | Phe | Ile | Thr | Phe | Ala | Pro |
| 65 | | | | | 70 | | | | | 75 | | | |

(2) INFORMATION FOR SEQ ID NO:48:

(i) SEQUENCE CHARACTERISTICS:
    (A) LENGTH: 89 amino acids
    (B) TYPE: amino acid
    (D) TOPOLOGY: linear (i i) MOLECULE TYPE: peptide (v i) ORIGINAL SOURCE:
    (A) ORGANISM: Ancyclostoma ceylanicum (x i) SEQUENCE DESCRIPTION: SEQ ID NO:48:

| Lys | Pro | Asn | Asn | Val | Met | Thr | Asn | Ala | Cys | Gly | Leu | Asn | Glu | Tyr | Phe |
| 1 | | | | 5 | | | | | 10 | | | | | 15 | |

| Ala | Glu | Cys | Gly | Asn | Met | Lys | Glu | Cys | Glu | His | Arg | Cys | Asn | Glu | Glu |
| | | | 20 | | | | 25 | | | | | 30 | | | |

| Glu | Asn | Glu | Glu | Arg | Asp | Glu | Glu | Arg | Ile | Thr | Ala | Cys | Leu | Ile | Arg |
| | | 35 | | | | | 40 | | | | | 45 | | | |

| Val | Cys | Phe | Arg | Pro | Gly | Ala | Cys | Val | Cys | Lys | Asp | Gly | Phe | Tyr | Arg |
| | 50 | | | | | 55 | | | | | 60 | | | | |

| Asn | Arg | Thr | Gly | Ser | Cys | Val | Glu | Glu | Asp | Asp | Cys | Glu | Tyr | Glu | Asn |
| 65 | | | | | 70 | | | | | 75 | | | | | 80 |

| Met | Glu | Phe | Ile | Thr | Phe | Ala | Pro | Glu |
| | | | | 85 | | | | |

(2) INFORMATION FOR SEQ ID NO:49:

(i) SEQUENCE CHARACTERISTICS:
    (A) LENGTH: 82 amino acids
    (B) TYPE: amino acid
    (D) TOPOLOGY: linear (i i) MOLECULE TYPE: peptide (v i) ORIGINAL SOURCE:
    (A) ORGANISM: Ancyclostoma ceylanicum (x i) SEQUENCE DESCRIPTION: SEQ ID NO:49:

| Val | Pro | Ile | Cys | Gly | Ser | Asn | Glu | Arg | Tyr | Ser | Asp | Cys | Gly | Asn | Asp |
| 1 | | | | 5 | | | | | 10 | | | | | 15 | |

| Lys | Gln | Cys | Glu | Arg | Lys | Cys | Asn | Glu | Asp | Asp | Tyr | Glu | Lys | Gly | Asp |
| | | | 20 | | | | 25 | | | | | 30 | | | |

| Glu | Ala | Cys | Arg | Ser | His | Val | Cys | Glu | Arg | Pro | Gly | Ala | Cys | Val | Cys |
| | | 35 | | | | | 40 | | | | | 45 | | | |

| Glu | Asp | Gly | Phe | Tyr | Arg | Asn | Lys | Lys | Gly | Ser | Cys | Val | Glu | Ser | Asp |
| | 50 | | | | | 55 | | | | | 60 | | | | |

Asp Cys Glu Tyr Asp Asn Met Asp Phe Ile Thr Phe Ala Pro Glu Thr
65                  70                  75                  80

Ser Arg ( 2 ) INFORMATION FOR SEQ ID NO:50:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:50:

Lys Ser Ala Lys Lys Cys Gly Leu Asn Glu Lys Leu Asp Cys Gly Asn
1               5                   10                  15

Leu Lys Ala Cys Glu Lys Lys Cys Ser Asp Leu Asp Asn Glu Glu Asp
            20                  25                  30

Tyr Lys Glu Glu Asp Glu Ser Lys Cys Arg Ser Arg Glu Cys Ser Arg
            35                  40                  45

Arg Val Cys Val Cys Asp Glu Gly Phe Tyr Arg Asn Lys Lys Gly Gln
            50                  55                  60

Cys Val Thr Arg Asp Asp Cys Glu Tyr Asp Asn Met Glu Ile Ile Thr
65                  70                  75                  80

Phe Pro Pro Glu ( 2 ) INFORMATION FOR SEQ ID NO:51:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:51:

Lys Ser Ala Lys Lys Cys Gly Leu Asn Glu Lys Leu Asp Cys Gly Asn
1               5                   10                  15

Leu Lys Ala Cys Glu Lys Lys Cys Ser Asp Leu Asp Asn Glu Glu Asp
            20                  25                  30

Tyr Gly Glu Glu Asp Glu Ser Lys Cys Arg Ser Arg Glu Cys Ile Gly
            35                  40                  45

Arg Val Cys Val Cys Asp Glu Gly Phe Tyr Arg Asn Lys Lys Gly Gln
            50                  55                  60

Cys Val Thr Arg Asp Asp Cys Glu Tyr Asp Asn Met Glu Ile Ile Thr
65                  70                  75                  80

Phe Pro Pro Glu ( 2 ) INFORMATION FOR SEQ ID NO:52:

( i ) SEQUENCE CHARACTERISTICS:
        ( A ) LENGTH: 83 amino acids
        ( B ) TYPE: amino acid
        ( D ) TOPOLOGY: linear ( i i ) MOLECULE TYPE: peptide ( v i ) ORIGINAL SOURCE:

(A) ORGANISM: Ancyclostoma duodenale (xi) SEQUENCE DESCRIPTION: SEQ ID NO:52:

```
Lys Ala Ala Lys Lys Cys Gly Leu Asn Glu Arg Leu Asp Cys Gly Asn
 1               5                  10                  15
Leu Lys Gln Cys Glu Pro Lys Cys Ser Asp Leu Glu Ser Glu Glu Tyr
                20                  25                  30
Glu Glu Glu Asp Glu Ser Lys Cys Arg Ser Arg Glu Cys Ser Arg Arg
            35                  40                  45
Val Cys Val Cys Asp Glu Gly Phe Tyr Arg Asn Lys Lys Gly Lys Cys
        50                  55                  60
Val Ala Lys Asp Val Cys Glu Asp Asp Asn Met Glu Ile Ile Thr Phe
 65                 70                  75                  80
Pro Pro Glu
```

(2) INFORMATION FOR SEQ ID NO:53:

(i) SEQUENCE CHARACTERISTICS:
        (A) LENGTH: 78 amino acids
        (B) TYPE: amino acid
        (D) TOPOLOGY: linear (ii) MOLECULE TYPE: peptide (vi) ORIGINAL SOURCE:
        (A) ORGANISM: Ancyclostoma caninum (xi) SEQUENCE DESCRIPTION: SEQ ID NO:53:

```
Asp Lys Cys Gly Pro Asp Glu Trp Phe Asp Trp Cys Gly Thr Tyr Lys
 1               5                  10                  15
Gln Cys Glu Arg Lys Cys Asn Lys Glu Leu Ser Glu Lys Asp Glu Glu
                20                  25                  30
Ala Cys Leu Ser Arg Ala Cys Thr Gly Arg Ala Cys Val Cys Asn Asp
            35                  40                  45
Gly Leu Tyr Arg Asp Asp Phe Gly Asn Cys Val Glu Lys Asp Glu Cys
        50                  55                  60
Asn Asp Met Glu Ile Ile Thr Phe Pro Pro Glu Thr Lys His
 65                 70                  75
```

(2) INFORMATION FOR SEQ ID NO:54:

(i) SEQUENCE CHARACTERISTICS:
        (A) LENGTH: 78 amino acids
        (B) TYPE: amino acid
        (D) TOPOLOGY: linear (ii) MOLECULE TYPE: peptide (vi) ORIGINAL SOURCE:
        (A) ORGANISM: Ancyclostoma caninum (xi) SEQUENCE DESCRIPTION: SEQ ID NO:54:

```
Asp Lys Cys Gly Pro Asp Glu Trp Phe Asp Trp Cys Gly Thr Tyr Lys
 1               5                  10                  15
Gln Cys Glu Arg Lys Cys Ser Glu Glu Leu Ser Glu Lys Asn Glu Glu
                20                  25                  30
Ala Cys Leu Ser Arg Ala Cys Thr Gly Arg Ala Cys Val Cys Asn Asp
            35                  40                  45
Gly Leu Tyr Arg Asp Asp Phe Gly Asn Cys Val Glu Lys Asp Glu Cys
        50                  55                  60
Asn Asp Met Glu Ile Ile Thr Phe Pro Pro Glu Thr Lys His
 65                 70                  75
```

( 2 ) INFORMATION FOR SEQ ID NO:55:

( i ) SEQUENCE CHARACTERISTICS:
        ( A ) LENGTH: 77 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma duodenale ( x i ) SEQUENCE DESCRIPTION: SEQ ID NO:55:

```
Lys Cys Pro Thr Asp Glu Trp Phe Asp Trp Cys Gly Thr Tyr Lys His
 1               5                  10                  15
Cys Glu Leu Lys Cys Asp Arg Glu Leu Thr Glu Lys Glu Glu Gln Ala
            20                  25                  30
Cys Leu Ser Arg Val Cys Glu Lys Ser Ala Cys Val Cys Asn Asp Gly
        35                  40                  45
Leu Tyr Arg Asp Lys Phe Gly Asn Cys Val Glu Lys Asp Glu Cys Asn
    50                  55                  60
Asp Met Glu Ile Ile Thr Phe Ala Pro Glu Glu Thr Lys
65                  70                  75
```

( 2 ) INFORMATION FOR SEQ ID NO:56:

( i ) SEQUENCE CHARACTERISTICS:
        ( A ) LENGTH: 78 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma duodenale ( x i ) SEQUENCE DESCRIPTION: SEQ ID NO:56:

```
Asp Glu Cys Gly Pro Asp Glu Trp Phe Asp Tyr Cys Gly Asn Tyr Lys
 1               5                  10                  15
Lys Cys Glu Arg Lys Cys Ser Glu Glu Thr Ser Glu Lys Asn Glu Glu
            20                  25                  30
Ala Cys Leu Ser Arg Ala Cys Thr Gly Arg Ala Cys Val Cys Lys Asp
        35                  40                  45
Gly Leu Tyr Arg Asp Asp Phe Gly Asn Cys Val Pro His Asp Glu Cys
    50                  55                  60
Asn Asp Met Glu Ile Ile Thr Phe Pro Pro Glu Thr Lys His
65                  70                  75
```

( 2 ) INFORMATION FOR SEQ ID NO:57:

( i ) SEQUENCE CHARACTERISTICS:
        ( A ) LENGTH: 75 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma ceylanicum ( x i ) SEQUENCE DESCRIPTION: SEQ ID NO:57:

```
Lys Ala Phe Pro Lys Cys Asp Val Asn Glu Arg Phe Glu Val Cys Gly
 1               5                  10                  15
Asn Leu Lys Glu Cys Glu Leu Lys Cys Asp Glu Asp Pro Lys Ile Cys
```

|  | 20 | 25 | 30 |
|---|---|---|---|

Ser Arg Ala Cys Ile Arg Pro Pro Ala Cys Val Cys Asp Asp Gly Phe
         35                        40                            45

Tyr Arg Asp Lys Tyr Gly Phe Cys Val Glu Glu Asp Glu Cys Asn Asp
    50                         55                         60

Met Glu Ile Ile Thr Phe Pro Pro Glu Thr Lys
65                     70                     75

(2) INFORMATION FOR SEQ ID NO:58:

(i) SEQUENCE CHARACTERISTICS:
        (A) LENGTH: 77 amino acids
        (B) TYPE: amino acid
        (D) TOPOLOGY: linear (ii) MOLECULE TYPE: peptide (vi) ORIGINAL SOURCE:
        (A) ORGANISM: Ancyclostoma ceylanicum (xi) SEQUENCE DESCRIPTION: SEQ ID NO:58:

Arg Thr Val Lys Lys Cys Gly Lys Asn Glu Arg Tyr Asp Asp Cys Gly
1                   5                    10                      15

Asn Ala Lys Asp Cys Glu Thr Lys Cys Gly Glu Glu Glu Lys Val Cys
          20                       25                     30

Arg Ser Arg Glu Cys Thr Ser Pro Gly Ala Cys Val Cys Glu Gln Gly
        35                       40                        45

Phe Tyr Arg Asp Pro Ala Gly Asp Cys Val Thr Asp Glu Glu Cys Asp
    50                         55                      60

Glu Trp Asn Asn Met Glu Ile Ile Thr Met Pro Lys Gln
65                     70                     75

(2) INFORMATION FOR SEQ ID NO:59:

(i) SEQUENCE CHARACTERISTICS:
        (A) LENGTH: 84 amino acids
        (B) TYPE: amino acid
        (D) TOPOLOGY: linear (ii) MOLECULE TYPE: peptide (vi) ORIGINAL SOURCE:
        (A) ORGANISM: Ancyclostoma caninum (xi) SEQUENCE DESCRIPTION: SEQ ID NO:59:

Lys Ala Thr Met Gln Cys Gly Glu Asn Glu Lys Tyr Asp Ser Cys Gly
1                   5                    10                      15

Ser Lys Glu Cys Asp Lys Lys Cys Lys Tyr Asp Gly Val Glu Glu Glu
          20                       25                     30

Asp Asp Glu Glu Pro Asn Val Pro Cys Leu Val Arg Val Cys His Gln
        35                       40                        45

Asp Cys Val Cys Glu Glu Gly Phe Tyr Arg Asn Lys Asp Asp Lys Cys
    50                         55                      60

Val Ser Ala Glu Asp Cys Glu Leu Asp Asn Met Asp Phe Ile Tyr Pro
65                     70                     75                     80

Gly Thr Arg Asn (2) INFORMATION FOR SEQ ID NO:60:

(i) SEQUENCE CHARACTERISTICS:
        (A) LENGTH: 58 amino acids
        (B) TYPE: amino acid
        (D) TOPOLOGY: linear (  i i  ) MOLECULE TYPE: peptide (  v i  ) ORIGINAL SOURCE:
    ( A ) ORGANISM: Heligmosomoides polygyrus (  x i  ) SEQUENCE DESCRIPTION: SEQ ID NO:60:

```
Lys Thr Cys Gly Pro Asn Glu Glu Tyr Thr Glu Cys Gly Thr Pro Cys
 1               5                  10                  15
Glu Pro Lys Cys Asn Glu Pro Met Pro Asp Ile Cys Thr Leu Asn Cys
            20                  25                  30
Ile Val Asn Val Cys Gln Cys Lys Pro Gly Phe Lys Arg Gly Pro Lys
        35                  40                  45
Gly Cys Val Ala Pro Gly Pro Gly Cys Lys
 50                  55
```

( 2 ) INFORMATION FOR SEQ ID NO:61:

( i ) SEQUENCE CHARACTERISTICS:
    ( A ) LENGTH: 61 amino acids
    ( B ) TYPE: amino acid
    ( D ) TOPOLOGY: linear (  i i  ) MOLECULE TYPE: peptide (  v i  ) ORIGINAL SOURCE:
    ( A ) ORGANISM: Necator americanus (  x i  ) SEQUENCE DESCRIPTION: SEQ ID NO:61:

```
Lys Arg Asp Cys Pro Ala Asn Glu Glu Trp Arg Glu Cys Gly Thr Pro
 1               5                  10                  15
Cys Glu Pro Lys Cys Asn Gln Pro Met Pro Asp Ile Cys Thr Met Asn
            20                  25                  30
Cys Ile Val Asp Val Cys Gln Cys Lys Glu Gly Tyr Lys Arg His Glu
        35                  40                  45
Thr Lys Gly Cys Leu Lys Glu Gly Ser Ala Asp Cys Lys
 50                  55                  60
```

( 2 ) INFORMATION FOR SEQ ID NO:62:

( i ) SEQUENCE CHARACTERISTICS:
    ( A ) LENGTH: 171 amino acids
    ( B ) TYPE: amino acid
    ( D ) TOPOLOGY: linear (  i i  ) MOLECULE TYPE: peptide (  v i  ) ORIGINAL SOURCE:
    ( A ) ORGANISM: Ancyclostoma ceylanicum (  x i  ) SEQUENCE DESCRIPTION: SEQ ID NO:62:

```
Lys Pro Asn Asn Val Met Thr Asn Ala Cys Gly Leu Asn Glu Tyr Phe
 1               5                  10                  15
Ala Glu Cys Gly Asn Met Lys Glu Cys Glu His Arg Cys Asn Glu Glu
            20                  25                  30
Glu Asn Glu Glu Arg Asp Glu Glu Arg Ile Thr Ala Cys Leu Ile Arg
        35                  40                  45
Val Cys Phe Arg Pro Gly Ala Cys Val Cys Lys Asp Gly Phe Tyr Arg
     50                  55                  60
Asn Arg Thr Gly Ser Cys Val Glu Glu Asp Asp Cys Glu Tyr Glu Asn
 65                  70                  75              80
Met Glu Phe Ile Thr Phe Ala Pro Glu Val Pro Ile Cys Gly Ser Asn
                85                  90                  95
```

| Glu | Arg | Tyr | Ser<br>100 | Asp | Cys | Gly | Asn | Asp<br>105 | Lys | Gln | Cys | Glu | Arg<br>110 | Lys | Cys |
| --- | --- | --- | --- | --- | --- | --- | --- | --- | --- | --- | --- | --- | --- | --- | --- |
| Asn | Glu | Asp<br>115 | Asp | Tyr | Glu | Lys | Gly<br>120 | Asp | Glu | Ala | Cys | Arg<br>125 | Ser | His | Val |
| Cys | Glu<br>130 | Arg | Pro | Gly | Ala | Cys<br>135 | Val | Cys | Glu | Asp | Gly<br>140 | Phe | Tyr | Arg | Asn |
| Lys<br>145 | Lys | Gly | Ser | Cys | Val<br>150 | Glu | Ser | Asp | Asp<br>155 | Cys | Glu | Tyr | Asp | Asn | Met<br>160 |
| Asp | Phe | Ile | Thr | Phe<br>165 | Ala | Pro | Glu | Thr | Ser<br>170 | Arg | | | | | |

( 2 ) INFORMATION FOR SEQ ID NO:63:

( i ) SEQUENCE CHARACTERISTICS:
        ( A ) LENGTH: 162 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:63:

| Lys<br>1 | Ser | Ala | Lys | Lys<br>5 | Cys | Gly | Leu | Asn | Glu<br>10 | Lys | Leu | Asp | Cys | Gly<br>15 | Asn |
| --- | --- | --- | --- | --- | --- | --- | --- | --- | --- | --- | --- | --- | --- | --- | --- |
| Leu | Lys | Ala | Cys<br>20 | Glu | Lys | Lys | Cys | Ser<br>25 | Asp | Leu | Asp | Asn | Glu<br>30 | Glu | Asp |
| Tyr | Lys | Glu<br>35 | Glu | Asp | Glu | Ser | Lys<br>40 | Cys | Arg | Ser | Arg | Glu<br>45 | Cys | Ser | Arg |
| Arg | Val<br>50 | Cys | Val | Cys | Asp | Glu<br>55 | Gly | Phe | Tyr | Arg | Asn<br>60 | Lys | Lys | Gly | Gln |
| Cys<br>65 | Val | Thr | Arg | Asp | Asp<br>70 | Cys | Glu | Tyr | Asp | Asn<br>75 | Met | Glu | Ile | Ile | Thr<br>80 |
| Phe | Pro | Pro | Glu | Asp<br>85 | Lys | Cys | Gly | Pro | Asp<br>90 | Glu | Trp | Phe | Asp | Trp<br>95 | Cys |
| Gly | Thr | Tyr | Lys<br>100 | Gln | Cys | Glu | Arg | Lys<br>105 | Cys | Asn | Lys | Glu | Leu<br>110 | Ser | Glu |
| Lys | Asp | Glu<br>115 | Glu | Ala | Cys | Leu | Ser<br>120 | Arg | Ala | Cys | Thr | Gly<br>125 | Arg | Ala | Cys |
| Val | Cys<br>130 | Asn | Asp | Gly | Leu | Tyr<br>135 | Arg | Asp | Asp | Phe | Gly<br>140 | Asn | Cys | Val | Glu |
| Lys<br>145 | Asp | Glu | Cys | Asn | Asp<br>150 | Met | Glu | Ile | Ile | Thr<br>155 | Phe | Pro | Pro | Glu | Thr<br>160 |
| Lys | His | | | | | | | | | | | | | | |

( 2 ) INFORMATION FOR SEQ ID NO:64:

( i ) SEQUENCE CHARACTERISTICS:
        ( A ) LENGTH: 162 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Ancyclostoma caninum ( x i ) SEQUENCE DESCRIPTION: SEQ ID NO:64:

| Lys<br>1 | Ser | Ala | Lys | Lys<br>5 | Cys | Gly | Leu | Asn | Glu<br>10 | Lys | Leu | Asp | Cys | Gly<br>15 | Asn |
| --- | --- | --- | --- | --- | --- | --- | --- | --- | --- | --- | --- | --- | --- | --- | --- |

Leu Lys Ala Cys Glu Lys Lys Cys Ser Asp Leu Asp Asn Glu Glu Asp
        20              25              30

Tyr Gly Glu Glu Asp Glu Ser Lys Cys Arg Ser Arg Glu Cys Ile Gly
            35              40              45

Arg Val Cys Val Cys Asp Gly Phe Tyr Arg Asn Lys Lys Gly Gln
    50              55              60

Cys Val Thr Arg Asp Asp Cys Glu Tyr Asp Asn Met Glu Ile Ile Thr
65              70              75              80

Phe Pro Pro Glu Asp Lys Cys Gly Pro Asp Glu Trp Phe Asp Trp Cys
                85              90              95

Gly Thr Tyr Lys Gln Cys Glu Arg Lys Cys Ser Glu Glu Leu Ser Glu
            100             105             110

Lys Asn Glu Glu Ala Cys Leu Ser Arg Ala Cys Thr Gly Arg Ala Cys
        115             120             125

Val Cys Asn Asp Gly Leu Tyr Arg Asp Asp Phe Gly Asn Cys Val Glu
    130             135             140

Lys Asp Glu Cys Asn Asp Met Glu Ile Ile Thr Phe Pro Pro Glu Thr
145             150             155             160

Lys His (2) INFORMATION FOR SEQ ID NO:65:

(i) SEQUENCE CHARACTERISTICS:
    (A) LENGTH: 161 amino acids
    (B) TYPE: amino acid
    (D) TOPOLOGY: linear (ii) MOLECULE TYPE: peptide (vi) ORIGINAL SOURCE:
    (A) ORGANISM: Ancyclostoma duodenale (xi) SEQUENCE DESCRIPTION: SEQ ID NO:65:

Lys Ala Ala Lys Lys Cys Gly Leu Asn Glu Arg Leu Asp Cys Gly Asn
1               5               10              15

Leu Lys Gln Cys Glu Pro Lys Cys Ser Asp Leu Glu Ser Glu Glu Tyr
        20              25              30

Glu Glu Glu Asp Glu Ser Lys Cys Arg Ser Arg Glu Cys Ser Arg Arg
            35              40              45

Val Cys Val Cys Asp Glu Gly Phe Tyr Arg Asn Lys Lys Gly Lys Cys
    50              55              60

Val Ala Lys Asp Val Cys Glu Asp Asn Met Glu Ile Ile Thr Phe
65              70              75              80

Pro Pro Glu Asp Glu Cys Gly Pro Asp Glu Trp Phe Asp Tyr Cys Gly
            85              90              95

Asn Tyr Lys Lys Cys Glu Arg Lys Cys Ser Glu Glu Thr Ser Glu Lys
        100             105             110

Asn Glu Glu Ala Cys Leu Ser Arg Ala Cys Thr Gly Arg Ala Cys Val
        115             120             125

Cys Lys Asp Gly Leu Tyr Arg Asp Asp Phe Gly Asn Cys Val Pro His
    130             135             140

Asp Glu Cys Asn Asp Met Glu Ile Ile Thr Phe Pro Pro Glu Thr Lys
145             150             155             160

His (2) INFORMATION FOR SEQ ID NO:66:

(i) SEQUENCE CHARACTERISTICS:

(A) LENGTH: 9 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 9
is an amino acid.

(xi) SEQUENCE DESCRIPTION: SEQ ID NO: 66:

Cys Xaa Xaa Xaa Xaa Xaa Xaa Xaa Xaa
1               5

(2) INFORMATION FOR SEQ ID NO: 67:

(i) SEQUENCE CHARACTERISTICS:
(A) LENGTH: 9 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 9 is
an amino acid.

(xi) SEQUENCE DESCRIPTION: SEQ ID NO: 67:

Cys Xaa Xaa Xaa Xaa Xaa Xaa Xaa Xaa
1               5

(2) INFORMATION FOR SEQ ID NO:68:

(i) SEQUENCE CHARACTERISTICS:
(A) LENGTH: 7 amino acids
(B) TYPE: amino acid
(D) TOPOLOGY: linear (ii) MOLECULE TYPE: peptide (v) FRAGMENT TYPE: internal fragment (ix) FEATURE:
(D) OTHER INFORMATION: Xaa at locations 1 and 2 is an amino
acid, provided that at least one of Xaa
at locations 1 and 2 is Glu or Asp, Xaa
in locations 3 to 8 is an amino acid.

(xi) SEQUENCE DESCRIPTION: SEQ ID NO:68:

Xaa Xaa Xaa Xaa Xaa Xaa Xaa
1               5

(2) INFORMATION FOR SEQ ID NO:69:

(i) SEQUENCE CHARACTERISTICS:
(A) LENGTH: 5 amino acids
(B) TYPE: amino acid
(D) TOPOLOGY: linear (ii) MOLECULE TYPE: peptide (v) FRAGMENT TYPE: internal fragment (xi) SEQUENCE DESCRIPTION: SEQ ID NO:69:

Gly Phe Tyr Arg Asp
1               5

(2) INFORMATION FOR SEQ ID NO:70:

(i) SEQUENCE CHARACTERISTICS:
(A) LENGTH: 5 amino acids
(B) TYPE: amino acid ( D ) TOPOLOGY: linear ( i i ) MOLECULE TYPE: peptide ( v ) FRAGMENT TYPE: internal fragment ( x i ) SEQUENCE DESCRIPTION: SEQ ID NO:70:

```
Gly  Phe  Tyr  Arg  Asn
 1                    5
```

( 2 ) INFORMATION FOR SEQ ID NO:71:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal fragment ( x i ) SEQUENCE DESCRIPTION: SEQ ID NO:71:

```
Gly  Tyr  Tyr  Arg  Asp
 1                    5
```

( 2 ) INFORMATION FOR SEQ ID NO:72:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal fragment ( x i ) SEQUENCE DESCRIPTION: SEQ ID NO:72:

```
Gly  Tyr  Tyr  Arg  Asn
 1                    5
```

( 2 ) INFORMATION FOR SEQ ID NO:73:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal fragment ( x i ) SEQUENCE DESCRIPTION: SEQ ID NO:73:

```
Gly  Leu  Tyr  Arg  Asp
 1                    5
```

( 2 ) INFORMATION FOR SEQ ID NO:74:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal fragment ( x i ) SEQUENCE DESCRIPTION: SEQ ID NO:74:

```
Glu  Ile  Ile  His  Val
 1                    5
```

( 2 ) INFORMATION FOR SEQ ID NO:75:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal fragment ( x i ) SEQUENCE DESCRIPTION: SEQ ID NO:75:

Asp Ile Ile Met Val
1               5

( 2 ) INFORMATION FOR SEQ ID NO:76:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal fragment ( x i ) SEQUENCE DESCRIPTION: SEQ ID NO:76:

Phe Ile Thr Phe Ala Pro
1               5

( 2 ) INFORMATION FOR SEQ ID NO:77:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal fragment ( x i ) SEQUENCE DESCRIPTION: SEQ ID NO:77:

Met Glu Ile Ile Thr
1               5

( 2 ) INFORMATION FOR SEQ ID NO:78:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal fragment ( i x ) FEATURE:
        ( D ) OTHER INFORMATION: Xaa in locations 1 and 2 is
        an amino acid, provided that at
        least one Xaa is Glu or Asp.

( x i ) SEQUENCE DESCRIPTION: SEQ ID NO:78:

Xaa Xaa Gly Phe Tyr Arg Asp
1               5

( 2 ) INFORMATION FOR SEQ ID NO:79:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal fragment ( i x ) FEATURE:
( D ) OTHER INFORMATION: Xaa in locations 1 and 2
is an amino acid, provided
that at least one Xaa is Glu or
Asp.

( x i ) SEQUENCE DESCRIPTION: SEQ ID NO:79:

Xaa  Xaa  Gly  Phe  Tyr  Arg  Asn
 1                    5

( 2 ) INFORMATION FOR SEQ ID NO:80:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( v ) FRAGMENT TYPE: internal fragment ( i x ) FEATURE:
( D ) OTHER INFORMATION: Xaa in locations 1 and 2 is an amino
acid, provided that at least one Xaa is
Glu or Asp.

( x i ) SEQUENCE DESCRIPTION: SEQ ID NO:80:

Xaa  Xaa  Gly  Tyr  Tyr  Arg  Asp
 1                    5

( 2 ) INFORMATION FOR SEQ ID NO:81:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( v ) FRAGMENT TYPE: internal fragment ( i x ) FEATURE:
( D ) OTHER INFORMATION: Xaa in locations 1 and 2 is an amino
acid, provided that at least one Xaa is
Glu or Asp.

( x i ) SEQUENCE DESCRIPTION: SEQ ID NO:81:

Xaa  Xaa  Gly  Tyr  Tyr  Arg  Asn
 1                    5

( 2 ) INFORMATION FOR SEQ ID NO:82:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( v ) FRAGMENT TYPE: internal fragment ( i x ) FEATURE:
( D ) OTHER INFORMATION: Xaa in locations 1 and 2 is an amino
acid, provided that at least one Xaa is
Glu or Asp.

( x i ) SEQUENCE DESCRIPTION: SEQ ID NO:82:

Xaa  Xaa  Gly  Leu  Tyr  Arg  Asp
 1                    5

( 2 ) INFORMATION FOR SEQ ID NO:83:

( i ) SEQUENCE CHARACTERISTICS:
        ( A ) LENGTH: 9 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 9 is
            an amino acid.

( x i ) SEQUENCE DESCRIPTION: SEQ ID NO: 83:

Cys  Xaa  Xaa  Xaa  Xaa  Xaa  Xaa  Xaa  Xaa
1                             5

( 2 ) INFORMATION FOR SEQ ID NO:84:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal fragment ( i x ) FEATURE:
        ( D ) OTHER INFORMATION: Xaa in location 1 is an amino
            acid, preferably Leu; Xaa in
            location 2 is an amino acid; Xaa
            in location 3 is an amino acid,
            preferably Arg; Xaa in location
            4 is an amino acid.

( x i ) SEQUENCE DESCRIPTION: SEQ ID NO:84:

Xaa  Xaa  Xaa  Xaa
1

( 2 ) INFORMATION FOR SEQ ID NO:85:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal fragment ( i x ) FEATURE:
        ( D ) OTHER INFORMATION: Xaa in locations 1 to 4
            is an amino acid.

( x i ) SEQUENCE DESCRIPTION: SEQ ID NO:85:

Xaa  Xaa  Xaa  Xaa
1

( 2 ) INFORMATION FOR SEQ ID NO: 86:

( i ) SEQUENCE CHARACTERISTICS:
        ( A ) LENGTH: 9 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 9 is
            an amino acid.

(x i) SEQUENCE DESCRIPTION: SEQ ID NO: 86:

Cys Xaa Xaa Xaa Xaa Xaa Xaa Xaa Xaa
1               5

(2) INFORMATION FOR SEQ ID NO:87:

(i) SEQUENCE CHARACTERISTICS:
        (A) LENGTH: 9 amino acids
        (B) TYPE: amino acid
        (D) TOPOLOGY: linear (v) FRAGMENT TYPE: internal fragment (i x) FEATURE:
        (D) OTHER INFORMATION: Xaa in locations 2 to 9 is
            an amino acid.

(x i) SEQUENCE DESCRIPTION: SEQ ID NO: 87:

Cys Xaa Xaa Xaa Xaa Xaa Xaa Xaa Xaa
1               5

(2) INFORMATION FOR SEQ ID NO:88:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (x i) SEQUENCE DESCRIPTION: SEQ ID NO:88:

TCAGACATGT ATAATCTCAT GTTGG    25

(2) INFORMATION FOR SEQ ID NO:89:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (x i) SEQUENCE DESCRIPTION: SEQ ID NO:89:

AAGGCATACC CGGAGTGTGG TG    22

(2) INFORMATION FOR SEQ ID NO:90:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i x) FEATURE:
        (D) OTHER INFORMATION: "R"stands for A or G; "N"stands for
            any base; "Y"stands for C or T; and
            "M"stands for A or C.

(x i) SEQUENCE DESCRIPTION: SEQ ID NO:90:

AARCCNTGYG ARMGGAARTG Y    21

(2) INFORMATION FOR SEQ ID NO:91:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i x) FEATURE:
        (D) OTHER INFORMATION: "W"stands for A or T; "R"stands for
            A or G; "N"stands for any base; and "Y"stands for C or T.

( x i ) SEQUENCE DESCRIPTION: SEQ ID NO:91:

TWRWANCCNT CYTTRCANAC RCA 23

( 2 ) INFORMATION FOR SEQ ID NO:92:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v ) FRAGMENT TYPE: N-terminal fragment ( v i ) ORIGINAL SOURCE:
        ( A ) ORGANISM: Ancyclostoma caninum ( x i ) SEQUENCE DESCRIPTION: SEQ ID NO:92:

Lys Ala Tyr Pro Glu Cys Gly Glu Asn Glu Trp Leu Asp
1               5                   10

( 2 ) INFORMATION FOR SEQ ID NO:93:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( v ) FRAGMENT TYPE: N-terminal fragment ( v i ) ORIGINAL SOURCE:
        ( A ) ORGANISM: Ancyclostoma caninum ( x i ) SEQUENCE DESCRIPTION: SEQ ID NO:93:

Lys Ala Tyr Pro Glu Cys Gly Glu Asn Glu Trp
1               5                   10

( 2 ) INFORMATION FOR SEQ ID NO:94:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i x ) FEATURE:
        ( D ) OTHER INFORMATION: "R"stands for A or G; "N"stands for
            inosine; and "Y"stands for C or T.

( x i ) SEQUENCE DESCRIPTION: SEQ ID NO:94:

AARGCNTAYC CNGARTGYGG NGARAAYGAR TGG 33

( 2 ) INFORMATION FOR SEQ ID NO:95:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:95:

AATTCGCGGC CGCTTTTTTT TTTTTTTT 28

( 2 ) INFORMATION FOR SEQ ID NO:96:

( i ) SEQUENCE CHARACTERISTICS:

(A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:96:

GGTGGCGACG ACTCCTGGAG CCCG                                                                                24

(2) INFORMATION FOR SEQ ID NO:97:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (v) FRAGMENT TYPE: N-terminal fragment (vi) ORIGINAL SOURCE:
            (A) ORGANISM: Ancyclostoma caninum (xi) SEQUENCE DESCRIPTION: SEQ ID NO:97:

Lys Ala Tyr Pro Glu Cys Gly Glu Asn Glu Trp Leu Asp Asp Cys Gly Thr
1               5                   10                  15

Gln Lys Pro
        20

(2) INFORMATION FOR SEQ ID NO:98:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:98:

CGGAATTCCG                                                                                                10

(2) INFORMATION FOR SEQ ID NO:99:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:99:

TGGCCTAGCG TCAGGAGT                                                                                       18

(2) INFORMATION FOR SEQ ID NO:100:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:100:

CCTGACGCTA GGCCATGG                                                                                       18

(2) INFORMATION FOR SEQ ID NO:101:

(i) SEQUENCE CHARACTERISTICS:
            (A) LENGTH: 24 base pairs
            (B) TYPE: nucleic acid
            (C) STRANDEDNESS: single
            (D) TOPOLOGY: linear ( x i ) SEQUENCE DESCRIPTION: SEQ ID NO:101:

AGCGGATAAC AATTTCACAC AGGA 24

( 2 ) INFORMATION FOR SEQ ID NO:102:

( i ) SEQUENCE CHARACTERISTICS:
      ( A ) LENGTH: 66 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:102:

ATGTTCTCTC CAATTTTGTC CTTGGAAATT ATTTTAGCTT TGGCTACTTT GCAATCTGTC 60

TTCGCT 66

( 2 ) INFORMATION FOR SEQ ID NO:103:

( i ) SEQUENCE CHARACTERISTICS:
      ( A ) LENGTH: 57 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:103:

CAGCCAGGTA TCTCCACTAC CGTTGGTTCC GCTGCCGAGG GTTCTTTGGA CAAGAGG 57

( 2 ) INFORMATION FOR SEQ ID NO:104:

( i ) SEQUENCE CHARACTERISTICS:
      ( A ) LENGTH: 51 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:104:

CCTATCCGCG GAATTCAGAT CTGAATGCGG CCGCTCGAGA CTAGTGGATC C 51

( 2 ) INFORMATION FOR SEQ ID NO:105:

( i ) SEQUENCE CHARACTERISTICS:
      ( A ) LENGTH: 41 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:105:

GCTCGCTCTA GAAGCTTCAG ACATGTATAA TCTCATGTTG G 41

( 2 ) INFORMATION FOR SEQ ID NO:106:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( v ) FRAGMENT TYPE: N-terminal fragment ( v i ) ORIGINAL SOURCE:
      ( A ) ORGANISM: Ancyclostoma caninum ( x i ) SEQUENCE DESCRIPTION: SEQ ID NO:106:

Lys Ala Tyr Pro Glu
 1               5

( 2 ) INFORMATION FOR SEQ ID NO:107:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:107:

GACCAGTCTA GACAATGAAG ATGCTTTACG CTATCG 36

( 2 ) INFORMATION FOR SEQ ID NO:108:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:108:

GTGGGAGACC TGATACTCTC AAG 23

( 2 ) INFORMATION FOR SEQ ID NO:109:

( i ) SEQUENCE CHARACTERISTICS:
  ( A ) LENGTH: 9 amino acids
  ( B ) TYPE: amino acid
  ( D ) TOPOLOGY: linear ( i i ) MOLECULE TYPE: peptide ( v ) FRAGMENT TYPE: N-terminal fragment ( v i ) ORIGINAL SOURCE:
  ( A ) ORGANISM: Ancyclostoma caninum ( x i ) SEQUENCE DESCRIPTION: SEQ ID NO:109:

Arg Thr Val Arg Lys Ala Tyr Pro Glu
 1               5

( 2 ) INFORMATION FOR SEQ ID NO:110:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( v ) FRAGMENT TYPE: N-terminal fragment ( v i ) ORIGINAL SOURCE:
  ( A ) ORGANISM: Ancyclostoma caninum ( x i ) SEQUENCE DESCRIPTION: SEQ ID NO:110:

Arg Thr Val Arg Lys
 1               5

( 2 ) INFORMATION FOR SEQ ID NO:111:

( i ) SEQUENCE CHARACTERISTICS:
  ( A ) LENGTH: 33 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:111:

ATCCGAAGCT TGCTAACAT ACTGCGTAAT AAG 33

( 2 ) INFORMATION FOR SEQ ID NO:112:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:112:

TATGGGATGG CCGACTTGGC CTCCGCCTGA GCCTCCACCT TTATCCCAAT CCAAATAAGA    60

( 2 ) INFORMATION FOR SEQ ID NO:113:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:113:

ATGGGATGGC CGACTTGGCC CTCCGCCTGA GCCTCCACCT TTATCCCAAT CCAAATAAGA    60

( 2 ) INFORMATION FOR SEQ ID NO:114:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:114:

TATGGGATGG CCGACTTGGC CGATCCGCCT GAGCCTCCAC CTTTATCCCA ATCCAAATAA    60

( 2 ) INFORMATION FOR SEQ ID NO:115:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:115:

AGGAGGGGAT CCGCGGCCGC GTGATATGGG ATGGCCGACT TGGCC    45

( 2 ) INFORMATION FOR SEQ ID NO:116:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:116:

CGCCAGGGTT TTCCCAGTCA CGAC    24

( 2 ) INFORMATION FOR SEQ ID NO:117:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:117:

GTTTCGAGTT CCGGGATATA TAAAGTCC    28

( 2 ) INFORMATION FOR SEQ ID NO:118:

( i ) SEQUENCE CHARACTERISTICS:
        ( A ) LENGTH: 7 amino acids (B) TYPE: amino acid
(D) TOPOLOGY: linear (i i) MOLECULE TYPE: peptide (i x) FEATURE:
(D) OTHER INFORMATION: Xaa in location 5 is Arg, Pro or Lys.

(x i) SEQUENCE DESCRIPTION: SEQ ID NO:118:

Lys Pro Cys Glu Xaa Lys Cys
1               5

(2) INFORMATION FOR SEQ ID NO:119:

(i) SEQUENCE CHARACTERISTICS:
(A) LENGTH: 8 amino acids
(B) TYPE: amino acid
(D) TOPOLOGY: linear (i i) MOLECULE TYPE: peptide (i x) FEATURE:
(D) OTHER INFORMATION: Xaa in location 2 is Val, Ile or Gln;
Xaa in location 4 is Lys, Asp, Glu or
Gln; Xaa in location 5 is Asp or
Glu; Xaa in location 7 is Phe or
Tyr.

(x i) SEQUENCE DESCRIPTION: SEQ ID NO:119:

Cys Xaa Cys Xaa Xaa Gly Xaa Tyr
1               5

(2) INFORMATION FOR SEQ ID NO:120:

(i) SEQUENCE CHARACTERISTICS:
(A) LENGTH: 44 base pairs
(B) TYPE: nucleic acid
(C) STRANDEDNESS: single
(D) TOPOLOGY: linear (x i) SEQUENCE DESCRIPTION: SEQ ID NO:120:

GACCAGTCTA GACCACCATG GCGGTGCTTT ATTCAGTAGC AATA      4 4

(2) INFORMATION FOR SEQ ID NO:121:

(i) SEQUENCE CHARACTERISTICS:
(A) LENGTH: 40 base pairs
(B) TYPE: nucleic acid
(C) STRANDEDNESS: single
(D) TOPOLOGY: linear (x i) SEQUENCE DESCRIPTION: SEQ ID NO:121:

GCTCGCTCTA GATTATCGTG AGGTTTCTGG TGCAAAAGTG      4 0

(2) INFORMATION FOR SEQ ID NO:122:

(i) SEQUENCE CHARACTERISTICS:
(A) LENGTH: 24 base pairs
(B) TYPE: nucleic acid
(C) STRANDEDNESS: single
(D) TOPOLOGY: linear (x i) SEQUENCE DESCRIPTION: SEQ ID NO:122:

AAAGCAACGA TGCAGTGTGG TGAG      2 4

(2) INFORMATION FOR SEQ ID NO:123:

(i) SEQUENCE CHARACTERISTICS:
(A) LENGTH: 47 base pairs
(B) TYPE: nucleic acid ( C ) STRANDEDNESS: single
( D ) TOPOLOGY: linear ( x i ) SEQUENCE DESCRIPTION: SEQ ID NO:123:

GCTCGCTCTA GAAGCTTCAG TTTCGAGTTC CGGGATATAT AAAGTCC 47

( 2 ) INFORMATION FOR SEQ ID NO:124:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:124:

GAGACTTTTA AATCACTGTG GGATCAGAAG 30

( 2 ) INFORMATION FOR SEQ ID NO:125:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:125:

TTCAGGACTA GTTCATGGTG CGAAAGTAAT AAA 33

( 2 ) INFORMATION FOR SEQ ID NO:126:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:126:

GCGTTTAAAG CAACGATGCA GTGTGGTG 28

( 2 ) INFORMATION FOR SEQ ID NO:127:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( x i ) SEQUENCE DESCRIPTION: SEQ ID NO:127:

CGCTCTAGAA GCTTCATGGG TTTCGAGTTC CGGGATATAT AAAGTC 46

( 2 ) INFORMATION FOR SEQ ID NO:128:

( i ) SEQUENCE CHARACTERISTICS:
( A ) LENGTH: 91 amino acids
( B ) TYPE: amino acid
( D ) TOPOLOGY: linear ( i i ) MOLECULE TYPE: peptide ( v i ) ORIGINAL SOURCE:
( A ) ORGANISM: Ancyclostoma caninum ( x i ) SEQUENCE DESCRIPTION: SEQ ID NO:128:

Leu Val Ser Tyr Cys Ser Gly Lys Ala Thr Met Gln Cys Gly Glu Asn
1               5                  10                 15

Glu Lys Tyr Asp Ser Cys Gly Ser Lys Glu Cys Asp Lys Lys Cys Lys
            20                 25                 30

```
Tyr  Asp  Gly  Val  Glu  Glu  Glu  Asp  Asp  Glu  Glu  Pro  Asn  Val  Pro  Cys
          35                      40                      45

Leu  Val  Arg  Val  Cys  His  Gln  Asp  Cys  Val  Cys  Glu  Glu  Gly  Phe  Tyr
     50                      55                      60

Arg  Asn  Lys  Asp  Asp  Lys  Cys  Val  Ser  Ala  Glu  Asp  Cys  Glu  Leu  Asp
65                      70                      75                      80

Asn  Met  Asp  Phe  Ile  Tyr  Pro  Gly  Thr  Arg  Asn
                    85                      90
```

( 2 ) INFORMATION FOR SEQ ID NO: 129:

( i ) SEQUENCE CHARACTERISTICS:
        ( A ) LENGTH: 8 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 8
            is an amino acid.

( x i ) SEQUENCE DESCRIPTION: SEQ ID NO: 129:

```
Cys  Xaa  Xaa  Xaa  Xaa  Xaa  Xaa  Xaa
1                        5
```

( 2 ) INFORMATION FOR SEQ ID NO: 130:

( i ) SEQUENCE CHARACTERISTICS:
        ( A ) LENGTH: 7 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 6
            is an amino acid.

( x i ) SEQUENCE DESCRIPTION: SEQ ID NO: 130:

```
Cys  Xaa  Xaa  Xaa  Xaa  Xaa  Cys
1                        5
```

( 2 ) INFORMATION FOR SEQ ID NO: 131:

( i ) SEQUENCE CHARACTERISTICS:
        ( A ) LENGTH: 6 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 5
            is an amino acid.

( x i ) SEQUENCE DESCRIPTION: SEQ ID NO: 131:

```
Cys  Xaa  Xaa  Xaa  Xaa  Cys
1                   5
```

( 2 ) INFORMATION FOR SEQ ID NO: 132:

( i ) SEQUENCE CHARACTERISTICS:
        ( A ) LENGTH: 5 amino acids
        ( B ) TYPE: amino acid
        ( D ) TOPOLOGY: linear ( v ) FRAGMENT TYPE: internal fragment ( i x ) FEATURE:

(D) OTHER INFORMATION: Xaa in locations 2 to 4
is an amino acid.

(xi) SEQUENCE DESCRIPTION: SEQ ID NO: 132:

Cys Xaa Xaa Xaa Cys
1               5

(2) INFORMATION FOR SEQ ID NO: 133:

(i) SEQUENCE CHARACTERISTICS:
(A) LENGTH: 4 amino acids
(B) TYPE: amino acid
(D) TOPOLOGY: linear (v) FRAGMENT TYPE: internal fragment (ix) FEATURE:
(D) OTHER INFORMATION: Xaa in locations 2 and 3
is an amino acid.

(xi) SEQUENCE DESCRIPTION: SEQ ID NO: 133:

Cys Xaa Xaa Cys
1

(2) INFORMATION FOR SEQ ID NO: 134:

(i) SEQUENCE CHARACTERISTICS:
(A) LENGTH: 21 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and 5
to 21 is an amino acid.

(xi) SEQUENCE DESCRIPTION: SEQ ID NO: 134:

Xaa Xaa Xaa Cys Xaa Xaa Xaa Xaa Xaa Xaa Xaa Xaa Xaa Xaa Xaa Xaa
1               5                           10                          15
Xaa Xaa Xaa Xaa Xaa
                20

(2) INFORMATION FOR SEQ ID NO: 135:

(i) SEQUENCE CHARACTERISTICS:
(A) LENGTH: 20 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and 5
to 20 is an amino acid.

(xi) SEQUENCE DESCRIPTION: SEQ ID NO: 135:

Xaa Xaa Xaa Cys Xaa Xaa Xaa Xaa Xaa Xaa Xaa Xaa Xaa Xaa Xaa Xaa
1               5                           10                          15
Xaa Xaa Xaa Xaa
                20

(2) INFORMATION FOR SEQ ID NO: 136:

(i) SEQUENCE CHARACTERISTICS:
(A) LENGTH: 19 amino acids
(B) TYPE: amino acid
(D) TOPOLOGY: linear (v) FRAGMENT TYPE: internal fragment ( i x ) FEATURE:
        ( D ) OTHER INFORMATION: Xaa in locations 1 to 3 and 5
              to 19 is an amino acid.

( x i ) SEQUENCE DESCRIPTION: SEQ ID NO: 136:

Xaa Xaa Xaa Cys Xaa Xaa Xaa Xaa Xaa Xaa Xaa Xaa Xaa Xaa Xaa Xaa
1                5                   10                  15
Xaa Xaa Xaa ( 2 ) INFORMATION FOR SEQ ID NO: 137:

( i ) SEQUENCE CHARACTERISTICS:
        ( A ) LENGTH: 18 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and 5
              to 18 is an amino acid.

( x i ) SEQUENCE DESCRIPTION: SEQ ID NO: 137:

Xaa Xaa Xaa Cys Xaa Xaa Xaa Xaa Xaa Xaa Xaa Xaa Xaa Xaa Xaa Xaa
1                5                   10                  15
Xaa Xaa ( 2 ) INFORMATION FOR SEQ ID NO: 138:

( i ) SEQUENCE CHARACTERISTICS:
        ( A ) LENGTH: 17 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and 5
              to 17 is an amino acid.

( x i ) SEQUENCE DESCRIPTION: SEQ ID NO: 138:

Xaa Xaa Xaa Cys Xaa Xaa Xaa Xaa Xaa Xaa Xaa Xaa Xaa Xaa Xaa Xaa
1                5                   10                  15
Xaa ( 2 ) INFORMATION FOR SEQ ID NO: 139:

( i ) SEQUENCE CHARACTERISTICS:
        ( A ) LENGTH: 16 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and 5
              to 16 is an amino acid.

( x i ) SEQUENCE DESCRIPTION: SEQ ID NO: 139:

Xaa Xaa Xaa Cys Xaa Xaa Xaa Xaa Xaa Xaa Xaa Xaa Xaa Xaa Xaa Xaa
1                5                   10                  15

( 2 ) INFORMATION FOR SEQ ID NO: 140:

( i ) SEQUENCE CHARACTERISTICS:
        ( A ) LENGTH: 15 amino acids
        ( B ) TYPE: amino acid
        ( D ) TOPOLOGY: linear (v) FRAGMENT TYPE: internal fragment (ix) FEATURE:
(D) OTHER INFORMATION: Xaa in locations 1 to 3 and 5 to 15 is an amino acid.

(xi) SEQUENCE DESCRIPTION: SEQ ID NO: 140:

Xaa Xaa Xaa Cys Xaa Xaa Xaa Xaa Xaa Xaa Xaa Xaa Xaa Xaa Xaa
1               5                   10                  15

(2) INFORMATION FOR SEQ ID NO: 141:

(i) SEQUENCE CHARACTERISTICS:
(A) LENGTH: 14 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and 5 to 14 is an amino acid.

(xi) SEQUENCE DESCRIPTION: SEQ ID NO: 141:

Xaa Xaa Xaa Cys Xaa Xaa Xaa Xaa Xaa Xaa Xaa Xaa Xaa Xaa
1               5                   10

(2) INFORMATION FOR SEQ ID NO: 142:

(i) SEQUENCE CHARACTERISTICS:
(A) LENGTH: 13 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and 5 to 13 is an amino acid.

(xi) SEQUENCE DESCRIPTION: SEQ ID NO: 142:

Xaa Xaa Xaa Cys Xaa Xaa Xaa Xaa Xaa Xaa Xaa Xaa Xaa
1               5                   10

(2) INFORMATION FOR SEQ ID NO: 143:

(i) SEQUENCE CHARACTERISTICS:
(A) LENGTH: 12 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and 5 to 12 is an amino acid.

(xi) SEQUENCE DESCRIPTION: SEQ ID NO: 143:

Xaa Xaa Xaa Cys Xaa Xaa Xaa Xaa Xaa Xaa Xaa Xaa
1               5                   10

(2) INFORMATION FOR SEQ ID NO: 144:

(i) SEQUENCE CHARACTERISTICS:
(A) LENGTH: 11 amino acids
(B) TYPE: amino acid
(D) TOPOLOGY: linear (v) FRAGMENT TYPE: internal fragment (ix) FEATURE:

(D) OTHER INFORMATION: Xaa in locations 1 to 3 and 5
to 11 is an amino acid.

(xi) SEQUENCE DESCRIPTION: SEQ ID NO: 144:

Xaa Xaa Xaa Cys Xaa Xaa Xaa Xaa Xaa Xaa Xaa
1               5                       10

(2) INFORMATION FOR SEQ ID NO: 145:

(i) SEQUENCE CHARACTERISTICS:
      (A) LENGTH: 10 amino acids
      (B) TYPE: amino acid
      (D) TOPOLOGY: linear (v) FRAGMENT TYPE: internal fragment (ix) FEATURE:
      (D) OTHER INFORMATION: Xaa in locations 1 to 3 and 5
      to 10 is an amino acid.

(xi) SEQUENCE DESCRIPTION: SEQ ID NO: 145:

Xaa Xaa Xaa Cys Xaa Xaa Xaa Xaa Xaa Xaa
1               5                   10

(2) INFORMATION FOR SEQ ID NO: 146:

(i) SEQUENCE CHARACTERISTICS:
      (A) LENGTH: 5 amino acids
      (B) TYPE: amino acid
      (D) TOPOLOGY: linear (v) FRAGMENT TYPE: internal fragment (ix) FEATURE:
      (D) OTHER INFORMATION: Xaa in locations 2 to 5 is an
      amino acid.

(xi) SEQUENCE DESCRIPTION: SEQ ID NO: 146:

Cys Xaa Xaa Xaa Xaa
1               5

(2) INFORMATION FOR SEQ ID NO: 147:

(i) SEQUENCE CHARACTERISTICS:
      (A) LENGTH: 4 amino acids
      (B) TYPE: amino acid
      (D) TOPOLOGY: linear (v) FRAGMENT TYPE: internal fragment (ix) FEATURE:
      (D) OTHER INFORMATION: Xaa in locations 2 to 4 is
      an amino acid.

(xi) SEQUENCE DESCRIPTION: SEQ ID NO: 147:

Cys Xaa Xaa Xaa
1

(2) INFORMATION FOR SEQ ID NO: 148:

(i) SEQUENCE CHARACTERISTICS:
      (A) LENGTH: 6 amino acids
      (B) TYPE: amino acid
      (D) TOPOLOGY: linear (v) FRAGMENT TYPE: internal fragment (ix) FEATURE:
      (D) OTHER INFORMATION: Xaa in locations 2 to 6 is
      an amino acid.

(xi) SEQUENCE DESCRIPTION: SEQ ID NO: 148:

Cys Xaa Xaa Xaa Xaa Xaa
1               5

(2) INFORMATION FOR SEQ ID NO: 149:

(i) SEQUENCE CHARACTERISTICS:
        (A) LENGTH: 5 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 5 is
        an amino acid.

(xi) SEQUENCE DESCRIPTION: SEQ ID NO: 149:

Cys Xaa Xaa Xaa Xaa
1               5

(2) INFORMATION FOR SEQ ID NO: 150:

(i) SEQUENCE CHARACTERISTICS:
        (A) LENGTH: 4 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 4 is
        an amino acid.

(xi) SEQUENCE DESCRIPTION: SEQ ID NO: 150:

Cys Xaa Xaa Xaa
1

(2) INFORMATION FOR SEQ ID NO: 151:

(i) SEQUENCE CHARACTERISTICS:
        (A) LENGTH: 15 amino acids
        (B) TYPE: amino acid
        (D) TOPOLOGY: linear (v) FRAGMENT TYPE: internal fragment (ix) FEATURE:
        (D) OTHER INFORMATION: Xaa in location 2 and locations
        4 to 15 is an amino acid.

(xi) SEQUENCE DESCRIPTION: SEQ ID NO: 151:

Cys Xaa Cys Xaa Xaa Xaa Xaa Xaa Xaa Xaa Xaa Xaa Xaa Xaa Xaa
1               5                   10                  15

(2) INFORMATION FOR SEQ ID NO: 152:

(i) SEQUENCE CHARACTERISTICS:
        (A) LENGTH: 14 amino acids
        (B) TYPE: amino acid
        (D) TOPOLOGY: linear (v) FRAGMENT TYPE: internal fragment (ix) FEATURE:
        (D) OTHER INFORMATION: Xaa in location 2 and locations
        4 to 14 is an amino acid.

(xi) SEQUENCE DESCRIPTION: SEQ ID NO: 152:

Cys Xaa Cys Xaa Xaa Xaa Xaa Xaa Xaa Xaa Xaa Xaa Xaa Xaa
1               5                   10

( 2 ) INFORMATION FOR SEQ ID NO: 153:

( i ) SEQUENCE CHARACTERISTICS:
        ( A ) LENGTH: 13 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in location 2 and locations
            4 to 13 is an amino acid.

( x i ) SEQUENCE DESCRIPTION: SEQ ID NO: 153:

```
Cys  Xaa  Cys  Xaa  Xaa  Xaa  Xaa  Xaa  Xaa  Xaa  Xaa  Xaa  Xaa
1              5                             10
```

( 2 ) INFORMATION FOR SEQ ID NO: 154:

( i ) SEQUENCE CHARACTERISTICS:
        ( A ) LENGTH: 8 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 7
            is an amino acid.

( x i ) SEQUENCE DESCRIPTION: SEQ ID NO: 154:

```
Cys  Xaa  Xaa  Xaa  Xaa  Xaa  Xaa  Cys
1              5
```

( 2 ) INFORMATION FOR SEQ ID NO: 155:

( i ) SEQUENCE CHARACTERISTICS:
        ( A ) LENGTH: 7 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 6
            is an amino acid.

( x i ) SEQUENCE DESCRIPTION: SEQ ID NO: 155:

```
Cys  Xaa  Xaa  Xaa  Xaa  Xaa  Cys
1              5
```

( 2 ) INFORMATION FOR SEQ ID NO: 156:

( i ) SEQUENCE CHARACTERISTICS:
        ( A ) LENGTH: 8 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 8 is
            an amino acid.

( x i ) SEQUENCE DESCRIPTION: SEQ ID NO: 156:

```
Cys  Xaa  Xaa  Xaa  Xaa  Xaa  Xaa  Xaa
1              5
```

( 2 ) INFORMATION FOR SEQ ID NO: 157:

( i ) SEQUENCE CHARACTERISTICS:

(A) LENGTH: 7 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 6 is
an amino acid.

(xi) SEQUENCE DESCRIPTION: SEQ ID NO: 157:

Cys Xaa Xaa Xaa Xaa Xaa Cys
1               5

(2) INFORMATION FOR SEQ ID NO: 158:

(i) SEQUENCE CHARACTERISTICS:
(A) LENGTH: 6 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 5 is
an amino acid.

(xi) SEQUENCE DESCRIPTION: SEQ ID NO: 158:

Cys Xaa Xaa Xaa Xaa Cys
1               5

(2) INFORMATION FOR SEQ ID NO: 159:

(i) SEQUENCE CHARACTERISTICS:
(A) LENGTH: 5 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 4 is
an amino acid.

(xi) SEQUENCE DESCRIPTION: SEQ ID NO: 159:

Cys Xaa Xaa Xaa Cys
1               5

(2) INFORMATION FOR SEQ ID NO: 160:

(i) SEQUENCE CHARACTERISTICS:
(A) LENGTH: 23 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and
locations 5 to 23 is an amino
acid.

(xi) SEQUENCE DESCRIPTION: SEQ ID NO: 160:

Xaa Xaa Xaa Cys Xaa Xaa Xaa Xaa Xaa Xaa Xaa Xaa Xaa Xaa Xaa Xaa
1               5                   10                  15
Xaa Xaa Xaa Xaa Xaa Xaa Xaa
            20

(2) INFORMATION FOR SEQ ID NO: 161:

(i) SEQUENCE CHARACTERISTICS:

(A) LENGTH: 22 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and locations 5 to 22 is an amino acid.

(xi) SEQUENCE DESCRIPTION: SEQ ID NO: 161:

Xaa Xaa Xaa Cys Xaa Xaa Xaa Xaa Xaa Xaa Xaa Xaa Xaa Xaa Xaa Xaa
1               5                           10                          15
Xaa Xaa Xaa Xaa Xaa Xaa
            20

(2) INFORMATION FOR SEQ ID NO: 162:

(i) SEQUENCE CHARACTERISTICS:
(A) LENGTH: 21 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and locations 5 to 21 is an amino acid.

(xi) SEQUENCE DESCRIPTION: SEQ ID NO: 162:

Xaa Xaa Xaa Cys Xaa Xaa Xaa Xaa Xaa Xaa Xaa Xaa Xaa Xaa Xaa Xaa
1               5                           10                          15
Xaa Xaa Xaa Xaa Xaa
            20

(2) INFORMATION FOR SEQ ID NO: 163:

(i) SEQUENCE CHARACTERISTICS:
(A) LENGTH: 20 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and locations 5 to 20 is an amino acid.

(xi) SEQUENCE DESCRIPTION: SEQ ID NO: 163:

Xaa Xaa Xaa Cys Xaa Xaa Xaa Xaa Xaa Xaa Xaa Xaa Xaa Xaa Xaa Xaa
1               5                           10                          15
Xaa Xaa Xaa Xaa
            20

(2) INFORMATION FOR SEQ ID NO: 164:

(i) SEQUENCE CHARACTERISTICS:
(A) LENGTH: 19 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and locations 5 to 19 is an amino acid.

(x i) SEQUENCE DESCRIPTION: SEQ ID NO: 164:

Xaa Xaa Xaa Cys Xaa Xaa Xaa Xaa Xaa Xaa Xaa Xaa Xaa Xaa Xaa Xaa
1               5                         1 0                        1 5

Xaa Xaa Xaa (2) INFORMATION FOR SEQ ID NO: 165:

(i) SEQUENCE CHARACTERISTICS:
        (A) LENGTH: 18 amino acids
        (B) TYPE: amino acid
        (D) TOPOLOGY: linear (v) FRAGMENT TYPE: internal fragment (i x) FEATURE:
        (D) OTHER INFORMATION: Xaa in locations 1 to 3 and
            locations 5 to 18 is an amino
            acid.

(x i) SEQUENCE DESCRIPTION: SEQ ID NO: 165:

Xaa Xaa Xaa Cys Xaa Xaa Xaa Xaa Xaa Xaa Xaa Xaa Xaa Xaa Xaa Xaa
1               5                         1 0                        1 5

Xaa Xaa (2) INFORMATION FOR SEQ ID NO: 166:

(i) SEQUENCE CHARACTERISTICS:
        (A) LENGTH: 17 amino acids
        (B) TYPE: amino acid
        (D) TOPOLOGY: linear (v) FRAGMENT TYPE: internal fragment (i x) FEATURE:
        (D) OTHER INFORMATION: Xaa in locations 1 to 3 and
            locations 5 to 17 is an amino
            acid.

(x i) SEQUENCE DESCRIPTION: SEQ ID NO: 166:

Xaa Xaa Xaa Cys Xaa Xaa Xaa Xaa Xaa Xaa Xaa Xaa Xaa Xaa Xaa Xaa
1               5                         1 0                        1 5

Xaa (2) INFORMATION FOR SEQ ID NO: 167:

(i) SEQUENCE CHARACTERISTICS:
        (A) LENGTH: 16 amino acids
        (B) TYPE: amino acid
        (D) TOPOLOGY: linear (v) FRAGMENT TYPE: internal fragment (i x) FEATURE:
        (D) OTHER INFORMATION: Xaa in locations 1 to 3 and
            locations 5 to 16 is an amino
            acid.

(x i) SEQUENCE DESCRIPTION: SEQ ID NO: 167:

Xaa Xaa Xaa Cys Xaa Xaa Xaa Xaa Xaa Xaa Xaa Xaa Xaa Xaa Xaa Xaa
1               5                         1 0                        1 5

(2) INFORMATION FOR SEQ ID NO: 168:

(i) SEQUENCE CHARACTERISTICS:
        (A) LENGTH: 15 amino acids
        (B) TYPE: amino acid
        (D) TOPOLOGY: linear (v) FRAGMENT TYPE: internal fragment ( i x ) FEATURE:
            ( D ) OTHER INFORMATION: Xaa in locations 1 to 3 and
                locations 5 to 15 is an amino
                acid.

( x i ) SEQUENCE DESCRIPTION: SEQ ID NO: 168:

Xaa  Xaa  Xaa  Cys  Xaa  Xaa  Xaa  Xaa  Xaa  Xaa  Xaa  Xaa  Xaa  Xaa  Xaa
1                  5                            1 0                           1 5

( 2 ) INFORMATION FOR SEQ ID NO: 169:

( i ) SEQUENCE CHARACTERISTICS:
                ( A ) LENGTH: 14 amino acids
                ( B ) TYPE: amino acid
                ( D ) TOPOLOGY: linear ( v ) FRAGMENT TYPE: internal fragment ( i x ) FEATURE:
                ( D ) OTHER INFORMATION: Xaa in locations 1 to 3 and
                    locations 5 to 14 is an amino
                    acid.

( x i ) SEQUENCE DESCRIPTION: SEQ ID NO: 169:

Xaa  Xaa  Xaa  Cys  Xaa  Xaa  Xaa  Xaa  Xaa  Xaa  Xaa  Xaa  Xaa  Xaa
1                  5                            1 0

( 2 ) INFORMATION FOR SEQ ID NO: 170:

( i ) SEQUENCE CHARACTERISTICS:
                ( A ) LENGTH: 13 amino acids
                ( B ) TYPE: amino acid
                ( D ) TOPOLOGY: linear ( v ) FRAGMENT TYPE: internal fragment ( i x ) FEATURE:
                ( D ) OTHER INFORMATION: Xaa in locations 1 to 3 and
                    locations 5 to 13 is an amino
                    acid.

( x i ) SEQUENCE DESCRIPTION: SEQ ID NO: 170:

Xaa  Xaa  Xaa  Cys  Xaa  Xaa  Xaa  Xaa  Xaa  Xaa  Xaa  Xaa  Xaa
1                  5                            1 0

( 2 ) INFORMATION FOR SEQ ID NO: 171:

( i ) SEQUENCE CHARACTERISTICS:
                ( A ) LENGTH: 12 amino acids
                ( B ) TYPE: amino acid
                ( D ) TOPOLOGY: linear ( v ) FRAGMENT TYPE: internal fragment ( i x ) FEATURE:
                ( D ) OTHER INFORMATION: Xaa in locations 1 to 3 and
                    locations 5 to 12 is an amino
                    acid.

( x i ) SEQUENCE DESCRIPTION: SEQ ID NO: 171:

Xaa  Xaa  Xaa  Cys  Xaa  Xaa  Xaa  Xaa  Xaa  Xaa  Xaa  Xaa
1                  5                            1 0

( 2 ) INFORMATION FOR SEQ ID NO: 172:

( i ) SEQUENCE CHARACTERISTICS:
                ( A ) LENGTH: 11 amino acids
                ( B ) TYPE: amino acid
                ( D ) TOPOLOGY: linear ( v ) FRAGMENT TYPE: internal fragment (ix) FEATURE:
     (D) OTHER INFORMATION: Xaa in locations 1 to 3 and
         locations 5 to 11 is an amino
         acid.

(xi) SEQUENCE DESCRIPTION: SEQ ID NO: 172:

Xaa Xaa Xaa Cys Xaa Xaa Xaa Xaa Xaa Xaa Xaa
1                 5                        10

(2) INFORMATION FOR SEQ ID NO: 173:

(i) SEQUENCE CHARACTERISTICS:
        (A) LENGTH: 10 amino acids
        (B) TYPE: amino acid
        (D) TOPOLOGY: linear (v) FRAGMENT TYPE: internal fragment (ix) FEATURE:
         (D) OTHER INFORMATION: Xaa in locations 1 to 3 and
             locations 5 to 10 is an amino
             acid.

(xi) SEQUENCE DESCRIPTION: SEQ ID NO: 173:

Xaa Xaa Xaa Cys Xaa Xaa Xaa Xaa Xaa Xaa
1                 5                    10

(2) INFORMATION FOR SEQ ID NO: 174:

(i) SEQUENCE CHARACTERISTICS:
        (A) LENGTH: 5 amino acids
        (B) TYPE: amino acid
        (D) TOPOLOGY: linear (v) FRAGMENT TYPE: internal fragment (ix) FEATURE:
         (D) OTHER INFORMATION: Xaa in locations 2 to 5 is
             an amino acid.

(xi) SEQUENCE DESCRIPTION: SEQ ID NO: 174:

Cys Xaa Xaa Xaa Xaa
1               5

(2) INFORMATION FOR SEQ ID NO: 175:

(i) SEQUENCE CHARACTERISTICS:
        (A) LENGTH: 4 amino acids
        (B) TYPE: amino acid
        (D) TOPOLOGY: linear (v) FRAGMENT TYPE: internal fragment (ix) FEATURE:
         (D) OTHER INFORMATION: Xaa in locations 2 to 4 is
             an amino acid.

(xi) SEQUENCE DESCRIPTION: SEQ ID NO: 175:

Cys Xaa Xaa Xaa
1

(2) INFORMATION FOR SEQ ID NO: 176:

(i) SEQUENCE CHARACTERISTICS:
        (A) LENGTH: 6 amino acids
        (B) TYPE: amino acid
        (D) TOPOLOGY: linear (v) FRAGMENT TYPE: internal fragment (ix) FEATURE:

(D) OTHER INFORMATION: Xaa in locations 2 to 6 is
    an amino acid.

(xi) SEQUENCE DESCRIPTION: SEQ ID NO: 176:

Cys Xaa Xaa Xaa Xaa Xaa
 1           5

(2) INFORMATION FOR SEQ ID NO: 177:

(i) SEQUENCE CHARACTERISTICS:
      (A) LENGTH: 5 amino acids
      (B) TYPE: amino acid
      (D) TOPOLOGY: linear (v) FRAGMENT TYPE: internal fragment (ix) FEATURE:
      (D) OTHER INFORMATION: Xaa in locations 2 to 5 is
           an amino acid.

(xi) SEQUENCE DESCRIPTION: SEQ ID NO: 177:

Cys Xaa Xaa Xaa Xaa
 1           5

(2) INFORMATION FOR SEQ ID NO: 178:

(i) SEQUENCE CHARACTERISTICS:
      (A) LENGTH: 4 amino acids
      (B) TYPE: amino acid
      (D) TOPOLOGY: linear (v) FRAGMENT TYPE: internal fragment (ix) FEATURE:
      (D) OTHER INFORMATION: Xaa in locations 2 to 4 is
           an amino acid.

(xi) SEQUENCE DESCRIPTION: SEQ ID NO: 178:

Cys Xaa Xaa Xaa
 1

(2) INFORMATION FOR SEQ ID NO: 179:

(i) SEQUENCE CHARACTERISTICS:
      (A) LENGTH: 15 amino acids
      (B) TYPE: amino acid
      (D) TOPOLOGY: linear (v) FRAGMENT TYPE: internal fragment (ix) FEATURE:
      (D) OTHER INFORMATION: Xaa in location 2 and
           locations 4 to 15 is an amino
           acid.

(xi) SEQUENCE DESCRIPTION: SEQ ID NO: 179:

Cys Xaa Cys Xaa Xaa Xaa Xaa Xaa Xaa Xaa Xaa Xaa Xaa Xaa Xaa
 1           5                   10                  15

(2) INFORMATION FOR SEQ ID NO: 180:

(i) SEQUENCE CHARACTERISTICS:
      (A) LENGTH: 14 amino acids
      (B) TYPE: amino acid
      (D) TOPOLOGY: linear (v) FRAGMENT TYPE: internal fragment (ix) FEATURE:
      (D) OTHER INFORMATION: Xaa in location 2 and
           locations 4 to 14 is an amino
           acid.

( x i ) SEQUENCE DESCRIPTION: SEQ ID NO: 180:

Cys Xaa Cys Xaa Xaa Xaa Xaa Xaa Xaa Xaa Xaa Xaa Xaa Xaa
1           5                           10

( 2 ) INFORMATION FOR SEQ ID NO: 181:

( i ) SEQUENCE CHARACTERISTICS:
        ( A ) LENGTH: 8 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 8 is
            an amino acid.

( x i ) SEQUENCE DESCRIPTION: SEQ ID NO: 181:

Cys Xaa Xaa Xaa Xaa Xaa Xaa Xaa
1           5

( 2 ) INFORMATION FOR SEQ ID NO: 182:

( i ) SEQUENCE CHARACTERISTICS:
        ( A ) LENGTH: 7 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 7 is
            an amino acid.

( x i ) SEQUENCE DESCRIPTION: SEQ ID NO: 182:

Cys Xaa Xaa Xaa Xaa Xaa Xaa
1           5

( 2 ) INFORMATION FOR SEQ ID NO: 183:

( i ) SEQUENCE CHARACTERISTICS:
        ( A ) LENGTH: 6 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 6 is
            an amino acid.

( x i ) SEQUENCE DESCRIPTION: SEQ ID NO: 183:

Cys Xaa Xaa Xaa Xaa Xaa
1           5

( 2 ) INFORMATION FOR SEQ ID NO: 184:

( i ) SEQUENCE CHARACTERISTICS:
        ( A ) LENGTH: 26 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 26 is an
            amino acid.

( x i ) SEQUENCE DESCRIPTION: SEQ ID NO: 184:

Cys Xaa Xaa Xaa Xaa Xaa Xaa Xaa Xaa Xaa Xaa Xaa Xaa Xaa Xaa Xaa

```
          1               5                    1 0                      1 5
Xaa  Xaa  Xaa  Xaa  Xaa  Xaa  Xaa  Xaa  Xaa  Xaa
                    2 0                      2 5
```

( 2 ) INFORMATION FOR SEQ ID NO: 185:

( i ) SEQUENCE CHARACTERISTICS:
        ( A ) LENGTH: 25 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 25 is an
            amino acid.

( x i ) SEQUENCE DESCRIPTION: SEQ ID NO: 185:

```
Cys  Xaa  Xaa  Xaa  Xaa  Xaa  Xaa  Xaa  Xaa  Xaa  Xaa  Xaa  Xaa  Xaa  Xaa  Xaa
1               5                    1 0                      1 5
Xaa  Xaa  Xaa  Xaa  Xaa  Xaa  Xaa  Xaa  Xaa
                    2 0                      2 5
```

( 2 ) INFORMATION FOR SEQ ID NO: 186:

( i ) SEQUENCE CHARACTERISTICS:
        ( A ) LENGTH: 24 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 24 is an
            amino acid.

( x i ) SEQUENCE DESCRIPTION: SEQ ID NO: 186:

```
Cys  Xaa  Xaa  Xaa  Xaa  Xaa  Xaa  Xaa  Xaa  Xaa  Xaa  Xaa  Xaa  Xaa  Xaa  Xaa
1               5                    1 0                      1 5
Xaa  Xaa  Xaa  Xaa  Xaa  Xaa  Xaa  Xaa
                    2 0
```

( 2 ) INFORMATION FOR SEQ ID NO: 187:

( i ) SEQUENCE CHARACTERISTICS:
        ( A ) LENGTH: 23 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 23 is an
            amino acid.

( x i ) SEQUENCE DESCRIPTION: SEQ ID NO: 187:

```
Cys  Xaa  Xaa  Xaa  Xaa  Xaa  Xaa  Xaa  Xaa  Xaa  Xaa  Xaa  Xaa  Xaa  Xaa  Xaa
1               5                    1 0                      1 5
Xaa  Xaa  Xaa  Xaa  Xaa  Xaa  Xaa
                    2 0
```

( 2 ) INFORMATION FOR SEQ ID NO: 188:

( i ) SEQUENCE CHARACTERISTICS:
        ( A ) LENGTH: 22 amino acids
        ( B ) TYPE: amino acid
        ( D ) TOPOLOGY: linear ( v ) FRAGMENT TYPE: internal fragment ( i x ) FEATURE:
  ( D ) OTHER INFORMATION: Xaa in locations 2 to 22 is an
    amino acid.

( x i ) SEQUENCE DESCRIPTION: SEQ ID NO: 188:

Cys Xaa Xaa Xaa Xaa Xaa Xaa Xaa Xaa Xaa Xaa Xaa Xaa Xaa Xaa Xaa
1               5                   10                  15
Xaa Xaa Xaa Xaa Xaa Xaa
          20

( 2 ) INFORMATION FOR SEQ ID NO: 189:

( i ) SEQUENCE CHARACTERISTICS:
    ( A ) LENGTH: 21 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in locations 2 to 21 is an
      amino acid.

( x i ) SEQUENCE DESCRIPTION: SEQ ID NO: 189:

Cys Xaa Xaa Xaa Xaa Xaa Xaa Xaa Xaa Xaa Xaa Xaa Xaa Xaa Xaa Xaa
1               5                   10                  15
Xaa Xaa Xaa Xaa Xaa
          20

( 2 ) INFORMATION FOR SEQ ID NO: 190:

( i ) SEQUENCE CHARACTERISTICS:
    ( A ) LENGTH: 20 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in locations 2 to 20 is an
      amino acid.

( x i ) SEQUENCE DESCRIPTION: SEQ ID NO: 190:

Cys Xaa Xaa Xaa Xaa Xaa Xaa Xaa Xaa Xaa Xaa Xaa Xaa Xaa Xaa Xaa
1               5                   10                  15
Xaa Xaa Xaa Xaa
          20

( 2 ) INFORMATION FOR SEQ ID NO: 191:

( i ) SEQUENCE CHARACTERISTICS:
    ( A ) LENGTH: 19 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in locations 2 to 19 is an
      amino acid.

( x i ) SEQUENCE DESCRIPTION: SEQ ID NO: 191:

Cys Xaa Xaa Xaa Xaa Xaa Xaa Xaa Xaa Xaa Xaa Xaa Xaa Xaa Xaa Xaa
1               5                   10                  15
Xaa Xaa Xaa ( 2 ) INFORMATION FOR SEQ ID NO: 192:

( i ) SEQUENCE CHARACTERISTICS:
    ( A ) LENGTH: 18 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in locations 2 to 18 is an amino acid.

( x i ) SEQUENCE DESCRIPTION: SEQ ID NO: 192:

```
Cys Xaa Xaa Xaa Xaa Xaa Xaa Xaa Xaa Xaa Xaa Xaa Xaa Xaa Xaa Xaa
1               5                   10                  15
Xaa Xaa
```

( 2 ) INFORMATION FOR SEQ ID NO: 193:

( i ) SEQUENCE CHARACTERISTICS:
    ( A ) LENGTH: 17 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in locations 2 to 17 is an amino acid.

( x i ) SEQUENCE DESCRIPTION: SEQ ID NO: 193:

```
Cys Xaa Xaa Xaa Xaa Xaa Xaa Xaa Xaa Xaa Xaa Xaa Xaa Xaa Xaa Xaa
1               5                   10                  15
Xaa
```

( 2 ) INFORMATION FOR SEQ ID NO: 194:

( i ) SEQUENCE CHARACTERISTICS:
    ( A ) LENGTH: 16 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in locations 2 to 16 is an amino acid.

( x i ) SEQUENCE DESCRIPTION: SEQ ID NO: 194:

```
Cys Xaa Xaa Xaa Xaa Xaa Xaa Xaa Xaa Xaa Xaa Xaa Xaa Xaa Xaa Xaa
1               5                   10                  15
```

( 2 ) INFORMATION FOR SEQ ID NO: 195:

( i ) SEQUENCE CHARACTERISTICS:
    ( A ) LENGTH: 15 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in locations 2 to 15 is an amino acid.

( x i ) SEQUENCE DESCRIPTION: SEQ ID NO: 195:

```
Cys Xaa Xaa Xaa Xaa Xaa Xaa Xaa Xaa Xaa Xaa Xaa Xaa Xaa Xaa
1               5                   10                  15
```

( 2 ) INFORMATION FOR SEQ ID NO: 196:

(  i  ) SEQUENCE CHARACTERISTICS:
( A ) LENGTH: 14 amino acids
( B ) TYPE: amino acid
( D ) TOPOLOGY: linear ( v ) FRAGMENT TYPE: internal fragment ( i x ) FEATURE:
( D ) OTHER INFORMATION: Xaa in locations 2 to 14 is an
amino acid.

( x i ) SEQUENCE DESCRIPTION: SEQ ID NO: 196:

Cys  Xaa  Xaa  Xaa  Xaa  Xaa  Xaa  Xaa  Xaa  Xaa  Xaa  Xaa  Xaa  Xaa
1                     5                               10

( 2 ) INFORMATION FOR SEQ ID NO: 197:

(  i  ) SEQUENCE CHARACTERISTICS:
( A ) LENGTH: 13 amino acids
( B ) TYPE: amino acid
( D ) TOPOLOGY: linear ( v ) FRAGMENT TYPE: internal fragment ( i x ) FEATURE:
( D ) OTHER INFORMATION: Xaa in locations 2 to 13 is an
amino acid.

( x i ) SEQUENCE DESCRIPTION: SEQ ID NO: 197:

Cys  Xaa  Xaa  Xaa  Xaa  Xaa  Xaa  Xaa  Xaa  Xaa  Xaa  Xaa  Xaa
1                     5                               10

( 2 ) INFORMATION FOR SEQ ID NO: 198:

(  i  ) SEQUENCE CHARACTERISTICS:
( A ) LENGTH: 12 amino acids
( B ) TYPE: amino acid
( D ) TOPOLOGY: linear ( v ) FRAGMENT TYPE: internal fragment ( i x ) FEATURE:
( D ) OTHER INFORMATION: Xaa in locations 2 to 12 is an
amino acid.

( x i ) SEQUENCE DESCRIPTION: SEQ ID NO: 198:

Cys  Xaa  Xaa  Xaa  Xaa  Xaa  Xaa  Xaa  Xaa  Xaa  Xaa  Xaa
1                     5                               10

( 2 ) INFORMATION FOR SEQ ID NO: 199:

(  i  ) SEQUENCE CHARACTERISTICS:
( A ) LENGTH: 11 amino acids
( B ) TYPE: amino acid
( D ) TOPOLOGY: linear ( v ) FRAGMENT TYPE: internal fragment ( i x ) FEATURE:
( D ) OTHER INFORMATION: Xaa in locations 2 to 11 is an
amino acid.

( x i ) SEQUENCE DESCRIPTION: SEQ ID NO: 199:

Cys  Xaa  Xaa  Xaa  Xaa  Xaa  Xaa  Xaa  Xaa  Xaa  Xaa
1                     5                               10

( 2 ) INFORMATION FOR SEQ ID NO: 200:

(  i  ) SEQUENCE CHARACTERISTICS:
( A ) LENGTH: 10 amino acids
( B ) TYPE: amino acid -continued ( D ) TOPOLOGY: linear ( v ) FRAGMENT TYPE: internal fragment ( i x ) FEATURE:
        ( D ) OTHER INFORMATION: Xaa in locations 2 to 10 is an
        amino acid.

( x i ) SEQUENCE DESCRIPTION: SEQ ID NO: 200:

```
Cys  Xaa  Xaa  Xaa  Xaa  Xaa  Xaa  Xaa  Xaa  Xaa
1                 5                          1 0
```

( 2 ) INFORMATION FOR SEQ ID NO: 201:

( i ) SEQUENCE CHARACTERISTICS:
        ( A ) LENGTH: 9 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 9 is an
        amino acid.

( x i ) SEQUENCE DESCRIPTION: SEQ ID NO: 201:

```
Cys  Xaa  Xaa  Xaa  Xaa  Xaa  Xaa  Xaa  Xaa
1                 5
```

( 2 ) INFORMATION FOR SEQ ID NO: 202:

( i ) SEQUENCE CHARACTERISTICS:
        ( A ) LENGTH: 8 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 8 is an
        amino acid.

( x i ) SEQUENCE DESCRIPTION: SEQ ID NO: 202:

```
Cys  Xaa  Xaa  Xaa  Xaa  Xaa  Xaa  Xaa
1                 5
```

( 2 ) INFORMATION FOR SEQ ID NO: 203:

( i ) SEQUENCE CHARACTERISTICS:
        ( A ) LENGTH: 7 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 7 is an
        amino acid.

( x i ) SEQUENCE DESCRIPTION: SEQ ID NO: 203:

```
Cys  Xaa  Xaa  Xaa  Xaa  Xaa  Xaa
1                 5
```

( 2 ) INFORMATION FOR SEQ ID NO: 204:

( i ) SEQUENCE CHARACTERISTICS:
        ( A ) LENGTH: 6 amino acids
        ( B ) TYPE: amino acid
        ( D ) TOPOLOGY: linear ( v ) FRAGMENT TYPE: internal fragment ( i x ) FEATURE:
    ( D ) OTHER INFORMATION: Xaa in locations 2 to 6 is an amino acid.

( x i ) SEQUENCE DESCRIPTION: SEQ ID NO: 204:

Cys Xaa Xaa Xaa Xaa Xaa
1               5

( 2 ) INFORMATION FOR SEQ ID NO: 205:

( i ) SEQUENCE CHARACTERISTICS:
        ( A ) LENGTH: 8 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 8 is an amino acid.

( x i ) SEQUENCE DESCRIPTION: SEQ ID NO: 205:

Cys Xaa Xaa Xaa Xaa Xaa Xaa Xaa
1               5

( 2 ) INFORMATION FOR SEQ ID NO: 206:

( i ) SEQUENCE CHARACTERISTICS:
        ( A ) LENGTH: 7 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 6 is an amino acid.

( x i ) SEQUENCE DESCRIPTION: SEQ ID NO: 206:

Cys Xaa Xaa Xaa Xaa Xaa Cys
1               5

( 2 ) INFORMATION FOR SEQ ID NO: 207:

( i ) SEQUENCE CHARACTERISTICS:
        ( A ) LENGTH: 6 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 5 is an amino acid.

( x i ) SEQUENCE DESCRIPTION: SEQ ID NO: 207:

Cys Xaa Xaa Xaa Xaa Cys
1               5

( 2 ) INFORMATION FOR SEQ ID NO: 208:

( i ) SEQUENCE CHARACTERISTICS:
        ( A ) LENGTH: 5 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 4 is an amino acid.

( x i ) SEQUENCE DESCRIPTION: SEQ ID NO: 208:

Cys Xaa Xaa Xaa Cys
1               5

( 2 ) INFORMATION FOR SEQ ID NO: 209:

( i ) SEQUENCE CHARACTERISTICS:
        ( A ) LENGTH: 23 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 23 is an amino
            acid.

( x i ) SEQUENCE DESCRIPTION: SEQ ID NO: 209:

Xaa Xaa Xaa Cys Xaa Xaa Xaa Xaa Xaa Xaa Xaa Xaa Xaa Xaa Xaa Xaa
1               5                       1 0                      1 5
Xaa Xaa Xaa Xaa Xaa Xaa Xaa
                2 0

( 2 ) INFORMATION FOR SEQ ID NO: 210:

( i ) SEQUENCE CHARACTERISTICS:
        ( A ) LENGTH: 22 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 22 is an amino
            acid.

( x i ) SEQUENCE DESCRIPTION: SEQ ID NO: 210:

Xaa Xaa Xaa Cys Xaa Xaa Xaa Xaa Xaa Xaa Xaa Xaa Xaa Xaa Xaa Xaa
1               5                       1 0                      1 5
Xaa Xaa Xaa Xaa Xaa Xaa
                2 0

( 2 ) INFORMATION FOR SEQ ID NO: 211:

( i ) SEQUENCE CHARACTERISTICS:
        ( A ) LENGTH: 21 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 21 is an amino
            acid.

( x i ) SEQUENCE DESCRIPTION: SEQ ID NO: 211:

Xaa Xaa Xaa Cys Xaa Xaa Xaa Xaa Xaa Xaa Xaa Xaa Xaa Xaa Xaa Xaa
1               5                       1 0                      1 5
Xaa Xaa Xaa Xaa Xaa
                2 0

( 2 ) INFORMATION FOR SEQ ID NO: 212:

( i ) SEQUENCE CHARACTERISTICS:
        ( A ) LENGTH: 20 amino acids
        ( B ) TYPE: amino acid (D) TOPOLOGY: linear (v) FRAGMENT TYPE: internal fragment (ix) FEATURE:
  (D) OTHER INFORMATION: Xaa in locations 1 to 3 and
    locations 5 to 20 is an amino
    acid.

(xi) SEQUENCE DESCRIPTION: SEQ ID NO: 212:

Xaa Xaa Xaa Cys Xaa Xaa Xaa Xaa Xaa Xaa Xaa Xaa Xaa Xaa Xaa
1               5                   10                  15
Xaa Xaa Xaa Xaa
            20

(2) INFORMATION FOR SEQ ID NO: 213:

(i) SEQUENCE CHARACTERISTICS:
    (A) LENGTH: 19 amino acids
    (B) TYPE: amino acid
    (D) TOPOLOGY: linear (v) FRAGMENT TYPE: internal fragment (ix) FEATURE:
    (D) OTHER INFORMATION: Xaa in locations 1 to 3 and
      locations 5 to 19 is an amino
      acid.

(xi) SEQUENCE DESCRIPTION: SEQ ID NO: 213:

Xaa Xaa Xaa Cys Xaa Xaa Xaa Xaa Xaa Xaa Xaa Xaa Xaa Xaa Xaa
1               5                   10                  15
Xaa Xaa Xaa (2) INFORMATION FOR SEQ ID NO: 214:

(i) SEQUENCE CHARACTERISTICS:
    (A) LENGTH: 18 amino acids
    (B) TYPE: amino acid
    (D) TOPOLOGY: linear (v) FRAGMENT TYPE: internal fragment (ix) FEATURE:
    (D) OTHER INFORMATION: Xaa in locations 1 to 3 and
      locations 5 to 18 is an amino
      acid.

(xi) SEQUENCE DESCRIPTION: SEQ ID NO: 214:

Xaa Xaa Xaa Cys Xaa Xaa Xaa Xaa Xaa Xaa Xaa Xaa Xaa Xaa Xaa
1               5                   10                  15
Xaa Xaa (2) INFORMATION FOR SEQ ID NO: 215:

(i) SEQUENCE CHARACTERISTICS:
    (A) LENGTH: 17 amino acids
    (B) TYPE: amino acid
    (D) TOPOLOGY: linear (v) FRAGMENT TYPE: internal fragment (ix) FEATURE:
    (D) OTHER INFORMATION: Xaa in locations 1 to 3 and
      locations 5 to 17 is an amino
      acid.

(xi) SEQUENCE DESCRIPTION: SEQ ID NO: 215:

Xaa Xaa Xaa Cys Xaa Xaa Xaa Xaa Xaa Xaa Xaa Xaa Xaa Xaa Xaa
1               5                   10                  15

Xaa (2) INFORMATION FOR SEQ ID NO: 216:

(i) SEQUENCE CHARACTERISTICS:
        (A) LENGTH: 16 amino acids
        (B) TYPE: amino acid
        (D) TOPOLOGY: linear (v) FRAGMENT TYPE: internal fragment (ix) FEATURE:
        (D) OTHER INFORMATION: Xaa in locations 1 to 3 and
            locations 5 to 16 is an amino
            acid.

(xi) SEQUENCE DESCRIPTION: SEQ ID NO: 216:

Xaa Xaa Xaa Cys Xaa Xaa Xaa Xaa Xaa Xaa Xaa Xaa Xaa Xaa Xaa Xaa
1             5                   10                  15

(2) INFORMATION FOR SEQ ID NO: 217:

(i) SEQUENCE CHARACTERISTICS:
        (A) LENGTH: 15 amino acids
        (B) TYPE: amino acid
        (D) TOPOLOGY: linear (v) FRAGMENT TYPE: internal fragment (ix) FEATURE:
        (D) OTHER INFORMATION: Xaa in locations 1 to 3 and
            locations 5 to 15 is an amino
            acid.

(xi) SEQUENCE DESCRIPTION: SEQ ID NO: 217:

Xaa Xaa Xaa Cys Xaa Xaa Xaa Xaa Xaa Xaa Xaa Xaa Xaa Xaa Xaa
1             5                   10                  15

(2) INFORMATION FOR SEQ ID NO: 218:

(i) SEQUENCE CHARACTERISTICS:
        (A) LENGTH: 14 amino acids
        (B) TYPE: amino acid
        (D) TOPOLOGY: linear (v) FRAGMENT TYPE: internal fragment (ix) FEATURE:
        (D) OTHER INFORMATION: Xaa in locations 1 to 3 and
            locations 5 to 14 is an amino
            acid.

(xi) SEQUENCE DESCRIPTION: SEQ ID NO: 218:

Xaa Xaa Xaa Cys Xaa Xaa Xaa Xaa Xaa Xaa Xaa Xaa Xaa Xaa
1             5                   10

(2) INFORMATION FOR SEQ ID NO: 219:

(i) SEQUENCE CHARACTERISTICS:
        (A) LENGTH: 13 amino acids
        (B) TYPE: amino acid
        (D) TOPOLOGY: linear (v) FRAGMENT TYPE: internal fragment (ix) FEATURE:
        (D) OTHER INFORMATION: Xaa in locations 1 to 3 and
            locations 5 to 13 is an amino
            acid.

(xi) SEQUENCE DESCRIPTION: SEQ ID NO: 219:

```
Xaa  Xaa  Xaa  Cys  Xaa  Xaa  Xaa  Xaa  Xaa  Xaa  Xaa  Xaa  Xaa
 1                 5                             10
```

( 2 ) INFORMATION FOR SEQ ID NO: 220:

( i ) SEQUENCE CHARACTERISTICS:
        ( A ) LENGTH: 12 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 12 is an amino
            acid.

( x i ) SEQUENCE DESCRIPTION: SEQ ID NO: 220:

```
Xaa  Xaa  Xaa  Cys  Xaa  Xaa  Xaa  Xaa  Xaa  Xaa  Xaa  Xaa
 1                 5                             10
```

( 2 ) INFORMATION FOR SEQ ID NO: 221:

( i ) SEQUENCE CHARACTERISTICS:
        ( A ) LENGTH: 11 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 11 is an amino
            acid.

( x i ) SEQUENCE DESCRIPTION: SEQ ID NO: 221:

```
Xaa  Xaa  Xaa  Cys  Xaa  Xaa  Xaa  Xaa  Xaa  Xaa  Xaa
 1                 5                             10
```

( 2 ) INFORMATION FOR SEQ ID NO: 222:

( i ) SEQUENCE CHARACTERISTICS:
        ( A ) LENGTH: 10 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 10 is an amino
            acid.

( x i ) SEQUENCE DESCRIPTION: SEQ ID NO: 222:

```
Xaa  Xaa  Xaa  Cys  Xaa  Xaa  Xaa  Xaa  Xaa  Xaa
 1                 5                             10
```

( 2 ) INFORMATION FOR SEQ ID NO: 223:

( i ) SEQUENCE CHARACTERISTICS:
        ( A ) LENGTH: 5 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 5 is
            an amino acid.

( x i ) SEQUENCE DESCRIPTION: SEQ ID NO: 223:

```
Cys  Xaa  Xaa  Xaa  Xaa
```

( 2 ) INFORMATION FOR SEQ ID NO: 224:

( i ) SEQUENCE CHARACTERISTICS:
        ( A ) LENGTH: 4 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 4 is an amino acid.

( x i ) SEQUENCE DESCRIPTION: SEQ ID NO: 224:

Cys Xaa Xaa Xaa
1

( 2 ) INFORMATION FOR SEQ ID NO: 225:

( i ) SEQUENCE CHARACTERISTICS:
        ( A ) LENGTH: 6 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 6 is an amino acid.

( x i ) SEQUENCE DESCRIPTION: SEQ ID NO: 225:

Cys Xaa Xaa Xaa Xaa Xaa
1                       5

( 2 ) INFORMATION FOR SEQ ID NO: 226:

( i ) SEQUENCE CHARACTERISTICS:
        ( A ) LENGTH: 5 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 5 is an amino acid.

( x i ) SEQUENCE DESCRIPTION: SEQ ID NO: 226:

Cys Xaa Xaa Xaa Xaa
1                 5

( 2 ) INFORMATION FOR SEQ ID NO: 227:

( i ) SEQUENCE CHARACTERISTICS:
        ( A ) LENGTH: 4 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 4 is an amino acid.

( x i ) SEQUENCE DESCRIPTION: SEQ ID NO: 227:

Cys Xaa Xaa Xaa
1

( 2 ) INFORMATION FOR SEQ ID NO: 228:

( i ) SEQUENCE CHARACTERISTICS:
 ( A ) LENGTH: 15 amino acids
 ( B ) TYPE: amino acid
 ( D ) TOPOLOGY: linear ( v ) FRAGMENT TYPE: internal fragment ( i x ) FEATURE:
 ( D ) OTHER INFORMATION: Xaa in location 2 and
 locations 4 to 15 is an amino
 acid.

( x i ) SEQUENCE DESCRIPTION: SEQ ID NO: 228:

Cys Xaa Cys Xaa Xaa Xaa Xaa Xaa Xaa Xaa Xaa Xaa Xaa Xaa Xaa
1               5                             10                            15

( 2 ) INFORMATION FOR SEQ ID NO: 229:

( i ) SEQUENCE CHARACTERISTICS:
  ( A ) LENGTH: 14 amino acids
  ( B ) TYPE: amino acid
  ( D ) TOPOLOGY: linear ( v ) FRAGMENT TYPE: internal fragment ( i x ) FEATURE:
  ( D ) OTHER INFORMATION: Xaa in location 2 and
  locations 4 to 14 is an amino
  acid.

( x i ) SEQUENCE DESCRIPTION: SEQ ID NO: 229:

Cys Xaa Cys Xaa Xaa Xaa Xaa Xaa Xaa Xaa Xaa Xaa Xaa Xaa
1               5                             10

( 2 ) INFORMATION FOR SEQ ID NO: 230:

( i ) SEQUENCE CHARACTERISTICS:
  ( A ) LENGTH: 8 amino acids
  ( B ) TYPE: amino acid
  ( D ) TOPOLOGY: linear ( v ) FRAGMENT TYPE: internal fragment ( i x ) FEATURE:
  ( D ) OTHER INFORMATION: Xaa in locations 2 to 8 is
  an amino acid.

( x i ) SEQUENCE DESCRIPTION: SEQ ID NO: 230:

Cys Xaa Xaa Xaa Xaa Xaa Xaa Xaa
1               5

( 2 ) INFORMATION FOR SEQ ID NO: 231:

( i ) SEQUENCE CHARACTERISTICS:
  ( A ) LENGTH: 7 amino acids
  ( B ) TYPE: amino acid
  ( D ) TOPOLOGY: linear ( v ) FRAGMENT TYPE: internal fragment ( i x ) FEATURE:
  ( D ) OTHER INFORMATION: Xaa in locations 2 to 7 is
  an amino acid.

( x i ) SEQUENCE DESCRIPTION: SEQ ID NO: 231:

Cys Xaa Xaa Xaa Xaa Xaa Xaa
1               5

( 2 ) INFORMATION FOR SEQ ID NO: 232:

( i ) SEQUENCE CHARACTERISTICS:

(A) LENGTH: 6 amino acids
                (B) TYPE: amino acid
                (D) TOPOLOGY: linear (v) FRAGMENT TYPE: internal fragment (ix) FEATURE:
                (D) OTHER INFORMATION: Xaa in locations 2 to 6 is
                    an amino acid.

(xi) SEQUENCE DESCRIPTION: SEQ ID NO: 232:

Cys  Xaa  Xaa  Xaa  Xaa  Xaa
1                    5

(2) INFORMATION FOR SEQ ID NO: 233:

(i) SEQUENCE CHARACTERISTICS:
                (A) LENGTH: 26 amino acids
                (B) TYPE: amino acid
                (D) TOPOLOGY: linear (v) FRAGMENT TYPE: internal fragment (ix) FEATURE:
                (D) OTHER INFORMATION: Xaa in locations 2 to 26 is an
                    amino acid.

(xi) SEQUENCE DESCRIPTION: SEQ ID NO: 233:

Cys  Xaa  Xaa  Xaa  Xaa  Xaa  Xaa  Xaa  Xaa  Xaa  Xaa  Xaa  Xaa  Xaa  Xaa  Xaa
1                    5                              10                             15

Xaa  Xaa  Xaa  Xaa  Xaa  Xaa  Xaa  Xaa  Xaa  Xaa
                    20                             25

(2) INFORMATION FOR SEQ ID NO: 234:

(i) SEQUENCE CHARACTERISTICS:
                (A) LENGTH: 25 amino acids
                (B) TYPE: amino acid
                (D) TOPOLOGY: linear (v) FRAGMENT TYPE: internal fragment (ix) FEATURE:
                (D) OTHER INFORMATION: Xaa in locations 2 to 25 is an
                    amino acid.

(xi) SEQUENCE DESCRIPTION: SEQ ID NO: 234:

Cys  Xaa  Xaa  Xaa  Xaa  Xaa  Xaa  Xaa  Xaa  Xaa  Xaa  Xaa  Xaa  Xaa  Xaa  Xaa
1                    5                              10                             15

Xaa  Xaa  Xaa  Xaa  Xaa  Xaa  Xaa  Xaa  Xaa
                    20                             25

(2) INFORMATION FOR SEQ ID NO: 235:

(i) SEQUENCE CHARACTERISTICS:
                (A) LENGTH: 24 amino acids
                (B) TYPE: amino acid
                (D) TOPOLOGY: linear (v) FRAGMENT TYPE: internal fragment (ix) FEATURE:
                (D) OTHER INFORMATION: Xaa in locations 2 to 24 is an
                    amino acid.

(xi) SEQUENCE DESCRIPTION: SEQ ID NO: 235:

Cys  Xaa  Xaa  Xaa  Xaa  Xaa  Xaa  Xaa  Xaa  Xaa  Xaa  Xaa  Xaa  Xaa  Xaa  Xaa
1                    5                              10                             15

Xaa  Xaa  Xaa  Xaa  Xaa  Xaa  Xaa  Xaa
                    20

( 2 ) INFORMATION FOR SEQ ID NO: 236:

( i ) SEQUENCE CHARACTERISTICS:
        ( A ) LENGTH: 23 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 23 is an
            amino acid.

( x i ) SEQUENCE DESCRIPTION: SEQ ID NO: 236:

Cys Xaa Xaa Xaa Xaa Xaa Xaa Xaa Xaa Xaa Xaa Xaa Xaa Xaa Xaa Xaa
1               5                    1 0                 1 5

Xaa Xaa Xaa Xaa Xaa Xaa Xaa
           2 0

( 2 ) INFORMATION FOR SEQ ID NO: 237:

( i ) SEQUENCE CHARACTERISTICS:
        ( A ) LENGTH: 22 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 22 is an
            amino acid.

( x i ) SEQUENCE DESCRIPTION: SEQ ID NO: 237:

Cys Xaa Xaa Xaa Xaa Xaa Xaa Xaa Xaa Xaa Xaa Xaa Xaa Xaa Xaa Xaa
1               5                    1 0                 1 5

Xaa Xaa Xaa Xaa Xaa Xaa
           2 0

( 2 ) INFORMATION FOR SEQ ID NO: 238:

( i ) SEQUENCE CHARACTERISTICS:
        ( A ) LENGTH: 21 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 21 is an
            amino acid.

( x i ) SEQUENCE DESCRIPTION: SEQ ID NO: 238:

Cys Xaa Xaa Xaa Xaa Xaa Xaa Xaa Xaa Xaa Xaa Xaa Xaa Xaa Xaa Xaa
1               5                    1 0                 1 5

Xaa Xaa Xaa Xaa Xaa
           2 0

( 2 ) INFORMATION FOR SEQ ID NO: 239:

( i ) SEQUENCE CHARACTERISTICS:
        ( A ) LENGTH: 20 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 20 is an
            amino acid.

( x i ) SEQUENCE DESCRIPTION: SEQ ID NO: 239:

Cys Xaa Xaa Xaa Xaa Xaa Xaa Xaa Xaa Xaa Xaa Xaa Xaa Xaa Xaa Xaa
1               5                       10                      15

Xaa Xaa Xaa Xaa
            20

( 2 ) INFORMATION FOR SEQ ID NO: 240:

( i ) SEQUENCE CHARACTERISTICS:
        ( A ) LENGTH: 19 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 19 is an amino acid.

( x i ) SEQUENCE DESCRIPTION: SEQ ID NO: 240:

Cys Xaa Xaa Xaa Xaa Xaa Xaa Xaa Xaa Xaa Xaa Xaa Xaa Xaa Xaa Xaa
1               5                       10                      15

Xaa Xaa Xaa ( 2 ) INFORMATION FOR SEQ ID NO: 241:

( i ) SEQUENCE CHARACTERISTICS:
        ( A ) LENGTH: 18 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 18 is an amino acid.

( x i ) SEQUENCE DESCRIPTION: SEQ ID NO: 241:

Cys Xaa Xaa Xaa Xaa Xaa Xaa Xaa Xaa Xaa Xaa Xaa Xaa Xaa Xaa Xaa
1               5                       10                      15

Xaa Xaa ( 2 ) INFORMATION FOR SEQ ID NO: 242:

( i ) SEQUENCE CHARACTERISTICS:
        ( A ) LENGTH: 17 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 17 is an amino acid.

( x i ) SEQUENCE DESCRIPTION: SEQ ID NO: 242:

Cys Xaa Xaa Xaa Xaa Xaa Xaa Xaa Xaa Xaa Xaa Xaa Xaa Xaa Xaa Xaa
1               5                       10                      15

Xaa ( 2 ) INFORMATION FOR SEQ ID NO: 243:

( i ) SEQUENCE CHARACTERISTICS:
        ( A ) LENGTH: 16 amino acids
        ( B ) TYPE: amino acid
        ( D ) TOPOLOGY: linear ( v ) FRAGMENT TYPE: internal fragment ( i x ) FEATURE:
                    ( D ) OTHER INFORMATION: Xaa in locations 2 to 16 is an
                          amino acid.

( x i ) SEQUENCE DESCRIPTION: SEQ ID NO: 243:

Cys  Xaa  Xaa  Xaa  Xaa  Xaa  Xaa  Xaa  Xaa  Xaa  Xaa  Xaa  Xaa  Xaa  Xaa  Xaa
1                  5                            10                           15

( 2 ) INFORMATION FOR SEQ ID NO: 244:

( i ) SEQUENCE CHARACTERISTICS:
                    ( A ) LENGTH: 15 amino acids
                    ( B ) TYPE: amino acid
                    ( D ) TOPOLOGY: linear ( v ) FRAGMENT TYPE: internal fragment ( i x ) FEATURE:
                    ( D ) OTHER INFORMATION: Xaa in locations 2 to 15 is an
                          amino acid.

( x i ) SEQUENCE DESCRIPTION: SEQ ID NO: 244:

Cys  Xaa  Xaa  Xaa  Xaa  Xaa  Xaa  Xaa  Xaa  Xaa  Xaa  Xaa  Xaa  Xaa  Xaa
1                  5                            10                       15

( 2 ) INFORMATION FOR SEQ ID NO: 245:

( i ) SEQUENCE CHARACTERISTICS:
                    ( A ) LENGTH: 14 amino acids
                    ( B ) TYPE: amino acid
                    ( D ) TOPOLOGY: linear ( v ) FRAGMENT TYPE: internal fragment ( i x ) FEATURE:
                    ( D ) OTHER INFORMATION: Xaa in locations 2 to 14 is an
                          amino acid.

( x i ) SEQUENCE DESCRIPTION: SEQ ID NO: 245:

Cys  Xaa  Xaa  Xaa  Xaa  Xaa  Xaa  Xaa  Xaa  Xaa  Xaa  Xaa  Xaa  Xaa
1                  5                            10

( 2 ) INFORMATION FOR SEQ ID NO: 246:

( i ) SEQUENCE CHARACTERISTICS:
                    ( A ) LENGTH: 13 amino acids
                    ( B ) TYPE: amino acid
                    ( D ) TOPOLOGY: linear ( v ) FRAGMENT TYPE: internal fragment ( i x ) FEATURE:
                    ( D ) OTHER INFORMATION: Xaa in locations 2 to 13 is an
                          amino acid.

( x i ) SEQUENCE DESCRIPTION: SEQ ID NO: 246:

Cys  Xaa  Xaa  Xaa  Xaa  Xaa  Xaa  Xaa  Xaa  Xaa  Xaa  Xaa  Xaa
1                  5                            10

( 2 ) INFORMATION FOR SEQ ID NO: 247:

( i ) SEQUENCE CHARACTERISTICS:
                    ( A ) LENGTH: 12 amino acids
                    ( B ) TYPE: amino acid
                    ( D ) TOPOLOGY: linear ( v ) FRAGMENT TYPE: internal fragment ( i x ) FEATURE:
                    ( D ) OTHER INFORMATION: Xaa in locations 2 to 12 is an amino acid.

( x i ) SEQUENCE DESCRIPTION: SEQ ID NO: 247:

Cys Xaa Xaa Xaa Xaa Xaa Xaa Xaa Xaa Xaa Xaa Xaa
1               5                           10

( 2 ) INFORMATION FOR SEQ ID NO: 248:

( i ) SEQUENCE CHARACTERISTICS:
        ( A ) LENGTH: 11 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 11 is an
            amino acid.

( x i ) SEQUENCE DESCRIPTION: SEQ ID NO: 248:

Cys Xaa Xaa Xaa Xaa Xaa Xaa Xaa Xaa Xaa Xaa
1               5                        10

( 2 ) INFORMATION FOR SEQ ID NO: 249:

( i ) SEQUENCE CHARACTERISTICS:
        ( A ) LENGTH: 10 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 10 is an
            amino acid.

( x i ) SEQUENCE DESCRIPTION: SEQ ID NO: 249:

Cys Xaa Xaa Xaa Xaa Xaa Xaa Xaa Xaa Xaa
1               5                    10

( 2 ) INFORMATION FOR SEQ ID NO: 250:

( i ) SEQUENCE CHARACTERISTICS:
        ( A ) LENGTH: 9 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 9 is an
            amino acid.

( x i ) SEQUENCE DESCRIPTION: SEQ ID NO: 250:

Cys Xaa Xaa Xaa Xaa Xaa Xaa Xaa Xaa
1               5

( 2 ) INFORMATION FOR SEQ ID NO: 251:

( i ) SEQUENCE CHARACTERISTICS:
        ( A ) LENGTH: 8 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 8 is an
            amino acid.

( x i ) SEQUENCE DESCRIPTION: SEQ ID NO: 251:

Cys Xaa Xaa Xaa Xaa Xaa Xaa Xaa
1               5

(2) INFORMATION FOR SEQ ID NO: 252:

(i) SEQUENCE CHARACTERISTICS:
        (A) LENGTH: 7 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 7 is an
            amino acid.

(xi) SEQUENCE DESCRIPTION: SEQ ID NO: 252:

Cys Xaa Xaa Xaa Xaa Xaa Xaa
1               5

(2) INFORMATION FOR SEQ ID NO: 253:

(i) SEQUENCE CHARACTERISTICS:
        (A) LENGTH: 6 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 6 is an
            amino acid.

(xi) SEQUENCE DESCRIPTION: SEQ ID NO: 253:

Cys Xaa Xaa Xaa Xaa Xaa
1               5

(2) INFORMATION FOR SEQ ID NO: 254:

(i) SEQUENCE CHARACTERISTICS:
        (A) LENGTH: 8 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 8
            is an amino acid.

(xi) SEQUENCE DESCRIPTION: SEQ ID NO: 254:

Cys Xaa Xaa Xaa Xaa Xaa Xaa Xaa
1               5

(2) INFORMATION FOR SEQ ID NO: 255:

(i) SEQUENCE CHARACTERISTICS:
        (A) LENGTH: 7 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 6 is
            an amino acid.

(xi) SEQUENCE DESCRIPTION: SEQ ID NO: 255:

Cys Xaa Xaa Xaa Xaa Xaa Cys
1               5

( 2 ) INFORMATION FOR SEQ ID NO: 256:

( i ) SEQUENCE CHARACTERISTICS:
        ( A ) LENGTH: 6 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 5 is
            an amino acid.

( x i ) SEQUENCE DESCRIPTION: SEQ ID NO: 256:

Cys  Xaa  Xaa  Xaa  Xaa  Cys
1                       5

( 2 ) INFORMATION FOR SEQ ID NO: 257:

( i ) SEQUENCE CHARACTERISTICS:
        ( A ) LENGTH: 5 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 4 is
            an amino acid.

( x i ) SEQUENCE DESCRIPTION: SEQ ID NO: 257:

Cys  Xaa  Xaa  Xaa  Cys
1                  5

( 2 ) INFORMATION FOR SEQ ID NO: 258:

( i ) SEQUENCE CHARACTERISTICS:
        ( A ) LENGTH: 23 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 23 is an amino
            acid.

( x i ) SEQUENCE DESCRIPTION: SEQ ID NO: 258:

Xaa  Xaa  Xaa  Cys  Xaa  Xaa  Xaa  Xaa  Xaa  Xaa  Xaa  Xaa  Xaa  Xaa  Xaa  Xaa
1                   5                             10                            15
Xaa  Xaa  Xaa  Xaa  Xaa  Xaa  Xaa
                    20

( 2 ) INFORMATION FOR SEQ ID NO: 259:

( i ) SEQUENCE CHARACTERISTICS:
        ( A ) LENGTH: 22 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 22 is an amino
            acid.

( x i ) SEQUENCE DESCRIPTION: SEQ ID NO: 259:

Xaa  Xaa  Xaa  Cys  Xaa  Xaa  Xaa  Xaa  Xaa  Xaa  Xaa  Xaa  Xaa  Xaa  Xaa  Xaa
1                   5                             10                            15

Xaa Xaa Xaa Xaa Xaa Xaa
                  20

( 2 ) INFORMATION FOR SEQ ID NO: 260:

( i ) SEQUENCE CHARACTERISTICS:
        ( A ) LENGTH: 21 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 21 is an amino
            acid.

( x i ) SEQUENCE DESCRIPTION: SEQ ID NO: 260:

Xaa Xaa Xaa Cys Xaa Xaa Xaa Xaa Xaa Xaa Xaa Xaa Xaa Xaa Xaa Xaa
1                 5                         1 0                        1 5
Xaa Xaa Xaa Xaa Xaa
                  20

( 2 ) INFORMATION FOR SEQ ID NO: 261:

( i ) SEQUENCE CHARACTERISTICS:
        ( A ) LENGTH: 20 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 20 is an amino
            acid.

( x i ) SEQUENCE DESCRIPTION: SEQ ID NO: 261:

Xaa Xaa Xaa Cys Xaa Xaa Xaa Xaa Xaa Xaa Xaa Xaa Xaa Xaa Xaa Xaa
1                 5                         1 0                        1 5
Xaa Xaa Xaa Xaa
              20

( 2 ) INFORMATION FOR SEQ ID NO: 262:

( i ) SEQUENCE CHARACTERISTICS:
        ( A ) LENGTH: 19 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 19 is an amino
            acid.

( x i ) SEQUENCE DESCRIPTION: SEQ ID NO: 262:

Xaa Xaa Xaa Cys Xaa Xaa Xaa Xaa Xaa Xaa Xaa Xaa Xaa Xaa Xaa Xaa
1                 5                         1 0                        1 5
Xaa Xaa Xaa ( 2 ) INFORMATION FOR SEQ ID NO: 263:

( i ) SEQUENCE CHARACTERISTICS:
        ( A ) LENGTH: 18 amino acids
        ( B ) TYPE: amino acid
        ( D ) TOPOLOGY: linear ( v ) FRAGMENT TYPE: internal fragment (ix) FEATURE:
    (D) OTHER INFORMATION: Xaa in locations 1 to 3 and
        locations 5 to 18 is an amino
        acid.

(xi) SEQUENCE DESCRIPTION: SEQ ID NO: 263:

Xaa Xaa Xaa Cys Xaa Xaa Xaa Xaa Xaa Xaa Xaa Xaa Xaa Xaa Xaa Xaa
1                    5                          10                     15

Xaa Xaa (2) INFORMATION FOR SEQ ID NO: 264:

(i) SEQUENCE CHARACTERISTICS:
        (A) LENGTH: 17 amino acids
        (B) TYPE: amino acid
        (D) TOPOLOGY: linear (v) FRAGMENT TYPE: internal fragment (ix) FEATURE:
        (D) OTHER INFORMATION: Xaa in locations 1 to 3 and
            locations 5 to 17 is an amino
            acid.

(xi) SEQUENCE DESCRIPTION: SEQ ID NO: 264:

Xaa Xaa Xaa Cys Xaa Xaa Xaa Xaa Xaa Xaa Xaa Xaa Xaa Xaa Xaa Xaa
1                    5                          10                     15

Xaa (2) INFORMATION FOR SEQ ID NO: 265:

(i) SEQUENCE CHARACTERISTICS:
        (A) LENGTH: 16 amino acids
        (B) TYPE: amino acid
        (D) TOPOLOGY: linear (v) FRAGMENT TYPE: internal fragment (ix) FEATURE:
        (D) OTHER INFORMATION: Xaa in locations 1 to 3 and
            locations 5 to 16 is an amino
            acid.

(xi) SEQUENCE DESCRIPTION: SEQ ID NO: 265:

Xaa Xaa Xaa Cys Xaa Xaa Xaa Xaa Xaa Xaa Xaa Xaa Xaa Xaa Xaa Xaa
1                    5                          10                     15

(2) INFORMATION FOR SEQ ID NO: 266:

(i) SEQUENCE CHARACTERISTICS:
        (A) LENGTH: 15 amino acids
        (B) TYPE: amino acid
        (D) TOPOLOGY: linear (v) FRAGMENT TYPE: internal fragment (ix) FEATURE:
        (D) OTHER INFORMATION: Xaa in locations 1 to 3 and
            locations 5 to 15 is an amino
            acid.

(xi) SEQUENCE DESCRIPTION: SEQ ID NO: 266:

Xaa Xaa Xaa Cys Xaa Xaa Xaa Xaa Xaa Xaa Xaa Xaa Xaa Xaa Xaa
1                    5                          10                     15

(2) INFORMATION FOR SEQ ID NO: 267:

(i) SEQUENCE CHARACTERISTICS:
        (A) LENGTH: 14 amino acids ( B ) TYPE: amino acid
              ( D ) TOPOLOGY: linear ( v ) FRAGMENT TYPE: internal fragment ( i x ) FEATURE:
              ( D ) OTHER INFORMATION: Xaa in locations 1 to 3 and
                    locations 5 to 14 is an amino
                    acid.

( x i ) SEQUENCE DESCRIPTION: SEQ ID NO: 267:

Xaa  Xaa  Xaa  Cys  Xaa  Xaa  Xaa  Xaa  Xaa  Xaa  Xaa  Xaa  Xaa  Xaa
 1              5                        10

( 2 ) INFORMATION FOR SEQ ID NO: 268:

( i ) SEQUENCE CHARACTERISTICS:
              ( A ) LENGTH: 13 amino acids
              ( B ) TYPE: amino acid
              ( D ) TOPOLOGY: linear ( v ) FRAGMENT TYPE: internal fragment ( i x ) FEATURE:
              ( D ) OTHER INFORMATION: Xaa in locations 1 to 3 and
                    locations 5 to 13 is an amino
                    acid.

( x i ) SEQUENCE DESCRIPTION: SEQ ID NO: 268:

Xaa  Xaa  Xaa  Cys  Xaa  Xaa  Xaa  Xaa  Xaa  Xaa  Xaa  Xaa  Xaa
 1              5                        10

( 2 ) INFORMATION FOR SEQ ID NO: 269:

( i ) SEQUENCE CHARACTERISTICS:
              ( A ) LENGTH: 12 amino acids
              ( B ) TYPE: amino acid
              ( D ) TOPOLOGY: linear ( v ) FRAGMENT TYPE: internal fragment ( i x ) FEATURE:
              ( D ) OTHER INFORMATION: Xaa in locations 1 to 3 and
                    locations 5 to 12 is an amino
                    acid.

( x i ) SEQUENCE DESCRIPTION: SEQ ID NO: 269:

Xaa  Xaa  Xaa  Cys  Xaa  Xaa  Xaa  Xaa  Xaa  Xaa  Xaa  Xaa
 1              5                        10

( 2 ) INFORMATION FOR SEQ ID NO: 270:

( i ) SEQUENCE CHARACTERISTICS:
              ( A ) LENGTH: 11 amino acids
              ( B ) TYPE: amino acid
              ( D ) TOPOLOGY: linear ( v ) FRAGMENT TYPE: internal fragment ( i x ) FEATURE:
              ( D ) OTHER INFORMATION: Xaa in locations 1 to 3 and
                    locations 5 to 11 is an amino
                    acid.

( x i ) SEQUENCE DESCRIPTION: SEQ ID NO: 270:

Xaa  Xaa  Xaa  Cys  Xaa  Xaa  Xaa  Xaa  Xaa  Xaa  Xaa
 1              5                        10

( 2 ) INFORMATION FOR SEQ ID NO: 271:

( i ) SEQUENCE CHARACTERISTICS:
              ( A ) LENGTH: 10 amino acids ( B ) TYPE: amino acid
                    ( D ) TOPOLOGY: linear ( v ) FRAGMENT TYPE: internal fragment ( i x ) FEATURE:
                    ( D ) OTHER INFORMATION: Xaa in locations 1 to 3 and
                        locations 5 to 10 is an amino
                        acid.

( x i ) SEQUENCE DESCRIPTION: SEQ ID NO: 271:

Xaa  Xaa  Xaa  Cys  Xaa  Xaa  Xaa  Xaa  Xaa  Xaa
1                  5                           10

( 2 ) INFORMATION FOR SEQ ID NO: 272:

( i ) SEQUENCE CHARACTERISTICS:
                    ( A ) LENGTH: 5 amino acids
                    ( B ) TYPE: amino acid
                    ( D ) TOPOLOGY: linear ( v ) FRAGMENT TYPE: internal fragment ( i x ) FEATURE:
                    ( D ) OTHER INFORMATION: Xaa in locations 2 to 5 is
                        an amino acid.

( x i ) SEQUENCE DESCRIPTION: SEQ ID NO: 272:

Cys  Xaa  Xaa  Xaa  Xaa
1                  5

( 2 ) INFORMATION FOR SEQ ID NO: 273:

( i ) SEQUENCE CHARACTERISTICS:
                    ( A ) LENGTH: 4 amino acids
                    ( B ) TYPE: amino acid
                    ( D ) TOPOLOGY: linear ( v ) FRAGMENT TYPE: internal fragment ( i x ) FEATURE:
                    ( D ) OTHER INFORMATION: Xaa in locations 2 to 4 is
                        an amino acid.

( x i ) SEQUENCE DESCRIPTION: SEQ ID NO: 273:

Cys  Xaa  Xaa  Xaa
1

( 2 ) INFORMATION FOR SEQ ID NO: 274:

( i ) SEQUENCE CHARACTERISTICS:
                    ( A ) LENGTH: 6 amino acids
                    ( B ) TYPE: amino acid
                    ( D ) TOPOLOGY: linear ( v ) FRAGMENT TYPE: internal fragment ( i x ) FEATURE:
                    ( D ) OTHER INFORMATION: Xaa in locations 2 to 6 is
                        an amino acid.

( x i ) SEQUENCE DESCRIPTION: SEQ ID NO: 274:

Cys  Xaa  Xaa  Xaa  Xaa  Xaa
1                  5

( 2 ) INFORMATION FOR SEQ ID NO: 275:

( i ) SEQUENCE CHARACTERISTICS:
                    ( A ) LENGTH: 5 amino acids
                    ( B ) TYPE: amino acid
                    ( D ) TOPOLOGY: linear ( v ) FRAGMENT TYPE: internal fragment ( i x ) FEATURE:
    ( D ) OTHER INFORMATION: Xaa in locations 2 to 5 is
    an amino acid.

( x i ) SEQUENCE DESCRIPTION: SEQ ID NO: 275:

Cys Xaa Xaa Xaa Xaa
1            5

( 2 ) INFORMATION FOR SEQ ID NO: 276:

( i ) SEQUENCE CHARACTERISTICS:
        ( A ) LENGTH: 4 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 4 is
        an amino acid.

( x i ) SEQUENCE DESCRIPTION: SEQ ID NO: 276:

Cys Xaa Xaa Xaa
1

( 2 ) INFORMATION FOR SEQ ID NO: 277:

( i ) SEQUENCE CHARACTERISTICS:
        ( A ) LENGTH: 15 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in location 2 and
        locations 4 to 15 is an amino
        acid.

( x i ) SEQUENCE DESCRIPTION: SEQ ID NO: 277:

Cys Xaa Cys Xaa Xaa Xaa Xaa Xaa Xaa Xaa Xaa Xaa Xaa Xaa Xaa
1            5                              10                             15

( 2 ) INFORMATION FOR SEQ ID NO: 278:

( i ) SEQUENCE CHARACTERISTICS:
        ( A ) LENGTH: 14 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in location 2 and
        locations 4 to 14 is an amino
        acid.

( x i ) SEQUENCE DESCRIPTION: SEQ ID NO: 278:

Cys Xaa Cys Xaa Xaa Xaa Xaa Xaa Xaa Xaa Xaa Xaa Xaa Xaa
1            5                              10

( 2 ) INFORMATION FOR SEQ ID NO: 279:

( i ) SEQUENCE CHARACTERISTICS:
        ( A ) LENGTH: 13 amino acids
        ( B ) TYPE: amino acid
        ( D ) TOPOLOGY: linear ( v ) FRAGMENT TYPE: internal fragment (ix) FEATURE:
    (D) OTHER INFORMATION: Xaa in location 2 and
    locations 4 to 13 is an amino
    acid.

(xi) SEQUENCE DESCRIPTION: SEQ ID NO: 279:

Cys Xaa Cys Xaa Xaa Xaa Xaa Xaa Xaa Xaa Xaa Xaa Xaa
1               5                                  10

(2) INFORMATION FOR SEQ ID NO: 280:

(i) SEQUENCE CHARACTERISTICS:
        (A) LENGTH: 8 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 8 is
        an amino acid.

(xi) SEQUENCE DESCRIPTION: SEQ ID NO: 280:

Cys Xaa Xaa Xaa Xaa Xaa Xaa Xaa
1               5

(2) INFORMATION FOR SEQ ID NO: 281:

(i) SEQUENCE CHARACTERISTICS:
        (A) LENGTH: 7 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 7 is
        an amino acid.

(xi) SEQUENCE DESCRIPTION: SEQ ID NO: 281:

Cys Xaa Xaa Xaa Xaa Xaa Xaa
1               5

(2) INFORMATION FOR SEQ ID NO: 282:

(i) SEQUENCE CHARACTERISTICS:
        (A) LENGTH: 6 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 6 is
        an amino acid.

(xi) SEQUENCE DESCRIPTION: SEQ ID NO: 282:

Cys Xaa Xaa Xaa Xaa Xaa
1               5

(2) INFORMATION FOR SEQ ID NO: 283:

(i) SEQUENCE CHARACTERISTICS:
        (A) LENGTH: 26 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 26 is an
        amino acid.

( x i ) SEQUENCE DESCRIPTION: SEQ ID NO: 283:

Cys Xaa Xaa Xaa Xaa Xaa Xaa Xaa Xaa Xaa Xaa Xaa Xaa Xaa Xaa Xaa
1               5                           10                          15

Xaa Xaa Xaa Xaa Xaa Xaa Xaa Xaa Xaa Xaa
                20                      25

( 2 ) INFORMATION FOR SEQ ID NO: 284:

( i ) SEQUENCE CHARACTERISTICS:
        ( A ) LENGTH: 25 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 25 is an
            amino acid.

( x i ) SEQUENCE DESCRIPTION: SEQ ID NO: 284:

Cys Xaa Xaa Xaa Xaa Xaa Xaa Xaa Xaa Xaa Xaa Xaa Xaa Xaa Xaa Xaa
1               5                           10                          15

Xaa Xaa Xaa Xaa Xaa Xaa Xaa Xaa Xaa
                20                      25

( 2 ) INFORMATION FOR SEQ ID NO: 285:

( i ) SEQUENCE CHARACTERISTICS:
        ( A ) LENGTH: 24 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 24 is an
            amino acid.

( x i ) SEQUENCE DESCRIPTION: SEQ ID NO: 285:

Cys Xaa Xaa Xaa Xaa Xaa Xaa Xaa Xaa Xaa Xaa Xaa Xaa Xaa Xaa Xaa
1               5                           10                          15

Xaa Xaa Xaa Xaa Xaa Xaa Xaa Xaa
                20

( 2 ) INFORMATION FOR SEQ ID NO: 286:

( i ) SEQUENCE CHARACTERISTICS:
        ( A ) LENGTH: 23 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 23 is an
            amino acid.

( x i ) SEQUENCE DESCRIPTION: SEQ ID NO: 286:

Cys Xaa Xaa Xaa Xaa Xaa Xaa Xaa Xaa Xaa Xaa Xaa Xaa Xaa Xaa Xaa
1               5                           10                          15

Xaa Xaa Xaa Xaa Xaa Xaa Xaa
                20

( 2 ) INFORMATION FOR SEQ ID NO: 287:

( i ) SEQUENCE CHARACTERISTICS:
        ( A ) LENGTH: 22 amino acids (B) TYPE: amino acid
(D) TOPOLOGY: linear (v) FRAGMENT TYPE: internal fragment (ix) FEATURE:
(D) OTHER INFORMATION: Xaa in locations 2 to 22 is an
amino acid.

(xi) SEQUENCE DESCRIPTION: SEQ ID NO: 287:

Cys Xaa Xaa Xaa Xaa Xaa Xaa Xaa Xaa Xaa Xaa Xaa Xaa Xaa Xaa Xaa
1               5                           10                          15

Xaa Xaa Xaa Xaa Xaa Xaa
            20

(2) INFORMATION FOR SEQ ID NO: 288:

(i) SEQUENCE CHARACTERISTICS:
(A) LENGTH: 21 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 21 is an
amino acid.

(xi) SEQUENCE DESCRIPTION: SEQ ID NO: 288:

Cys Xaa Xaa Xaa Xaa Xaa Xaa Xaa Xaa Xaa Xaa Xaa Xaa Xaa Xaa Xaa
1               5                           10                          15

Xaa Xaa Xaa Xaa Xaa
            20

(2) INFORMATION FOR SEQ ID NO: 289:

(i) SEQUENCE CHARACTERISTICS:
(A) LENGTH: 20 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 20 is an
amino acid.

(xi) SEQUENCE DESCRIPTION: SEQ ID NO: 289:

Cys Xaa Xaa Xaa Xaa Xaa Xaa Xaa Xaa Xaa Xaa Xaa Xaa Xaa Xaa Xaa
1               5                           10                          15

Xaa Xaa Xaa Xaa
            20

(2) INFORMATION FOR SEQ ID NO: 290:

(i) SEQUENCE CHARACTERISTICS:
(A) LENGTH: 19 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 19 is an
amino acid.

(xi) SEQUENCE DESCRIPTION: SEQ ID NO: 290:

Cys Xaa Xaa Xaa Xaa Xaa Xaa Xaa Xaa Xaa Xaa Xaa Xaa Xaa Xaa Xaa
1               5                           10                          15

Xaa Xaa Xaa ( 2 ) INFORMATION FOR SEQ ID NO: 291:

( i ) SEQUENCE CHARACTERISTICS:
        ( A ) LENGTH: 18 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 18 is an
            amino acid.

( x i ) SEQUENCE DESCRIPTION: SEQ ID NO: 291:

Cys Xaa Xaa Xaa Xaa Xaa Xaa Xaa Xaa Xaa Xaa Xaa Xaa Xaa Xaa Xaa
1               5                   10                  15
Xaa Xaa ( 2 ) INFORMATION FOR SEQ ID NO: 292:

( i ) SEQUENCE CHARACTERISTICS:
        ( A ) LENGTH: 17 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 17 is an
            amino acid.

( x i ) SEQUENCE DESCRIPTION: SEQ ID NO: 292:

Cys Xaa Xaa Xaa Xaa Xaa Xaa Xaa Xaa Xaa Xaa Xaa Xaa Xaa Xaa Xaa
1               5                   10                  15
Xaa ( 2 ) INFORMATION FOR SEQ ID NO: 293:

( i ) SEQUENCE CHARACTERISTICS:
        ( A ) LENGTH: 16 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 16 is an
            amino acid.

( x i ) SEQUENCE DESCRIPTION: SEQ ID NO: 293:

Cys Xaa Xaa Xaa Xaa Xaa Xaa Xaa Xaa Xaa Xaa Xaa Xaa Xaa Xaa Xaa
1               5                   10                  15

( 2 ) INFORMATION FOR SEQ ID NO: 294:

( i ) SEQUENCE CHARACTERISTICS:
        ( A ) LENGTH: 15 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 15 is an
            amino acid.

( x i ) SEQUENCE DESCRIPTION: SEQ ID NO: 294:

Cys Xaa Xaa Xaa Xaa Xaa Xaa Xaa Xaa Xaa Xaa Xaa Xaa Xaa Xaa (2) INFORMATION FOR SEQ ID NO: 295:

(i) SEQUENCE CHARACTERISTICS:
        (A) LENGTH: 14 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 14 is an amino acid.

(xi) SEQUENCE DESCRIPTION: SEQ ID NO: 295:

Cys Xaa Xaa Xaa Xaa Xaa Xaa Xaa Xaa Xaa Xaa Xaa Xaa Xaa
1               5                       10

(2) INFORMATION FOR SEQ ID NO: 296:

(i) SEQUENCE CHARACTERISTICS:
        (A) LENGTH: 13 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 13 is an amino acid.

(xi) SEQUENCE DESCRIPTION: SEQ ID NO: 296:

Cys Xaa Xaa Xaa Xaa Xaa Xaa Xaa Xaa Xaa Xaa Xaa Xaa
1               5                       10

(2) INFORMATION FOR SEQ ID NO: 297:

(i) SEQUENCE CHARACTERISTICS:
        (A) LENGTH: 12 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 12 is an amino acid.

(xi) SEQUENCE DESCRIPTION: SEQ ID NO: 297:

Cys Xaa Xaa Xaa Xaa Xaa Xaa Xaa Xaa Xaa Xaa Xaa
1               5                       10

(2) INFORMATION FOR SEQ ID NO: 298:

(i) SEQUENCE CHARACTERISTICS:
        (A) LENGTH: 11 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 11 is an amino acid.

(xi) SEQUENCE DESCRIPTION: SEQ ID NO: 298:

Cys Xaa Xaa Xaa Xaa Xaa Xaa Xaa Xaa Xaa Xaa
1               5                       10

(2) INFORMATION FOR SEQ ID NO: 299:

( i ) SEQUENCE CHARACTERISTICS:
    ( A ) LENGTH: 10 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in locations 2 to 10 is an amino acid.

( x i ) SEQUENCE DESCRIPTION: SEQ ID NO: 299:

```
Cys  Xaa  Xaa  Xaa  Xaa  Xaa  Xaa  Xaa  Xaa  Xaa
1                 5                            10
```

( 2 ) INFORMATION FOR SEQ ID NO: 300:

( i ) SEQUENCE CHARACTERISTICS:
    ( A ) LENGTH: 9 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in locations 2 to 9 is an amino acid.

( x i ) SEQUENCE DESCRIPTION: SEQ ID NO: 300:

```
Cys  Xaa  Xaa  Xaa  Xaa  Xaa  Xaa  Xaa  Xaa
1                 5
```

( 2 ) INFORMATION FOR SEQ ID NO: 301:

( i ) SEQUENCE CHARACTERISTICS:
    ( A ) LENGTH: 8 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in locations 2 to 8 is an amino acid.

( x i ) SEQUENCE DESCRIPTION: SEQ ID NO: 301:

```
Cys  Xaa  Xaa  Xaa  Xaa  Xaa  Xaa  Xaa
1                 5
```

( 2 ) INFORMATION FOR SEQ ID NO: 302:

( i ) SEQUENCE CHARACTERISTICS:
    ( A ) LENGTH: 7 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in locations 2 to 7 is an amino acid.

( x i ) SEQUENCE DESCRIPTION: SEQ ID NO: 302:

```
Cys  Xaa  Xaa  Xaa  Xaa  Xaa  Xaa
1                 5
```

( 2 ) INFORMATION FOR SEQ ID NO: 303:

( i ) SEQUENCE CHARACTERISTICS:
    ( A ) LENGTH: 6 amino acids
    ( B ) TYPE: amino acid (D) TOPOLOGY: linear (v) FRAGMENT TYPE: internal fragment (ix) FEATURE:
   (D) OTHER INFORMATION: Xaa in locations 2 to 6 is an amino acid.

(xi) SEQUENCE DESCRIPTION: SEQ ID NO: 303:

Cys Xaa Xaa Xaa Xaa Xaa
1                     5

(2) INFORMATION FOR SEQ ID NO: 304:

(i) SEQUENCE CHARACTERISTICS:
      (A) LENGTH: 5 amino acids
      (B) TYPE: amino acid
      (D) TOPOLOGY: linear (v) FRAGMENT TYPE: internal fragment (ix) FEATURE:
      (D) OTHER INFORMATION: Xaa in locations 2 to 5 is an amino acid.

(xi) SEQUENCE DESCRIPTION: SEQ ID NO: 304:

Cys Xaa Xaa Xaa Xaa
1                 5

(2) INFORMATION FOR SEQ ID NO: 305:

(i) SEQUENCE CHARACTERISTICS:
      (A) LENGTH: 4 amino acids
      (B) TYPE: amino acid
      (D) TOPOLOGY: linear (v) FRAGMENT TYPE: internal fragment (ix) FEATURE:
      (D) OTHER INFORMATION: Xaa in locations 2 to 4 is an amino acid.

(xi) SEQUENCE DESCRIPTION: SEQ ID NO: 305:

Cys Xaa Xaa Xaa
1

(2) INFORMATION FOR SEQ ID NO: 306:

(i) SEQUENCE CHARACTERISTICS:
      (A) LENGTH: 3 amino acids
      (B) TYPE: amino acid
      (D) TOPOLOGY: linear (v) FRAGMENT TYPE: internal fragment (ix) FEATURE:
      (D) OTHER INFORMATION: Xaa in location 2 and 3 is an amino acid.

(xi) SEQUENCE DESCRIPTION: SEQ ID NO: 306:

Cys Xaa Xaa
1

(2) INFORMATION FOR SEQ ID NO: 307:

(i) SEQUENCE CHARACTERISTICS:
      (A) LENGTH: 2 amino acids
      (B) TYPE: amino acid
      (D) TOPOLOGY: linear (v) FRAGMENT TYPE: internal fragment ( i x ) FEATURE:
      ( D ) OTHER INFORMATION: Xaa in location 2 is an
            amino acid.

( x i ) SEQUENCE DESCRIPTION: SEQ ID NO: 307:

Cys  Xaa
1

( 2 ) INFORMATION FOR SEQ ID NO: 308:

( i ) SEQUENCE CHARACTERISTICS:
            ( A ) LENGTH: 8 amino acids
            ( B ) TYPE: amino acid
            ( D ) TOPOLOGY: linear ( v ) FRAGMENT TYPE: internal fragment ( i x ) FEATURE:
            ( D ) OTHER INFORMATION: Xaa in locations 2 to 8
                  is an amino acid.

( x i ) SEQUENCE DESCRIPTION: SEQ ID NO: 308:

Cys  Xaa  Xaa  Xaa  Xaa  Xaa  Xaa  Xaa
1                 5

( 2 ) INFORMATION FOR SEQ ID NO: 309:

( i ) SEQUENCE CHARACTERISTICS:
            ( A ) LENGTH: 7 amino acids
            ( B ) TYPE: amino acid
            ( D ) TOPOLOGY: linear ( v ) FRAGMENT TYPE: internal fragment ( i x ) FEATURE:
            ( D ) OTHER INFORMATION: Xaa in locations 2 to 6 is
                  an amino acid.

( x i ) SEQUENCE DESCRIPTION: SEQ ID NO: 309:

Cys  Xaa  Xaa  Xaa  Xaa  Xaa  Cys
1                 5

( 2 ) INFORMATION FOR SEQ ID NO: 310:

( i ) SEQUENCE CHARACTERISTICS:
            ( A ) LENGTH: 6 amino acids
            ( B ) TYPE: amino acid
            ( D ) TOPOLOGY: linear ( v ) FRAGMENT TYPE: internal fragment ( i x ) FEATURE:
            ( D ) OTHER INFORMATION: Xaa in locations 2 to 5 is
                  an amino acid.

( x i ) SEQUENCE DESCRIPTION: SEQ ID NO: 310:

Cys  Xaa  Xaa  Xaa  Xaa  Cys
1                 5

( 2 ) INFORMATION FOR SEQ ID NO: 311:

( i ) SEQUENCE CHARACTERISTICS:
            ( A ) LENGTH: 5 amino acids
            ( B ) TYPE: amino acid
            ( D ) TOPOLOGY: linear ( v ) FRAGMENT TYPE: internal fragment ( i x ) FEATURE:
            ( D ) OTHER INFORMATION: Xaa in locations 2 to 4 is
                  an amino acid.

( x i ) SEQUENCE DESCRIPTION: SEQ ID NO: 311:

Cys  Xaa  Xaa  Xaa  Cys
1                    5

( 2 ) INFORMATION FOR SEQ ID NO: 312:

( i ) SEQUENCE CHARACTERISTICS:
        ( A ) LENGTH: 23 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 23 is an amino
            acid.

( x i ) SEQUENCE DESCRIPTION: SEQ ID NO: 312:

Xaa  Xaa  Xaa  Cys  Xaa  Xaa  Xaa  Xaa  Xaa  Xaa  Xaa  Xaa  Xaa  Xaa  Xaa  Xaa
1              5                        10                       15

Xaa  Xaa  Xaa  Xaa  Xaa  Xaa  Xaa
               20

( 2 ) INFORMATION FOR SEQ ID NO: 313:

( i ) SEQUENCE CHARACTERISTICS:
        ( A ) LENGTH: 22 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 22 is an amino
            acid.

( x i ) SEQUENCE DESCRIPTION: SEQ ID NO: 313:

Xaa  Xaa  Xaa  Cys  Xaa  Xaa  Xaa  Xaa  Xaa  Xaa  Xaa  Xaa  Xaa  Xaa  Xaa  Xaa
1              5                        10                       15

Xaa  Xaa  Xaa  Xaa  Xaa  Xaa
               20

( 2 ) INFORMATION FOR SEQ ID NO: 314:

( i ) SEQUENCE CHARACTERISTICS:
        ( A ) LENGTH: 21 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 1 to 3 and
            locations 5 to 21 is an amino
            acid.

( x i ) SEQUENCE DESCRIPTION: SEQ ID NO: 314:

Xaa  Xaa  Xaa  Cys  Xaa  Xaa  Xaa  Xaa  Xaa  Xaa  Xaa  Xaa  Xaa  Xaa  Xaa  Xaa
1              5                        10                       15

Xaa  Xaa  Xaa  Xaa  Xaa
               20

( 2 ) INFORMATION FOR SEQ ID NO: 315:

( i ) SEQUENCE CHARACTERISTICS:
        ( A ) LENGTH: 20 amino acids
        ( B ) TYPE: amino acid (D) TOPOLOGY: linear (v) FRAGMENT TYPE: internal fragment (ix) FEATURE:
  (D) OTHER INFORMATION: Xaa in locations 1 to 3 and
      locations 5 to 20 is an amino
      acid.

(xi) SEQUENCE DESCRIPTION: SEQ ID NO: 315:

Xaa Xaa Xaa Cys Xaa Xaa Xaa Xaa Xaa Xaa Xaa Xaa Xaa Xaa Xaa
1               5                   10                  15
Xaa Xaa Xaa Xaa
        20

(2) INFORMATION FOR SEQ ID NO: 316:

(i) SEQUENCE CHARACTERISTICS:
    (A) LENGTH: 19 amino acids
    (B) TYPE: amino acid
    (D) TOPOLOGY: linear (v) FRAGMENT TYPE: internal fragment (ix) FEATURE:
    (D) OTHER INFORMATION: Xaa in locations 1 to 3 and
        locations 5 to 19 is an amino
        acid.

(xi) SEQUENCE DESCRIPTION: SEQ ID NO: 316:

Xaa Xaa Xaa Cys Xaa Xaa Xaa Xaa Xaa Xaa Xaa Xaa Xaa Xaa Xaa
1               5                   10                  15
Xaa Xaa Xaa (2) INFORMATION FOR SEQ ID NO: 317:

(i) SEQUENCE CHARACTERISTICS:
    (A) LENGTH: 18 amino acids
    (B) TYPE: amino acid
    (D) TOPOLOGY: linear (v) FRAGMENT TYPE: internal fragment (ix) FEATURE:
    (D) OTHER INFORMATION: Xaa in locations 1 to 3 and
        locations 5 to 18 is an amino
        acid.

(xi) SEQUENCE DESCRIPTION: SEQ ID NO: 317:

Xaa Xaa Xaa Cys Xaa Xaa Xaa Xaa Xaa Xaa Xaa Xaa Xaa Xaa Xaa
1               5                   10                  15
Xaa Xaa (2) INFORMATION FOR SEQ ID NO: 318:

(i) SEQUENCE CHARACTERISTICS:
    (A) LENGTH: 17 amino acids
    (B) TYPE: amino acid
    (D) TOPOLOGY: linear (v) FRAGMENT TYPE: internal fragment (ix) FEATURE:
    (D) OTHER INFORMATION: Xaa in locations 1 to 3 and
        locations 5 to 17 is an amino
        acid.

(xi) SEQUENCE DESCRIPTION: SEQ ID NO: 318:

Xaa Xaa Xaa Cys Xaa Xaa Xaa Xaa Xaa Xaa Xaa Xaa Xaa Xaa Xaa
1               5                   10                  15

Xaa (2) INFORMATION FOR SEQ ID NO: 319:

(i) SEQUENCE CHARACTERISTICS:
(A) LENGTH: 16 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and locations 5 to 16 is an amino acid.

(xi) SEQUENCE DESCRIPTION: SEQ ID NO: 319:

Xaa Xaa Xaa Cys Xaa Xaa Xaa Xaa Xaa Xaa Xaa Xaa Xaa Xaa Xaa Xaa
1               5                       10                      15

(2) INFORMATION FOR SEQ ID NO: 320:

(i) SEQUENCE CHARACTERISTICS:
(A) LENGTH: 15 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and locations 5 to 15 is an amino acid.

(xi) SEQUENCE DESCRIPTION: SEQ ID NO: 320:

Xaa Xaa Xaa Cys Xaa Xaa Xaa Xaa Xaa Xaa Xaa Xaa Xaa Xaa Xaa
1               5                       10                  15

(2) INFORMATION FOR SEQ ID NO: 321:

(i) SEQUENCE CHARACTERISTICS:
(A) LENGTH: 14 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and locations 5 to 14 is an amino acid.

(xi) SEQUENCE DESCRIPTION: SEQ ID NO: 321:

Xaa Xaa Xaa Cys Xaa Xaa Xaa Xaa Xaa Xaa Xaa Xaa Xaa Xaa
1               5                       10

(2) INFORMATION FOR SEQ ID NO: 322:

(i) SEQUENCE CHARACTERISTICS:
(A) LENGTH: 13 amino acids
(B) TYPE: amino acid
(D) TOPOLOGY: linear (v) FRAGMENT TYPE: internal fragment (ix) FEATURE:
(D) OTHER INFORMATION: Xaa in locations 1 to 3 and locations 5 to 13 is an amino acid.

(xi) SEQUENCE DESCRIPTION: SEQ ID NO: 322:

Xaa Xaa Xaa Cys Xaa Xaa Xaa Xaa Xaa Xaa Xaa Xaa Xaa
1               5                           10

(2) INFORMATION FOR SEQ ID NO: 323:

(i) SEQUENCE CHARACTERISTICS:
        (A) LENGTH: 12 amino acids
        (B) TYPE: amino acid
        (D) TOPOLOGY: linear (v) FRAGMENT TYPE: internal fragment (ix) FEATURE:
        (D) OTHER INFORMATION: Xaa in locations 1 to 3 and
            locations 5 to 12 is an amino
            acid.

(xi) SEQUENCE DESCRIPTION: SEQ ID NO: 323:

Xaa Xaa Xaa Cys Xaa Xaa Xaa Xaa Xaa Xaa Xaa Xaa
1               5                           10

(2) INFORMATION FOR SEQ ID NO: 324:

(i) SEQUENCE CHARACTERISTICS:
        (A) LENGTH: 11 amino acids
        (B) TYPE: amino acid
        (D) TOPOLOGY: linear (v) FRAGMENT TYPE: internal fragment (ix) FEATURE:
        (D) OTHER INFORMATION: Xaa in locations 1 to 3 and
            locations 5 to 11 is an amino
            acid.

(xi) SEQUENCE DESCRIPTION: SEQ ID NO: 324:

Xaa Xaa Xaa Cys Xaa Xaa Xaa Xaa Xaa Xaa Xaa
1               5                           10

(2) INFORMATION FOR SEQ ID NO: 325:

(i) SEQUENCE CHARACTERISTICS:
        (A) LENGTH: 10 amino acids
        (B) TYPE: amino acid
        (D) TOPOLOGY: linear (v) FRAGMENT TYPE: internal fragment (ix) FEATURE:
        (D) OTHER INFORMATION: Xaa in locations 1 to 3 and
            locations 5 to 10 is an amino
            acid.

(xi) SEQUENCE DESCRIPTION: SEQ ID NO: 325:

Xaa Xaa Xaa Cys Xaa Xaa Xaa Xaa Xaa Xaa
1               5                       10

(2) INFORMATION FOR SEQ ID NO: 326:

(i) SEQUENCE CHARACTERISTICS:
        (A) LENGTH: 5 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 5 is
            an amino acid.

(xi) SEQUENCE DESCRIPTION: SEQ ID NO: 326:

Cys Xaa Xaa Xaa Xaa (2) INFORMATION FOR SEQ ID NO: 327:

(i) SEQUENCE CHARACTERISTICS:
        (A) LENGTH: 4 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 4 is
            an amino acid.

(xi) SEQUENCE DESCRIPTION: SEQ ID NO: 327:

Cys Xaa Xaa Xaa
1

(2) INFORMATION FOR SEQ ID NO: 328:

(i) SEQUENCE CHARACTERISTICS:
        (A) LENGTH: 6 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 6 is
            an amino acid.

(xi) SEQUENCE DESCRIPTION: SEQ ID NO: 328:

Cys Xaa Xaa Xaa Xaa Xaa
1                    5

(2) INFORMATION FOR SEQ ID NO: 329:

(i) SEQUENCE CHARACTERISTICS:
        (A) LENGTH: 5 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 5 is
            an amino acid.

(xi) SEQUENCE DESCRIPTION: SEQ ID NO: 329:

Cys Xaa Xaa Xaa Xaa
1              5

(2) INFORMATION FOR SEQ ID NO: 330:

(i) SEQUENCE CHARACTERISTICS:
        (A) LENGTH: 4 amino acids
        (B) TYPE: amino acid
        (D) TOPOLOGY: linear (v) FRAGMENT TYPE: internal fragment (ix) FEATURE:
        (D) OTHER INFORMATION: Xaa in locations 2 to 4 is
            an amino acid.

(xi) SEQUENCE DESCRIPTION: SEQ ID NO: 330:

Cys Xaa Xaa Xaa
1

(2) INFORMATION FOR SEQ ID NO: 331:

( i ) SEQUENCE CHARACTERISTICS:
    ( A ) LENGTH: 15 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in location 2 and
        locations 4 to 15 is an amino
        acid.

( x i ) SEQUENCE DESCRIPTION: SEQ ID NO: 331:

```
Cys Xaa Cys Xaa Xaa Xaa Xaa Xaa Xaa Xaa Xaa Xaa Xaa Xaa Xaa
1               5                        10                        15
```

( 2 ) INFORMATION FOR SEQ ID NO: 332:

( i ) SEQUENCE CHARACTERISTICS:
        ( A ) LENGTH: 14 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in location 2 and
            locations 4 to 14 is an amino
            acid.

( x i ) SEQUENCE DESCRIPTION: SEQ ID NO: 332:

```
Cys Xaa Cys Xaa Xaa Xaa Xaa Xaa Xaa Xaa Xaa Xaa Xaa Xaa
1               5                        10
```

( 2 ) INFORMATION FOR SEQ ID NO: 333:

( i ) SEQUENCE CHARACTERISTICS:
        ( A ) LENGTH: 8 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 8 is
            an amino acid.

( x i ) SEQUENCE DESCRIPTION: SEQ ID NO: 333:

```
Cys Xaa Xaa Xaa Xaa Xaa Xaa Xaa
1               5
```

( 2 ) INFORMATION FOR SEQ ID NO: 334:

( i ) SEQUENCE CHARACTERISTICS:
        ( A ) LENGTH: 7 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 7 is
            an amino acid.

( x i ) SEQUENCE DESCRIPTION: SEQ ID NO: 334:

```
Cys Xaa Xaa Xaa Xaa Xaa Xaa
1               5
```

( 2 ) INFORMATION FOR SEQ ID NO: 335:

( i ) SEQUENCE CHARACTERISTICS:

(A) LENGTH: 6 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 6 is an amino acid.

(xi) SEQUENCE DESCRIPTION: SEQ ID NO: 335:

Cys Xaa Xaa Xaa Xaa Xaa
1               5

(2) INFORMATION FOR SEQ ID NO: 336:

(i) SEQUENCE CHARACTERISTICS:
(A) LENGTH: 26 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 26 is an amino acid.

(xi) SEQUENCE DESCRIPTION: SEQ ID NO: 336:

Cys Xaa Xaa Xaa Xaa Xaa Xaa Xaa Xaa Xaa Xaa Xaa Xaa Xaa Xaa Xaa
1               5                   10                  15
Xaa Xaa Xaa Xaa Xaa Xaa Xaa Xaa Xaa Xaa
            20                  25

(2) INFORMATION FOR SEQ ID NO: 337:

(i) SEQUENCE CHARACTERISTICS:
(A) LENGTH: 25 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 25 is an amino acid.

(xi) SEQUENCE DESCRIPTION: SEQ ID NO: 337:

Cys Xaa Xaa Xaa Xaa Xaa Xaa Xaa Xaa Xaa Xaa Xaa Xaa Xaa Xaa Xaa
1               5                   10                  15
Xaa Xaa Xaa Xaa Xaa Xaa Xaa Xaa Xaa
            20                  25

(2) INFORMATION FOR SEQ ID NO: 338:

(i) SEQUENCE CHARACTERISTICS:
(A) LENGTH: 24 amino acids
(B) TYPE: amino acid
(D) TOPOLOGY: linear (v) FRAGMENT TYPE: internal fragment (ix) FEATURE:
(D) OTHER INFORMATION: Xaa in locations 2 to 24 is an amino acid.

(xi) SEQUENCE DESCRIPTION: SEQ ID NO: 338:

Cys Xaa Xaa Xaa Xaa Xaa Xaa Xaa Xaa Xaa Xaa Xaa Xaa Xaa Xaa Xaa
1               5                   10                  15
Xaa Xaa Xaa Xaa Xaa Xaa Xaa Xaa
            20

( 2 ) INFORMATION FOR SEQ ID NO: 339:

( i ) SEQUENCE CHARACTERISTICS:
        ( A ) LENGTH: 23 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 23 is an
            amino acid.

( x i ) SEQUENCE DESCRIPTION: SEQ ID NO: 339:

```
Cys Xaa Xaa Xaa Xaa Xaa Xaa Xaa Xaa Xaa Xaa Xaa Xaa Xaa Xaa Xaa
  1               5                  10                  15
Xaa Xaa Xaa Xaa Xaa Xaa Xaa
             20
```

( 2 ) INFORMATION FOR SEQ ID NO: 340:

( i ) SEQUENCE CHARACTERISTICS:
        ( A ) LENGTH: 22 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 22 is an
            amino acid.

( x i ) SEQUENCE DESCRIPTION: SEQ ID NO: 340:

```
Cys Xaa Xaa Xaa Xaa Xaa Xaa Xaa Xaa Xaa Xaa Xaa Xaa Xaa Xaa Xaa
  1               5                  10                  15
Xaa Xaa Xaa Xaa Xaa Xaa
             20
```

( 2 ) INFORMATION FOR SEQ ID NO: 341:

( i ) SEQUENCE CHARACTERISTICS:
        ( A ) LENGTH: 21 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 21 is an
            amino acid.

( x i ) SEQUENCE DESCRIPTION: SEQ ID NO: 341:

```
Cys Xaa Xaa Xaa Xaa Xaa Xaa Xaa Xaa Xaa Xaa Xaa Xaa Xaa Xaa Xaa
  1               5                  10                  15
Xaa Xaa Xaa Xaa Xaa
             20
```

( 2 ) INFORMATION FOR SEQ ID NO: 342:

( i ) SEQUENCE CHARACTERISTICS:
        ( A ) LENGTH: 20 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 20 is an
            amino acid.

( x i ) SEQUENCE DESCRIPTION: SEQ ID NO: 342:

Cys Xaa Xaa Xaa Xaa Xaa Xaa Xaa Xaa Xaa Xaa Xaa Xaa Xaa Xaa Xaa
1               5                       10                          15

Xaa Xaa Xaa Xaa
            20

( 2 ) INFORMATION FOR SEQ ID NO: 343:

( i ) SEQUENCE CHARACTERISTICS:
        ( A ) LENGTH: 19 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 19 is an
            amino acid.

( x i ) SEQUENCE DESCRIPTION: SEQ ID NO: 343:

Cys Xaa Xaa Xaa Xaa Xaa Xaa Xaa Xaa Xaa Xaa Xaa Xaa Xaa Xaa Xaa
1               5                       10                          15

Xaa Xaa Xaa ( 2 ) INFORMATION FOR SEQ ID NO: 344:

( i ) SEQUENCE CHARACTERISTICS:
        ( A ) LENGTH: 18 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 18 is an
            amino acid.

( x i ) SEQUENCE DESCRIPTION: SEQ ID NO: 344:

Cys Xaa Xaa Xaa Xaa Xaa Xaa Xaa Xaa Xaa Xaa Xaa Xaa Xaa Xaa Xaa
1               5                       10                          15

Xaa Xaa ( 2 ) INFORMATION FOR SEQ ID NO: 345:

( i ) SEQUENCE CHARACTERISTICS:
        ( A ) LENGTH: 17 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 17 is an
            amino acid.

( x i ) SEQUENCE DESCRIPTION: SEQ ID NO: 345:

Cys Xaa Xaa Xaa Xaa Xaa Xaa Xaa Xaa Xaa Xaa Xaa Xaa Xaa Xaa Xaa
1               5                       10                          15

Xaa ( 2 ) INFORMATION FOR SEQ ID NO: 346:

( i ) SEQUENCE CHARACTERISTICS:
        ( A ) LENGTH: 16 amino acids
        ( B ) TYPE: amino acid
        ( D ) TOPOLOGY: linear ( v ) FRAGMENT TYPE: internal fragment ( i x ) FEATURE:
( D ) OTHER INFORMATION: Xaa in locations 2 to 16 is an amino acid.

( x i ) SEQUENCE DESCRIPTION: SEQ ID NO: 346:

Cys Xaa Xaa Xaa Xaa Xaa Xaa Xaa Xaa Xaa Xaa Xaa Xaa Xaa Xaa Xaa
1               5                   10                  15

( 2 ) INFORMATION FOR SEQ ID NO: 347:

( i ) SEQUENCE CHARACTERISTICS:
( A ) LENGTH: 15 amino acids
( B ) TYPE: amino acid
( D ) TOPOLOGY: linear ( v ) FRAGMENT TYPE: internal fragment ( i x ) FEATURE:
( D ) OTHER INFORMATION: Xaa in locations 2 to 15 is an amino acid.

( x i ) SEQUENCE DESCRIPTION: SEQ ID NO: 347:

Cys Xaa Xaa Xaa Xaa Xaa Xaa Xaa Xaa Xaa Xaa Xaa Xaa Xaa Xaa
1               5                   10                  15

( 2 ) INFORMATION FOR SEQ ID NO: 348:

( i ) SEQUENCE CHARACTERISTICS:
( A ) LENGTH: 14 amino acids
( B ) TYPE: amino acid
( D ) TOPOLOGY: linear ( v ) FRAGMENT TYPE: internal fragment ( i x ) FEATURE:
( D ) OTHER INFORMATION: Xaa in locations 2 to 14 is an amino acid.

( x i ) SEQUENCE DESCRIPTION: SEQ ID NO: 348:

Cys Xaa Xaa Xaa Xaa Xaa Xaa Xaa Xaa Xaa Xaa Xaa Xaa Xaa
1               5                   10

( 2 ) INFORMATION FOR SEQ ID NO: 349:

( i ) SEQUENCE CHARACTERISTICS:
( A ) LENGTH: 13 amino acids
( B ) TYPE: amino acid
( D ) TOPOLOGY: linear ( v ) FRAGMENT TYPE: internal fragment ( i x ) FEATURE:
( D ) OTHER INFORMATION: Xaa in locations 2 to 13 is an amino acid.

( x i ) SEQUENCE DESCRIPTION: SEQ ID NO: 349:

Cys Xaa Xaa Xaa Xaa Xaa Xaa Xaa Xaa Xaa Xaa Xaa Xaa
1               5                   10

( 2 ) INFORMATION FOR SEQ ID NO: 350:

( i ) SEQUENCE CHARACTERISTICS:
( A ) LENGTH: 12 amino acids
( B ) TYPE: amino acid
( D ) TOPOLOGY: linear ( v ) FRAGMENT TYPE: internal fragment ( i x ) FEATURE:
( D ) OTHER INFORMATION: Xaa in locations 2 to 12 is an amino acid.

(x i) SEQUENCE DESCRIPTION: SEQ ID NO: 350:

Cys Xaa Xaa Xaa Xaa Xaa Xaa Xaa Xaa Xaa Xaa Xaa
1               5                           1 0

(2) INFORMATION FOR SEQ ID NO: 351:

(i) SEQUENCE CHARACTERISTICS:
        (A) LENGTH: 11 amino acids
        (B) TYPE: amino acid
        (D) TOPOLOGY: linear (v) FRAGMENT TYPE: internal fragment (i x) FEATURE:
        (D) OTHER INFORMATION: Xaa in locations 2 to 11 is an
        amino acid.

(x i) SEQUENCE DESCRIPTION: SEQ ID NO: 351:

Cys Xaa Xaa Xaa Xaa Xaa Xaa Xaa Xaa Xaa Xaa
1               5                       1 0

(2) INFORMATION FOR SEQ ID NO: 352:

(i) SEQUENCE CHARACTERISTICS:
        (A) LENGTH: 10 amino acids
        (B) TYPE: amino acid
        (D) TOPOLOGY: linear (v) FRAGMENT TYPE: internal fragment (i x) FEATURE:
        (D) OTHER INFORMATION: Xaa in locations 2 to 10 is an
        amino acid.

(x i) SEQUENCE DESCRIPTION: SEQ ID NO: 352:

Cys Xaa Xaa Xaa Xaa Xaa Xaa Xaa Xaa Xaa
1               5                   1 0

(2) INFORMATION FOR SEQ ID NO: 353:

(i) SEQUENCE CHARACTERISTICS:
        (A) LENGTH: 9 amino acids
        (B) TYPE: amino acid
        (D) TOPOLOGY: linear (v) FRAGMENT TYPE: internal fragment (i x) FEATURE:
        (D) OTHER INFORMATION: Xaa in locations 2 to 9 is an
        amino acid.

(x i) SEQUENCE DESCRIPTION: SEQ ID NO: 353:

Cys Xaa Xaa Xaa Xaa Xaa Xaa Xaa Xaa
1               5

(2) INFORMATION FOR SEQ ID NO: 354:

(i) SEQUENCE CHARACTERISTICS:
        (A) LENGTH: 8 amino acids
        (B) TYPE: amino acid
        (D) TOPOLOGY: linear (v) FRAGMENT TYPE: internal fragment (i x) FEATURE:
        (D) OTHER INFORMATION: Xaa in locations 2 to 8 is an
        amino acid.

(x i) SEQUENCE DESCRIPTION: SEQ ID NO: 354:

```
Cys  Xaa  Xaa  Xaa  Xaa  Xaa  Xaa  Xaa
1                     5
```

( 2 ) INFORMATION FOR SEQ ID NO: 355:

( i ) SEQUENCE CHARACTERISTICS:
        ( A ) LENGTH: 7 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 7 is an amino acid.

( x i ) SEQUENCE DESCRIPTION: SEQ ID NO: 355:

```
Cys  Xaa  Xaa  Xaa  Xaa  Xaa  Xaa
1                     5
```

( 2 ) INFORMATION FOR SEQ ID NO: 356:

( i ) SEQUENCE CHARACTERISTICS:
        ( A ) LENGTH: 6 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in locations 2 to 6 is an amino acid.

( x i ) SEQUENCE DESCRIPTION: SEQ ID NO: 356:

```
Cys  Xaa  Xaa  Xaa  Xaa  Xaa
1                     5
```

( 2 ) INFORMATION FOR SEQ ID NO: 357:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( v ) FRAGMENT TYPE: internal fragment ( i x ) FEATURE:
        ( D ) OTHER INFORMATION: Xaa in locations 2 and 4 is an amino acid.

( x i ) SEQUENCE DESCRIPTION: SEQ ID NO: 357:

```
Leu  Xaa  Arg  Xaa
1
```

NEMATODE-EXTRACTED ANTICOAGULANT PROTEIN

CROSS REFERENCE TO RELATED APPLICATION

This application is a Continuation-in-Part of U.S. Ser. No. 08/326,110, filed Oct. 18, 1994, the disclosure of which is incorporated herein by reference.

FIELD OF THE INVENTION

The present invention relates to specific proteins as well as recombinant versions of these proteins which are potent anticoagulants in human plasma. These proteins include certain proteins extracted from nematodes. In another aspect, the present invention relates to compositions comprising these proteins, which are useful as potent and specific inhibitors of blood coagulation enzymes in vitro and in vivo, and methods for their use as in vitro diagnostic agents, or as in vivo therapeutic agents, to prevent the clotting of blood. In a further aspect, the invention relates to nucleic acid sequences, including mRNA and DNA, encoding the proteins and their use in vectors to transfect or transform host cells and as probes to isolate certain related genes in other species and organisms.

BACKGROUND AND INTRODUCTION TO THE INVENTION

Normal hemostasis is the result of a delicate balance between the processes of clot formation (blood coagulation) and clot dissolution (fibrinolysis). The complex interactions between blood cells, specific plasma proteins and the vascular surface, maintain the fluidity of blood unless injury occurs. Damage to the endothelial barrier lining the vascular wall exposes underlying tissue to these blood components. This in turn triggers a series of biochemical reactions altering the hemostatic balance in favor of blood coagulation which can either result in the desired formation of a hemostatic plug stemming the loss of blood or the undesirable formation of an occlusive intravascular thrombus resulting in reduced or complete lack of blood flow to the affected organ.

The blood coagulation response is the culmination of a series of amplified reactions in which several specific zymogens of serine proteases in plasma are activated by limited proteolysis. This series of reactions results in the formation of an insoluble matrix composed of fibrin and cellular components which is required for the stabilization of the primary hemostatic plug or thrombus. The initiation and propagation of the proteolytic activation reactions occurs through a series of amplified pathways which are localized to membranous surfaces at the site of vascular injury (Mann, K. G., Nesheim, M. E., Church, W. R., Haley, P. and Krishnaswamy, S. (1990) *Blood* 76: 1–16. and Lawson, J. H., Kalafatis, M., Stram, S.,and Mann, K. G. (1994) *J. Biol. Chem.* 269: 23357–23366).

Initiation of the blood coagulation response to vascular injury follows the formation of a catalytic complex composed of serine protease factor VIIa and the non-enzymatic co-factor, tissue factor (TF)(Rappaport, S. I. and Rao, L. V. M. (1992) *Arteriosclerosis and Thrombosis* 12: 1112–1121). This response appears to be exclusively regulated by the exposure of subendothelial TF to trace circulating levels of factor VIIa and its zymogen factor VII, following a focal breakdown in vascular integrity. Autoactivation results in an increase in the number of factor VIIa/TF complexes which are responsible for the formation of the serine protease factor Xa. It is believed that in addition to the factor VIIa/TF complex, the small amount of factor Xa which is formed primes the coagulation response through the proteolytic modification of factor IX to factor $IX_{alpha}$ which in turn is converted to the active serine protease factor $IXa_{beta}$ by the factor VIIa/TF complex (Mann, K. G., Krishnaswamy, S. and Lawson, J. H. (1992) *Sem. Hematology* 29: 213–226.). It is factor $IXa_{beta}$ in complex with activated factor VIIIa, which appears to be responsible for the production of significant quantities of factor Xa which subsequently catalyzes the penultimate step in the blood coagulation cascade; the formation of the serine protease thrombin.

Factor Xa catalyzes the formation of thrombin following the assembly of the prothrombinase complex which is composed of factor Xa, the non-enzymatic co-factor Va and the substrate prothrombin (factor II) assembled in most cases, on the surface of activated platelets which are adhered at the site of injury (Fuster, V., Badimon, L., Badimon, J. J. and Chesebro, J. H. (1992) *New Engl. J. Med.* 326: 310–318). In the arterial vasculature, the resulting amplified "burst" of thrombin generation catalyzed by prothrombinase results locally high levels of this protease which is responsible for the formation of fibrin and the further recruitment of additional platelets as well as the covalent stabilization of the clot through the activation of the transglutaminase zymogen factor XIII. In addition, the coagulation response is further propagated through the thrombin-mediated proteolytic feedback activation of the non-enzymatic co-factors V and VIII resulting in more prothrombinase formation and subsequent thrombin generation (Hemker, H. C. and Kessels, H. (1991) *Haemostasis* 21: 189–196).

Substances which interfere in the process of blood coagulation (anticoagulants) have been demonstrated to be important therapeutic agents in the treatment and prevention of thrombotic disorders (Kessler, C. M. (1991) *Chest* 99: 97S–112S and Cairns, J. A., Hirsh, J., Lewis, H. D., Resnekov, L., and Theroux, P. (1992) *Chest* 102: 456S–481S). The currently approved clinical anticoagulants have been associated with a number of adverse effects owing to the relatively non-specific nature of their effect on the blood coagulation cascade (Levine, M. N., Hirsh, J., Landefeld, S., and Raskob, G. (1992) *Chest* 102: 352S–363S). This has stimulated the search for more effective anticoagulant agents which can more effectively control the activity of the coagulation cascade by selectively interfering with specific reactions in this process which may have a positive effect in reducing the complications of anticoagulant therapy (Weitz, J., and Hirsh, J. (1993) *J. Lab. Clin. Med.* 122: 364–373). In another aspect, this search has focused on normal human proteins which serve as endogenous anticoagulants in controlling the activity of the blood coagulation cascade. In addition, various hematophageous organisms have been investigated because of their ability to effectively anticoagulate the blood meal during and following feeding on their hosts suggesting that they have evolved effective anticoagulant strategies which may be useful as therapeutic agents.

A plasma protein, Tissue Factor Pathway Inhibitor (TFPI), contains three consecutive Kunitz domains and has been reported to inhibit the enzyme activity of factor Xa directly and, in a factor Xa-dependent manner, inhibit the enzyme activity the factor VIIa-tissue factor complex. Salvensen,G., and Pizzo, S. V., "Proteinase Inhibitors: α-Macroglobulins, Serpins, and Kunis", "Hemostasis and Thrombosis", Third Edition, pp. 251–253, J. B. Lippincott Company (Edit. R. W. Colman et al. 1994). A cDNA sequence encoding TFPI has been reported, and the cloned protein was reported to have a molecular weight of 31,950 daltons and contain 276 amino acids. Broze, G. J. and Girad, T. J., U.S. Pat. No. 5,106,833, col. 1, (1992). Various recombinant proteins derived from TFPI have been reported. Girad, T. J. and Broze, G. J., EP 439,442 (1991); Rasmussen, J. S. and Nordfand, O. J., WO 91/02753 (1991); and Broze, G. J. and Girad, T. J., U.S. Pat. No. 5,106,833, col. 1, (1992).

Antistasin, a protein comprised of 119 amino acids and found in the salivary gland of the Mexican leech, *Haementeria officinalis,* has been reported to inhibit the enzyme activity of factor Xa. Tuszynski et al., J. Biol. Chem, 262:9718 (1987); Nutt, et al., J. Biol. Chem, 263:10162 (1988). A 6,000 daltons recombinant protein containing 58 amino acids with a high degree homology to antistasin's amino-terminus amino acids 1 through 58 has been reported to inhibit the enzyme activity of factor Xa. Tung, J. et al., EP 454,372 (Oct. 30, 1991); Tung, J. et al., U.S. Pat. No. 5,189,019 (Feb. 23, 1993).

Tick Anticoagulant Peptide (TAP), a protein comprised of 60 amino acids and isolated from the soft tick, *Ornithodoros moubata,* has been reported to inhibit the enzyme activity of factor Xa but not factor VIIa. Waxman, L. et al., Science, 248:593 (1990). TAP made by recombinant methods has been reported. Vlausk, G. P. et al., EP 419,099 (1991) and Vlausk, G. P. et al., U.S. Pat. No 5,239,058 (1993).

The dog hookworm, *Ancylostoma caninum,* which can also infect humans, has been reported to contain a potent anticoagulant substance which inhibited coagulation of blood in vitro. Loeb, L. and Smith, A. J., Proc. Pathol. Soc. Philadelphia, 7:173–187 (1904). Extracts of *A. caninum* were reported to prolong prothrombin time and partial thromboplastin time in human plasma with the anticoagulant effect being reported attributable to inhibition of factor Xa but not thrombin. Spellman, Jr., J. J. and Nossel, H. L., Am. J. Physiol., 220:922–927 (1971). More recently, soluble protein extracts of *A. caninum* were reported to prolong prothrombin time and partial thromboplastin time in human plasma in vitro. The anticoagulant effect was reported to be attributable to inhibition of human factor Xa but not thrombin, Cappello, M, et al., J. Infect. Diseases, 167:1474–1477 (1993), and to inhibition of factor Xa and factor VIIa (W094/25000).

The human hookworm, *Ancylostoma ceylanicum,* has also been reported to contain an anticoagulant. Extracts of *A. ceylanicum* have been reported to prolong prothrombin time and partial thromboplastin time in dog and human plasma in vitro. Carroll, S. M., et al., Thromb. Haemostas. (Stuttgart), 51:222–227 (1984).

Soluble extracts of the non-hematophagous parasite, *Ascaris suum,* have been reported to contain an anticoagulant. These extracts were reported to prolong the clotting of whole blood, as well as clotting time in the kaolin-activated partial thromboplastin time test but not in the prothrombin time test. Crawford, G. P. M. et al., J. Parasitol., 68: 1044–1047 (1982). Chymotrypsin/elastase inhibitor and its major isoforms, trypsin inhibitor-1 and chymotrypsin/ elastase inhibitor-4, isolated from *Ascaris suum,* were reported to be serine protease inhibitors and share a common pattern of five-disulfide bridges. Bernard, V. D. and Peanasky, R. J., Arch. Biochem. Biophys., 303:367–376 (1993); Huang, K. et al., Structure, 2:679–689 (1994); and Grasberger, B. L. et al., Structure, 2:669–678 (1994). There was no indication that the reported serine protease inhibitors had anticoagulant activity.

Secretions of the hookworm *Necator americanus* are reported to prolong human plasma clotting times, inhibit the amidolytic activity of human FXa using a fluorogenic substrate, inhibit multiple agonist-induced platelet dense granule release, and degrade fibrinogen. Pritchard, D. I. and B. Furmidge, Thromb. Haemost. 73: 546 (1995).

SUMMARY OF THE INVENTION

The present invention is directed to isolated proteins having anticoagulant activity and including at least one NAP domain. We refer to these proteins as Nematode-extracted Anticoagulant Proteins or "NAPs". "NAP domain" refers to a sequence of the isolated protein, or NAP, believed to have anticoagulant activity. The anticoagulant activity of these proteins may be assessed by their activities in increasing clotting time of human plasma in the prothrombin time (PT) and activated partial thromboplastin time (aPTT) assays, as well as by their ability to inhibit the blood coagulation enzymes factor Xa or factor VIIa/TF. It is believed that the NAP domain is responsible for the observed anticoagulant activity of these proteins. Certain of these proteins have at least one NAP domain which is an amino acid sequence containing less than about 120 amino acid residues, and containing 10 cysteine amino acid residues.

In another aspect, the present invention is directed to a method of preparing and isolating a cDNA molecule encoding a protein exhibiting anticoagulant activity and having a NAP domain, and to a recombinant cDNA molecule made by this method. This method comprises the steps of: (a) constructing a cDNA library from a species of nematode; (b) ligating said cDNA library into an appropriate cloning vector; (c) introducing said cloning vector containing said cDNA library into an appropriate host cell; (d) contacting the cDNA molecules of said host cell with a solution containing a hybridization probe having a nucleic acid sequence comprising AAR GCi TAY CCi GAR TGY GGi GAR AAY GAR TGG, [SEQ. ID. NO. 87] wherein R is A or G, Y is T or C, and i is inosine; (e) detecting a recombinant cDNA molecule which hybridizes to said probe; and (f) isolating said recombinant cDNA molecule.

In another aspect, the present invention is directed to a method of making a recombinant protein encoded by said cDNA which has anticoagulant activity and which includes a NAP domain and to recombinant proteins made by this method. This method comprises the steps of: (a) constructing a cDNA library from a species of nematode; (b) ligating said cDNA library into an appropriate cloning vector; (c) introducing said cloning vector containing said cDNA library into an appropriate host cell; (d) contacting the cDNA molecules of said host cell with a solution containing a hybridization probe having a nucleic acid sequence comprising AAR GCi TAY CCi GAR TGY GGi GAR AAY GAR TGG, wherein R is A or G, Y is T or C, and i is inosine [SEQ. ID. NO. 94]; (e) detecting a recombinant cDNA molecule which hybridizes to said probe; (f) isolating said recombinant cDNA molecule; (g) ligating the nucleic acid sequence of said cDNA molecule which encodes said recombinant protein into an appropriate expression cloning vector; (h) transforming a second host cell with said expression cloning vector containing said nucleic acid sequence of said cDNA molecule which encodes said recombinant protein; (i) culturing the transformed second host cell; and (j) isolating said recombinant protein expressed by said second host cell. It is noted that when describing production of recombinant proteins in certain expression systems such as COS cells, the term "transfection" is conventionally used in place of (and sometimes interchangeably with) "transformation".

In another aspect, the present invention is directed to a method of making a recombinant CDNA encoding a recombinant protein having anticoagulant activity and having a NAP domain, comprising the steps of: (a) isolating a cDNA library from a nematode; (b) ligating said cDNA library into a cloning vector;

(c) introducing said cloning vector containing said CDNA library into a host cell; (d) contacting the CDNA molecules of said host cells with a solution comprising first and second hybridization probes, wherein said first hybridization probe has the nucleic acid sequence comprising AAG GCA TAC CCG GAG TGT GGT GAG AAT GAA TGG CTC GAC GAC TGT GGA ACT CAG AAG CCA TGC GAG GCC AAG TGC AAT GAG GAA CCC CCT GAG GAG GAA GAT CCG ATA TGC CGC TCA CGT GGT TGT TTA TTA CCT CCT GCT TGC GTA TGC AAA GAC GGA TTC TAC AGA GAC ACG GTG ATC GGC GAC TGT GTT AGG GAA GAA GAA TGC GAC CAA CAT GAG ATT ATA CAT GTC TGA [SEQ. ID. NO. 1], and said second hybridization probe has the nucleic acid sequence comprising AAG GCA TAC CCG GAG TGT GGT GAG AAT GAA TGG CTC GAC GTC TGT GGA ACT AAG AAG CCA TGC GAG GCC AAG TGC AGT GAG GAA GAG GAG GAA GAT CCG ATA TGC CGA TCA TTT TCT TGT CCG GGT CCC GCT GCT TGC GTA TGC GAA GAC GGA TTC TAC AGA GAC ACG GTG ATC GGC GAC TGT GTT AAG GAA GAA GAA TGC GAC CAA CAT GAG ATT ATA CAT GTC TGA [SEQ. ID. NO. 2];

(e) detecting a recombinant cDNA molecule which hybridizes to said mixture of said probes; and (f) isolating said recombinant cDNA molecule.

In yet another aspect, the present invention is directed to a method of making a recombinant cDNA encoding a protein having anticoagulant activity and which encodes a NAP domain, comprising the steps of: (a) isolating a cDNA library from a nematode; (b) ligating said cDNA library into an appropriate phagemid expression cloning vector; (c) transforming host cells with said vector containing said cDNA library; (d) culturing said host cells; (e) infecting said host cells with a helper phage; (f) separating phage containing said cDNA library from said host cells; (g) combining a solution of said phage containing said cDNA library with a solution of biotinylated human factor Xa; (h) contacting a streptavidin-coated solid phase with said solution containing said phages containing said cDNA library, and said biotinylated human factor Xa; (i) isolating phages which bind to said streptavidin-coated solid phase; and (j) isolating the recombinant cDNA molecule from phages which bind to said streptavidin-coated solid phase.

In one preferred aspect, the present invention is directed to a recombinant cDNA having a nucleic acid sequence selected from the nucleic acid sequences depicted in FIGS. 7A–F, FIG. 9, FIGS. 13A–H, and FIG. 14.

The present invention also is directed to NAPs that inhibit the catalytic activity of FXa, to NAPs that inhibit the catalytic activity of the FVIIa/TF complex, and to NAPs that inhibit the catalytic activity of a serine protease, as well as nucleic acids encoding such NAPs and their methods of use.

Definitions

The term "amino acid" refers to the natural L-amino acids. Natural L-amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val).

The term "amino acid residue" refers to radicals having the structure: (1) —NH—CH(R)C(=O)—, wherein R is the alpha-carbon side-chain group of an L-amino acid, except for L-proline; or (2)

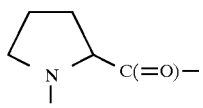

for L-proline.

The term "peptide" refers to a sequence of amino acids linked together through their alpha-amino and carboxylate groups by peptide bonds. Such sequences as shown herein are presented in the amino to carboxy direction, from left to right.

The term "protein" refers to a molecule comprised of one or more peptides.

The term "CDNA" refers to complementary DNA.

The term "nucleic acid" refers to polymers in which bases (e.g., purines or pyrimidines) are attached to a sugar phosphate backbone. Nucleic acids include DNA and RNA.

The term "nucleic acid sequence" refers to the sequence of nucleosides comprising a nucleic acid. Such sequences as shown herein are presented in the 5' to 3' direction, from left to right.

The term "recombinant DNA molecule" refers to a DNA molecule created by ligating together pieces of DNA that are not normally continguous.

The term "mRNA" refers to messenger ribonucleic acid.

The term "homology" refers to the degree of similarity of DNA or peptide sequences.

The terms "Factor Xa" or "fXa" or "FXa" are synonymous and are commonly known to mean a serine protease within the blood coagulation cascade of enzymes that functions to form the enzyme thrombin as part of the prothrombinase complex.

The phrase "Factor Xa inhibitory activity" means an activity that inhibits the catalytic activity of fXa toward its substrate.

The phrase "Factor Xa selective inhibitory activity" means inhibitory activity that is selective toward Factor Xa compared to other related enzymes, such as other serine proteases.

The phrase "Factor Xa inhibitor" is a compound having Factor Xa inhibitory activity.

The terms "Factor VIIa/Tissue Factor" or "fVIIa/TF" or "FVIIa/TF" are synonymous and are commonly known to mean a catalytically active complex of the serine protease coagulation factor VIIa (fVIIa) and the non-enzymatic protein Tissue Factor (TF), wherein the complex is assembled on the surface of a phospholipid membrane of defined composition.

The phrase "fVIIa/TF inhibitory activity" means an activity that inhibits the catalytic activity of the fVIIa/TF complex in the presence of fXa or catalytically inactive fXa derivative. The phrase "fVIIa/TF selective inhibitory activity" means inhibitory activity that is selective toward fVIIa/TF compared to other related enzymes, such as other serine proteases, including FVIIa and fXa.

The phrase a "fVIIa/TF inhibitor" is a compound having fVIIa/TF inhibitory activity in the presence of fXa or catalytically inactive fXa derivatives.

The phrase "serine protease" is commonly known to mean an enzyme, comprising a triad of the amino acids histidine, aspartic acid and serine, that catalytically cleaves an amide bond, wherein the serine residue within the triad is involved in a covalent manner in the catalytic cleavage. Serine proteases are rendered catalytically inactive by covalent modification of the serine residue within the catalytic triad by diisopropylfluorophosphate (DFP).

The phrase "serine protease inhibitory activity" means an activity that inhibits the catalytic activity of a serine protease.

The phrase "serine protease selective inhibitory activity" means inhibitory activity that is selective toward one serine protease compared to other serine proteases.

The phrase "serine protease inhibitor" is a compound having serine protease inhibitory activity.

The term "prothrombinase" is commonly known to mean a catalytically active complex of the serine protease coagulation Factor Xa (fXa) and the non-enzymatic protein Factor Va (fVa), wherein the complex is assembled on the surface of a phospholipid membrane of defined composition.

The phrase "anticoagulant activity" means an activity that inhibits the clotting of blood, which includes the clotting of plasma.

The term "selective", "selectivity", and permutations thereof, when referring to NAP activity toward a certain enzyme, mean the NAP inhibits the specified enzyme with at least 10-fold higher potency than it inhibits other, related enzymes. Thus, the NAP activity is selective toward that specified enzyme.

The term "substantially the same" when used to refer to proteins, amino acid sequences, cDNAs, nucleotide sequences and the like refer to proteins, cDNAs or sequences having at least about 90% homology with the other protein, cDNA, or sequence.

BRIEF DESCRIPTION OF THE DRAWINGS

FIG. 1 depicts the nucleotide sequence of the AcaNAP5 cDNA [SEQ. ID. NO. 3]. The numbering starts at the first nucleotide of the cDNA. Translation starts at the first ATG codon (position 14); a second in frame ATG is present at position 20.

FIG. 2 depicts the amino acid sequence of mature AcaNAP5 [SEQ. ID. NO. 4].

FIG. 3 depicts the nucleotide sequence of the AcaNAP6 cDNA [SEQ. ID. NO. 5]. The numbering starts at the first nucleotide of the cDNA. Translation starts at the first ATG codon (position 14); a second in frame ATG is present at position 20.

FIG. 4 depicts the amino acid sequence of mature AcaNAP6 [SEQ. ID. NO. 6]. Amino acids that differ from AcaNAP5 are underlined. In addition to these amino acid substitutions, AcaNAP6 contains a two amino acid deletion (Pro-Pro) when compared to AcaNAP5.

FIG. 5 depicts the amino acid sequence of Pro-AcaNAP5 [SEQ. ID. NO. 7].

FIG. 6 depicts the amino acid sequence of Pro-AcaNAP6 [SEQ. ID. NO. 8]. Amino acids that differ from Pro-AcaNAP5 are underlined. In addition to these amino acid substitutions, Pro-AcaNAP6 contains a two amino acid deletion (Pro-Pro) when compared to Pro-AcaNAP5.

FIGS. 7A-1 through 7F depict the nucleotide sequences of the cDNAs and deduced amino acid sequences of certain NAP proteins isolated from Ancylostoma ceylanicum, Ancylostoma duodenale, and Heligmosomoides polygyrus. FIGS. 7A-1 to 7A-2 depicts sequences for the recombinant cDNA molecule, AceNAP4, isolated from Ancylostoma ceylanicum [SEQ. ID. NO. 9]. FIG. 7B depicts sequences for the recombinant cDNA molecule, AceNAP5, isolated from Ancylostoma ceylanicum [SEQ. ID. NO. 10]. FIG. 7C depicts sequences for the recombinant cDNA molecule, AceNAP7, isolated from Ancylostoma ceylanicum [SEQ. ID. NO. 11]. FIG. 7D depicts sequences for the recombinant cDNA molecule, AduNAP4, isolated from Ancylostoma duodenale [SEQ. ID. NO. 12]. FIGS. 7E-1 and 7E-2 depicts sequences for the recombinant cDNA molecule, AduNAP7, isolated from Ancylostoma duodenale [SEQ. ID. NO. 13]. FIG. 7F depicts sequences for the recombinant cDNA molecule, HpoNAP5, isolated from Heligmosomoides polygyrus [SEQ. ID. NO. 14]. The EcoRI site, corresponding to the 5'-end of the recombinant cDNA molecule, is indicated in all cases (underlined). Numbering of each sequence starts at this EcoRI site. AceNAP4 and AduNAP7, each encode a protein which has two NAP domains; all other clones in this Figure code for a protein having a single NAP domain. The AduNAP4 cDNA clone is not full-length, i.e., the recombinant CDNA molecule lacks the 5'-terminal part of the coding region based on comparison with other isoforms.

FIGS. 8A through 8C depict the nucleotide sequence of the vectors, pDONG61 (FIG. 8A) [SEQ. ID. NO. 15], pDONG62 (FIG. 8B) [SEQ. ID. NO. 16], and pDONG63 (FIG. 8C) [SEQ. ID. NO. 17]. The HindIII-BamHI fragment which is shown is located between the HindIII and BamHI sites of pUC119. The vectors allow the cloning of cDNAs, as SfiI-NotI fragments, in the three different reading frames downstream of the filamentous phage gene 6. All relevant restriction sites are indicated. The AAA Lys-triplet at position 373–375 is the last codon of gene 6. The gene 6 encoded protein is followed by a Gly-Gly-Gly-Ser-Gly-Gly [SEQ. ID. NO. 18] linker sequence.

FIG. 9 depicts the nucleotide sequence of the recombinant cDNA molecule, AcaNAPc2 cDNA [SEQ. ID. NO. 19]. The EcoRI site, corresponding to the 5'-end of the cDNA, is indicated (underlined). Numbering starts at this EcoRI site. The deduced amino acid sequence is also shown; the translational reading frame was determined by the gene 6 fusion partner. The AcaNAPc2 CDNA lacks a portion of the 5'-terminal part of the coding region; the homology with AcaNAP5 and AcaNAP6 predicts that the first seven amino acid residues belong to the secretion signal.

FIGS. 11-1 to 11-9 depicts the alignment of the amino acid sequences encoded by certain NAP cDNAs isolated from various nematodes. AcaNAP5 [SEQ. ID. NO. 20], AcaNAP6 [SEQ. ID. NO. 21], and AcaNAPc2 [SEQ. ID. NO. 128] were isolated from Ancylostoma caninum. AceNAP5 [SEQ. ID. NO. 22], AceNAP7 [SEQ. ID. NO. 23], and AceNAP4 (AceNAP4d1 [SEQ. ID. NO. 24] and AceNAP4d2 [SEQ. ID. NO. 25] were isolated from Ancylostoma ceylanicum. AduNAP4 [SEQ. ID. NO. 26] and AduNAP7 (AduNAP7d1 [SEQ. ID. NO. 27] and AduNAP7d2 [SEQ. ID. NO. 28]) were isolated from Ancylostoma duodenale. HpoNAP5 [SEQ. ID. NO. 29] was isolated from Heligmosomoides polygyrus. The amino acid sequences shown in this figure are as given in FIGS. 1, 3, 7A-1 through 7F, and 9. The sequences of mature AcaNAP5 [SEQ. ID. NO. 4] and AcaNAP6 [SEQ. ID. NO. 6] (see FIGS. 2 and 4) are characterized, in part, by ten cysteine residues (numbered one through ten and shown in bold). All of the amino acid sequences in this Figure contain at least one NAP domain. The AceNAP4 cDNA consists of two adjacent regions, named AceNAP4d1 [SEQ. ID. NO. 24] and AceNAP4d2 [SEQ. ID. NO. 25], which encode a first (d1) and second (d2) NAP-domain; similarly, the AduNAP7 cDNA contains two adjacent regions, AduNAP7d1 [SEQ. ID. NO. 27] and AduNAP7d2 [SEQ. ID. NO. 28], encoding a first (d1) and second (d2) NAP-domain. The alignment of the amino acid sequences of all NAP-domains is guided by the cysteines; dashes (- - -) were introduced at certain positions to maintain the cysteine alignment and indicate the absence of an amino acid at that position. The carboxy-terminal residue of a cDNA encoded protein is followed by the word "end".

FIG. 12, Part B depicts the following contiguous DNA sequences which are incorporated in pYAM7SP8: the acid phosphatase (PH01) secretion signal sequence, pro sequence and multicloning site (MCS) sequence. The ATG start codon of the PH01 secretion signal is underlined.

FIGS. 13A through 13H depict the nucleotide sequences of the cDNAs and deduced amino acid sequences of certain NAP proteins isolated from *Ancylostoma caninum*. FIG. 13A depicts sequences for the recombinant cDNA molecule AcaNAP23 [SEQ. ID. NO. 31]. FIG. 13B depicts sequences for the recombinant cDNA molecule AcaNAP24 [SEQ. ID. NO. 32]. FIG. 13C depicts sequences for the recombinant cDNA molecule AcaNAP25 [SEQ. ID. NO. 33]. FIG. 13D depicts sequences for the recombinant cDNA molecules AcaNAP31, AcaNAP42, and AcaNAP46, all of which are identical [SEQ. ID. NO. 34]. FIG. 13E depicts sequences for the recombinant cDNA molecule AcaNAP44 [SEQ. ID. NO. 35]. FIG. 13F depicts sequences for the recombinant cDNA molecule AcaNAP45 [SEQ. ID. NO. 36]. FIG. 13G depicts sequences for the recombinant cDNA molecule AcaNAP47 [SEQ. ID. NO. 37]. FIG. 13H depicts sequences for the recombinant cDNA molecule AcaNAP48 [SEQ. ID. NO. 38]. The EcoRI site, corresponding to the 5'-end of the recombinant cDNA molecule, is indicated in all cases (underlined). Numbering of each sequence starts at this EcoRI site. AcaNAP45 and AcaNAP47, each encode a protein which has two NAP domains; all other clones in this Figure code for a protein having a single NAP domain.

FIG. 14 depicts the nucleotide, and deduced amino acid, sequence of the recombinant cDNA molecule NamNAP [SEQ. ID. NO. 39].

FIG. 16 presents the alignment of amino acid sequences corresponding to mature NAPs isolated according to the procedures disclosed herein: namely AcaNAP5 [SEQ. ID. NO. 40], AcaNAP6 [SEQ. ID. NO. 41], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP31, 42, 46 [SEQ. ID. NO. 47], AceNAP4d1 [SEQ. ID. NO. 48], AceNAP4d2 [SEQ. ID. NO. 49], AcaNAP45d1 [SEQ. ID. NO. 50], AcaNAP47d1 [SEQ. ID. NO. 51], AduNAP7d1 [SEQ. ID. NO. 52], AcaNAP45d2 [SEQ. ID. NO. 53], AcaNAP47d2 [SEQ. ID. NO. 54], AduNAP4 [SEQ. ID. NO. 55], AduNAP7d2 [SEQ. ID. NO. 56], AceNAP5 [SEQ. ID. NO. 57], AceNAP7 [SEQ. ID. NO. 58], AcaNAPc2 [SEQ. ID. NO. 59], HpoNAP5 [SEQ. ID. NO. 60], and NamNAP [SEQ. ID. NO. 61]. Each NAP domain comprises ten cysteine residues, which are used to align the sequences, and amino acid sequences between the cysteines. A1 through A10 represent the amino acid sequences between the cysteine residues.

FIG. 17 depicts the amino acid sequence of mature AceNAP4 [SEQ. ID. NO. 62] having two NAP domains.

FIG. 18 depicts the amino acid sequence of mature AcaNAP45 [SEQ. ID. NO. 63] having two NAP domains.

FIG. 19 depicts the amino acid sequence of mature AcaNAP47 [SEQ. ID. NO. 64] having two NAP domains.

FIG. 20 depicts the amino acid sequence for mature AduNAP7 [SEQ. ID. NO. 65] having two NAP domains.

DETAILED DESCRIPTION OF THE INVENTION

Figure 10A:
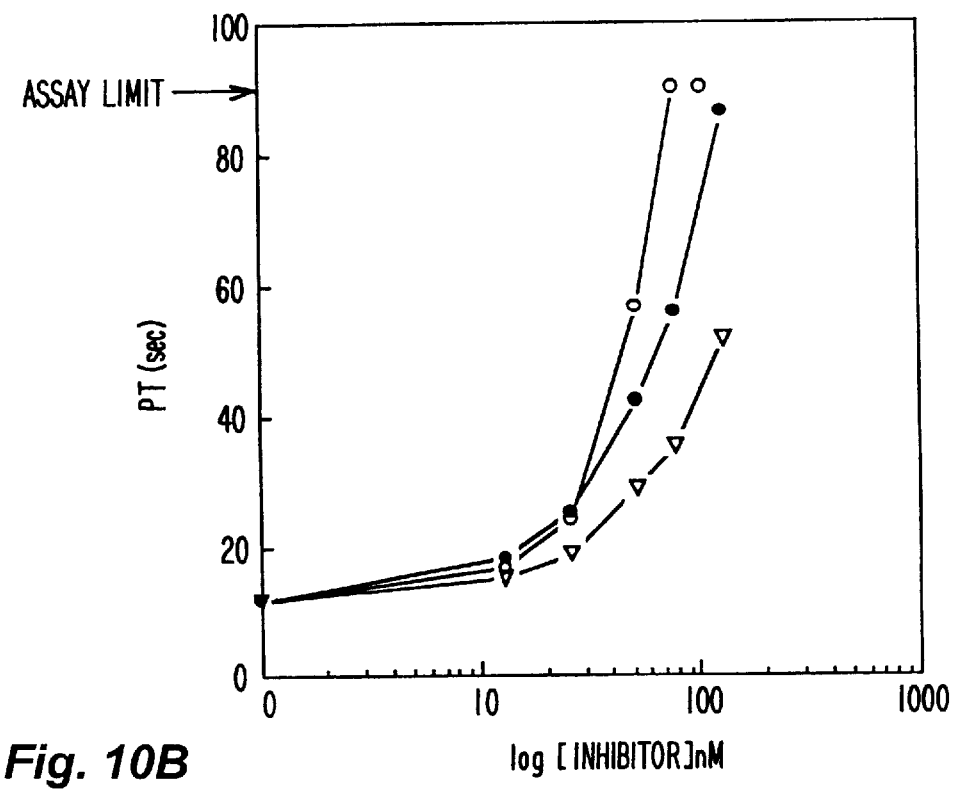
FIG. 10 Parts A and B depict the comparative effects of certain NAP proteins on the prothrombin time (PT) measurement (FIG. 10 Part A) and the activated partial thromboplastin time (aPTT) (FIG. 10 Part B) of normal citrated human plasma. Solid circles, (•), represent Pro-AcaNAP5; open triangles, (Δ), represent AcaNAP5; and open circles, (○), represent native AcaNAP.

This invention provides a family of proteins, collectively referred to as Nematode-extracted Anticoagulant Proteins (NAPs). These proteins are so designated because the first member originally isolated was extracted from a nematode, the canine hookworm, *Ancyclostoma caninum*. However, the designation NAP or NAP domain should not be considered to limit the proteins of the present invention by this or other natural source.

Individual NAP proteins are characterized by having at least one NAP domain and by having anticoagulant activity. Such anticoagulant activity may be assessed by increases in clotting time in both the PT and aPTT assays described herein, by the inhibition of factor Xa or factor VIIa/TF activity, or by demonstration of activity in vivo. Preferably, blood or plasma used in such assays derives from species known to be infected by nematodes, such as pigs, humans, primates, and the like. The NAP domain is an amino acid sequence. It is believed that the NAP domain is responsible for the observed anticoagulant activity. Certain representative NAP domains include the amino acid sequences depicted in FIGS. 11 and 16, particularly the sequences between the cysteines designated as Cysteine 1 and Cysteine 10 in FIG. 11 and the sequence following cysteine 10. The characteristics broadly defining this family of proteins, as well as the nucleic acid molecules, including mRNAs sequences and DNA sequences which encode such proteins, are provided. Methods of making these proteins, as well as methods of making nucleic acid molecules encoding such proteins, are also provided. The specific examples provided are exemplary only and other members of the NAP family of proteins, as well as nucleic acid sequences encoding them, can be obtained by following the procedures outlined in these examples and described herein.

The proteins of the present invention include isolated NAPs which comprise proteins having anticoagulant activity and including at least one NAP domain.

With respect to "anticoagulant activity", the purified proteins of the present invention are active as anticoagulants, and as such, are characterized by inhibiting the clotting of blood which includes the clotting of plasma. In one aspect, the preferred isolated proteins of the present invention include those which increase the clotting time of human plasma as measured in both the prothrombin time (PT) and activated partial thromboplastin time (aPTT) assays.

In the PT assay, clotting is initiated by the addition of a fixed amount of tissue factor-phospholipid micelle complex (thromboplastin) to human plasma. Anticoagulants interfere with certain interactions on the surface of this complex and increase the time required to achieve clotting relative to the clotting observed in the absence of the anticoagulant. The measurement of PT is particularly relevant for assessing NAP anticoagulant activity because the series of specific biochemical events required to cause clotting in this assay are similar to those that must be overcome by the hookworm in nature to facilitate feeding. Thus, the ability of NAP to act as an inhibitor in this assay can parallel its activity in nature, and is predictive of anticoagulant activity in vivo. In both the assay and in nature, the coagulation response is initiated by the formation of a binary complex of the serine protease factor VIIa (fVIIa) and the protein tissue factor (TF) (fVIIa/TF), resulting in the generation of fXa. The subsequent assembly of fXa into the prothrombinase complex is the key event responsible for the formation of thrombin and eventual clot formation.

In the aPTT assay, clotting is initiated by the addition of a certain fixed amount of negatively charged phospholipid micelle (activator) to the human plasma. Substances acting as anticoagulants will interfere with certain interactions on the surface of the complex and again increase the time to achieve a certain amount of clotting relative to that observed in the absence of the anticoagulant. Example B describes such PT and aPTT assays. These assays can be used to assess anticoagulant activity of the isolated NAPs of the present invention.

The preferred isolated NAPs of the present invention include those which double the clotting time of human plasma in the PT assay when present at a concentration of about 1 to about 500 nanomolar and which also double the clotting time of human plasma in the aPTT assay when present at a concentration of about 1 to about 500 nanomolar. Especially preferably are those proteins which double the clotting time of human plasma in the PT assay when present at a concentration of about 5 to about 100 nanomolar, and which also double the clotting time of human plasma in the aPTT assay when present at a concentration of about 5 to about 200 nanomolar. More especially preferred are those proteins which double the clotting time of human plasma in the PT assay when present at a concentration about 10 to about 50 nanomolar, and which also double the clotting time of human plasma in the aPTT assay when present at a concentration of about 10 to about 100 nanomolar.

Figure 15:
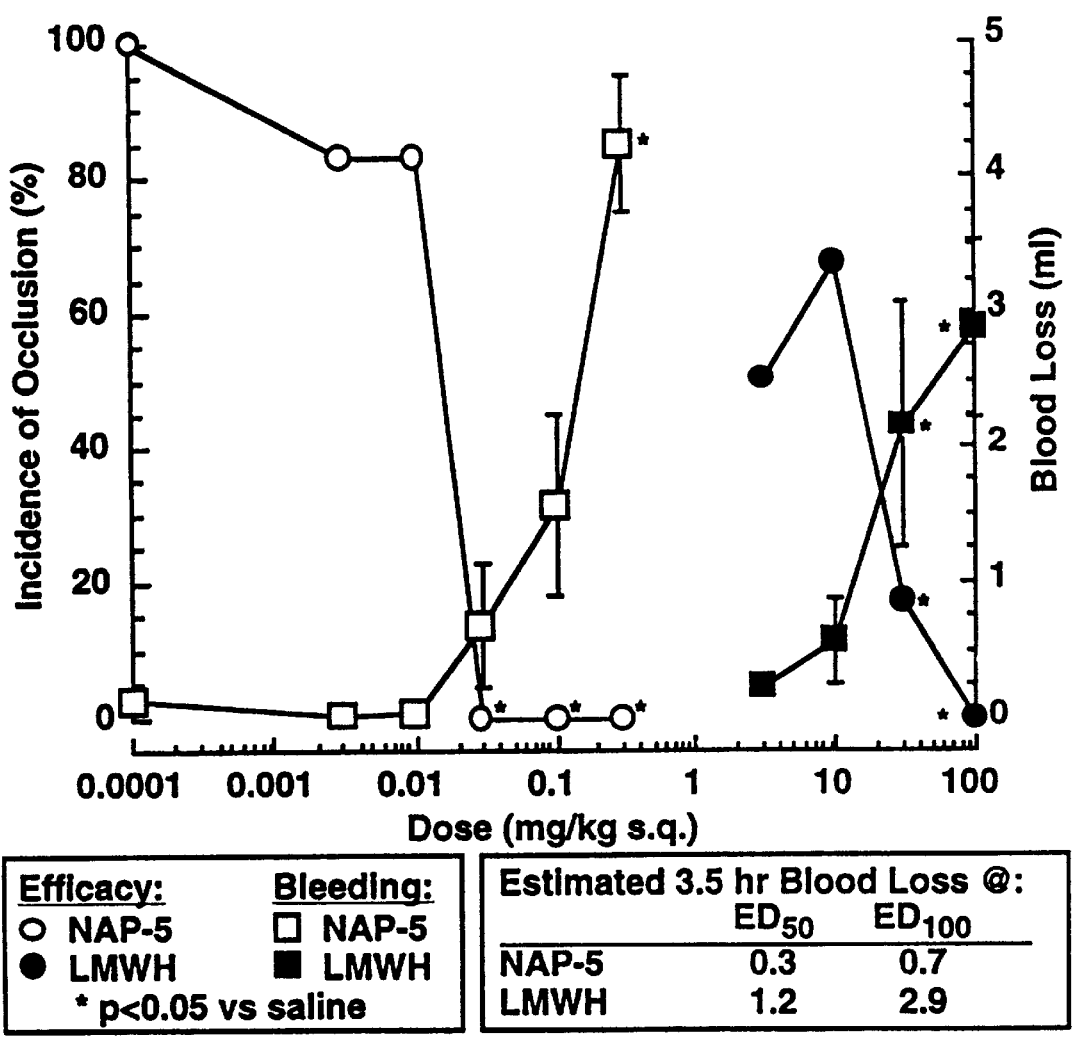
FIG. 15 presents the antithrombotic activity of AcaNAP5 and Low Molecular Weight Heparin (LMWH; Enoxaparin™) evaluated in the $FeCl_3$ model of arterial thrombosis. Activity data is represented as the percent incidence of occlusive thrombus formation in the carotid artery (circles). Thrombus formation began 150 minutes after subcutaneous (s.c.) administration of test agent. Deep wound bleeding was quantified in a separate group of animals that were treated in an identical manner but without addition of $FeCl_3$ (squares). Blood loss at a deep surgical wound in the neck was quantified over a total of 210 minutes after subcutaneous compound administration.

Anticoagulant, or antithrombotic, activity of NAPs of the present invention also can be evaluated using the in vivo models presented in Example F. The rat $FeCl_3$ model described in part A of that Example is a model of platelet dependent, arterial thrombosis that is commonly used to assess antithrombotic compounds. The model evaluates the ability of a test compound to prevent the formation of an occlusive thrombus induced by $FeCl_3$ in a segment of the rat carotid artery. NAPs of the present invention are effective anticoagulants in this model when administered intravenously or subcutaneously. The deep wound bleeding assay described in part B of Example F allows measurement of blood loss after administration of an anticoagulant compound. A desired effect of an anticoagulant is that it inhibits blood coagulation, or thrombus formation, but must not be so active as to prevent clotting altogether and thereby potentiate bleeding. Thus, the deep wound bleeding assay measures the amount of blood loss over the 3.5 hour period after administration of anticoagulant. The data presented in FIG. 15 show NAP of the present invention to be an effective antithrombotic compound at a dose that does not cause excessive bleeding. In contrast, the dose of low molecular weight heparin (LMWH) that correlated with 0% occlusion caused about three times more bleeding than the effective dose of NAP.

General NAP Domain [FORMULA I]

With respect to "NAP domain", the isolated proteins (or NAPs) of the present invention include at least one NAP domain in their amino acid sequence. Certain NAP domains have an amino acid sequence having a molecular weight of about 5.0 to 8.0 kilodaltons and containing 10 cysteine amino acid residues.

Certain preferred isolated NAPs of the present invention include those which contain at least one NAP domain, wherein each such NAP domain is further characterized by including the amino acid sequence: $Cys-A_1-Cys-A_2-Cys-A_3-Cys-A_4-Cys-A_5-Cys-A_6-Cys-A_7-Cys-A_8-Cys-A_9-Cys$ ("FORMULA I"), wherein: (a) $A_1$ is an amino acid sequence containing 7 to 8 amino acid residues; (b) $A_2$ is an amino acid sequence containing 2 to 5 amino acid residues; (c) $A_3$ is an amino acid sequence containing 3 amino acid residues; (d) $A_4$ is an amino acid sequence containing 6 to 17 amino acid residues; (e) $A_5$ is an amino acid sequence containing 3 to 4 amino acid residues; (f) $A_6$ is an amino acid sequence containing 3 to 5 amino acid residues; (g) $A_7$ is an amino acid residue; (h) $A_8$ is an amino acid sequence containing 10 to 12 amino acid residues; and (i) $A_9$ is an amino acid sequence containing 5 to 6 amino acid residues. Other NAPs having slightly different NAP domains (See FORMULAS II to V) are encompassed within the present invention.

Especially preferred NAP domains include those wherein $A_2$ is an amino acid sequence containing 4 to 5 amino acid residues and $A_4$ is an amino acid sequence containing 6 to 16 amino acid residues. More preferred are NAP domains wherein: (a) $A_1$ has Glu as its fourth amino acid residue; (b) $A_2$ has Gly as its first amino acid residue; (c) $A_8$ has Gly as its third amino acid residue and Arg as its sixth amino acid residue; and (d) $A_9$ has Val as its first amino acid residue. More preferably, $A_3$ has Asp or Glu as its first amino acid residue and Lys or Arg as its third amino acid residue and $A_7$ is Val or Gln. Also, more preferably $A_8$ has Leu or Phe as its fourth amino acid residue and Lys or Tyr as its fifth amino acid residue. Also preferred are NAP domains where, when $A_8$ has 11 or 12 amino acid residues, Asp or Gly is its penultimate amino acid residue, and, where when $A_8$ has 10 amino acids, Gly is its tenth amino acid residue. For expression of recombinant protein in certain expression systems, a recombinant NAP may additionally include an amino acid sequence for an appropriate secretion signal. Certain representative NAP domains include the sequences depicted in FIG. 11 and FIG. 16, particularly the sequences between (and including) the cysteines designated as Cysteine 1 and Cysteine 10 and following Cysteine 10.

Certain NAPs of the present invention demonstrate specificity toward inhibiting a particular component in the coagulation cascade, such as fXa or the fVIIa/TF complex. The specificity of a NAP's inhibitory activity toward a component in the coagualtion cascade can be evaluated using the protocol in Example D. There, the ability of a NAP to inhibit the activity of a variety of serine proteases involved in coagulation is measured and compared. The ability of a NAP to inhibit the fVIIa/TF complex also can be assessed using the protocols in Examples E, which measure the ability of a NAP to bind fXa in either an inhibitory or noninhibitory manner and to inhibit FVIIa when complexed with TF. AcaNAP5 and AcaNAP6 are examples of proteins having NAP domains that specifically inhibit fXa. AcaNAPc2 is a protein having a NAP domain that demonstrates selective inhibition of the fVIIa/TF complex.

NAPs having Factor Xa Inhibitory Activity
(FORMULA II)

Thus, in one aspect NAPs of the present invention also include an isolated protein having Factor Xa inhibitory activity and having one or more NAP domains, wherein each NAP domain includes the sequence: Cys-A1-Cys-A2-Cys-A3-Cys-A4-Cys-A5-Cys-A6-Cys-A7-Cys-A8-Cys-A9-Cys-A10 ("FORMULA II"), wherein (a) A1 is an amino acid sequence of 7 to 8 amino acid residues;

(b) A2 is an amino acid sequence;

(c) A3 is an amino acid sequence of 3 amino acid residues;

(d) A4 is an amino acid sequence;

(e) A5 is an amino acid sequence of 3 to 4 amino acid residues;

(f) A6 is an amino acid sequence;

(g) A7 is an amino acid;

(h) A8 is an amino acid sequence of 11 to 12 amino acid residues;

(i) A9 is an amino acid sequence of 5 to 7 amino acid residues; and (j) A10 is an amino acid sequence; wherein each of A2, A4, A6 and A10 has an independently selected number of independently selected amino acid residues and each sequence is selected such that each NAP domain has in total less than about 120 amino acid residues.

Pharmaceutical compositions comprising NAP proteins according to this aspect, and methods of inhibiting blood coagulation comprising administering NAP proteins according to this aspect also are contemplated by this invention.

NAP proteins within this aspect of the invention have at least one NAP domain. Preferred are NAPs having one or two NAP domains. NAP proteins AcaNAP5 [SEQ. ID. NOS. 4 and 40] and AcaNAP6 [SEQ. ID. NOS. 6 and 41] have one NAP domain and are preferred NAPs according to this aspect of the invention.

Preferred NAP proteins according to one embodiment of this aspect of the invention are those in which A2 is an amino acid sequence of 3 to 5 amino acid residues, A4 is an amino acid sequence of 6 to 19 amino acid residues, A6 is an amino acid sequence of 3 to 5 amino acid residues, and A10 is an amino acid sequence of 5 to 25 amino acid residues.

In another preferred embodiment of this aspect of the invention, A3 has the sequence Glu-A3$_a$-A3$_b$, wherein A3$_a$ and A3$_b$ are independently selected amino acid residues. More preferably, A3$_a$ is selected from the group consisting of Ala, Arg, Pro, Lys, Ile, His, Leu, and Thr, and A3$_b$ is selected from the group consisting of Lys, Thr, and Arg. Especially preferred A3 sequences are selected from the group consisting of Glu-Ala-Lys, Glu-Arg-Lys, Glu-Pro-Lys, Glu-Lys-Lys, Glu-Ile-Thr, Glu-His-Arg, Glu-Leu-Lys, and Glu-Thr-Lys.

In an additional preferred embodiment of this aspect of the invention, A4 is an amino acid sequence having a net anionic charge.

According to this aspect of the invention, a preferred A7 amino acid residue is Val or Ile.

Another preferred embodiment of this aspect of the invention is one in which A8 includes the amino acid sequence A8$_a$-A8$_b$-A8$_c$-A8$_d$-A8$_e$-A8$_f$-A8$_g$- [SEQ. ID. NO. 68], wherein (a) A8$_a$ is the first amino acid residue in A8, (b) at least one of A8$_a$ and A8$_b$ is selected from the group consisting of Glu or Asp, and (c) A8$_c$ through A8$_g$ are independently selected amino acid residues.

Preferably, A8$_c$ is Gly, A8$_d$ is selected from the group consisting of Phe, Tyr, and Leu, A8$_e$ is Tyr, A8$_f$ is Arg, and A8$_g$ is selected from Asp and Asn. An especially preferred A8$_c$-A8$_d$-A8$_e$-A8$_f$-A8$_g$- sequence is selected from the group consisting of Gly-Phe-Tyr-Arg-Asp [SEQ. ID. NO. 69], Gly-Phe-Tyr-Arg-Asn [SEQ. ID. NO. 70], Gly-Tyr-Tyr-Arg-Asp [SEQ, ID. NO. 71], Gly-Tyr-Tyr-Arg-Asn [SEQ. ID. NO. 72], and Gly-Leu-Tyr-Arg-Asp [SEQ. ID. NO. 73].

An additional preferred embodiment is one in which A10 includes an amino sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77].

NAP proteins AcaNAP5 and AcaNAP6 include the amino acid sequence Glu-Ile-Ile-His-Val [SEQ. ID. NO. 74] in A10, and are preferred NAPs according to this embodiment of the invention.

In one embodiment of this aspect of the invention, a preferred NAP molecule is one wherein (a) A3 has the sequence Glu-A3$_a$-A3$_b$, wherein A$^3$$_a$ and A3$_b$ are independently selected amino acid residues;

(b) A4 is an amino acid sequence having a net anionic charge;

(c) A7 is selected from the group consisting of Val and Ile;

(d) A8 includes an amino acid sequence selected from the group consisting of Gly-Phe-Tyr-Arg-Asp [SEQ. ID. NO. 69], Gly-Phe-Tyr-Arg-Asn [SEQ. ID. NO. 70], Gly-Tyr-Tyr-Arg-Asp [SEQ. ID. NO. 71], Gly-Tyr-Tyr-Arg-Asn [SEQ. ID. NO. 72], and Gly-Leu-Tyr-Arg-Asp [SEQ. ID. NO. 73]; and (e) A10 includes an amino sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77].

Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP proteins AcaNAP5 and AcaNAP6 have one NAP domain and are preferred NAPs according to this embodiment of the invention.

In another preferred embodiment, a NAP molecule is one wherein (a) A3 is selected from the group consisting of Glu-Ala-Lys, Glu-Arg-Lys, Glu-Pro-Lys, Glu-Lys-Lys, Glu-Ile-Thr, Glu-His-Arg, Glu-Leu-Lys, and Glu-Thr-Lys;

(b) A4 is an amino acid sequence having a net anionic charge;

(c) A7 is Val or Ile;

(d) A8 includes an amino acid sequence selected from the group consisting of $A8_a$-$A8_b$-Gly-Phe-Tyr-Arg-Asp [SEQ. ID. NO. 78], $A8_a$-$A8_b$-Gly-Phe-Tyr-Arg-Asn [SEQ. ID. NO. 79], $A8_a$-$A8_b$-Gly-Tyr-Tyr-Arg-Asp [SEQ. ID. NO. 80], $A8_a$-$A8_b$-Gly-Tyr-Tyr-Arg-Asn [SEQ. ID. NO. 81], and $A8_a$-$A8_b$-Gly-Leu-Tyr-Arg-Asp [SEQ. ID. NO. 82], wherein at least one of $A8_a$ and $A8_b$ is Glu or Asp;

(e) A9 is an amino acid sequence of five amino acid residues; and (f) A10 includes an amino acid sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77]. Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. Preferred are proteins having at least one NAP domain that is substantially the same as that of either AcaNAP5 [SEQ. ID. NO. 40] or AcaNAP6 [SEQ. ID. NO. 41]. NAP proteins AcaNAP5 [SEQ. ID. NOS. 4 and 40] and AcaNAP6 [SEQ. ID. NOS. 6 and 41] have one NAP domain and are especially preferred NAPs according to this embodiment of the invention.

Preferred NAP proteins having Factor Xa inhibitory activity, according to all the embodiments recited above for this aspect of the invention, are derived from a nematode species. A preferred nematode species is selected from the group consisting of *Ancylostoma caninum, Ancylostoma ceylanicum, Ancylostoma duodenale, Necator americanus,* and *Heligomosomoides polygyrus*. Particularly preferred are NAP proteins AcaNAP5 and AcaNAP6 derived from *Ancylostoma caninum*.

This aspect of the invention also contemplates isolated recombinant cDNA molecules encoding a protein having Factor Xa inhibitory activity, wherein the protein is defined according to each of the embodiments recited above for isolated NAP protein having Factor Xa inhibitory activity. Preferred cDNAs according to this aspect of the invention code for AcaNAP5 and AcaNAP6.

The Factor Xa inhibitory activity of NAPs within this aspect of the invention can be determined using protocols described herein. Example A describes one such method. In brief, a NAP is incubated with factor Xa for a period of time, after which a factor Xa substrate is added. The rate of substrate hydrolysis is measured, with a slower rate compared to the rate in the absence of NAP indicative of NAP inhibition of factor Xa. Example C provides another method of detecting NAP's inhibitory activity toward factor Xa when it is assembled into the prothrombinase complex, which more accurately reflects its normal physiological function in vivo. As described therein, factor Xa assembled in the prothrombinase complex is incubated with NAP, followed by addition of substrate. fxa-mediated thrombin generation by the prothrombinase complex is measured by the rate of thrombin generation from this mixture.

NAPs having Factor VIIa/TF Inhibitory Activity
(FORMULA III)

In another aspect, NAPs of the present invention also include an isolated protein having Factor VIIa/TF inhibitory activity and having one or more NAP domains, wherein each NAP domain includes the sequence: Cys-A1-Cys-A2-Cys-A3-Cys-A4-Cys-A5-Cys-A6-Cys-A7-Cys-A8-Cys-A9-Cys-A10 ("FORMULA III"), wherein (a) A1 is an amino acid sequence of 7 to 8 amino acid residues;

(b) A2 is an amino acid sequence;

(c) A3 is an amino acid sequence of 3 amino acid residues;

(d) A4 is an amino acid sequence;

(e) A5 is an amino acid sequence of 3 to 4 amino acid residues;

(f) A6 is an amino acid sequence;

(g) A7 is an amino acid;

(h) A8 is an amino acid sequence of 11 to 12 amino acid residues;

(i) A9 is an amino acid sequence of 5 to 7 amino acid residues; and (j) A10 is an amino acid sequence; wherein each of A2, A4, A6 and A10 has an independently selected number of independently selected amino acid residues and each sequence is selected such that each NAP domain has in total less than about 120 amino acid residues.

Pharmaceutical compositions comprising NAP proteins according to this aspeact, and methods of inhibiting blood coagulation comprising administering NAP proteins according to this aspect also are contemplated by this invention. NAP proteins within this aspect of the invention have at least one NAP domain. Preferred are NAPs having one or two NAP domains. Preferred are proteins having at least one NAP domain substantially the same as that of AcaNAPc2 [SEQ. ID. NO. 59]. NAP protein AcaNAPc2 [SEQ. ID. NO. 59] has one NAP domain and is an especially preferred NAP according to this aspect of the invention.

Preferred NAP proteins according to this aspect of the invention are those in which A2 is an amino acid sequence of 3 to 5 amino acid residues, A4 is an amino acid sequence of 6 to 19 amino acid residues, A6 is an amino acid sequence of 3 to 5 amino acid residues, and A10 is an amino acid sequence of 5 to 25 amino acid residues.

In another preferred embodiment according to this aspect of the invention, A3 has the sequence Asp-$A3_a$-$A3_b$, wherein $A3_a$ and $A3_b$ are independently selected amino acid residues. More preferably, A3 is Asp-Lys-Lys.

In an additional preferred embodiment, A4 is an amino acid sequence having a net anionic charge.

In another preferred embodiment of this aspect of the invention, A5 has the sequence $A5_a$-$A5_b$-$A5_c$-$A5_d$ [SEQ. ID. NO. 84], wherein $A5_a$ through $A5_d$ are independently selected amino acid residues. Preferably, $A5_a$ is Leu and $A5_c$ is Arg.

According to this aspect of the invention, a preferred A7 amino acid residue is Val or Ile, more preferably Val.

An additional preferred embodiment of this aspect of the invention is one in which A8 includes the amino acid sequence $A8_a$-$A8_b$-$A8_c$-$A8_d$-$A8_e$-$A8_f$-$A8_g$- [SEQ. ID. NO. 68], wherein (a) $A8_a$ is the first amino acid residue in A8, (b) at least one of $A8_a$ and $A8_b$ is selected from the group consisting of Glu or Asp, and (c) $A8_c$ through $A8_g$ are independently selected amino acid residues.

Preferably, $A8_c$ is Gly, $A8_d$ is selected from the group consisting of Phe, Tyr, and Leu, $A8_e$ is Tyr, $A8_f$ is Arg, and $A8_g$ is selected from Asp and Asn. A preferred $A8_c$-$A8_d$-$A8_e$-$A8_f$-$A8_g$- sequence is Gly-Phe-Tyr-Arg-Asn [SEQ. ID. NO. 70].

In one embodiment, a preferred NAP molecule is one wherein (a) A3 has the sequence Asp-$A3_a$-$A3_b$, wherein $A3_a$ and $A3_b$ are independently selected amino acid residues;

(b) A4 is an amino acid sequence having a net anionic charge;

(c) A5 has the sequence $A5_a$-$A5_b$-$A5_c$-$A5_d$, wherein $A5_a$ through $A5_d$ are independently selected amino acid residues, and (d) A7 is selected from the group consisting of Val and Ile. Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP protein AcaNAPc2 has one NAP domain and is a preferred NAP according to this embodiment of the invention.

In another preferred embodiment, a NAP molecule is one wherein (a) A3 is Asp-Lys-Lys;

(b) A4 is an amino acid sequence having a net anionic charge;

(c) A5 has the sequence $a5_a$-$A5_b$-$A5_c$-$A5_d$ [SEQ. ID. NO. 85], wherein $A5_a$ through $A5_d$ are independently selected amino acid residues;

(d) A7 is Val;

(e) A8 includes an amino acid sequence $A8_a$-$A8_b$-Gly-Phe-Tyr-Arg-Asn [SEQ. ID. NO. 79], wherein at least one of $A8_a$ and $A8_b$ is Glu or Asp. Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP protein AcaNAPc2 [SEQ. ID. NO. 59] has one NAP domain and is a preferred NAP according to this embodiment of the invention.

Preferred NAP proteins having Factor VIIa/TF inhibitory activity, according to all the embodiments recited above for this aspect of the invention, are derived from a nematode species. A preferred nematode species is selected from the group consisting of *Ancylostoma caninum, Ancylostoma ceylanicum, Ancylostoma duodenale, Necator americanus,* and *Heligomosomoides polygyrus*. Particularly preferred is NAP protein AcaNAPc2 derived from *Ancylostoma caninum*.

This aspect of the invention also contemplates isolated recombinant cDNA molecules encoding a protein having Factor VIIa/TF inhibitory activity, wherein the protein is defined according to each of the embodiments recited above for isolated NAP protein having Factor VIIa/TF inhibitory activity. A preferred cDNA according to this aspect has a nucleotide sequence [SEQ. ID. NO. 19] and codes for AcaNAPc2 [SEQ. ID. NO. 59].

The fVIIa/TF inhibitory activity of NAPs within this aspect of the invention can be determined using protocols described herein. Example E describes fVIIa/TF assays. There, the fVIIa/TF-mediated cleavage and liberation of the tritiated activation peptide from radiolabeled human factor IX ($^3$H-FIX) or the amidolytic hydrolysis of a chromogenic peptidyl substrate are measured. Interestingly, NAP fVIIa/TF inhibitors of the present invention require the presence of fXa in order to be active fVIIa/TF inhibitors. However, NAP fVIIa/TF inhibitors were equally effective in the presence of fXa in which the active site had been irreversibly occupied with the peptidyl chloromethyl ketone H-Glu-Gly-Arg-CMK (EGR), and thereby rendered catalytically inactive (EGR-fXa). While not wishing to be bound by any one explanation, it appears that the NAP having fVIIa/TF inhibition activity forms a binary complex with fXa by binding to a specific recognition site on the enzyme that is distinct from the primary recognition sites $P_4$-$P_1$, within the catalytic center of the enzyme. This is followed by the formation of a quaternary inhibitory complex with the fVIIa/TF complex. Consistent with this hypothesis is that EGR-fXa can fully support the inhibition of fVIIa/TF by NAPs inhibitory for fVIIa/TF despite covalent occupancy of the primary recognition sites ($P_4$-$P_1$) within the catalytic site of fXa by the tripeptidyl-chloromethyl ketone (EGR-CMK).

The fVIIa/TF inhibitory activity of NAPs also can be determined using the protocol in Example D, as well as the fXa assays described above, and in Examples A and C. There, the ability of a NAP to inhibit the catalytic activity of a variety of enzymes is measured and compared to its inhibitory activity toward the fVIIa/TF complex. Specific inhibition of fVIIa/TF by a NAP is a desired characteristic for certain applications.

A further aspect of the invention includes an isolated protein having anticoagulant activity, and cDNAs coding for the protein, wherein said protein specifically inhibits the catalytic activity of the fVIIa/TF complex in the presence of fXa or catalytically inactive fXa derivative, but does not specifically inhibit the activity of FVIIa in the absence of TF or specifically inhibit prothrombinase. Preferred proteins according to this aspect of the invention have the characteristics described above for an isolated protein having Factor VIIa/TF inhibitory activity and having one or more NAP domains. A preferred protein according to this aspect of the invention is AcaNAPc2.

NAPs within this aspect of the invention are identified by their fVIIa/TF inhibitory activity in the presence of fXa or a fXa derivative, whether the derivative is catalytically active or not. The protocols described in Examples B, C, and F are useful in determining the anticoagulant activity of such NAPs. The protocol in Example A can detect a NAP's inactivity toward free fXa or prothrombinase. Data generated using the protcols in Example E will identify NAPs that require either catalytically active or inactive fXa to inhibit fVIIa/TF complex.

NAPs having Serine Protease Inhibitory Activity (FORMULA IV)

In an additional aspect, NAPs of the present invention also include an isolated protein having serine protease inhibitory activity and having one or more NAP domains, wherein each NAP domain includes the sequence: Cys-A1-Cys-A2-Cys-A3-Cys-A4-Cys-A5-Cys-A6-Cys-A7-Cys-A8-Cys-A9-Cys-A10, [SEQ. ID. NO. 86] ("FORMULA IV") wherein (a) A1 is an amino acid sequence of 7 to 8 amino acid residues;

(b) A2 is an amino acid sequence;

(c) A3 is an amino acid sequence of 3 amino acid residues;

(d) A4 is an amino acid sequence;

(e) A5 is an amino acid sequence of 3 to 4 amino acid residues;

(f) A6 is an amino acid sequence;

(g) A7 is an amino acid;

(h) A8 is an amino acid sequence of 10 to 12 amino acid residues;

(i) A9 is an amino acid sequence of 5 to 7 amino acid residues; and (j) A10 is an amino acid sequence;

wherein each of A2, A4, A6 and A10 has an independently selected number of independently selected amino acid residues and each sequence is selected such that each NAP domain has in total less than about 120 amino acid residues. Pharmaceutical compositions comprising NAP proteins according to this aspect, and methods of inhibiting blood coagulation comprising administering NAP proteins according to this aspect also are contemplated by this invention. NAP proteins within this aspect of the invention have at least one NAP domain. Preferred are NAPs having one or two NAP domains. Preferred are NAP domains that have amino acid sequences that are substantially the same as the NAP domains of HpoNAP5 [SEQ. ID. NO. 60] or NamNAP [SEQ. ID. NO. 61]. NAP proteins HpoNAP5 [SEQ. ID. NO. 60] and NamNAP [SEQ. ID. NO. 61] have one NAP domain and are preferred NAPs according to this aspect of the invention.

Preferred NAP proteins according to this aspect of the invention are those in which A2 is an amino acid sequence of 3 to 5 amino acid residues, A4 is an amino acid sequence of 6 to 19 amino acid residues, A6 is an amino acid sequence of 3 to 5 amino acid residues, and A10 is an amino acid sequence of 1 to 25 amino acid residues.

In another preferred embodiment, A3 has the sequence Glu-A3$_a$-A3$_b$, wherein A3$_a$ and A3$_b$ are independently selected amino acid residues. More preferably, A3 is Glu-Pro-Lys.

In an additional preferred embodiment, A4 is an amino acid sequence having a net anionic charge.

In another preferred embodiment, A5 has the sequence A5$_a$-A5$_b$-A5$_c$, wherein A5$_a$ through A5$_c$ are independently selected amino acid residues. Preferably, A5$_a$ is Thr and A5$_c$ is Asn. An especially preferred A5 sequence includes Thr-Leu-Asn or Thr-Met-Asn.

According to this aspect of the invention, a preferred A7 amino acid residue is Gln.

In one embodiment of this aspect of the invention, a preferred NAP molecule is one wherein (a) A3 has the sequence Glu-A3$_a$-A3$_b$, wherein A3$_a$ and A3$_b$ are independently selected amino acid residues;

(b) A4 is an amino acid sequence having a net anionic charge;

(c) A5 has the sequence A5$_a$-A5$_b$-A5$_c$, wherein A5$_a$ through A5$_c$ are independently selected amino acid residues, and (d) A7 is Gln. Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP proteins HpoNAP5 [SEQ. ID. NO. 60] and NamNAP [SEQ. ID. NO. 61] have one NAP domain and are preferred NAPs according to this embodiment of the invention.

In another preferred embodiment, a NAP molecule is one wherein (a) A3 is Glu-Pro-Lys;

(b) A4 is an amino acid sequence having a net anionic charge;

(c) A5 is selected from Thr-Leu-Asn and Thr-Met-Asn; and (d) A7 is Gln. Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP proteins HpoNAP5 [SEQ. ID. NO. 60] and NamNAP [SEQ. ID. NO. 61] have one NAP domain and are preferred NAPs according to this embodiment of the invention.

Preferred NAP proteins having serine protease inhibitory activity, according to all the embodiments recited above for this aspect of the invention, are derived from a nematode species. A preferred nematode species is selected from the group consisting of *Ancylostoma caninum, Ancylostoma ceylanicum, Ancylostoma duodenale, Necator americanus*, and *Heligomosomoides polygyrus*. Particularly preferred are NAP proteins HpoNAP5 and NamNAP derived from *Heligomosomoides polygyrus* and *Necator americanus*, respectively.

This aspect of the invention also contemplates isolated recombinant cDNA molecules encoding a protein having serine protease inhibitory activity, wherein the protein is defined according to each of the embodiments recited above for isolated NAP protein having serine protease inhibitory activity. Preferred cDNAs according to this aspect have nucleotide sequences [SEQ. ID. NO. 14] (HpoNAP5) and [SEQ. ID. NO. 39] (NamNAP) and code for HpoNAP5 [SEQ. ID. NO. 60] and NamNAP [SEQ. ID. NO. 61].

The serine protease inhibitory activity can be determined using any of the assays disclosed in Examples A through F, or any commonly used enzymatic assay for measuring inhibition of serine protease activity. Procedures for a multitude of enzymatic assays can be found in the volumes of *Methods of Enzymology* or similar reference materials. Preferred NAPs have serine protease inhibitory activity directed toward enzymes in the blood coagulation cascade or toward trypsin/elastase.

NAPs having Anticoagulant Activity (FORMULA V)

In another aspect of the invention, NAPs of the present invention also include an isolated protein having anticoagulant activity and having one or more NAP domains, wherein each NAP domain includes the sequence: Cys-A1-Cys-A2-Cys-A3-Cys-A4-Cys-A5-Cys-A6-Cys-A7-Cys-A8-Cys-A9-Cys-A10 ("FORMULA V"), wherein (a) A1 is an amino acid sequence of 7 to 8 amino acid residues;

(b) A2 is an amino acid sequence;

(c) A3 is an amino acid sequence of 3 amino acid residues;

(d) A4 is an amino acid sequence;

(e) A5 is an amino acid sequence of 3 to 4 amino acid residues;

(f) A6 is an amino acid sequence;

(g) A7 is an amino acid;

(h) A8 is an amino acid sequence of 11 to 12 amino acid residues;

(i) A9 is an amino acid sequence of 5 to 7 amino acid residues; AND (j) A10 is an amino acid sequence;

wherein each of A2, A4, A6 and A10 has an independently selected number of independently selected amino acid residues and each sequence is selected such that each NAP domain has in total less than about 120 amino acid residues. Pharmaceutical compositions comprising NAP proteins according to this aspeact, and methods of inhibiting blood coagulation comprising administering NAP proteins according to this aspect also are contemplated by this invention. NAP proteins within this aspect of the invention have at least one NAP domain. Preferred are NAPs having one or two NAP domains. Preferred NAPs include those having at least one NAP domain having an amino acid sequence substantially the same as any of [SEQ. ID. NOS. 40 to 61]. NAP proteins AcaNAP5 [SEQ. ID. NO. 40], AcaNAP6 [SEQ. ID. NO. 41], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP31 [SEQ. ID. NO. 47], AduNAP4 [SEQ. ID. NO. 55], AceNAP5 [SEQ. ID. NO. 57], and AceNAP7 [SEQ. ID. NO. 58] have one NAP domain and are preferred NAPs according to this aspect of the invention. NAP proteins AceNAP4 [SEQ. ID. NO. 62], AcaNAP45 [SEQ. ID. NO. 63], AcaNAP47 [SEQ. ID. NO. 64], and AduNAP7 [SEQ. ID. NO. 65] have two NAP domains and are preferred NAPs according to this aspect of the invention.

Preferred NAP proteins according to this aspect of the invention are those in which A2 is an amino acid sequence of 3 to 5 amino acid residues, A4 is an amino acid sequence of 6 to 19 amino acid residues, A6 is an amino acid sequence of 3 to 5 amino acid residues, and A10 is an amino acid sequence of 5 to 25 amino acid residues.

In another preferred embodiment, A3 has the sequence Glu-$A3_a$-$A3_b$, wherein $A3_a$ and $A3_b$ are independently selected amino acid residues. More preferably, $A3_a$ is selected from the group consisting of Ala, Arg, Pro, Lys, Ile, His, Leu, and Thr, and $A3_b$ is selected from the group consisting of Lys, Thr, and Arg. Especially preferred A3 sequences are selected from the group consisting of Glu-Ala-Lys, Glu-Arg-Lys, Glu-Pro-Lys, Glu-Lys-Lys, Glu-Ile-Thr, Glu-His-Arg, Glu-Leu-Lys, and Glu-Thr-Lys.

In an additional preferred embodiment, A4 is an amino acid sequence having a net anionic charge.

According to this aspect of the invention, a preferred A7 amino acid residue is Val or Ile.

Another preferred embodiment of the invention is one in which A8 includes the amino acid sequence $A8_a$-$A8^8_b$-$A8_c$-$A8_d$-$A8_e$-$A8_f$-$A8_g$- [SEQ. ID. NO. 68], wherein (a) $A8^8_a$ is the first amino acid residue in A8, (b) at least one of $A8_a$ and $A8_b$ is selected from the group consisting of Glu or Asp, and (c) $A8_c$ through $A8_g$ are independently selected amino acid residues.

Preferably, $A8_c$ is Gly, $A8_d$ is selected from the group consisting of Phe, Tyr, and Leu, $A8_e$ is Tyr, $A8_f$ is Arg, and $A8_g$ is selected from Asp and Asn. A preferred $A8_c$-$A8_d$-$A8_e$-$A8_f$-$A8_g$- sequence is selected from the group consisting of Gly-Phe-Tyr-Arg-Asp [SEQ. ID. NO. 69], Gly-Phe-Tyr-Arg-Asn [SEQ. ID. NO. 70], Gly-Tyr-Tyr-Arg-Asp [SEQ. ID. NO. 71], Gly-Tyr-Tyr-Arg-Asn [SEQ. ID. NO. 72], and Gly-Leu-Tyr-Arg-Asp [SEQ. ID. NO. 73].

Another preferred embodiment is one in which A10includes an amino sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77]. NAP proteins AcaNAP5 [SEQ. ID. NOS. 4 and 40] and AcaNAP6 [SEQ. ID. NOS. 6 and 41] include the amino acid sequence Glu-Ile-Ile-His-Val [SEQ. ID. NO. 74] in A10, and are preferred NAPs according to this embodiment of the invention. NAP protein AcaNAP48 [SEQ. ID. NO. 42] includes the amino acid sequence Asp-Ile-Ile-Met-Val [SEQ. ID. NO. 75] in A10 and is a preferred NAP according to this embodiment of the invention. NAP proteins AcaNAp23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAp31 [SEQ. ID. NO. 47], and AceNAP4 [SEQ. ID. NO. 48, 49 AND 62] include the amino acid sequence Phe-Ile-Thr-Phe-Ala-Pro [SEQ. ID. NO. 76] and are preferred NAPs according to this embodiment of the invention. NAP proteins AcaNAP45 [SEQ. ID. NOS. 50, 53 AND 63], AcaNAP47 [SEQ. ID. NO. 51, 54 AND 64], AduNAP7 [SEQ. ID. NO. 52, 56 AND 65], AduNAP4 [SEQ. ID. NO. 55], AceNAP5 [SEQ. ID. NO. 57], and AceNAP7 [SEQ. ID. NO. 58] include the amino acid sequence Met-Glu-Ile-Ile-Thr [SEQ. ID. NO. 77] and are preferred NAPs according to this embodiment of the invention.

In one embodiment, a preferred NAP molecule is one wherein (a) A3 has the sequence Glu-$A3_a$-$A3_b$, wherein $A^3_a$ and $A3_b$ are independently selected amino acid residues;

(b) A4 is an amino acid sequence having a net anionic charge;

(c) A7 is selected from the group consisting of Val and Ile;

(d) A8 includes an amino acid sequence selected from the group consisting of Gly-Phe-Tyr-Arg-Asp [SEQ. ID. NO. 69], Gly-Phe-Tyr-Arg-Asn [SEQ. ID. NO. 70], Gly-Tyr-Tyr-Arg-Asp [SEQ. ID. NO. 71], Gly-Tyr-Tyr-Arg-Asn [SEQ. ID. NO. 72], and Gly-Leu-Tyr-Arg-Asp [SEQ. ID. NO. 73]; and (e) A10 includes an amino sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77]. Pharmaceutical compositions comprising NAP proteins according to this embodiment, and methods of inhibiting blood coagulation comprising administering NAP proteins according to this embodiment also are contemplated by this invention. NAP proteins within this aspect of the invention have at least one NAP domain. Preferred are NAPs having one or two NAP domains. NAP proteins AcaNAP5 [SEQ. ID. NOS. 4 and 40], AcaNAP6 [SEQ. ID. NOS. 6 and 41], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP31 [SEQ. ID. NO. 47], AduNAP4 [SEQ. ID. NO. 55], AceNAP5 [SEQ. ID. NO. 57], and AceNAP7 [SEQ. ID. NO. 58] have one NAP domain and are preferred NAPs according to this embodiment. NAP proteins AceNAP4 [SEQ. ID. NO. 62], AcaNAP45 [SEQ. ID. NO. 63], AcaNAP47 [SEQ. ID. NO. 64], and AduNAP7 [SEQ. ID. NO. 65] have two NAP domains and are preferred NAPs according to this embodiment.

In another preferred embodiment, a NAP molecule is one wherein (a) A3 is selected from the group consisting of Glu-Ala-Lys, Glu-Arg-Lys, Glu-Pro-Lys, Glu-Lys-Lys, Glu-Ile-Thr, Glu-His-Arg, Glu-Leu-Lys, and Glu-Thr-Lys;

(b) A4 is an amino acid sequence having a net anionic charge;

(c) A7 is Val or Ile;

(d) A8 includes an amino acid sequence selected from the group consisting of $A8_a$-$A8_b$-Gly-Phe-Tyr-Arg-Asp [SEQ. ID. NO. 78], $A8_a$-$A8_b$-Gly-Phe-Tyr-Arg-Asn [SEQ. ID. NO. 79], $A8_a$-$A8_b$-Gly-Tyr-Tyr-Arg-Asp [SEQ. ID. NO. 80], $A8_a$-$A8_b$-Gly-Tyr-Tyr-Arg-Asn [SEQ. ID. NO. 81], and $A8_a$-$A8_b$-Gly-Leu-Tyr-Arg-Asp [SEQ. ID. NO. 82], wherein at least one of $A8_a$ and $A8_b$ is Glu or Asp;

(e) A9 is an amino acid sequence of five amino acid residues; and (f) A10 includes an amino acid sequence selected from the group consisting of Glu-Ile-Ile-His-Val [SEQ. ID. NO. 74], Asp-Ile-Ile-Met-Val [SEQ. ID. NO. 75], Phe-Ile-Thr-Phe-Ala-Pro [SEQ. ID. NO. 76], and Met-Glu-Ile-Ile-Thr [SEQ. ID. NO. 77]. Pharmaceutical compositions comprising NAP proteins according to this embodiment, and methods of inhibiting blood coagulation comprising administering NAP proteins according to this embodiment also are contemplated by this invention. NAP proteins within this embodiment of the invention have at least one NAP domain. Preferred are NAPs having one or two NAP domains. NAP proteins AcaNAP5 [SEQ. ID. NOS. 4 and 40], AcaNAP6 [SEQ. ID. NOS. 6 and 41], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP31 [SEQ. ID. NO. 47], AduNAP4 [SEQ. ID. NO. 55], AceNAP5 [SEQ. ID. NO. 57], and AceNAP7 [SEQ. ID. NO. 58] have one NAP domain and are preferred NAPs according to this embodiment. NAP proteins AceNAP4 [SEQ. ID. NO. 62], AcaNAP45 [SEQ. ID. NO. 63], AcaNAP47 [SEQ. ID. NO. 64], and AduNAP7 [SEQ. ID. NO. 65] have two NAP domains and are preferred NAPs according to this embodiment.

Preferred NAP proteins having anticoagulant activity, according to all the embodiments recited above for this aspect of the invention, are derived from a nematode species. A preferred nematode species is selected from the group consisting of *Ancylostoma caninum, Ancylostoma ceylanicum, Ancylostoma duodenale, Necator americanus,* and *Heligomosomoides polygyrus*. Particularly preferred are NAP proteins AcaNAP5 [SEQ. ID. NO. 4 and 40], AcaNAP6 [SEQ. ID. NO. 6 and 41], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP45 [SEQ. ID. NO. 63], AcaNAP47 [SEQ. ID. NO. 64], and AcaNAP31 [SEQ. ID. NO. 47] derived from *Ancylostoma caninum;* AceNAP4 [SEQ. ID. NO. 62], AceNAPS [SEQ. ID. NO. 57], and AceNAP7 [SEQ. ID. NO. 58] derived from *Ancylostoma ceylanicum;* and AduNAP7 [SEQ. ID. NO. 65] and AduNAP4 [SEQ. ID. NO. 55] derived from *Ancylostoma duodenale*.

This aspect of the invention also contemplates isolated recombinant cDNA molecules encoding a protein having anticoagulant activity, wherein the protein is defined according to each of the embodiments recited above for isolated NAP protein having anticoagulant activity. Preferred cDNAs according to this aspect include AcaNAP5 [SEQ. ID. NO. 3], AcaNAP6 [SEQ. ID. NO. 5], AcaNAP48 [SEQ. ID. NO. 38], AcaNAP23 [SEQ. ID. NO. 31], AcaNAP24 [SEQ. ID. NO. 32], AcaNAP25 [SEQ. ID. NO. 33], AcaNAP44 [SEQ. ID. NO. 35], AcaNAP31 [SEQ. ID. NO. 34], AduNAP4 [SEQ. ID. NO. 12], AceNAP5 [SEQ. ID. NO. 10], AceNAP7 [SEQ. ID. NO. 11], AceNAP4 [SEQ. ID. NO. 9], AcaNAP45 [SEQ. ID. NO. 36], AcaNAP47 [SEQ. ID. NO. 37], and AduNAP7 [SEQ. ID. NO. 13].

The anticoagulation activity of NAPs within this aspect of the invention can be determined using protocols described herein. Examples B and F present particulary useful methods for assessing a NAP's anticoagulation activity. The procedures described for detecting NAPs having fXa inhibitory activity (Examples A,C) and fVIIa/TF inhibitory activity (Example E) also are useful in evaluating a NAP's anticoagulation activity.

Oligonucleotides

Another aspect of this invention is an oligonucleotide comprising a sequence selected from

YG109: TCAGACATGT-ATAATCTCAT-GTTGG [SEQ. ID. NO. 88],

YG103: AAGGCATACC-CGGAGTGTGG-TG [SEQ. ID. NO. 89],

NAP-1: AAR-CCN-TGY-GAR-MGG-AAR-TGY [SEQ. ID. NO. 90], and

NAP-4.RC: TW-RWA-NCC-NTC-YTT-RCA-NAC-RCA [SEQ. ID. NO. 91].

These oligonucleotide sequences hybridize to nucleic acid sequences coding for NAP protein.

The isolated NAPs of the present invention include those having variations in the disclosed amino acid sequence or sequences, including fragments, naturally occurring mutations, allelic variants, randomly generated artificial mutants and intentional sequence variations, all of which conserve anticoagulant activity. The term "fragments" refers to any part of the sequence which contains fewer amino acids than the complete protein, as for example, partial sequences excluding portions at the amino-terminus, carboxy-terminus or between the amino-terminus and carboxy-terminus of the complete protein.

The isolated NAPs of the present invention also include proteins having a recombinant amino acid sequence or sequences which conserve the anticoagulant activity of the NAP domain amino acid sequence or sequences. Thus, as used herein, the phrase "NAP protein" or the term "protein" when referring to a protein comprising a NAP domain, means, without discrimination, native NAP protein and NAP protein made by recombinant means. These recombinant proteins include hybrid proteins, such as fusion proteins, proteins resulting from the expression of multiple genes within the expression vector, proteins resulting from expression of multiple genes within the chromosome of the host cell, and may include a polypeptide having anticoagulant activity of a disclosed protein linked by peptide bonds to a second polypeptide. The recombinant proteins also include variants of the NAP domain amino acid sequence or sequences of the present invention that differ only by conservative amino acid substitution. Conservative amino acid substitutions are defined as "sets" in Table 1 of Taylor, W. R., J. Mol. Biol., 188:233 (1986). The recombinant proteins also include variants of the disclosed isolated NAP domain amino acid sequence or sequences of the present invention in which amino acid substitutions or deletions are made which conserve the anticoagulant activity of the isolated NAP domain sequence or sequences.

One preferred embodiment of the present invention is a protein isolated by biochemical methods from the nematode, *Ancylostoma caninum,* as described in Example 1. This protein increases the clotting time of human plasma in the PT and aPTT assays, contains one NAP domain, and is characterized by an N-terminus having the amino acid sequence, Lys-Ala-Tyr-Pro-Glu-Cys-Gly-Glu-Asn-Glu-Trp-Leu-Asp [SEQ. ID. NO. 92], and a molecular weight of about 8.7 kilodaltons to about 8.8 kilodaltons as determined by mass spectrometry.

Further preferred embodiments of the present invention include the proteins having anticoagulant activity made by recombinant methods from the cDNA library isolated from the nematode, *Ancylostoma caninum,* for example, AcaNAP5 [SEQ. ID. NO. 4 or 40], AcaNAP6 [SEQ. ID. NO. 6 or 41], Pro-AcaNAP5 [SEQ. ID. NO. 7], Pro-AcaNAP6 [SEQ. ID. NO. 8], AcaNAP48 [SEQ. ID. NO. 42], AcaNAP23 [SEQ. ID. NO. 43], AcaNAP24 [SEQ. ID. NO. 44], AcaNAP25 [SEQ. ID. NO. 45], AcaNAP44 [SEQ. ID. NO. 46], AcaNAP31 [SEQ. ID. NO. 47], AcaNAP45 [SEQ. ID. NO. 63], AcaNAP47 [SEQ. ID. NO. 64], and AcaNAPc2 [SEQ. ID. NO. 59]; isolated from the nematode, *Ancyclostoma ceylanium,* for example, AceNAP4 [SEQ. ID. NO. 62], AceNAP5 [SEQ. ID. NO. 57], and AceNAP7 [SEQ. ID. NO. 58]; isolated from the nematode, *Ancyclostoma duodenale,* for example, AduNAP4 [SEQ. ID. NO. 55] and AduNAP7 [SEQ. ID. NO. 65]; isolated from the nematode *Heligmosmoides polygyrus,* for example, HpoNAP5 [SEQ. ID. NO. 60]; and the nematode *Necator americanus,* for example, NamNAP [SEQ. ID. NO. 61]. The amino acid sequences of these proteins are shown in FIGS. 11 and 16 and elsewhere. Each such preferred embodiment increases the clotting time of human plasma in the PT and aPTT assays and contains at least one NAP domain.

With respect to "isolated proteins", the proteins of the present invention are isolated by methods of protein purification well known in the art, or as disclosed below. They may be isolated from a natural source, from a chemical mixture after chemical synthesis on a solid phase or in solution such as solid-phase automated peptide synthesis, or from a cell culture after production by recombinant methods.

As described further hereinbelow, the present invention also contemplates pharmaceutical compositions comprising NAP and methods of using NAP to inhibit the process of blood coagulation and associated thrombosis. Oligonucleotide probes useful for identifying NAP nucleic acid in a sample also are within the purview of the present invention, as described more fully hereinbelow.

1. NAP Isolated from Natural Sources.

The preferred isolated proteins (NAPs) of the present invention may be isolated and purified from natural sources. Preferred as natural sources are nematodes; suitable nematodes include intestinal nematodes such as *Ancylostoma caninum, Ancylostoma ceylanicum, Ancylostoma duodenale, Necator americanus* and *Heligmosomoides polygyrus.* Especially preferred as a natural source is the hematophagous nematode, the hookworm, *Ancylostoma caninum.*

The preferred proteins of the present invention are isolated and purified from their natural sources by methods known in the biochemical arts. These methods include preparing a soluble extract and enriching the extract using chromatographic methods on different solid support matrices. Preferred methods of purification would include preparation of a soluble extract of a nematode in 0.02M Tris-HCl, pH 7.4 buffer containing various protease inhibitors, followed by sequential chromatography of the extract through columns containing Concanavalin-A Sepharose matrix, Poros20 HQ cation-ion exchange matrix, Superdex30 gel filtration matrix and a C18 reverse-phase matrix. The fractions collected from such chromatography columns may be selected by their ability to increase the clotting time of human plasma, as measured by the PT and aPTT assays, or their ability to inhibit factor Xa amidolytic activity as measured in a calorimetric amidolytic assay using purified enzyme, or by other methods disclosed in Examples A to F herein. An example of a preferred method of purification of an isolated protein of the present invention would include that as disclosed in Example 1.

The preferred proteins of the present invention, when purified from a natural source, such as *Ancylostoma caninum,* as described, include those which contain the amino acid sequence: Lys-Ala-Tyr-Pro-Glu-Cys-Gly-Glu-Asn-Glu-Trp-Leu-Asp [SEQ. ID. NO. 92]. Especially preferred are the purified proteins having this amino acid sequence at its amino terminus, such as shown in FIG. 2 (AcaNAP5 [SEQ. ID. NO. 4]) or FIG. 4 (AcaNAP6 [SEQ. ID. NO. 6]). One preferred protein of the present invention was demonstrated to have the amino acid sequence, Lys-Ala-Tyr-Pro-Glu-Cys-Gly-Glu-Asn-Glu-Trp-Leu-Asp [SEQ. ID. NO. 92] at its amino-terminus and a molecular weight of 8.7 to 8.8 kilodaltons, as determined by mass spectrometry.

2. NAP made by Chemical Synthesis.

The preferred isolated NAPs of the present invention may be synthesized by standard methods known in the chemical arts.

The isolated proteins of the present invention may be prepared using solid-phase synthesis, such as that described by Merrifield, J. Amer. Chem. Soc., 85:2149 (1964) or other equivalent methods known in the chemical arts, such as the method described by Houghten in Proc. Natl. Acad. Sci., 82:5132 (1985).

Solid-phase synthesis is commenced from the C-terminus of the peptide by coupling a protected amino acid or peptide to a suitable insoluble resin. Suitable resins include those containing chloromethyl, bromomethyl, hydroxylmethyl, aminomethyl, benzhydryl, and t-alkyloxycarbonylhydrazide groups to which the amino acid can be directly coupled.

In this solid phase synthesis, the carboxy terminal amino acid, having its alpha amino group and, if necessary, its reactive side chain group suitably protected, is first coupled to the insoluble resin. After removal of the alpha amino protecting group, such as by treatment with trifluoroacetic acid in a suitable solvent, the next amino acid or peptide, also having its alpha amino group and, if necessary, any reactive side chain group or groups suitably protected, is coupled to the free alpha amino group of the amino acid coupled to the resin. Additional suitably protected amino acids or peptides are coupled in the same manner to the growing peptide chain until the desired amino acid sequence is achieved. The synthesis may be done manually, by using automated peptide synthesizers, or by a combination of these.

The coupling of the suitably protected amino acid or peptide to the free alpha amino group of the resin-bound amino acid can be carried out according to conventional coupling methods, such as the azide method, mixed anhydride method, DCC (dicyclohexylcarbodiimide) method, activated ester method (p-nitrophenyl ester or N-hydroxysuccinimide ester), BOP (benzotriazole-1-yl-oxy-tris (diamino) phosphonium hexafluorophosphate) method or Woodward reagent K method.

It is common in peptide synthesis that the protecting groups for the alpha amino group of the amino acids or peptides coupled to the growing peptide chain attached to the insoluble resin will be removed under conditions which do not remove the side chain protecting groups. Upon completion of the synthesis, it is also common that the peptide is removed from the insoluble resin, and during or after such removal, the side chain protecting groups are removed.

Suitable protecting groups for the alpha amino group of all amino acids and the omega amino group of lysine include benzyloxycarbonyl, isonicotinyloxycarbonyl, o-chlorobenzyloxycarbonyl, p-nitrophenyloxycarbonyl, p-methoxyphenyloxycarbonyl, t-butoxycarbonyl, t-amyloxycarbonyl, adamantyloxycarbonyl, 2-(4-biphenyl)-2-propyloxycarbonyl, 9-fluorenylmethoxycarbonyl, methylsulfonylethoxylcarbonyl, trifluroacetyl, phthalyl, formyl, 2-nitrophenylsulfphenyl, diphenylphosphinothioyl, dimethylphosphinothioyl, and the like.

Suitable protecting groups for the carboxy group of aspartic acid and glutamic acid include benzyl ester, cyclohexyl ester, 4-nitrobenzyl ester, t-butyl ester, 4-pyridylmethyl ester, and the like.

Suitable protecting groups for the guanidino group of arginine include nitro, p-toluenesulfonyl, benzyloxycarbonyl, adamantyloxycarbonyl, p-methoxybenzenesulfonyl, 4-methoxy-2,6-dimethylbenzenesulfonyl, 1,3,5-trimethylphenylsulfonyl, and the like.

Suitable protecting groups for the thiol group of cysteine include p-methoxybenzyl, triphenylmethyl, acetylaminomethyl, ethylcarbamoyl, 4-methylbenzyl, 2,4,6-trimethylbenzyl, and the like.

Suitable protecting groups for the hydroxy group of serine include benzyl, t-butyl, acetyl, tetrahydropyranyl, and the like.

The completed peptide may be cleaved from the resin by treatment with liquid hydrofluoric acid containing one or more thio-containing scavengers at reduced temperatures. The cleavage of the peptide from the resin by such treatment will also remove all side chain protecting groups from the peptide.

The cleaved peptide is dissolved in dilute acetic acid followed by filtration, then is allowed to refold and establish proper disulfide bond formation by dilution to a peptide concentration of about 0.5 mM to about 2 mM in a 0.1M acetic acid solution. The pH of this solution is adjusted to about 8.0 using ammonium hydroxide and the solution is stirred open to air for about 24 to about 72 hours.

The refolded peptide is purified by chromatography, preferably by high pressure liquid chromatography on a reverse phase column, eluting with gradient of acetonitrile in water (also containing 0.1% trifluoroacetic acid), with the preferred gradient running from 0 to about 80% acetonitrile in water. Upon collection of fractions containing the pure peptide, the fractions are pooled and lyophilized to the solid peptide.

3. NAP made by Recombinant Methods.

Alternatively, the preferred isolated NAPs of the present invention may be made by recombinant DNA methods taught herein and well known in the biological arts. Sambrook, J., Fritsch, E. F. and Maniatis, T., *Molecular Cloning, A Laboratory Manual, Second Edition,* volumes 1 to 3, Cold Spring Harbor Laboratory Press (1989).

Recombinant DNA methods allow segments of genetic information, DNA, from different organisms, to be joined together outside of the organisms from which the DNA was obtained and this hybrid DNA to be incorporated into a cell that will allow the production of the protein for which the original DNA encodes.

Genetic information encoding a protein of the present invention may be obtained from the genomic DNA or mRNA of an organism by methods well known in the art. Preferred methods of obtaining this genetic information include isolating mRNA from an organism, converting it to its complementary DNA (cDNA), incorporating the cDNA into an appropriate cloning vector, and identifying the clone which contains the recombinant cDNA encoding the desired protein by means of hybridization with appropriate oligonucleotide probes constructed from known sequences of the protein.

The genetic information in the recombinant cDNA encoding a protein of the present invention may be ligated into an expression vector, the vector introduced into host cells, and the genetic information expressed as the protein encoded for.

(A) Preparation of cDNA Library.

Preferred natural sources of mRNA from which to construct a cDNA library are nematodes which include intestinal nematodes such as *Ancylostoma caninum, Ancylostoma ceylanicum, Ancylostoma duodenale, Necator americanus* and *Heligmosomoides polygyrus.* Especially preferred as a natural source of mRNA is the hookworm nematode, *Ancylostoma caninum.*

Preferred methods of isolating mRNA encoding a protein of the present invention, along with other mRNA, from an organism include chromatography on poly U or poly T affinity gels. Especially preferred methods of isolating the mRNA from nematodes include the procedure and materials provided in the QuickPrep mRNA Purification kit (Pharmacia).

Preferred methods of obtaining double-stranded cDNA from isolated mRNA include synthesizing a single-stranded cDNA on the mRNA template using a reverse transcriptase, degrading the RNA hybridized to the cDNA strand using a ribonuclease (RNase), and synthesizing a complementary DNA strand by using a DNA polymerase to give a double-stranded cDNA. Especially preferred methods include those wherein about 3 micrograms of mRNA isolated from a nematode is converted into double-stranded cDNA making use of Avian Myeloblastosis Virus reverse transcriptase, RNase H, and *E. coli* DNA polymerase I and T4 DNA polymerase.

cDNA encoding a protein of the present invention, along with the other cDNA in the library constructed as above, are then ligated into cloning vectors. Cloning vectors include a DNA sequence which accommodates the cDNA from the cDNA library. The vectors containing the cDNA library are introduced into host cells that can exist in a stable manner and provide a environment in which the cloning vector is replicated. Suitable cloning vectors include plasmids, bacteriophages, viruses and cosmids. Preferred cloning vectors include the bacteriophages. Cloning vectors which are especially preferred include the bacteriophage, lambda gt11 Sfi-Not vector.

The construction of suitable cloning vectors containing the cDNA library and control sequences employs standard ligation and restriction techniques which are well known in the art. Isolated plasmids, DNA sequences or synthesized oligonucleotides are cleaved, tailored and religated in the form desired.

With respect to restriction techniques, site-specific cleavage of cDNA is performed by treating with suitable restriction enzyme under conditions which are generally understood in the art, and the particulars of which are specified by the manufacturer of these commercially available restriction enzymes. For example, see the product catalogs of New England Biolabs, Promega and Stratagene Cloning Systems.

Generally, about 1 microgram of the cDNA is cleaved by treatment in about one unit of a restriction enzyme in about 20 microliters of buffer solution. Typically, an excess of restriction enzyme is used to ensure complete cleavage of the cDNA. Incubation times of about 1 to 2 hours at about 37° C. are usually used, though exceptions are known. After each cleavage reaction, the protein may be removed by extraction with phenol/chloroform, optionally followed by chromatography over a gel filtration column, such as Sephadex® G50. Alternatively, cleaved cDNA fragments may be separated by their sizes by electrophoresis in polyacrylamide or agarose gels and isolated using standard techniques. A general description of size separations is found in Methods of Enzymology, 65:499–560 (1980).

The restriction enzyme-cleaved cDNA fragments are then ligated into a cloning vector.

With respect to ligation techniques, blunt-end ligations are usually performed in about 15 to about 30 microliters of a pH 7.5 buffer comprising about 1 mM ATP and about 0.3 to 0.6 (Weiss) units of T4 DNA ligase at about 14° C. Intermolecular "sticky end" ligations are usually performed at about 5 to 100 nanomolar total-end DNA concentrations. Intermolecular blunt-end ligations (usually employing about 10 to 30-fold molar excess of linkers) are performed at about 1 micromolar total-end DNA concentrations.

(B) Preparation of cDNA Encoding NAP.

Cloning vectors containing the cDNA library prepared as disclosed are introduced into host cells, the host cells are cultured, plated, and then probed with a hybridization probe to identify clones which contain the recombinant cDNA encoding a protein of the present invention. Preferred host cells include bacteria when phage cloning vectors are used. Especially preferred host cells include E. coli strains such as strain Y1090.

Alternatively, the recombinant cDNA encoding a protein of the present invention may be obtained by expression of such protein on the outer surface of a filamentous phage and then isolating such phage by binding them to a target protein involved in blood coagulation.

An important and well known feature of the genetic code is its redundancy-more than one triplet nucleotide sequence codes for one amino acid. Thus, a number of different nucleotide sequences are possible for recombinant cDNA molecules which encode a particular amino acid sequence for a NAP of the present invention. Such nucleotide sequences are considered functionally equivalent since they can result in the production of the same amino acid sequence in all organisms. Occasionally, a methylated variant of a purine or pyrimidine may be incorporated into a given nucleotide sequence. However, such methylations do not affect the coding relationship in any way.

(1) Using Oligonucleotide Probes.

Hybridization probes and primers are oligonucleotide sequences which are complementary to all or part of the recombinant cDNA molecule that is desired. They may be prepared using any suitable method, for example, the phosphotriester and phosphodiester methods, described respectively in Narang, S. A. et al., Methods in Enzymology, 68:90 (1979) and Brown, E. L. et al., Methods in Enzymology, 68:109 (1979), or automated embodiments thereof. In one such embodiment, diethylphosphoramidites are used as starting materials and may be synthesized as described by Beaucage et al, Tetrahedron Letters, 22:1859–1862 (1981). One method for synthesizing oligonucleotides on a modified solid support is described in U.S. Pat. No. 4,458,066. Probes differ from primers in that they are labelled with an enzyme, such as horseradish peroxidase, or radioactive atom, such as $^{32}P$, to facilitate their detection. A synthesized probe is radiolabeled by nick translation using E. coli DNA polymerase I or by end labeling using alkaline phosphatase and T4 bacteriophage polynucleotide kinase.

Preferred hybridization probes include oligonucleotide sequences which are complementary to a stretch of the single-stranded cDNA encoding a portion of the amino acid sequence of a NAP purified from a nematode, such as the hookworm, Ancylostoma caninum. For example, a portion of the amino acid sequence shown in FIG. 2 (AcaNAP5) [SEQ. ID. NO. 4] or FIG. 4 (AcaNAP6 [SEQ. ID. NO. 6]) can be used. Especially preferred hybridization probes include those wherein their oligonucleotide sequence is complementary to the stretch of the single-stranded cDNA encoding the amino acid sequence: Lys-Ala-Tyr-Pro-Glu-Cys-Gly-Glu-Asn-Glu-Trp [SEQ. ID. NO. 93]. Such hybridization probes include the degenerate probe having the oligonucleotide sequence: AAR GCi TAY CCi GAR TGY GGi GAR AAY GAR TGG [SEQ. ID. NO. 94], wherein R is A or G, Y is T or C, and i is inosine. A preferred recombinant cDNA molecule encoding a protein of the present invention is identified by its ability to hybridize to this probe.

Preferred hybridization probes also include the pair NAP-1 [SEQ. ID. NO. 90] and NAP-4.RC [SEQ. ID. NO. 91], and the pair YG109 [SEQ. ID. NO. 88] and YG103 [SEQ. ID. NO. 89], both of which are described in Examples 13 and 12, respectively.

Upon identification of the clone containing the desired cDNA, amplification is used to produce large quantities of a gene encoding a protein of the present invention in the form of a recombinant cDNA molecule.

Preferred methods of amplification include the use of the polymerase chain reaction (PCR). See, e.g., *PCR Technology*, W. H. Freeman and Company, New York (Edit. Erlich, H. A. 1992). PCR is an in vitro amplification method for the synthesis of specific DNA sequences. In PCR, two oligonucleotide primers that hybridize to opposite strands and flank the region of interest in the cDNA of the clone are used. A repetitive series of cycles involving cDNA denaturation into single strands, primer annealing to the single-stranded cDNA, and the extension of the annealed primers by DNA polymerase results in number of copies of cDNA, whose termini are defined by the 5-ends of the primers, approximately doubling at every cycle. *Ibid.*, p.1. Through PCR amplification, the coding domain and any additional primer encoded information such as restriction sites or translational signals (signal sequences, start codons and/or stop codons) of the recombinant cDNA molecule to be isolated is obtained.

Preferred conditions for amplification of cDNA include those using Taq polymerase and involving 30 temperature cycles of: 1 minute at 95° C.; 1 minute at 50° C.; 1.5 minutes at 72° C. Preferred primers include the oligo(dT)-NotI primer, AATTCGCGGC CGC(T)$_{15}$ [SEQ. ID. NO. 95], obtained from Promega Corp. in combination with either (i) the degenerate primer having the oligonucleotide sequence: AAR GCi TAY CCi GAR TGY GGi GAR AAY GAR TGG [SEQ. ID. NO. 94], wherein R is A or G, Y is T or C, and i is inosine, or (ii) the lambda gt11 primer #1218, GGTG-GCGACG ACTCCTGGAG CCCG [SEQ. ID. NO. 96], obtained from New England Biolabs.

The nucleic acid sequence of a recombinant cDNA molecule made as disclosed is determined by methods based on the dideoxy method of Sanger, F. et al, Proc. Natl. Acad. Sci. USA, 74:5463 (1977) as further described by Messing, et al., Nucleic Acids Res., 9:309 (1981).

Preferred recombinant cDNA molecules made as disclosed include those having the nucleic acid sequences of FIGS. 1, 3, 7, 9, 13, and 14.

(2) Using NAP cDNAs As Probes.

Also especially preferred as hybridization probes are oligonucleotide sequences encoding substantially all of the amino acid sequence of NAP purified from the nematode, the hookworm, Ancylostoma caninum. Especially preferred probes include those derived from the AcaNAp5 and AcaNAp6 gene and having the following nucleic acid sequences (AcaNAP5 gene): AAG GCA TAC CCG GAG TGT GGT GAG AAT GAA TGG CTC GAC GAC TGT GGA ACT CAG AAG CCA TGC GAG GCC AAG TGC AAT GAG GAA CCC CCT GAG GAG GAA GAT CCG ATA TGC CGC TCA CGT GGT TGT TTA TTA CCT CCT GCT TGC GTA TGC AAA GAC GGA TTC TAC AGA GAC ACG GTG ATC GGC GAC TGT GTT AGG GAA GAA GAA TGC GAC CAA CAT GAG ATT ATA CAT GTC TGA [SEQ. ID. NO. 1], or FIG. 3 (AcaNAP6 gene): AAG GCA TAC CCG GAG TGT GGT GAG AAT GAA TGG CTC GAC GTC TGT GGA ACT AAG AAG CCA TGC GAG GCC AAG TGC AGT GAG GAA GAG GAG GAA GAT CCG ATA TGC CGA TCA TTT TCT TGT CCG GGT CCC GCT GCT TGC GTA TGC GAA GAC GGA TTC TAC AGA GAC ACG GTG ATC GGC GAC TGT GTT AAG GAA GAA GAA TGC GAC CAA CAT GAG ATT ATA CAT GTC TGA [SEQ. ID. NO. 2].

Preferred hybridization probes also include sequenes encoding a substantial part of the amino acid sequence of a NAP, such as the PCR fragment generated with the primer couple NAP-1 [SEQ. ID. NO. 90] and NAP-4.RC [SEQ. ID. NO. 91] as described in Example 13.

(3) Using Phage Display.

Disclosed herein is a method to select cDNAs encoding the proteins of the present invention from whole cDNA libraries making use of filamentous phage display technology. Current display technology with filamentous phage relies on the in-frame insertion of coding regions of interest into gene 3 or gene 8 which code for the attachment protein and major coat protein of the phage, respectively. Those skilled in the art will recognize that various difficulties are inherent in performing this with a vast mixture of cDNAs of unknown sequence and that the most practical way to obtain functional display of cDNA products would consist of fusing the cDNAs through their 5'-end. Indeed, cDNA libraries of sufficient size may contain several cDNAs which derive from the same mRNA but which are 5'-terminally truncated at various positions such that some of them may be expressed as fusion products. A strategy along this line, which relies on the ability of the leucine zippers Jun and Fos to form heterodimers was recently described. See, Crameri, R. and Suter, M., Gene, 137:69–75 (1993).

We have found a novel alternative and direct way to convalently link cDNA gene products to the phage surface; the finding is based on the observation that proteins fused to the C-terminus of phage coat protein 6 can be functionally displayed. This observation has led to the development of a phagemid system as described herein which allows the expression of functionally displayed cDNA products, which in turn permits the affinity-selection of phage particles which contain the cDNA required for the production of the displayed cDNA product. This system provides the basis for the isolation of cDNAs which encode a protein of the present invention. Once isolated, recombinant cDNA molecules containing such cDNA can be used for expression of the proteins of the present invention in other expression systems. The recombinant cDNA molecules made in this way are considered to be within the scope of the present invention.

Recombinant cDNA molecules of the present invention are isolated by preparing a cDNA library from a natural source (as for example, a nematode such as a hookworm), ligating this cDNA library into appropriate phagemid vectors, transforming host cells with these vectors containing the cDNAs, culturing the host cells, infecting the transformed cells with an appropriate helper phage, separating phage from the host cell culture, separating phage expressing a protein of the present invention on its surface, isolating these phage, and isolating a recombinant cDNA molecule from such phage.

The phagemid vectors are constructed using the pUC119 expression vector described by Vieira, J. and Messing, J., Methods in Enzymology, 153:3–11 (1987). The filamentous phage gene 6 encoding a surface protein of the phage is modified on its 5' and 3' ends by the addition of HindIII and SfiI restriction sites, respectively, by use of three forward primers and one backward primer using PCR. This results in three DNA fragments which are further modified by addition to their 3' ends of NotI and BamHI restriction sites by PCR. After separate digestion of the three DNA fragments with HindIII and BamHI, the three DNA fragments are ligated into the pUC119 to give pDONG61, pDONG62 and pDONG63 expression vectors. These vectors permit the insertion of cDNA as SfiI-NotI fragments into them. cDNA libraries are prepared from natural sources, such as nematodes, as described in Example 2. Preferred nematodes from which to make such libraries include the intestinal nematodes such as *Ancylostoma caninum, Ancylostoma ceylanicum, Ancylostoma duodenale, Necator americanus* and *Heligmosomoides polygyrus*.

A cDNA library as SfiI-NotI fragments may be directly directionally ligated into the phagemid vectors pDONG61, pDONG62 and pDONG63. Alternatively, a cDNA library which has been ligated into the lambda gt11 phage vector as described in Example 2 can be recovered by PCR, followed by isolation with electrophoresis and then directional ligation into these vectors. In the latter approach, preferred conditions for PCR use Taq polymerase; the primers, lambda gt11 primer #1218 having the sequence GGTGGCGACG ACTCCTGGAG CCCG (New England Biolabs, Beverly, Mass., USA) [SEQ. ID. NO. 96] and the oligo(dT)-NotI primer having the sequence, AATTCGCGGC CGC(T)15, (Promega Corp.) [SEQ. ID. NO. 95]; and 20 temperature cycles of 1 minute at 95° C., 1 minute at 50° C., and 3 minutes at 72° C., followed by 10 minutes at 65° C.

Host cells are transformed with the pDONG expression vectors containing a cDNA library. Preferred host cells include *E. coli* strains, with strain TG1 being especially preferred. Preferred methods for the transformation of *E. coli* host cells include electroporation.

The transformed cells are cultured at 37° C. in LB medium supplemented with 1% glucose and 100 micrograms/ml carbenicillin until the optical absorbance at 600 nm reaches the value of 0.5 and then are infected with VCSM13 helper phage (Stratagene) at a multiplicity of infection (moi) of 20.

The phage are separated from the culture by centrifugation, then are purified by precipitations with polyethylene glycol/sodium chloride.

The phage which express a NAP of the present invention on their surface are isolated by taking advantage of the ability of the NAP to bind to a target protein involved in blood coagulation, for example, Factor Xa.

Preferred methods of isolating such phage include a method comprising the steps of:
(1) combining a solution of factor Xa labelled to biotin with a solution of such phage;
(2) incubating this mixture;
(3) contacting a solid phase labelled with streptavidin with this mixture;
(4) incubating the solid phase with the mixture;
(5) removing the solid phase from the mixture and contacting the solid phase with buffer to remove unbound phage;

(6) contacting the solid phase with a second buffer to
(7) isolating such phage;
(8) transforming host cells with such phage;
(9) culturing the transformed host cells;
(10) infecting transformed host cells with VCSM13 helper phage;
(11) isolating the phage from the host cell culture; and
(12) repeating steps (1) to (11) four more times.

An especially preferred method of isolating such phage include the method as detailed in Example 10.

Single-stranded DNA was prepared from the isolated phages and their inserts 3' to the filamentous phage gene 6 sequenced.

FIG. 9 depicts the recombinant cDNA molecule, AcaNAPc2, isolated by the phage display method. The deduced amino acid sequence of the protein of the present invention encoded by AcaNAPc2 is also shown in this figure.

(C) Preparation of Recombinant NAP.

The recombinant cDNA molecules of the present invention when isolated as disclosed are used to obtain expression of the NAPs of the present invention. Generally, a recombinant cDNA molecule of the present invention is incorporated into an expression vector, this expression vector is introduced into an appropriate host cell, the host cell is cultured, and the expressed protein is isolated.

Expression vectors are DNA sequences that are required for the transcription of cloned copies of genes and translation of their mRNAs in an appropriate host. These vectors can express either procaryotic or eucaryotic genes in a variety of cells such as bacteria, yeast, mammalian, plant and insect cells. Proteins may also be expressed in a number of virus systems.

Suitably constructed expression vectors contain an origin of replication for autonomous replication in host cells, or are capable of integrating into the host cell chromosomes. Such vectors will also contain selective markers, a limited number of useful restriction enzyme sites, a high copy number, and strong promoters. Promoters are DNA sequences that direct RNA polymerase to bind to DNA and initiate RNA synthesis; strong promoters cause such initiation at high frequency. The preferred expression vectors of the present invention are operatively linked to a recombinant cDNA molecule of the present invention, i.e., the vectors are capable directing both replication of the attached recombinant cDNA molecule and expression of the protein encoded by the recombinant cDNA molecule. Expression vectors may include, but are not limited to cloning vectors, modified cloning vectors and specifically designed plasmids or viruses.

Suitable host cells for expression of the proteins of the present invention include bacteria, yeast, mammalian, plant and insect cells. With each type of cell and species therein certain expression vectors are appropriate as will be disclosed below.

Procaryotes may be used for expression of the proteins of the present invention. Suitable bacteria host cells include the various strains of *E. coli, Bacillus subtilis,* and various species of Pseudomonas. In these systems, plasmid vectors which contain replication sites and control sequences derived from species compatible with the host are used. Suitable vectors for *E. coli* are derivatives of pBR322, a plasmid derived from an *E. coli* species by Bolivar et al., Gene, 2:95 (1977). Common procaryotic control sequences, which are defined herein to include promoters for transcription, initiation, optionally with an operator, along with ribosome binding site sequences, include the beta-lactamase and lactose promoter systems (Chang et al., Nature, 198:1056 (1977)), the tryptophan promoter system (Goeddel et al., Nucleic Acids Res., 8:4057 (1980)) and the lambda-derived-$P_L$ promoter and N-gene ribosome binding site (Shimatake et al., Nature, 292:128 (1981)). However, any available promoter system compatible with procaryotes can be used. Preferred procaryote expression systems include *E. coli* and their expression vectors.

Eucaryotes may be used for expression of the proteins of the present invention. Eucaryotes are usually represented by the yeast and mammalian cells. Suitable yeast host cells include *Saccharomyces cerevisiae* and *Pichia pastoris*. Suitable mammalian host cells include COS and CHO (chinese hamster ovary) cells.

Expression vectors for the eucaryotes are comprised of promoters derived from appropriate eucaryotic genes. Suitable promoters for yeast cell expression vectors, include promoters for synthesis of glycolytic enzymes, including those for 3-phosphoglycerate kinase gene in *Saccharomyces cerevisiae* (Hitzman et al., J. Biol. Chem., 255:2073 (1980)) and those for the metabolism of methanol as the alcohol oxidase gene in *Pichia pastoris* (Stroman et al., U.S. Pat. Nos. 4,808,537 and 4,855,231). Other suitable promoters include those from the enolase gene (Holland, M. J. et al., J. Biol. Chem., 256:1385 (1981)) or the Leu2 gene obtained from YEp13 (Broach, J. et al., Gene, 8:121 (1978)).

Preferred yeast expression systems include *Pichia pastoris* and their expression vectors. NAP-encoding cDNAs expressed in *Pichia pastoris* optionally may be mutated to encode a NAP protein that incorporates a proline residue at the C-terminus. In some instances the NAP protein is expressed at a higher level and can be more resistant to unwanted proteolysis. One such cDNA, and its expression in *Pichia pastoris,* is described in Example 17.

Suitable promoters for mammalian cell expression vectors include the early and late promoters from SV40 (Fiers, et al., Nature, 273:113 (1978)) or other viral promoters such as those derived from polyoma, adenovirus II, bovine papilloma virus or avian sarcoma viruses. Suitable viral and mammalian enhancers may also be incorporated into these expression vectors.

Suitable promoters for plant cell expression vectors include the nopaline synthesis promoter described by Depicker, A. et al., Mol. Appl. Gen., 1:561 (1978).

Suitable promoters for insect cell expression vectors include modified versions of the system described by Smith et al., U.S. Pat. No. 4,745,051. The expression vector comprises a baculovirus polyhedrin promoter under whose control a cDNA molecule encoding a protein can be placed.

Host cells are transformed by introduction of expression vectors of the present invention into them. Transformation is done using standard techniques appropriate for each type of cell. The calcium treatment employing calcium chloride described in Cohen, S. N., Proc. Natl. Acad. Sci. USA, 69:2110 (1972), or the RbCl method described in Maniatis et al., *Molecular Cloning: A Laboratory Manual,* p. 254, Cold Spring Harbor Press (1982) is used for procaryotes or other cells which contain substantial cell wall barriers. The transformation of yeast is carried out as described in Van Solingen, P. et al., J. Bacter., 130:946 (1977) and Hsiao, C. L. et al., Proc. Natl. Acad. Sci. USA, 76:3829 (1979). Mammalian cells without much cell wall are transformed using the calcium phosphate procedure of Graham and van der Eb, Virology, 52:546 (1978). Plant cells are transformed by infection with *Agrobacterium tumefaciens* as described in Shaw, C. et al, Gene, 23:315 (1983). Preferred methods of transforming *E. coli* and *Pichia pastoris* with expression vectors include electroporation.

Transformed host cells are cultured under conditions, such as type of media, temperature, oxygen content, fluid motion, etc., well known in the biological arts.

The recombinant proteins of the present invention are isolated from the host cell or media by standard methods well known in the biochemical arts, which include the use chromatography methods. Preferred methods of purification would include sequential chromatography of an extract through columns containing Poros20 HQ anion-ion exchange matrix or Poros20 HS cation exchange matrix, Superdex30 gel filtration matrix and a C18 reverse-phase matrix. The fractions collected after one such chromatography column may be selected by their ability to increase the clotting time of human plasma, as measured by the PT and aPTT assays, or their ability to inhibit factor Xa amidolytic activity as measured in a calorimetric assay, or demonstration of activity in any of the other assays disclosed herein. Examples of preferred methods of purification of a recombinant protein of the present invention are disclosed in Examples 3, 4, 6, 8, 14 and 15.

4. Methods of using NAP.

In one aspect, the present invention includes methods of collecting mammalian plasma such that clotting of said plasma is inhibited, comprising adding to a blood collection tube an amount of a protein of the present invention sufficient to inhibit the formation of a clot when mammalian blood is drawn into the tube, adding mammalian blood to said tube, separating the red blood cells from the mammalian plasma, and collecting the mammalian plasma.

Blood collection tubes include stoppered test tubes having a vacuum therein as a means to draw blood obtained by venipuncture into the tubes. Preferred test tubes include those which are made of borosilicate glass, and have the dimensions of, for example, 10.25×47 mm, 10.25×50 mm, 10.25×64 mm, 10.25×82 mm, 13×75 mm, 13×100 mm, 16×75 mm, 16×100 mm or 16×125 mm. Preferred stoppers include those which can be easily punctured by a blood collection needle and which when placed onto the test tube provide a seal sufficient to prevent leaking of air into the tube.

The proteins of the present invention are added to the blood collection tubes in variety of forms well known in the art, such as a liquid composition thereof, a solid composition thereof, or a liquid composition which is lyophilized to a solid in the tube. The amount added to such tubes is that amount sufficient to inhibit the formation of a clot when mammalian blood is drawn into the tube. The proteins of the present invention are added to blood collection tubes in such amounts that, when combined with 2 to 10 ml of mammalian blood, the concentration of such proteins will be sufficient to inhibit clot formation. Typically, this effective concentration will be about 1 to 10,000 nM, with 10 to 1000 nM being preferred. Alternatively, the proteins of the present invention may be added to such tubes in combination with other clot-inhibiting additives, such as heparin salts, EDTA salts, citrate salts or oxalate salts.

After mammalian blood is drawn into a blood collection tube containing either a protein of the present invention or the same in combination with other clot-inhibiting additives, the red blood cells are separated from the mammalian plasma by centrifugation. The centrifugation is performed at g-forces, temperatures and times well known in the medical arts. Typical conditions for separating plasma from red blood cells include centrifugation at a centrifugal force of about 100×g to about 1500×g, at a temperatures of about 5° to about 25° C., and for a time of about 10 to about 60 minutes.

The mammalian plasma may be collected by pouring it off into a separate container, by withdrawing it into a pipette or by other means well known to those skilled in the medical arts.

In another aspect, the present invention includes methods for preventing or inhibiting thrombosis (clot formation) or blood coagulation in a mammal, comprising administering to said mammal a therapeutically effective amount of a protein or a pharmaceutical composition of the present invention.

The proteins or pharmaceutical compositions of the present invention are administered in vivo, ordinarily in a mammal, preferably in a human. In employing them in vivo, the proteins or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets, capsules or elixers taken on a daily basis.

In practicing the methods of the present invention, the proteins or pharmaceutical compositions of the present invention are administered alone or in combination with one another, or in combination with other therapeutic or in vivo diagnostic agents.

As is apparent to one skilled in the medical art, a therapeutically effective amount of the proteins or pharmaceutical compositions of the present invention will vary depending upon the age, weight and mammalian species treated, the particular proteins employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts.

Typically, administration of the proteins or pharmaceutical composition of the present invention is commenced at lower dosage levels, with dosage levels being increased until the desired effect of preventing in vivo thrombosis is achieved which would define a therapeutically effective amount. For the proteins of the present invention, alone or as part of a pharmaceutical composition, such doses are between about 0.01 mg/kg and 100 mg/kg body weight, preferably between about 0.01 and 10 mg/kg, body weight.

5. Utility.

Proteins of the present invention when made and selected as disclosed are useful as potent inhibitors of blood coagulation in vitro and in vivo. As such, these proteins are useful as in vitro diagnostic reagents to prevent the clotting of blood and are also useful as in vivo pharmaceutical agents to prevent or inhibit thrombosis or blood coagulation in mammals.

The proteins of the present invention are useful as in vitro diagnostic reagents for inhibiting clotting in blood drawing tubes. The use of stoppered test tubes having a vacuum therein as a means to draw blood obtained by venipuncture into the tube is well known in the medical arts. Kasten, B. L., "Specimen Collection", *Laboratory Test Handbook,* 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The proteins of the present invention are potent inhibitors of blood clotting and as such, can be incorporated into blood collection tubes to prevent clotting of the mammalian blood drawn into them.

The proteins of the present invention are used alone, in combination of other proteins of the present invention, or in combination with other known inhibitors of clotting, in the blood collection tubes, for example, with heparin salts, EDTA salts, citrate salts or oxalate salts.

The amount to be added to such tubes, or effective amount, is that amount sufficient to inhibit the formation of a blood clot when mammalian blood is drawn into the tube. The proteins of the present invention are added to blood collection tubes in such amounts that, when combined with 2 to 10 ml of mammalian blood, the concentration of such proteins will be sufficient to inhibit the formation of blood clots. Typically, this effective amount is that required to give a final concentration in the blood of about 1 to 10,000 nM, with 10 to 1000 nM being preferred.

The proteins of the present invention may also be used to prepare diagnostic compositions. In one embodiment, diagnostic compositions are prepared by dissolving the proteins of the present invention into diagnostically acceptable carriers, which carriers include phosphate buffered saline (0.01M sodium phosphate+0.15M sodium chloride, pH 7.2 or Tris buffered saline (0.05M Tris-HCl +0.15M sodium chloride, pH 8.0). In another embodiment, the proteins of the present invention may be blended with other solid diagnostically acceptable carriers by methods well known in the art to provide solid diagnostic compositions. These carriers include buffer salts.

The addition of the proteins of the present invention to blood collection tubes may be accomplished by methods well known in the art, which methods include introduction of a liquid diagnostic composition thereof, a solid diagnostic composition thereof, or a liquid diagnostic composition which is lyophilized in such tubes to a solid plug of a solid diagnostic composition.

The use of blood collection tubes containing the diagnostic compositions of the present invention comprises contacting a effective amount of such diagnostic composition with mammalian blood drawn into the tube. Typically, when a sample of 2 to 10 ml of mammalian blood is drawn into a blood collection tube and contacted with such diagnostic composition therein; the effective amount to be used will include those concentrations of the proteins formulated as a diagnostic composition which in the blood sample are sufficient to inhibit the formation of blood clots. Preferred effective concentrations would be about 1 to 10,000 nM, with 10 to 1000 nM being especially preferred.

According to an alternate aspect of our invention, the proteins of the present invention are also useful as pharmaceutical agents for preventing or inhibiting thrombosis or blood coagulationin a mammal. This prevention or inhibition of thrombosis or blood coagulation includes preventing or inhibiting abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, and also characterizes the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition for pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The NAP proteins of the present invention also are useful immunogens against which antibodies are raised. Antibodies, both monoclonal and polyclonal, directed to a NAP are useful for diagnostic purposes and for the identification of concentration levels of NAP in various biological fluids. Immunoassay utilizing these antibodies may be used as a diagnostic test, such as to detect infection of a mammalian host by a parasitic worm or to detect NAP from a parasitic worm in a tissue of the mammalian host. Also, such immunoassays may be used in the detection and isolation of NAP from tissue homogenates, cloned cells and the like.

NAP can be used, with suitable adjuvants, as a vaccine against parasitic worm infections in mammals. Immunization with NAP vaccine may be used in both the prophylaxis and therapy of parasitic infections. Disease conditions caused by parasitic worms may be treated by administering to an animal infected with these parasites anti-NAP antibody.

NAP proteins of this invention having serine protease inhibitory activity also are useful in conditions or assays where the inhibition of serine protease is desired. For example, NAP proteins that inhibit the serine protease trypsin or elastase are useful for treatment of acute pancreatitis or acute inflammatory response, mediated by leukocytes, respectively.

The recombinant cDNA molecules encoding the proteins of the present invention are useful in one aspect for isolating other recombinant cDNA molecules which also encode the proteins of the present invention. In another aspect, they are useful for expression in host cells of the proteins of the present invention.

The nucleotide probes of the present invention are useful to identify and isolate nucleic acid encoding NAPs from nematodes or other organisms. Additionally, the nucleotide probes are useful diagnostic reagents to detect the presence of nematode-encoding nucleic acid in a sample, such as a bodily fluid or tissue from a mammal suspected of infection by nematode. The probes can be used directly, with appropriate label for detection, to detect the presence of nematode nucleic acid, or can be used in a more indirect manner, such as in a PCR-type reaction, to amplify nematode nucleic acid that may be present in the sample for detection. The conditions of such methods and diagnostic assays are readily available in the art.

To assist in understanding, the present invention will now be be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Isolation of Novel Anticoagulant Protein (NAP) from *Ancylostoma caninum*.

(A) Preparation of the *Ancylostoma caniumum* Lysate.

Frozen canine hookworms, *Ancylostoma caninum*, were obtained from Antibody Systems (Bedford, Tex). Hookworms were stored at −80° C. until used for homogenate.

Hookworms were frozen in liquid nitrogen frozen and ground in a mortar followed by a homogenization on ice in homogenization buffer using a PotterS homogenizer with a teflon piston (B.Braun Melsungen AG, Germany). The homogenization buffer contained: 0.02M Tris-HCl pH 7.4, 0.05M NaCl, 0.001M $MgCl_2$, 0.001M $CaCl_2$, $1.0 \times 10^{-5}$M E 64 protease inhibitor (Boehringer Mannheim, Germany), $1.0 \times 10^{-5}$M pepstatin A (isovaleryl-Val-Val-4-amino-3-hydroxy-6-methyl-heptanoyl-Ala-4-amino-3-hydroxy-6-methylheptanoic acid, ICN Biomedicals, CA), $1.0 \times 10^{-5}$M chymostatin (Boehringer), $1.0 \times 10^{-5}$M leupeptin (ICN), $5 \times 10^{-5}$M AEBSF (4-(2-aminoethyl)-benzenesulfonyl fluoride, ICN), and 5% (v/v) glycerol. Approximately 4 ml of homogenization buffer was used to homogenize each gram of frozen worms (approximately 500 worms). Insoluble material was pelleted by two sequential centrifugation steps: $19,000 \times g_{max}$ at 4° C. for 30 minutes followed by $110,000 \times g_{max}$ at 4° C. for 40 minutes. The supernatant solution was clarified by passage through a 0.45 micrometer cellulose acetate filter (Corning, N.Y.) to give *Ancylostoma caniumum* lysate.

(B) Concanavalin A Sepharose Chromatography.

*Ancylostoma caniumum* lysate (100 ml) was adsorbed onto 22 ml of Concanavalin A Sepharose (Pharmacia, Sweden) pre-equilibrated with Con A buffer (0.02M Tris-HCl, pH 7.4, 1M NaCl, 0.002M $CaCl_2$) by loading it onto a 1.6×11 cm column of this gel at a flow rate of 3 ml/minute (90 cm/hour). The column was at ambient temperature while the reservoir of lysate was maintained at ice bath temperature throughout the procedure. The column was subsequently washed with 2 column volumes of Con A buffer. The column flow-through and wash were collected (approximately 150 ml) and stored at −80° C. until further processing was done.

(C) Anion-Exchange Chromatography.

The flow-through and wash of the Concanavalin A Sepharose column was buffered by adding solid sodium acetate to a final concentration of 12.5 mM. The conductivity was reduced by dilution with milliQ water and the pH was adjusted with HCl to pH 5.3. The precipitate formed during pH adjustment was pelleted by centrifugation $15,000 \times g_{max}$ at 4° C. for 15 minutes. The supernatant solution was clarified by passage through a 0.2 micrometer cellulose acetate filter (Corning, N.Y.).

This clarified solution (total volume approximately 600 ml) was loaded on to a Poros20 HQ (Perseptive Biosystems, MA) 1×2 cm column pre-equilibrated with Anion buffer (0.05M Na acetate, pH 5.3, 0.1M NaCl) at a flow rate of 10 ml/minute (800 cm/hour). The column and the solution added were at ambient temperature throughout this purification step. The column was subsequently washed with 10 column volumes of Anion buffer.

Material that had inhibitory activity, detected following the procedure below, in the factor Xa amidolytic assay was eluted with Cation buffer containing 0.55M NaCl at a flow rate of 5 ml/minute (400 cm/hour).

A sample of solution was tested in a factor Xa amidolytic assay as follows. Reaction mixtures (150 microliters) were prepared in 96-well plates containing factor Xa and various dilutions of the sample in assay buffer (100 mM Tris-HCl pH 7.4; 140 mM NaCl; 0.1% BSA). Human factor X was purchased from Enzyme Research Laboratories (South Bend, Ind., USA) and activated with Russell's Viper venom using the procedure of Bock, P. E., Craig, P. A., Olson, S. T., and Singh P., Arch. Biochem. Biophys., 273: 375–388 (1989). Following a 30 minute incubation at ambient temperature, the enzymatic reactions were initiated by addition of 50 microliters of a 1 mM substrate solution in water (N-alpha-benzyloxycarbonyl-D-arginyl-L-glycyl-L-arginine p-nitroanilide-dihydrochloride; S-2765; Chromogenix, Mölndal, Sweden) to yield final concentrations of 0.2 nM factor Xa and 0.25 mM S-2765. Substrate hydrolysis was monitored by continuously measuring absorbance at 405 nm using a Vmax kinetic plate reader (Molecular Devices, Menlo Park, Calif., USA).

(D) Heat Treatment.

Half of the 0.55M NaCl elution pool (3 ml) from anion-exchange chromatography was neutralized by adding 1M Tris-HCl, pH 7.5 to a final concentration of 50 mM, incubated for 5 minutes at 90° C. in a glass tube and subsequently cooled rapidly on ice. Insoluble material was pelleted by centrifugation $19,000 \times g_{max}$ at 4° C. for 20 minutes. The supernatant contained material which inhibited factor Xa in the factor Xa amidolytic assay. About 89% of the factor Xa inhibitory activity was recovered in the supernatant, after this heat treatment after accounting for dilution.

(E) Molecular Sieve Chromatography using Superdex30 (alternative for the heat treatment step).

Half of the 0.55M NaCl elution pool (3 ml) from anion-exchange chromatography was loaded on a Superdex30 PG (Pharmacia, Sweden) 1.6×66 cm column pre-equilibrated with 0.01M sodium phosphate, pH 7.4, 0.15M NaCl at 24° C. The chromatography was conducted at a flow rate of 2 ml/minute. The factor Xa inhibitory activity (determined in the factor Xa amidolytic assay) eluted 56–64 ml into the run ($K_{av}$ of 0.207). This elution volume would be expected for a globular protein with a molecular mass of 14,000 daltons.

(F) Reverse Phase Chromatography.

Hookworm lysate which was fractionated by chromatography on Concanavalin A Sepharose, anion-exchange and Superdex30 (or with the alternative heat treatment step) was loaded on to a 0.46×25 cm C18 column (218TP54 Vydac; Hesperia, Calif.) which was then developed with a linear gradient of 10–35% acetonitrile in 0.1% (v/v) trifluoroacetic acid at a flow rate of 1 ml/minute with a rate of 0.625% change in acetonitrile/minute. FXa inhibitory activity (determined in the factor Xa amidolytic assay) eluted at approximately 30% acetonitrile. The HPLC runs were performed on a Vista 5500 connected with a Polychrom 9600 detector set at 215 nm (Varian, Calif.). Detector signals were integrated on a 4290 integrator obtained from the same company. Factor Xa inhibitory activity containing fractions were vacuum dried and then redissolved in PBS (0.01M sodium phosphate, pH 7.4, 0.15M NaCl).

These fractions were pooled and then loaded on to a 0.46×25 cm C18 column (218TP54 Vydac; Hesperia, Calif.) which was developed with a linear gradient of 10–35% acetonitrile in 0.1% trifluoroacetic acid at a flow rate of 1 ml/minute with a slower rate of 0.4% change in acetonitrile/minute. Factor Xa inhibitory activity containing fractions were pooled and subsequently vacuum dried.

(G) Molecular Weight Determination of NAP from *Ancylostoma caninum*.

The estimated mass for NAP isolated as described in this example was determined using electrospray ionisation mass spectrometry.

A vacuum-dried pellet of NAP was dissolved in 50% (v/v) acetonitrile, 1% (v/v) formic acid. Mass analysis was performed using a VG Bio-Q (Fisons Instruments, Manchester UK).

The NAP sample was pumped through a capillary and at its tip a high voltage of 4 kV was applied. Under the influence of the high electric field, the sample was sprayed out in droplets containing the protein molecules. Aided by the drying effect of a neutral gas ($N_2$) at 60° C., the droplets were further reduced in size until all the solvent had been evaporated and only the protein species remained in the gaseous form. A population of protein species arose which differed from each other in one charge. With a quadrupole analyzer, the different Da/e (mass/charge)-values were detected. Calibration of the instrument was accomplished using Horse Heart Myoglobin (Sigma, Miss.).

The estimated mass of NAP isolated as described in sections A, B, C, D, and F of this example is 8734.60 daltons. The estimated mass of native NAP isolated as described in sections A, B, C, E, and F is 8735.67 daltons.

(H) Amino Acid Sequencing of NAP from *Ancylostoma caninum*.

Amino acid determination was performed on a 476-A Protein/Peptide Sequencer with On Board Microgradient PTH Analyzer and Model 610A Data Analysis System (Applied Biosystems, CA). Quantification of the residues was performed by on-line analysis on the system computer (Applied Biosystems, CA); residue assignment was performed by visual analysis of the HPLC chromatograms. The first twenty amino acids of the amino-terminus of native NAP were determined to be:

Lys Ala Tyr Pro Glu Cys Gly Glu Asn Glu Trp Leu Asp Asp Cys Gly Thr Gln Lys Pro [SEQ. ID. NO. 97].

The cysteine residues were not directly detected in this analysis because the sample was not reduced and subsequently alkylated. Cysteines were assigned to the positions where no specific amino acid was identified.

Example 2

Cloning and Sequencing of NAP from *Ancylostoma caninum*.

(A) Preparation of Hybridization Probe.

Full-length cDNA clones encoding NAP were isolated by screening a cDNA library, prepared from the mRNA isolated from the nematode, *Ancylostoma caninum*, using as a hybridization probe—a radiolabeled degenerate oligonucleotide whose sequence was based on the first eleven amino acids of the amino-terminus of NAP from *A. caninum*:

Lys Ala Tyr Pro Glu Cys Gly Glu Asn Glu Trp [SEQ. ID. NO. 93].

The 33-mer oligonucleotide hybridization probe, designated YG99, had the following sequence:

AAR GCi TAY CCi GAR TGY GGi GAR AAY GAR TGG [SEQ. ID. NO. 94]

where "R" refers to A or G; "Y" refers to T or C; and "i" refers to inosine. YG99 was radiolabeled by enzymatic 5'-end phosphorylation (5'-end labeling kit; Amersham, Buckinghamshire, England) using gamma-$^{32}$P-ATP (specific activity >7000 Ci/mmole; ICN, Costa Mesa, Calif., USA) and subsequently passed over a NAP™10 column (Pharmacia, Uppsala, Sweden).

(B) Preparation of CDNA Library.

A cDNA library was constructed using described procedures (Promega Protocols and Applications Guide 2nd Ed.; Promega Corp., Madison, Wis., USA).

Adult hookworms, *Ancylostoma caninum*, were purchased from Antibody Systems (Bedford, Tex.). Poly(A+) RNA was prepared using the QuickPrep mRNA Purification Kit (Pharmacia). About 3 micrograms of mRNA was reverse transcribed using an oligo(dT)-NotI primer/adaptor, AATTCGCGGCCGC(T)$_{15}$ [SEQ. ID. NO. 95], (Promega Corp.) and AMV (Avian Myeloblastosis Virus) reverse transcriptase (Boehringer, Mannheim, Germany). The enzymes used for double-stranded cDNA synthesis were the following: *E. coli* DNA polymerase I and RNaseH from Life Technologies (Gaithersburg, Md., USA) and T4 DNA polymerase from Pharmacia.

EcoRI linkers (pCGGAATTCCG) [SEQ. ID. NO. 98] were ligated onto the obtained cDNA after treatment with EcoRI methylase (RiboClone EcoRI Linker Ligation System; Promega).

The cDNAs were digested with NotI and EcoRI, passed over a 1.5% agarose gel (all sizeable material was eluted using the Geneclean protocol, BIO101 Inc., La Jolla, Calif.), and unidirectionally ligated into the EcoRI-NotI arms of the lambda gt11 Sfi-NotI vector (Promega). After in vitro packaging (GigapackII-Gold, Stratagene, La Jolla, Calif.) recombinant phage were obtained by infecting strain Y1090 (Promega).

The usefulness of the cDNA library was demonstrated by PCR analysis (Taq polymerase from Boehringer; 30 temperature cycles: 1 minute at 95° C.; 1 minute at 50° C.; 3 minutes at 72° C.) of a number of randomly picked clones using the lambda gt11 primer #1218, having the sequence, GGTGGCGACG ACTCCTGGAG CCCG (New England Biolabs, Beverly, Mass., USA) [SEQ. ID. NO. 96]; targeting sequences located upstream of the cDNA insert) in combination with the above-mentioned oligo(dT)-NotI primer/adaptor; the majority of the clones was found to contain cDNA inserts of variable size.

(C) Identification of Clones.

Approximately $1 \times 10^6$ cDNA clones (duplicate plaque-lift filters were prepared using Hybond™-N; Amersham) were screened with the radiolabeled YG99 oligonucleotide using the following pre-hybridization and hybridization conditions: 5× SSC (SSC: 150 mM NaCl, 15 mM trisodium citrate), 5× Denhardt's solution, 0.5% SDS, 100 micrograms/ml sonicated fish sperm DNA (Boehringer), overnight at 42° C. The filters were washed 4 times in 2× SSC, 0.1% SDS at 37° C. After exposure (about 72 hours) to X-ray film, a total of between 350 and 500 hybridization spots were identified.

Twenty-four positive clones, designated NAP1 through NAP24, were subjected to a second hybridization round at lower plaque-density; except for NAP24, single plaques containing a homogeneous population of lambda phage were identified. The retained clones were analyzed by PCR amplifications (Taq polymerase from Boehringer; 30 temperature cycles: 1 minute at 95° C.; 1 minute at 50° C.; 1.5 minutes at 72° C.) using the oligo(dT)-NotI primer (AATTCGCGGC CGC(T)$_{15}$) [SEQ. ID. NO. 95] in combination with either (i) YG99 or (ii) the lambda gt11 primer #1218. The majority of the clones (20 out of 23) yielded a fragment of about 400 bp when the oligo(dT)-NotI/YG99 primer set was used and a fragment of about 520 bp when the oligo(dT)-NotI/#1218 primer couple was used. Nineteen such possibly full-length clones were further characterized.

The cDNA inserts of five clones were subcloned as SfiI-NotI fragments on both pGEM-5Zf(-) and pGEM-9Zf (-) (Promega). Because the SfiI sites of lambda gt11 and pGEM-5Zf(-) are not compatible with one another, the cloning on this vector required the use of a small adaptor fragment obtained after annealing the following two 5'-end hosphorylated oligonucleotides: pTGGCCTAGCG TCAG-GAGT [SEQ. ID. NO. 99] and pCCTGACGCTA GGC- CATGG [SEQ. ID. NO. 100]. Following preparation of single-stranded DNA, the sequence of these cDNAs was determined with the dideoxy chain termination method using primer #1233 having the sequence, AGCGGATAAC AATTTCACAC AGGA (New England Biolabs) [SEQ. ID. NO. 101]. All five clones were found to be full-length including a complete secretion signal. Clones NAP5, NAP7 and NAP22 were found to have an identical coding region. Clones NAP6 and NAP11 are also identical but differ from the NAP5 type of coding region. FIG. 1 depicts the nucleotide sequence of the NAP5 gene and FIG. 2 depicts the amino acid sequence of the protein encoded, AcaNAP5. Likewise, FIG. 3 depicts the nucleotide sequence of the NAP6 [SEQ. ID. NO. 5] gene and FIG. 4 depicts the amino acid sequence of the protein encoded, AcaNAP6 [SEQ. ID. NO. 6].

Fourteen other possibly full-length clones were subjected to a restriction analysis. The above mentioned 400 bp PCR product obtained with the YG99/oligo(dT)-NotI primer couple, was digested with four different enzymes capable of discriminating between a NAP5- and NAP6-type of clone: Sau96I, Sau3AI, DdeI, and HpaII. The results were consistent with 10 out of the 14 clones being NAP5-type (e.g. NAP4, NAP8, NAP9, NAP15, NAP16, NAP17, NAP18, NAP20, NAP21, and NAP23) while the remaining four were NAP6-type (e.g. NAP10, NAP12, NAP14, and NAP19).

These clones were renamed to reflect origin from *Ancylostoma caninum* by placing the letters Aca immediately before the NAP designation. For example, NAP5 became AcaNAP5, NAP6 became AcaNAP6 and so forth.

Example 3
Production and Purification of Recombinant AcaNAP5 in *P. pastoris*.

(A) Expression Vector Construction.

The *Pichia pastoris* yeast expression system, including the *E. coli*/*P. pastoris* shuttle vector, pHILD2, has been described in a number of United States Patents. See, e.g., U.S. Pat. Nos. 5,330,901; 5,268,273; 5,204,261; 5,166,329; 5,135,868; 5,122,465; 5,032,516; 5,004,688; 5,002,876; 4,895,800; 4,885,242; 4,882,279; 4,879,231; 4,857,467; 4,855,231; 4,837,148; 4,818,700; 4,812,405; 4,808,537; 4,777,242; and 4,683,293.

The pYAM7SP8 vector used to direct expression and secretion of recombinant AcaNAP5 in *P. pastoris* was a derivative of the pHILD2 plasmid (Despreaux, C. W. and Manning, R. F., Gene 131: 35–41 (1993)), having the same general structure. In addition to the transcription and recombination elements of pHILD2 required for expression and chromosomal integration in *P. pastoris* (see Stroman, D. W. et al., U.S. Pat. No. 4,855,231), this vector contained a chimeric prepro leader sequence inserted downstream of the alcohol oxidase (AOX1) promoter. The prepro leader consisted of the *P. pastoris* acid phosphatase (PHO1) secretion signal fused to a synthetic 19-amino acid pro-sequence. This pro-sequence was one of the two 19-aa pro-sequences designed by Clements et al., Gene 106: 267–272 (1991) on the basis of the *Saccharomyces cerevisiae* alpha-factor leader sequence. Engineered immediately downstream from the prepro leader sequence was a synthetic multi-cloning site with recognition sequences for the enzymes StuI, SacII, EcoRI, BglII, NotI, XhoI, SpeI and BamHI to facilitate the cloning of foreign genes. NAP as expressed from pYAM7SP8 in *Pichia pastoris* was first translated as a prepro-product and subsequently processed by the host cell to remove the pre- and pro-sequences.

Figures 12A, 12B:
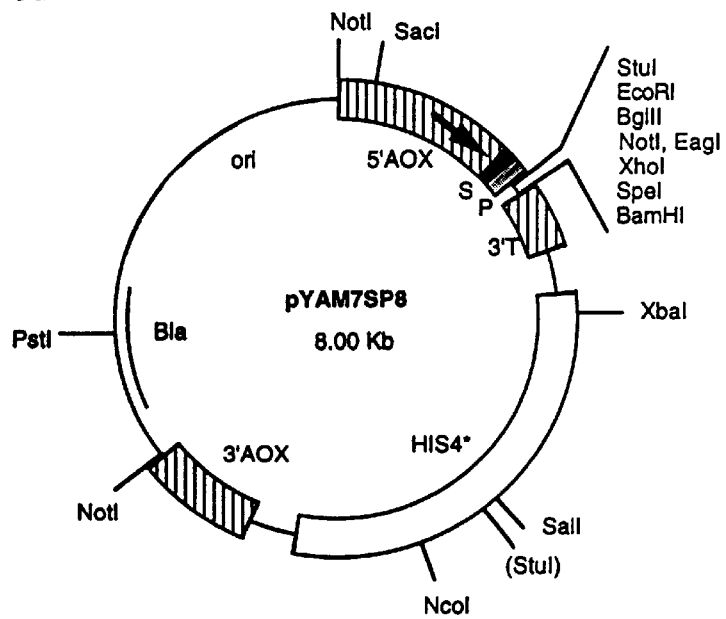
FIG. 12 Parts A and B depict a map of the *P. pastoris* pYAM7SP8 expression/secretion vector (FIG. 12 Part A) and sequences included in the vector (FIG. 12, Part B) [SEQ. ID. NO. 30]. As depicted in FIG. 12, Part A, this plasmid contains the following elements inserted between the methanol-induced AOX1 promoter (dark arrow in the 5'AOX untranslated region) and the AOX1 transcription termination signal (3'T): a synthetic DNA fragment encoding the acid phosphatase secretion signal (S), a synthetic 19-amino acid pro sequence (P) ending with a Lys-Arg processing site for the KEX2 protease and a multicloning site. The HIS4 gene which serves as a selection marker in GS115 transformation was modified by site directed mutagenesis to eliminate the Stu1 recognition sequence (HIS4*). pBR322 sequences, including the Bla gene and origin (ori) for propagation in *E. coli* are represented by a single line.

The structure of this vector is shown in FIG. 12. The signal sequence (S) has the nucleic acid sequence: ATG TTC TCT CCA ATT TTG TCC TTG GAA ATT ATT TTA GCT TTG GCT ACT TTG CAA TCT GTC TTC GCT [SEQ. ID. NO. 102]. The pro sequence (P) has the nucleic acid sequence: CAG CCA GGT ATC TCC ACT ACC GTT GGT TCC GCT GCC GAG GGT TCT TTG GAC AAG AGG [SEQ. ID. NO. 103]. The multiple cloning site (MCS) has the nucleic acid sequence: CCT ATC CGC GGA ATT CAG ATC TGA ATG CGG CCG CTC GAG ACT AGT GGA TCC [SEQ. ID. NO. 104].

The pGEM-9Zf(-) vector (Promega) containing the AcaNAP5 CDNA was used to isolate by amplification ("PCR-rescue") the region encoding the mature AcaNAP5 protein (using Vent polymerase from New England Biolabs, Beverly, Mass.; 20 temperature cycles: 1 minute at 94° C., 1 minute at 50° C., and 1.5 minutes at 72° C.). The following oligonucleotide primers were used:

YG101: GCTCGCTCTA-GAAGCTTCAG-ACATGTATAA-TCTCATGTTG-G [SEQ. ID. NO. 105]

YG103: AAGGCATACC-CGGAGTGTGG-TG [SEQ. ID. NO. 89]

The YG101 primer, targeting C-terminal sequences, contained a non-annealing extension which included XbaI and HindIII restriction sites (underlined).

Following digestion with XbaI enzyme, the amplification product, having the expected size, was isolated from gel and subsequently enzymatically phosphorylated (T4 polynucleotide kinase from New England Biolabs, Beverly, Mass.). After heat-inactivation (10 minutes at at 70° C.) of the kinase, the blunt-ended/XbaI fragment was directionally cloned into the vector pYAM7SP8 for expression purposes. The recipient vector-fragment from pYAM7SP8 was prepared by StuI-SpeI restriction, and purified from agarose gel. The *E. coli* strain, WK6 [Zell, R. and Fritz, H.-J., EMBO J., 6: 1809–1815 (1987)], was transformed with the ligation mixture, and ampicillin resistant clones were selected.

Based on restriction analysis, a plasmid clone containing an insert of the expected size, designated pYAM7SP-NAP5, was retained for further characterization. Sequence determination of the clone pYAM7SP-NAP5 confirmed the precise insertion of the mature AcaNAP5 coding region in fusion with the prepro leader signal, as predicted by the construction scheme, as well as the absence of unwanted mutations in the coding region.

(B) Expression of Recombinant AcaNAP5 in *P. pastoris*.

The *Pichia pastoris* strain GTS115 (his4) has been described in Stroman, D. W. et al., U.S. Pat. No. 4,855,231. All of the *P. pastoris* manipulations were performed essentially as described in Stroman, D. W. et al., U.S. Pat. No. 4,855,231.

About 1 microgram of pYAM7SP-NAP5 plasmid DNA was electroporated into the strain GTS115 using a standard electroporation protocol. The plasmid was previously linearized by SalI digestion, which theoretically facilitates the targeting and integration of the plasmid into the his4 chromosomal locus.

The selection of a AcaNAP5 high-expresser strain was performed essentially as described hereinbelow. His+ transformants were recovered on MD plates (Yeast Nitrogen Base without amino acids (DIFCO), 13.4 g/l; Biotin, 400 micrograms/L; D-glucose, 20 g/l; agar, 15 g/l). Single colonies (n=60) originating from the electroporation were inoculated into 100 microliters of FM22-glycerol-PTM1 medium in wells of a 96-well plate and were allowed to grow on a plate-agitator at 30° C. for 24 hours. One liter of FM22-glycerol-PTM1 medium contained 42.87 g $KH_2PO_4$, 5 g $(NH_4)_2SO_4$, 1 g $CaSO_4.2H_2O$, 14.28 g $K_2SO_4$, 11.7 g $MgSO_4.7H_2O$, 50 g glycerol sterilized as a 100 ml solution, and 1 ml of PTM1 trace mineral mix filter-sterilized. The FM22 part of the medium was prepared as a 900 ml solution adjusted to pH 4.9 with KOH and sterile filtered. One liter of the PTM1 mix contained 6 g $CuSO_4.5H_2O$, 0.8 g KI, 3 g $MnSO_4.H_2O$, 0.2 g $NaMoO_4.2H_2O$, 0.02 g $H_3BO_3$, 0.5 g $CoCl_2.6H_2O$, 20 g $ZnCl_2$, 5 ml $H_2SO_4$, 65 g $FeSO_4.7H_2O$, 0.2 g biotin.

The cells were then pelleted and resuspended in fresh FM22-methanol-PTM1 medium (same composition as above except that the 50 g glycerol was replaced by 0.5% (v/v) methanol in order to induce expression of the AOX1 promoter). After an additional incubation period of 24 hours at 30° C., the supernatants of the mini-cultures were tested for the presence of secreted AcaNAP5. Two clones were selected that directed high synthesis and secretion of AcaNAP5, as was shown by the appearance of high factor Xa inhibitory activity in the culture medium (as measured by the amidolytic factor Xa assay described in Example 1). After a second screening round, using the same procedure, but this time at the shake-flask level, one isolated host cell was chosen and designated *P. pastoris* GTS115/7SP-NAP5.

The host cell, GTS115/7SP-NAP5, was shown to have a wild type methanol-utilisation phenotype (Mut+), which demonstrated that the integration of the expression cassette into the chromosome of GTS115 did not alter the functionality of the genomic AOX1 gene.

Subsequent production of recombinant AcaNAP5 material was performed in shake flask cultures, as described in Stroman, D. W. et al., U.S. Pat. No. 4,855,231. The recombinant product was purified from *Pichia pastoris* cell supernatant as described below.

(C) Purification of Recombinant AcaNAP5.

(1) Cation Exchange Chromatography.

Following expression, the culture supernatant from GTS115/75SP-NAP5 (100 ml) was centrifuged at 16000 r.p.m. (about 30,000×g) for 20 minutes before the pH was adjusted with 1N HCl to pH 3. The conductivity of the supernatant was decreased to less than 10 mS/cm by adding MilliQ water. The diluted supernatant was clarified by passage through a 0.22 micrometer cellulose acetate filter (Corning Inc., Corning, N.Y., USA)

The total volume (approximately 500 ml) of supernatant was loaded on a Poros20 HS (Perseptive Biosystems,MA) 1×2 cm column pre-equilibrated with Cation Buffer (0.05M sodium citrate, pH 3) at a flow rate of 5 ml/minute (400 cm/hour). The column and the sample were at ambient temperature throughout this purification step. The column was subsequently washed with 50 column volumes Cation Buffer. Material that had inhibitory activity in a factor Xa amidolytic assay was eluted with Cation Buffer containing 1M NaCl at a flow rate of 2 ml/minute.

(2) Molecular Sieve Chromatography using Superdex30.

The 1M NaCl elution pool containing the inhibitory material (3 ml) from the cation-exchange column was loaded on a Superdex30 PG (Pharmacia, Sweden) 1.6×66 cm column pre-equilibrated with 0.01M sodium phosphate, pH 7.4, 0.15M NaCl at ambient temperature. The chromatography was conducted at a flow rate of 2 ml/minute. The factor Xa inhibitory activity eluted 56–64 ml into the run ($K_{av}$ of 0.207). This is the same elution volume as determined for the native molecule (Example 1, part E).

(3) Reverse Phase Chromatography.

1 ml of the pooled fractions from the gel filtration chromatography was loaded on to a 0.46×25 cm C18 column (218TP54 Vydac; Hesperia, Calif.) which was then developed with a linear gradient of 10–35 % acetonitrile in 0.1% (v/v) trifluoroacetic acid at 1 ml/minute with a rate of 0.4% change in acetonitrile/minute. Factor Xa inhibitory activity, assayed in Example 6 (1)) eluted around 30–35% acetonitrile and was present in several fractions. HPLC runs were performed on the same system as described in Example 1. Fractions from several runs on this column containing the factor Xa inhibitory activity were pooled and vacuum dried.

(4) Molecular Weight Determination of Recombinant AcaNAP5

The estimated mass for the main constituent isolated as described in sections (1) to (3) of this example were determined using the same electrospray ionisation mass spectrometry system as described in Example 1.

The estimated mass of recombinant AcaNAP5 is 8735.69 daltons.

(5) Amino Acid Sequencing of Recombinant AcaNAP5.

Following purification by section (1) to (3) of this example, the recombinant AcaNAP5 from *Pichia pastoris* was subjected to amino acid sequence analysis as described in Example 1. The first five amino acids of the aminoterminus of AcaNAP5 were determined to be: Lys-Ala-Tyr-Pro-Glu [SEQ. ID. NO. 106]. The sequence was identical to the native NAP protein (see Example 1).

Example 4

Production and Purification of Recombinant AcaNAP6 in *P. pastoris*.

(A) Expression Vector Construction.

The expression vector, pYAM7SP-NAP6, was made in the same manner as described for pYAM7SP-NAP5 in Example 3.

(B) Expression of Recombinant AcaNAP6 in *P. pastoris*.

The vector, pYAM7SP-NAP6, was used to transform the Pichia strain GTS115 (his4) as described in Example 3.

(C) Purification of AcaNAP6.

The recombinant AcaNAP6, expressed from Pichia strain GTS115 (his4) transformed with the expression vector, pYAM7SP-NAP6, was purified as described for recombinant AcaNAP5 in Example 3.

The estimated mass of recombinant AcaNAP6 was determined, as described in Example 3, to be 8393.84 daltons.

The majority of the AcaNAP6 preparation had the following amino-terminus: Lys-Ala-Tyr-Pro-Glu [SEQ. ID. NO. 106].

Example 5

Expression of Recombinant Pro-AcaNAP5 in COS Cells (A) Expression Vector Construction.

The pGEM-9Zf(-) vector (Promega Corporation, Madison, Wis., USA) onto which the NAP5 cDNA was subcloned, served as target for PCR-rescue of the entire AcaNAP5 coding region, including the native secretion signal (using Vent polymerase from New England Biolabs, Beverly, Mass., USA; 20 temperature cycles: 1 minute at 95° C., 1 minute at 50° C., and 1.5 minutes at 72° C.). The oligonucleotide primers used were: (1) YG101, targeting the 3'-end of the gene encoding a NAP and having the sequence, GCTCGCTCTA GAAGCTTCAG ACATGTATAA TCT-CATGTTG G [SEQ, ID. NO. 105], and (2) YG102, targeting the 5'-end of the gene encoding a NAP and having the sequence, GACCAGTCTA GACAATGAAG ATGCTT-TACG CTATCG [SEQ. ID. NO. 107]. These primers contain non-annealing extensions which include XbaI restriction sites (underlined).

Following digestion with XbaI enzyme, the amplification product having the expected size was isolated from an agarose gel and subsequently substituted for the about 450 basepair XbaI stuffer fragment of the pEF-BOS vector

[Mizushima, S. and Nagata, S., Nucl. Acids Res., 18: 5322 (1990)] for expression purposes. The recipient vector-fragment was prepared by XbaI digestion and purified from an agarose gel.

E. coli strain WK6 [Zell, R. and Fritz, H.-J., EMBO J., 6: 1809–1815 (1987)] was transformed with the ligation mixture. Thirty randomly picked ampicillin-resistant transformants were subjected to PCR analysis (Taq polymerase from Life Technologies Inc., Gaithersburg, Md., USA; 30 cycles of amplification with the following temperature program: 1 minute at 95° C., 1 minute at 50° C., and 1 minute at 72° C.). Oligonucleotide primers used were: (i) YG103 having the sequence, AAGGCATACC CGGAGTGTGG TG [SEQ. ID. NO. 89], and matching the amino-terminus of the region encoding mature NAP, and (ii) YG60 having the sequence, GTGGGAGACC TGATACTCTC AAG [SEQ. ID. NO. 108], and targeting vector sequences downstream of the site of insertion, i.e., in the 3'-untranslated region of the pEF-BOS expression cassette. Only clones that harbor the insert in the desired orientation can yield a PCR fragment of predictable length (about 250 basepair). Two such clones were further characterized by sequence determination and were found to contain the desired XbaI insert. One of the clones, designated pEF-BOS-NAP5, was used to transfect COS cells.

(B) Transfection of COS Cells.

COS-7 cells (ATCC CRL 1651) were transfected with pEF-BOS-NAP5, pEF-BOS containing an irrelevant insert or with omission of DNA (mock transfections) using DEAE-dextran. The following media and stock solutions are used with the DEAE-dextran method:

(1) COS-medium: DMEM; 10% FBS (incubated for 30 minutes at 56° C.); 0.03% L-glutamine; penicillin (50 I.U./ml) and streptomycin (50 micrograms/ml) (all products from Life Technologies).

(2) MEM-HEPES: MEM medium from Life Technologies Inc., reconstituted according to the manufacturer's specifications; containing a 25 mM final concentration of HEPES; adjusted to pH 7.1 before filtration (0.22 micrometer).

(3) DNA solution: 6 micrograms DNA per 3 ml MEM-HEPES (4) DEAE-dextran solution: 30 microliters DEAE-dextran stock (Pharmacia, Uppsala, Sweden; 100 mg/ml in $H_2O$) per 3 ml MEM-HEPES.

(5) Transfection mixture: 3 ml of the DEAE-dextran solution is added to 3 ml of the DNA solution and the mixture is left to stand for 30 minutes at ambient temperature.

(6) Chloroquine solution: a 1:100 dilution of chloroquine stock (Sigma, St.Louis, Mo., USA; 10 mM in water; filtered through a 0.22 micrometer membrane) in COS medium.

Transient transfection of the COS cells is performed as follows. COS cells (about $3.5 \times 10^6$), cultured in a 175 $cm^2$ Nunc TC-flask (Life Technologies Inc.) were washed once with MEM-HEPES. Six ml of the Transfection mixture was pipetted onto the washed cells. After incubation for 30 minutes at ambient temperature, 48 ml of the chloroquine solution was added and the cells were incubated for another 4 hours at 37° C. The cells were washed one time with fresh COS-medium and finally incubated in 50 ml of the same medium at 37° C.

(C) Culturinc of Transfected COS Cells.

Three, four, and five days after transfection a sample of the culture supernatants was tested in a factor Xa amidolytic assay according to the procedure in Example 1. The results clearly demonstrated that factor Xa inhibitory activity was accumulating in the culture supernatant of the cells transfected with pEF-BOS-NAP5.

The COS culture supernatant was harvested five days after transfection and the NAP protein purified as described in Example 6.

Example 6

Purification of Recombinant Pro-AcaNAP5.

(A) Anion Exchange Chromatography.

The COS culture supernatant containing Pro-AcaNAP5 was centrifuged at 1500 r.p.m. (about 500×g) for 10 minutes before adding solid sodium acetate to a final concentration of 50 mM. The following protease inhibitors were added (all protease inhibitors from ICN Biomedicals Inc, Costa Mesa, Calif., USA): $1.0 \times 10^{-5}$M pepstatin A (isovaleryl-Val-Val-4-amino-3-hydroxy-6-methyl-heptanoyl-Ala-4-amino-3-hydroxy-6-methylheptanoic acid), $1.0 \times 10^{-5}$M leupeptin, $5 \times 10^{-5}$M AEBSF (4-(2-aminoethyl)-benzenesulfonyl fluoride). The pH was adjusted with HCl to pH 5.3. The supernatant was clarified by passage through a 0.2 micrometer cellulose acetate filter (Corning Inc., Corning, N.Y., USA).

The clarified supernatant (total volume approximately 300 ml) was loaded on a Poros20 HQ (Perseptive Biosystems, MA) 1×2 cm column pre-equilibrated with Anion buffer (0.05M sodium acetate, pH 5.3, 0.1M NaCl) at a flow rate of 10 ml/minute (800 cm/hour). The column and the sample were at ambient temperature throughout this purification step. The column was subsequently washed with at least 10 column volumes of Anion buffer. Material that had inhibitory activity in a factor Xa amidolytic assay was eluted with Anion buffer containing 0.55M NaCl at a flow rate of 5 ml/minute (400 cm/hour) and was collected.

(B) Molecular Sieve Chromatography using Superdex30.

The 0.55M NaCl elution pool (3 ml) from the anion-exchange chromatography was loaded on a Superdex30 PG (Pharmacia, Sweden) 1.6×66 cm column pre-equilibrated with 0.01M sodium phosphate, pH 7.4, 0.15M NaCl at 24° C. The chromatography was conducted at a flow rate of 2 ml/minute. Material which was inhibitory in the Factor Xa amidolytic assay eluted 56–64 ml into the run ($K_{av}$ of 0.207). This was exactly the same elution volume as determined for the native molecule.

(C) Heat Treatment.

The total pool of fractions having factor Xa inhibitory activity was incubated for 5 minutes at 90° C. in a glass tube and subsequently cooled rapidly on ice. Insoluble material was pelleted by centrifugation $19,000 \times g_{max}$ at 4° C. for 20 minutes. The supernatant contained all of the factor Xa inhibitory activity.

(D) Reverse Phase HPLC Chromatography.

The supernatant of the heat-treated sample was loaded onto a 0.46×25 cm C18 column (218TP54 Vydac; Hesperia, Calif.) which was then developed with a linear gradient of 10–35% acetonitrile in 0.1% (v/v) trifluoroacetic acid at 1 ml/minute with a rate of 0.4% change in acetonitrile/minute. Factor Xa inhibitory activity eluted at approximately 30% acetonitrile. The HPLC runs were performed on the same system as described in Example 1. Factor Xa inhibitory activity containing-fractions were vacuum dried.

(E) Molecular Weight Determination.

The estimated mass for recombinant Pro-AcaNAP5, isolated as described in sections A–D of this example, was determined using the same electrospray ionisation mass spectrometry system as described in Example 1.

The estimated mass of recombinant Pro-AcaNAP5 was 9248.4 daltons.

(F) Amino Acid Sequencing.

Following purification, the recombinant Pro-AcaNAP5 from COS cells was subjected to amino acid analysis to determine its amino-terminus sequence, as described in Example 1. The first nine amino acids of the amino-terminus of Pro-AcaNAP5 was determined to be: Arg Thr Val Arg Lys Ala Tyr Pro Glu [SEQ. ID. NO. 109]. Compared to the native AcaNAP5 protein (see Example 1), Pro-AcaNAP5 possesses four additional amino acids on its N-terminus. The amino acid sequence of Pro-AcaNAP5 is shown in FIG. 5.

Example 7
Expression of Recombinant Pro-AcaNAP6 in COS Cells

Pro-AcaNAP6 was transiently produced in COS cells essentially as described for Pro-AcaNAP5 in Example 5.

The AcaNAP6 coding region, including the secretion signal, was PCR-rescued with the same two oligonucleotide primers used for AcaNAP5: (1) YG101 targeting the 3'-end of the gene and having the sequence, GCTCGCTCTA GAAGCTTCAG ACATGTATAA TCTCATGTTG G [SEQ. ID. NO. 105], and (2) YG102 targeting the 5'-end of the gene and having the sequence, GACCAGTCTA GACAATGAAG ATGCTTTACG CTATCG [SEQ. ID. NO. 107]. The YG101-primer contains a non-matching nucleotide when used with AcaNAP6 as target (underlined T-residue; compare with FIG. 1 and FIG. 3); this mismatch results in the replacement an ATT Ile-codon by an ATA Ile-codon. The mismatch did not markedly influence the amplification efficiency.

The following modification from Example 5 was introduced: twenty-four hours after transfection of the COS cells (which is described in Example 5, section B) the COS-medium containing 10% FBS was replaced 50 ml of a medium consisting of a 1:1 mixture of DMEM and Nutrient Mixture Ham's F-12 (Life Technologies). The cells were then further incubated at 37° C. and the production of factor Xa inhibitory activity detected as described in Example 5.

Example 8
Purification of Recombinant Pro-AcaNAP6.

(A) Anion Exchange Chromatography.

The COS culture supernatant containing Pro-AcaNAP6 was centrifuged at 1500 r.p.m. for 10 minutes before adding solid sodium acetate to a final concentration of 50 mM. The following protease inhibitors were added (all protease inhibitors from ICN Biomedicals Inc, Costa Mesa, Calif., USA): $1.0 \times 10^{-5}$M pepstatin A (isovaleryl-Val-Val-4-amino-3-hydroxy-6-methyl-heptanoyl-Ala-4-amino-3-hydroxy-6-methylheptanoic acid), $1.0 \times 10^{-5}$M leupeptin, $5 \times 10^{-5}$M AEBSF (4-(2-aminoethyl)-benzenesulfonyl fluoride). The pH was adjusted with HCl to pH 5.3. The supernatant was clarified by passage through a 0.2 micrometer cellulose acetate filter (Corning Inc., Corning, N.Y., USA).

The clarified supernatant (total volume approximately 450 ml) was loaded on a Poros20 HQ (Perseptive Biosystems,MA) 1×2 cm column pre-equilibrated with Anion buffer (0.05M Na sodium acetate, pH 5.3, 0.1M NaCl) at a flow rate of 10 ml/minute (800 cm/hour). The column and the sample were at ambient temperature throughout this purification step. The column was subsequently washed with at least 10 column volumes of Anion buffer. Material that had inhibitory activity in a factor Xa amidolytic assay was eluted with Anion buffer containing 0.55M NaCl at a flow rate of 5 ml/minute (400 cm/hour) and was collected.

(B) Molecular Sieve Chromatography using Superdex30.

The 0.55M NaCl elution pool (3 ml) from the anion-exchange chromatography was loaded on a Superdex30 PG (Pharmacia, Sweden) 1.6×66 cm column pre-equilibrated with 0.01M sodium phosphate, pH 7.4, 0.15M NaCl at 24° C. The chromatography was conducted at a flow rate of 2 ml/minute. Material which was inhibitory in the Factor Xa amidolytic assay eluted 56–64 ml into the run ($K_{av}$ of 0.207). This was exactly the same elution volume as determined for the native NAP.

(C) Reverse Phase HPLC Chromatography.

The pooled fractions from the gel filtration were loaded onto a 0.46×25 cm C18 column (218TP54 Vydac; Hesperia, Calif.) which was then developed with a linear gradient of 10–35% acetonitrile in 0.1% (v/v) trifluoroacetic acid at a flow rate of 1 ml/minute with a rate of 0.4% change in acetonitrile/minute. Factor Xa inhibitory activity (assayed according to Example 1) eluted at approximately 30% acetonitrile. The HPLC runs were performed on the same system as described in Example 1. Factor Xa inhibitory activity containing-fractions were vacuum dried.

(D) Molecular Weight Determination.

The estimated mass for recombinant Pro-AcaNAP6, isolated as described in sections A to C of this example, was determined using the same electrospray ionisation mass spectrometry system as described in Example 1.

The estimated mass of recombinant Pro-AcaNAP6 was 8906.9 daltons.

(E) Amino Acid Sequencing.

Following purification, the recombinant Pro-AcaNAP6 from COS cells was subjected to amino acid sequence analysis as described in Example 1. The first five amino acids of the N-terminus of Pro-AcaNAP6 was determined to be: Arg Thr Val Arg Lys [SEQ. ID. NO. 110]. Compared to the native NAP protein (see Example 1), Pro-AcaNAP6 possesses four additional amino acids on its amino-terminus. The amino acid sequence of Pro-AcaNAP6 is shown in FIG. 6 [SEQ. ID. NO. 8].

Example 9
The use of NAP DNA Sequences to Isolate Genes Encoding Other NAP Proteins.

The AcaNAP5 and AcaNAP6 cDNA sequences (from Example 2) were used to isolate related molecules from other parasitic species by cross-hybridization.

The pGEM-9Zf(−) vectors (Promega) containing the AcaNAP5 and AcaNAP6 cDNAs were used to PCR-rescue the regions encoding the mature NAP proteins (Taq polymerase from Life Technologies; 20 temperature cycles: 1 minute at 95° C., 1 minute at 50° C., and 1.5 minutes at 72° C.). The oligonucleotide primers used were: (1) YG109, targeting the C-terminal sequences of cDNA encoding NAP, and having the sequence, TCAGACATGT-ATAATCTCAT-GTTGG [SEQ. ID. NO. 88], and (2) YG103 having the sequence, AAGGCATACC-CGGAGTGTGG-TG [SEQ. ID. NO. 89]. The YG109 primer contains a single nucleotide mismatch (underlined T-residue; compare with the sequences shown in FIGS. 1 and 3) when used with AcaNAP6 as target. This did not markedly influence the amplification efficiency. The correctly sized PCR products (about 230 basepairs) were both isolated from a 1.5% agarose gel. An equimolar mixture was radiolabeled by random primer extension (T7 QuickPrime kit; Pharmacia) and subsequently passed over a Bio-Spin 30 column (Bio-Rad, Richmond, Calif., USA).

*Ancylostoma ceylanicum* (Ace), *Ancylostoma duodenale* (Adu), and *Heligmosomoides polygyrus* (Hpo) cDNA libraries were prepared essentially as described for *Ancylostoma caninum* in Example 2.

*Ancylostoma ceylanicum* and *Heligmosomoides polygyrus* were purchased from Dr. D. I. Pritchard, Department of Life Science, University of Nottingham, Nottingham, UK. *Ancylostoma duodenale* was purchased from Dr. G. A. Schad, The School of Veterinary Medicine, Department of Pathobiology, University of Pennsylvania, Philadelphia, Pa., USA.

In each case, the cDNAs were directionally cloned as EcoRI-NotI fragments in lambda gt11. Approximately 2×10[5] cDNA clones from each library (duplicate plaque-lift filters were prepared using Hybond™-N; Amersham) were screened with the radiolabeled AcaNAP5 and AcaNAP6 fragments using the following prehybridization and hybridization conditions: 5× SSC (SSC: 150 mM NaCl, 15 mM trisodium citrate), 5× Denhardt's solution, 0.5% SDS, 20% formamide, 100 micrograms/ml sonicated fish sperm DNA (Boehringer), overnight at 42° C. The filters were washed 4 times for 30 minutes in 2× SSC, 0.1% SDS at 37° C. After exposure (about 60 hours) to X-ray film, a total of between 100 and 200 hybridization spots were identified in the case of Ace and Adu. A small number of very faint spots were visible in the case of the Hpo cDNA library. For each of the libraries, eight positives were subjected to a second hybridization round at lower plaque-density so as to isolate single plaques.

The retained clones were further characterized by a PCR amplification of the cDNA-inserts using the oligo(dT)-NotI primer (Promega; this is the same primer used to prepare first strand cDNA; see Example 2) [SEQ. ID. NO. 95] in combination with the lambda-gt11 primer #1218 having the sequence, GGTGGCGACG ACTCCTGGAG CCCG [SEQ. ID. NO. 96] (New England Biolabs; primer #1218 targets lambda sequences located upstream of the site of cDNA insertion). PCR amplifications were performed as follows: Taq polymerase from Boehringer; 30 temperature cycles: 1 minute at 95° C.; 1 minute at 50° C.; 1.5 minutes at 72° C. Gel-electrophoretic analysis of the PCR products clearly demonstrated that cDNAs of roughly the same size as the AcaNAP5 cDNA (e.g., 400 to 500 bp) were obtained for each species. In addition to these AcaNAP5-sized cDNAs, some Ace and Adu cDNAs were estimated to be about 700 bp long.

A number of clones, containing either a 500 bp or an 800 bp insert, were chosen for sequence determination. To that end the cDNA inserts were subcloned, as SfiI-NotI fragments, onto pGEM-type phagemids (Promega; refer to Example 2 for details) which permit the preparation of single stranded DNA. The sequencing results led to the identification of six different new NAP-like proteins, designated as follows: AceNAP4, AceNAP5, AceNAP7, AduNAP4, AduNAP7, and HpoNAP5. The nucleotide sequences of the cDNAs as well as the deduced amino acid sequences of the encoded proteins are shown in FIG. 7A (AceNAP4 [SEQ. ID. NO. 9]), FIG. 7B (AceNAP5) [SEQ. ID. NO. 10], FIG. 7C (AceNAP7) [SEQ. ID. NO. 11], FIG. 7D (AduNAP4) [SEQ. ID. NO. 12], FIG. 7E (AduNAP7) [SEQ. ID. NO. 13], and FIG. 7F (HpoNAP5) [SEQ. ID. NO. 14]. The AceNAP4 [SEQ. ID. NO. 9] and AduNAP7 [SEQ. ID. NO. 13] cDNAs, each about 700 bp long, each encoded proteins which incorporated two NAP domains; the other cDNAs isolated coded for a protein having a single NAP domain. The AduNAP4 cDNA clone [SEQ. ID. NO. 12] was not full-length, i.e., the clone lacked the 5'-terminal part of the coding region; the correct reading frame could, however, be assigned based on amino acid sequence homology with the NAP family of related molecules.

The identified cDNA sequences can be used to produce the encoded proteins as disclosed in Examples 3, 4, 5, and 7 using the same or alternative suitable expression systems. Conditioned media or cell lysates, depending on the system used, can be tested as such or after fractionation (using such methodology as outlined in Example 3, 4, 6 and 8) for protease inhibitory and anticoagulant activity. Proteins that are encoded by cDNAs which hybridize to probes derived from fragments of the NAP5 gene (FIG. 1) [SEQ. ID. NO. 3] and/or the NAP6 gene (FIG. 3) [SEQ. ID. NO. 5] and that possess anticoagulant properties are considered to belong to the AP family of related molecules.

Example 10
Identification of NAP by Functional Display of cDNA Encoded Proteins.
(A) The pDONG Series of Vectors.

The nucleotide sequences of the pDONG vectors, pDONG61 [SEQ. ID. NO. 15], pDONG62 [SEQ. ID. NO. 16] and pDONG63 [SEQ. ID. NO. 17], derivatives of pUC119 [Vieira, J. and Messing, J., Methods in Enzymology, 153:3–11 (1987)], are depicted in FIGS. 8A to 8C respectively.

To construct these three vectors, HindIII and SfiI restriction sites were added at the 5'-end and 3'-end of the filamentous phage gene 6 by PCR amplification of the M13K07 single stranded DNA [Vieira, J. and Messing, J., Ibid] with the G6BACKHIND backward primer and G6FORSFI61, G6FORSFI62 or G6FORSFI63 as forward primers. In a second PCR, the three obtained fragments were re-amplified with G6BACKHIND and G6FORNOTBAMH as forward primer to append NotI and BamHI sites at the 3'-end of the fragments. The sequences of the above mentioned PCR-primers are as follows (restriction sites are underlined):

G6BACKHIND: ATCCGAAGCT TGCTAACAT ACTGCGTAAT AAG [SEQ. ID. NO. 111]

G6FORSFI61: TATGGGATGG CCGACTTGGC CTCCGCCTGA GCCTCCACCT TTATCCCAAT CCAAATAAGA [SEQ. ID. NO. 112]

G6FORSFI62: ATGGGATGGC CGACTTGGCC CTCCGCCTGA GCCTCCACCT TTATCCCAAT CCAAATAAGA [SEQ. ID. NO. 113]

G6FORSFI63: TATGGGATGG CCGACTTGGC CGATCCGCCT GAGCCTCCAC CTTTATCCCA ATCCAAATAA [SEQ. ID. NO. 114]

GAG6FORNOTBAMH: AGGAGGGGAT CCGCGGCCGC GTGATATGGG ATGGCCGACT TGGCC [SEQ. ID. NO. 115]

Finally, the PCR products were gel-purified, individually digested with HindIII and BamHI and inserted between the corresponding sites of pUC119. Sequence determination confirmed that pDONG61, pDONG62, and pDONG63 all contained the intended insert.

The pDONG series of vectors permit the cloning of cDNAs, as SfiI-NotI fragments. This cloning fuses the cDNAs in each of the three reading (translation) frames to the 3'-end of filamentous phage gene 6 which encodes one of the phage's coat proteins. Infection of a male-specific *E. coli* strain harboring a pDONG-derivative, with VCSM13 helper phage (Stratagene, La Jolla, Calif.), results in the rescuing of pseudo-virions which encapsidate one specific single strand of the pDONG-derivative and which may also incorporate a recombinant protein 6 (p6) fusion protein in their coat. cDNAs which are such that the encoded protein is functionally displayed on the phage surface as a recombinant p6 fusion protein become identifiable by means of a panning experiment described below.

(B) Transfer of the *Ancylostoma caninum* cDNA Library from Lambda gt11 to the ODONG Series of Vectors.

A phage lambda preparation of the pooled *A. caninum* cDNA clones (about 1×10[6] plaques, see Example 2) was used to PCR-rescue the cDNA inserts (Taq polymerase from Life Technologies, Gaithersburg, Md., USA; 20 temperature cycles: 1 minute at 95° C., 1 minute at 50° C., and 3 minutes at 72° C. followed by 10 minutes at 65° C.), with the lambda gt11 primer #1218 having the sequence, GGTGGCGACG ACTCCTGGAG CCCG [SEQ. ID. NO. 96] (New England Biolabs, Beverly, Mass., USA; targeting sequences located upstream of the cDNA insert) in combination with the oligo(dT)-NotI primer/adaptor (Promega) used for first strand cDNA synthesis. Following digestion with the restriction enzymes SfiI and NotI, the whole size-range of amplification products were recovered from agarose gel.

All fragments were directionally cloned into the pDONG61, pDONG62, and pDONG63 vectors. The recipient vector-fragments were prepared by digestion of the CsCl purified vectors with SfiI and NotI and purification with the "Wizard™ PCR Preps DNA Purification System" (Promega Corp, Madison, Wis., USA).

E. coli strain TG1 [Sambrook, J., Fritsch, E. F. and Maniatis, T., *Molecular Cloning, A Laboratory Manual, Second Edition*, volumes 1 to 3, Cold Spring Harbor Laboratory Press (1989)] was transformed by electroporation with the pDONG/cDNA ligation mixtures. Electrotransformed cells were incubated 1 hour at 37° C. in SOC medium [Sambrook, J. et al., *Ibid.*] and plated on LB-agar containing 0.1% glucose and 100 micrograms/ml carbenicillin (245×245×25 mm plates; Nunc). $2.2\times10^6$, $1.6\times10^6$, and $1.4\times10^6$ carbenicillin resistant transformants were obtained with pDONG61, pDONG62, and pDONG63, respectively. From each respective library, designated 20L, 21L and 22L, a number of randomly picked transformants were subjected to PCR analysis (Taq polymerase from Life Technologies; 30 cycles of amplification with the following temperature program: 1 minute at 95° C., 1 minute at 50° C., and 1 to 3 minutes at 72° C.) using two primers that match with sequences flanking the multiple cloning site of pUC119 (primers #1224 having the sequence, CGCCAGGGTTTTC-CCAGTCA CGAC [SEQ. ID. NO. 116], and #1233 having the sequence, AGCGGATAAC AATTTCACAC AGGA [SEQ. ID. NO. 101]; New England Biolabs). The results showed that the vast majority of the clones contained a cDNA-insert of variable size.

(C) Factor Xa Based Affinity-Selection of cDNA Clones Encoding a NAP Protein.

Phage particles from the 20L, 21L and 22L libraries were rescued as follows: each library was scraped from the plates and grown at 37° C. in 100 ml LB medium supplemented with 1% glucose and 100 micrograms/ml carbenicillin until the optical absorbance at 600 nm reaches the value of 0.5. After addition of VCSM13 helper phage (Stratagene) at a multiplicity of infection (moi) of 20, the culture was left to stand for 30 minutes at 37° C. and then slowly shaken for another 30 minutes. The cells were pelleted by centrifugation and resuspended in 250 ml LB medium supplemented with 100 micrograms/ml carbenicillin and 50 micrograms/ml kanamycin. These cultures were allowed to grow overnight at 30° C. under vigorous agitation. The resulting phage particles were purified by two consecutive precipitations with polyethylene glycol/NaCl and resuspended at $1\times10^{13}$ virions per ml in TRIS-buffered saline (0.05M Tris, 0.15M sodium chloride, pH 7.4) (TBS). Equal amounts of phage particles from the 20L, 21L and 22L were then mixed together.

Human factor Xa (see Example 1 for preparation) was biotinylated with biotin-XX-NHS according to manufacturer's instructions (Pierce). The amidolytic activity of the protease was not affected by this modification as shown by an enzymatic assay using the chromogenic substrate S-2765 (Chromogenix; see Example 1). Streptavidin-coated magnetic beads (Dynal; 1 mg per panning round) were washed three times with TBS and blocked in TBS supplemented with 2% skim milk (Difco) at ambient temperature. After one hour, the magnetic beads were washed twice with TBS before use.

For the first round of panning, $1\times10^{13}$ phage from the pooled libraries were incubated for 75 minutes at 4° C. in 200 microliters of TBS buffer supplemented with 250 nM biotinylated factor Xa, 5 mM $CaCl_2$ and 2% skim milk. After this time, 1 mg blocked streptavidin-coated magnetic beads, resuspended in 200 microliters of TBS containing 5 mM $CaCl_2$ and 2% skim milk, was added to the phage solution and incubated for 1 hour at 4° C. with gentle agitation. With a magnet (Dynal), the magnetic beads were then rinsed ten times with 500 microliters of TBS containing 0.1% Tween-20. Bound phage were eluted from the magnetic beads by incubating them with 500 microliters of 0.1M glycine-HCl buffer (pH 2.0) for 10 minutes. The supernatant was neutralized with 150 microliters 1M Tris-HCl buffer (pH 8.0).

For phage propagation, E. coli strain TG1 [Sambrook, J., Fritsch, E. F. and Maniatis, T., *Molecular Cloning, A Laboratory Manual, Second Edition*, volumes 1 to 3, Cold Spring Harbor Laboratory Press (1989)] was grown at 37° C. in 10 ml LB medium until the optical absorbance at 600 nm reached the value of 0.5. The culture was infected with 650 microliters of phage eluted from the magnetic beads and briefly incubated at 37° C. with no shaking. After centrifugation, the infected cells were resuspended in 2 ml LB medium and plated onto 245×245×25 mm plates filled with LB-agar containing 1% glucose and 100 micrograms/ml carbenicillin. After overnight incubation at 37° C., the cells were scraped from the plates and resuspended in 40 ml LB medium supplemented with 1% glucose and 100 micrograms/ml carbenicillin. A cell aliquot corresponding to 15 optical densities at 600 nm was then used to inoculate 100 ml LB medium containing 1% glucose and 100 micrograms/ml carbenicillin. Phage rescue for the next panning round was done as outlined above.

For the second panning round, $6\times10^{12}$ phage were incubated during 90 minutes with 1 mg blocked streptavidin-coated magnetic beads in 200 microliters of TBS containing 2.5 mM $Ca^{2+}$ and 2% skim milk (this step was introduced in the procedure to avoid selection of streptavidin-binding clones). After removal of the beads, the same protocol was followed as for round 1. Rounds 3, 4 and 5 were accomplished as round 2, except that the phage input was lowered to $2\times10^{12}$ phage.

Twenty-four individual carbenicillin resistant clones that were isolated after five rounds of panning against biotinylated factor Xa, were then analysed by ELISA. Streptavidin-coated 96-well plates (Pierce) were blocked for 1 hour with 200 microliters of TBS containing 2% skim milk per well, then were incubated for 1 hour with 100 microliters of 20 nM biotinylated factor Xa in TBS per well. For each clone, about 1010 phage diluted in 100 microliters TBS containing 2% skim milk and 0.1% Tween-20 were added to the wells. After a 2-hour incubation, the wells were rinsed four times with 200 microliters TBS containing 0.1% Tween-20. Bound phage were visualized by consecutively incubating with a rabbit anti-M13 anti-serum (see Example 11), an alkaline phosphatase conjugated anti- rabbit serum (Sigma), and p-nitrophenylphosphate as substrate (Sigma). Absorbances were taken at 405 nm after 20 minutes. Out of the 24 clones, five bound strongly to factor Xa. No significant non-specific binding was observed with these phage when tested in the same ELISA with omission of biotinylated factor Xa.

Single stranded DNA was then prepared from the five positive clones and the inserts 3' to the gene 6 were submitted to automated DNA sequencing using the primer #1224 having the sequence, CGCCAGGGTT TTC-CCAGTCA CGAC [SEQ. ID. NO. 116] (New England Biolabs). All five clones were found to contain the same 470 bp 5'-truncated cDNA fused in frame to gene 6 in pDONG63. The nucleotide sequence of this cDNA as well as the deduced amino acid sequence are depicted in FIG. 9 [SEQ. ID. NO. 19]. The cDNA, designated AcaNAPc2, encodes a protein, designated NAP isoform c2, that belongs to the NAP family of related proteins.

Example 11

Preparation of Antiserum Against M13 Phage

Antiserum against M13 phage was prepared in rabbits by subcutaneous injections of about $10^{13}$ M13K07 phage in 500 microliters of PBS (0.01M sodium phosphate, pH 7.4+ 0.15M sodium chloride) combined with an equal volume of adjuvant. The M13KO7 phage were CsCl-purified essentially as described by Glaser-Wuttke, G., Keppner, J., and Rasched, I., Biochim. Biophys. Acta, 985: 239–247 (1989). The initial injection was done with Complete Freunds adjuvant on day 0, followed by subsequent injections with Incomplete Freunds adjuvant on days 7, 14 and 35. Antiserum was harvested on day 42.

The IgG fraction of the antiserum was enriched by passage over a Protein A-Sepharose column using conditions well known in the art.

Example 12

The Use of AcaNAP5 and AcaNAP6 DNA Sequences to Isolate Additional NAP-Encoding Sequences from *A. caninum*

The AcaNAP5 and AcaNAP6 cDNA sequences (from Example 2) were used to isolate related molecules from the same parasitic species by cross-hybridization.

The pGEM-9Zf(-) vectors (Promega, Madison, Wis.) containing the AcaNAP5 and AcaNAP6 cDNAs were used to PCR-rescue the regions encoding the mature NAP proteins (Taq polymerase from Life Technologies (Gaithersburg, Md.); 20 temperature cycles: 1 minute at 95° C., 1 minute at 50° C., and 1.5 minutes at 72° C.). The oligonucleotide primers used were: (1) YG109, targeting the C-terminal-encoding sequences of cDNA encoding AcaNAP5 and AcaNAP6, and having the sequence, TCAGACATGT-ATAATCTCAT-GTTGG [SEQ. ID. NO. 88], and (2) YG103, targeting the N-terminal-encoding sequences of mature AcaNAP5 and AcaNAP6, having the sequence, AAGGCATACC-CGGAGTGTGG-TG [SEQ. ID. NO. 89]. The YG109 primer contains a single nucleotide mismatch when used with AcaNAP6 as target (underlined T-residue; compare with the sequence shown in FIG. 3 [SEQ. ID. NO. 5]). This mismatch did not markedly influence the amplification efficiency. The correctly sized PCR products (about 230 basepairs) for AcaNAP5 and AcaNAP6 were both isolated from a 1.5% agarose gel. An equimolar mixture was radiolabeled by random primer extension (T7 QuickPrime kit; Pharmacia (Sweden) and subsequently passed over a Bio-Spin 30 column (Bio-Rad, Richmond, Calif., USA).

Approximately 750,000 *Ancylostoma caninum* (Aca) cDNA clones (refer to Example 2 (B); duplicate plaque-lift filters were prepared using Hybond™-N; Amersham (Buckinghamshire, England) were screened with the radiolabeled AcaNAP5 and AcaNAP6 cDNA fragments using the following prehybridization and hybridization conditions: 5× SSC (SSC: 150 mM NaCl, 15 mM trisodium citrate), 5× Denhardt's solution, 0.5% SDS, 20% formamide, 100 micrograms/ml sonicated fish sperm DNA (Boehringer), overnight at 42° C. The filters were washed 4 times for 30 minutes in 2× SSC, 0.1% SDS at 37° C. After exposure to X-ray film, a total of about 300 positives were identified.

48 of the 300 positives were subjected to PCR-amplification (Taq polymerase from Boehringer Mannheim, Germany; 30 temperature cycles: 1 minute at 95° C.; 1 minute at 50° C.; 1.5 minutes at 72° C.) using the above mentioned YG109 primer, specific for the C-terminus-encoding sequence of AcaNAP5 and AcaNAP6 cDNAs, and primer #1218 which targets lambda-gt11 sequences located upstream of the site of cDNA insertion (New England Biolabs, Beverly, Mass.; GGTGGCGACG ACTCCTGGAG CCCG [SEQ. ID. NO. 96]). 31 out of the 48 positives yielded a PCR product of a size similar to that expected for a AcaNAP5/6-type cDNA.

The remaining 17 positives were used as template for amplification with primer #1218 and an AcaNAPc2 specific primer (e.g., LJ189, targeting the AcaNAPc2 C-terminus and having the sequence GTTTCGAGTT CCGGGATATA TAAAGTCC [SEQ. ID. NO. 117]; refer to Example 10 and FIG. 9). None of the clones yielded a PCR product. All 17 positives were then subjected to a second hybridization round at lower plaque-density; single isolated clones were identified in all cases. The 17 isolated cDNA clones were re-analyzed by PCR using the primer couples #1218/YG109 and #1218/LJ189. Three out of the 17 clones yielded an amplification product with the #1218/YG109 primers.

The remaining 14 clones were further analyzed by PCR amplification with the primers #1218 and oligo(dT)-Not (Promega, Madison, Wis.; this is the same primer used to prepare first strand cDNA; see Example 2). All 14 clones yielded a PCR product. Gel-electrophoretic analysis of the PCR products indicated that some cDNAs were considerably longer than the AcaNAP5 cDNA insert.

Ten clones, including those having the largest cDNA inserts, were chosen for sequence determination. To that end the cDNA inserts were subcloned as SfiI-NotI fragments onto pGEM-type phagemids (Promega, Madison, Wis.), as described in Example 2. The sequencing identified eight additional NAP protein sequences, designated as follows: AcaNAP23, AcaNAP24, AcaNAP25, AcaNAP31, AcaNAP44, AcaNAP45, AcaNAP47, and AcaNAP48. Two additional cDNA clones, designated AcaNAP42 and AcaNAP46, encoded proteins identical to those encoded by AcaNAP31 [SEQ. ID. NO. 34]. The nucleotide sequences of the cDNAs as well as the deduced amino acid sequences of the encoded proteins are shown in FIG. 13A (AcaNAP23 [SEQ. ID. NO. 31]), FIG. 13B (AcaNAP24 [SEQ. ID. NO. 32]), FIG. 13C (AcaNAP25 [SEQ. ID. NO. 33]), FIG. 13D (AcaNAP31 [SEQ. ID. NO. 34]), FIG. 13E (AcaNAP44 [SEQ. ID. NO. 35]), FIG. 13F (AcaNAP45 [SEQ. ID. NO. 36]), FIG. 13G (AcaNAP47 [SEQ. ID. NO. 37]), and FIG. 13H (AcaNAP48 [SEQ. ID. NO. 38]). All clones were full-length and included a complete secretion signal. The AcaNAP45 [SEQ. ID. NO. 36] and AcaNAP47 [SEQ. ID. NO. 37] cDNAs, each encode proteins which incorporate two NAP domains; the other cDNAs code for a protein having a single NAP domain.

Example 13

The Use of NAP DNA Sequences to Isolate Sequences Encoding a NAP Protein from *Necator americanus*

The sequences of AcaNAP5 [SEQ. ID. NO. 3], AcaNAP6 [SEQ. ID. NO. 5], AcaNAPc2 [SEQ. ID. NO. 19], AcaNAP23 [SEQ. ID. NO. 31], AcaNAP24 [SEQ. ID. NO. 32], AcaNAP25 [SEQ. ID. NO. 33], AcaNAP31 [SEQ. ID. NO. 34], AcaNAP44 [SEQ. ID. NO. 35], AcaNAP45 [SEQ. ID. NO. 36], AcaNAP47 [SEQ. ID. NO. 37], AcaNAP48 [SEQ. ID. NO. 38], AceNAP4 [SEQ. ID. NO. 9], AceNAP5 [SEQ. ID. NO. 10], AceNAP7 [SEQ. ID. NO. 11], AduNAP4 [SEQ. ID. NO. 12], AduNAP7 [SEQ. ID. NO. 13], and HpoNAP5 [SEQ. ID. NO. 14] (see FIGS. 1, 3, 7, and 13) were used to isolate related molecules from the hematophageous parasite Necator americanus by PCR-cloning.

Consensus amino acid sequences were generated from regions of homology among the NAP proteins. These consensus sequences were then used to design the following degenerate PCR primers: NAP-1, 5' -AAR-CCN-TGY-GAR-MGG-AAR-TGY-3' [SEQ. ID. NO. 90] corresponding to the amino acid sequence NH$_2$-Lys-Pro-Cys-Glu-(Arg/Pro/Lys)-Lys-Cys [SEQ. ID. NO. 118]; NAP-4.RC, 5'-TW-RWA-NCC-NTC-YTT-RCA-NAC-RCA-3' [SEQ. ID. NO. 91], corresponding to the sequence NH$_2$-Cys-(Val/Ile/Gln)-Cys-(Lys/Asp/Glu/Gln)-(Asp/Glu)-Gly-(Phe/Tyr)-Tyr [SEQ. ID. NO. 119]. These primers were used pairwise to generate NAP-specific probes by PCR using N. americanus cDNA as template.

Adult worms, N. americanus, were purchased from Dr. David Pritchard, University of Nottingham. Poly(A+) RNA was prepared using the QuickPrep mRNA Purification Kit (Pharmacia, Piscataway, N.J.). One microgram of mRNA was reverse transcribed using AMV reverse transcriptase and random hexamer primers (Amersham, Arlington Hills, Ill.). One fiftieth of the single-stranded cDNA reaction product was used as template for ~400 pmole of each of NAP-1 and NAP-4.RC, with PCR GeneAmp (Perkin Elmer, Norwalk, Conn.) reagents, on a Perkin-Elmer DNA thermal cycler. PCR conditions were: cycles 1–3, denaturation at 96° C. for 2 minutes, annealing at 37° C. for 1 minute, and elongation at 72° C. for 3 minutes (ramp time between 37° C. and 72° C. was 2 minutes); cycles 4–5, denaturation at 94° C. for 1 minute, annealing at 37° C. for 1 minute, and elongation at 72° C. for 2 minutes (ramp time between 37° C. and 72° C. was 2 minutes); cycles 6–45, denaturation at 94° C. for 1 minute, annealing at 37° C. for 1 minute, and elongation at 72° C. for 2 minutes. Elongation times were incremented by 3 seconds/cycle for cycles 6–45.

PCR amplification of N. americanus cDNA with NAP-1 and NAP-4.RC resulted in an approximately 100 bp amplification product. The PCR product was labeled with [a-32P]-dCTP (Amersham) using random primer labeling (Stratagene, La Jolla, Calif.), and labeled DNA was separated from unincorporated nucleotides using a Chromaspin-10 column (Clonetech, Palo Alto, Calif.).

A cDNA library was constructed using the following procedure. Double stranded cDNA was synthesized from 1 μg of N. americanus poly(A+) RNA using AMV reverse transcriptase and random hexamer primers (Amersham, Arlington Hills, Ill.). cDNA fragments larger than approximately 300 bp were purified on a 6% polyacrylamide gel and ligated to EcoRI linkers (Stratagene, San Diego, Calif.) using standard procedures. Linkered cDNA was ligated into EcoRI-cut and dephosphorylated lambda gt10 (Stratagene, San Diego, Calif.) and packaged using a Gigapack Gold II packaging kit (Stratagene, San Diego, Calif.).

Prehybridization and hybridization conditions were 6× SSC (SSC: 150 mM NaCl, 15 mM trisodium citrate, pH 7.0), 0.02M sodium phosphate pH 6.5, 5× Denhardt's solution, 100 μg/ml sheared, denatured salmon sperm DNA, 0.23% dextran sulfate. Prehybridization and hybridization were at 42° C., and the filters were washed for 30 minutes at 45° C. with 2× SSC after two prewashes with 2× SSC for 20 minutes. The filters were exposed overnight to X-ray film with two intensifying screens at −70° C.

Approximately 400,000 recombinant phage of the random primed N. americanus library (unamplified) were screened with the NAP-1/NAP-4.RC PCR fragment. About eleven recombinant phage hybridized to this probe, of which four were isolated for nucleotide sequencing analysis. Double stranded sequencing was effected by subcloning the EcoRI cDNA fragments contained in these phage isolates into pBluescript II KS+ vector (Stratagene, San Diego, Calif.). DNA was sequenced using the Sequenase version 2.0 kit (Amersham, Arlington Hills, Ill.)) and M13 oligonucleotide primers (Stratagene, San Diego, Calif.).

The four lambda isolates contained DNA that encoded a single 79 amino acid NAP polypeptide that resembles NAP sequences from Ancylostoma spp. and H. polygyrus. The NAP polypeptide from N. americanus has a calculated molecular weight of 8859.6 Daltons. The nucleotide and deduced amino acid sequences are shown in FIG. 14.

Example 14

Expression Of Recombinant AceNAP4 In COS Cells

A. Expression

AceNAP4 was transiently produced in COS cells essentially as described for Pro-AcaNAP5 in Example 5 and Pro-AcaNAP6 in Example 7.

A pGEM-type phagemid that harbors the AceNAP4 cDNA (from Example 9), served as target for PCR-rescue of the entire AceNAP4 coding region, including the secretion signal, using two XbaI-appending oligonucleotide primers. The primers used were: (1) SHPCR4, targeting the 5'-end of the gene and having the sequence, GACCAGTCTA GAC-CACCATG GCGGTGCTTT ATTCAGTAGC AATA [SEQ. ID. NO. 120], and (2) SHPCR5, targeting the 3'-end of the gene and having the sequence, GCTCGCTCTA GAT-TATCGTG AGGTTTCTGG TGCAAAAGTG [SEQ. ID. NO. 121]. The XbaI restriction sites included in the primers are underlined. The primers were used to amplify the AceNAP4 sequence according to the conditions described in Example 5.

Following digestion with XbaI enzyme, the amplification product, having the expected size, was isolated from an agarose gel and subsequently substituted for the about 450 basepair XbaI stuffer fragment of the pEF-BOS vector [Mizushima, S. and Nagata, S., Nucl. Acids Res., 18: 5322 (1990)]. The protocol described in Example 5 was followed to yield clone pEF-BOS-AceNAP4, which was first shown to harbor the XbaI-insert in the desired orientation by PCR using primers SHPCR4 and YG60, and subsequently confirmed by sequence determination. This clone was used to transfect COS cells according to the methods in Example 5.

Twenty-four hours after transfection of the COS cells (refer to Example 5, section B) the COS-medium containing 10% FBS was replaced with 50 ml of a medium consisting of a 1:1 mixture of DMEM and Nutrient Mixture Ham's F-12 (Life Technologies (Gaithersburg, Md.). The cells were then further incubated at 37° C. and the production of EGR-factor Xa dependent TF/factor VIIa inhibitory activity detected as described in Example E.

B. Purification of AceNAP4

1. Anion-exchange chromatography

The COS culture supernatant from the AceNAP4-expressing cells was centrifuged at 1500 r.p.m.(about 500× g) for 10 minutes before the following protease inhibitors (ICN Biomedicals Inc., Costa Mesa, Calif.) were added ($1.0 \times 10^{-5}$M pepstatinA (isovaleryl-Val-Val-4-amino-3-hydroxy-6-methyl-heptanoyl -Ala-4-amino-3hydroxy-6-methylheptanoic acid), $1.0 \times 10^{-5}$M AEBSF (4-(2-amonoethyl)-benzenesulfonyl fluoride). Solid sodium acetate was added to a final concentration of 50 mM before the pH was adjusted with 1N HCl to pH 5.3. The supernatant was clarified by passage through a 0.22 micrometer cellulose acetate filter (Corning Inc., Corning, N.Y., USA).

The clarified supernatant (total volume approximately 450 ml) was loaded on a Poros20 HQ (Perseptive Biosystems, Mass.) 1×2 cm column preequilibrated with Anion Buffer (0.05M sodium acetate 0.1M NaCl, pH 5.3) at a flow rate of 5 ml/minute. The column and the sample were at ambient temperature throughout this purification step. The column was subsequently washed with 10 column volumes of Anion Buffer and 10 column volumes of 50 mM sodium acetate, 0.37M NaCl, pH5.3.

Material that had EGR-FXa dependent fVIIa/TF amidolytic inhibitory activity (see Example E) was eluted with 50 mM sodium acetate, 1M NaCl, pH5.3 at a flow of 2 ml/minute.

2. Reverse-phase chromatography

An aliqout of the pool of fractions collected after anion exchange chromatography was loaded onto a 0.46×25 cm C18 column (218TP54 Vydac; Hesperia, Calif.) which was then developed with a linear gradient of 10–35% acetonitrile in 0.1% (v/v) trifluoroacetic acid at 1 ml/minute with a rate of 0.4% change in acetonitrile/minute. EGR-FXa dependent TF/FVIIa amidolytic inhibitory activity (see Example E) was monitored and fractions containing this inhibitory activity were isolated and vacuum-dried.

3. Characterization of recombinant AceNAP4

The AceNAP4 compound demonstrated SDS-PAGE mobility on a 4–20% gel, consistent with its size predicted from the sequence of the cDNA (Coomassie stained gel of material after RP-chromatography).

Example 15

Production and Purification Of Recombinant AcaNAPc2 In *P. pastoris*.

A. Expression Vector Construction

Expression of the AcaNAPc2 gene in *P. pastoris* was accomplished using the protocol detailed in Example 3 for the expression of AcaNAP5 with the following modifications.

The pDONG63 vector containing the AcaNAPc2 cDNA described in Example 10, was used to isolate by amplification ("PCR-rescue") the region encoding mature AcaNAPc2 protein (using Vent polymerase from New England Biolabs, Beverly, Mass.; 20 temperature cycles: 1 minute at 94° C., 1 minute at 50° C., and 1.5 minutes at 72° C.). The following oligonucleotide primers were used:
LJ190: AAAGCAACGA-TGCAGTGTGG-TGAG [SEQ. ID. NO. 122]
LJ191: GCTCGCTCTA-GAAGCTTCAG-TTTCGAGTTC-CGGGATATAT-AAAGTCC [SEQ. ID. NO. 123]

The LJ191 primer, targeting C-terminal sequences, contained a non-annealing extension which included XbaI and HindIII restriction sites (underlined).

Following digestion with XbaI enzyme, the amplification product, having the expected size, was isolated from gel and subsequently enzymatically phosphorylated (T4 polynucle-otide kinase from New England Biolabs, Beverly, Mass.). After heat-inactivation (10 minutes at at 70° C.) of the kinase, the blunt-ended/XbaI fragment was directionally cloned into the vector pYAM7SP8 for expression purposes. The recipient vector-fragment from pYAM7SP8 was prepared by StuI-SpeI restriction, and purified from agarose gel. The *E. coli* strain, WK6 [Zell, R. and Fritz, H. -J., EMBO J., 6: 1809–1815 (1987)], was transformed with the ligation mixture, and ampicillin resistant clones were selected.

Based on restriction analysis, a plasmid clone containing an insert of the expected size, designated pYAM7SP-NAPC2, was retained for further characterization. Sequence determination of the clone pYAM7SP-NAPC2 confirmed the precise insertion of the mature AcaNAPC2 coding region in fusion with the prepro leader signal, as predicted by the construction scheme, as well as the absence of unwanted mutations in the coding region.

B. Expression Of Recombinant AcaNAPc2 In *P. pastoris*

The Pichia strain GTS115 (his4) has been described in Stroman, D. W. et al., U.S. Pat. No. 4,855,231. All of the *P. pastoris* manipulations were performed essentially as described in Stroman, D. W. et al., U.S. Pat. No. 4,855,231.

About 1 microgram of pYAM7SP-NAPC2 plasmid DNA was electroporated into the strain GTS115 using a standard electroporation protocol. The plasmid was previously linearized by SalI digestion, theoretically targeting the integration event into the his4 chromosomal locus.

The selection of a AcaNAPc2 high-expresser strain was performed as described In Example 3 for NAP isoform 5 using mini-culture screening. The mini-cultures were tested for the presence of secreted AcaNAPc2 using the fVIIa/TF-EGR-fXa assay (Example E) resulting in the selection of two clones. After a second screening round, using the same procedure, but this time at the shake-flask level, one isolated host cell was chosen and designated *P. pastoris* GTS115/7SP-NAPc2.

The host cell, GTS115/7SP-NAPc2, was shown to have a wild type methanol-utilisation phenotype (Mut$^+$), which demonstrated that the integration of the expression cassette into the chromosome of GTS115 did not alter the functionality of the genomic AOX1 gene.

Subsequent production of recombinant AcaNAPc2 material was performed in shake flask cultures, as described in Stroman, D. W. et al., U.S. Pat. No. 4,855,231. The recombinant product was purified from *Pichia pastoris* cell supernatant as described below.

C. Purification of recombinant AcaNAPc2

1. Cation Exchange chromatography

The culture supernatant (100 ml) was centrifuged at 16000 rpm (about 30,000× g) for 20 minutes before the pH was adjusted with 1N HCl to pH 3. The conductivity of the supernatant was decreased to less than 10 mS/cm by adding MilliQ water. The diluted supernatant was clarified by passage through a 0.22 micrometer cellulose acetate filter (Corning Inc., Corning, N.Y., USA).

The total volume (approximately 500 ml) of the supernatant was loaded onto a Poros20HS (Perseptive Biosystems, Mass.) 1×2 cm column pre-equilibrated with Cation Buffer (50 mM sodium citrate pH 3) at a flow-rate of 5 ml/minute. The column and the diluted fermentation supernatant were at room temperature throughout this purification step. The column was subsequently washed with 50 column volumes Cation Buffer and 10 column volumes Cation Buffer containing 0.1M NaCl. Material that had inhibitory activity in a prothrombinase assay was eluted with Cation Buffer containing 1M NaCl at a flow rate of 2 ml/min.

2. Molecular Sieve Chromatography using Superdex30

The 1M NaCl elution pool containing the EGR-fXa-fVIIa/TF inhibitory material (3 ml; see Example C) from the cation-exchange column was loaded onto a Superdex30 PG (Pharmacia, Sweden) 1.6×60 cm column pre-equilibrated with 0.1M sodium phosphate pH7.4, 0.15M NaCl at ambient temperature. The chromatography was conducted at a flow-rate of 2 ml/minute. The prothrombinase inhibitory activity (Example C) eluted 56–64ml into the run and was pooled.

3. Reverse Phase Chromatography

One ml of the pooled fractions from the gel filtration chromatography was loaded onto a 0.46×25 cm C18 column (218TP54 Vydac; Hesperia, Calif.) which was then developed with a linear gradient 10–30% acetonitrile in 0.1% (v/v) trifluoroacetic acid with a rate of 0.5% change in acetonitrile/minute. The major peak which eluted around 20–25% acetonitrile, was manually collected and displayed prothrombinase inhibitory activity.

4. Molecular Mass Determination

The estimated mass for the main constituent isolated as described in section (1) to (3) of this example was determined using electrospray ionisation mass spectrometry. The estimated mass of the recombinant AcaNAPc2 was 9640 daltons, fully in agreement with the calculated molecular mass of this molecule derived from the cDNA sequence.

Example 16

Expression of AcaNAP42 in *P. pastoris*

The pGEM-9zf(-) vector (Promega) containing the AcaNAP42 cDNA (Example 12) was used to isolate the region encoding the mature AcaNAP42 protein by PCR amplification (using Taq polymerase from Perkin Elmer, Branchburg, N.J.; 25 temperature cycles: 1 minute at 94° C., 1 minute at 50° C., and 1 minute at 72° C.). The following oligonucleotide primers were used:

oligo3: $^{5'}$GAG ACT TTT AAA TCA CTG TGG GAT CAG AAG$^{3'}$ [SEQ. ID. NO. 124]

oligo2: $^{5'}$TTC AGG ACT AGT TCA TGG TGC GAA AGT AAT AAA$^{3'}$ [SEQ. ID. NO. 125]

The oligo 3 primer, targeting the N-terminal sequence, contained a non-annealing extension which includes DraI restriction site (underlined). The oligo 2 primer, targeting the C-terminal sequence, contained SpeI restriction site.

The NAP amplification product, having the expected approximately 250 bp size, was digested with DraI and SpeI enzymes, purified by extraction with phenol: chloroform: iso-amyl alcohol (25:24:1, volume/volume) and precipitated in ethyl alcohol. The recipient vector-fragment from pYAM7SP8 (Example 3) was prepared by StuI-SpeI restriction, purified by extraction with phenol: chloroform:iso-amyl alcohol (25:24:1, volume/volume) and precipitated in ethyl alcohol. The *E. coli* strain, XL1-Blue [Bullock, W. O., Fernande, J. M., and Short, J. M. Biotechniques 5: 376–379 (1987)], was transformed with the ligation mixture that contained the above DNA fragments, and ampicillin resistant clones were selected.

Based on restriction analysis, a plasmid clone containing an insert of the expected size, designated pYAM7SP8-NAP42, was retained for further characterization. Sequence determination of the clone confirmed correct insertion of the mature coding region in fusion with the PHO1/alpha-factor prepro leader signal, as predicted by the construction scheme, as well as the absence of unwanted mutations in the coding region.

About 10 micrograms of pYAM 7SP-NAP 42 plasmid was electroporated into Pichia strain GTS115 (his4), described in Example 3. The plasmid was previously digested by NotI enzyme, targeting the integration event at the AOX1 chromosomal locus.

The His+ transformants were selected as described in Example 3. Single colonies (n=90) from the electroporation were grown in wells of a 96-well plate containing 100 microliters of glycerol-minimal medium for 24 hours on a plate-shaker at room temperature. One liter of the glycerol-minimal medium contained 13.4 g Yeast Nitrogen Base without amino acids (DIFCO); 400 microgram biotin; 10 ml glycerol; and 10 mM potassium phosphate (pH 6.0).

The cells were pelleted and resuspended in fresh methanol-minimal medium (same composition as above except that the 10 ml glycerol was replaced by 5 ml methanol) to induce the AOX1 promoter. After an additional incubation period of 24 hours with agitation at room temperature, 10 microliters of culture supernatants were tested by the Prothrombin Time Assay (Example B). The presence of secreted AcaNAP42 was detected by the prolongation of the coagulation time of human plasma.

Example 17

Expression of AcaNAPc2/Proline in *P. pastoris*

To enhance stability and the expression level of AcaNAPc2, a mutant cDNA was constructed that encoded an additional proline residue at the C-terminus of the protein (AcaNAPc2/Proline). The expression vector, pYAM7SP8-NAPc2/Proline, was made in the same manner as described in Example 16. The oligo 8 primer is the N-terminal primer with DraI restriction site and the oligo 9 primer is the C-terminal primer containing XbaI site and the amino acid codon, TGG, to add one Proline residue to the C-terminal of the natural form of AcaNAPc2.

oligo 8: $^{5'}$GCG TTT AAA GCA ACG ATG CAG TGT GGT G$^{3'}$ [SEQ. ID. NO. 126]

oligo 9: $^{5'}$C GCT CTA GAA GCT TCA TGG GTT TCG AGT TCC GGG ATA TAT AAA GTC$^{3'}$ [SEQ. ID. NO. 127]

Following digestion of the amplification product (approximately 270 bp) with DraI and XbaI, the amplification product was purified and ligated with the vector-fragment from pYAM7SP8 prepared by StuI-SpeI restriction. A plasmid clone containing the AcaNAPc2/Proline insert was confirmed by DNA sequencing and designated pYAM7SP8-NAPc2/Proline.

The vector, pYAM7SP8-NAPc2/Proline, was used to transform strain GTS115 (his) as described in Example 16. Transformants were selected and grown according to Example 16. The presence of secreted AcaNAPc2/proline in the growth media was detected by the prolongation of the coagulation time of human plasma (see Example B).

Example A

Factor Xa Amidolytic Assay

The ability of NAPs of the present invention to act as inhibitors of factor Xa catalytic activity was assessed by determining the NAP-induced inhibition of amidolytic activity catalyzed by the human enzyme, as represented by Ki* values.

The buffer used for all assays was HBSA (10 mM HEPES, pH 7.5, 150 mM sodium chloride, 0.1% bovine serum albumin). All reagents were from Sigma Chemical Co. (St. Louis, Mo.), unless otherwise indicated.

The assay was conducted by combining in appropriate wells of a Corning microtiter plate, 50 microliters of HBSA, 50 microliters of the test NAP compound diluted (0.025–25 nM) in HBSA (or HBSA alone for uninhibited velocity measurement), and 50 microliters of the Factor Xa enzyme diluted in HBSA (prepared from purified human factor X obtained from Enzyme Research Laboratories (South Bend, Ind.) according to the method described by Bock, P. E. et al., Archives of Biochem, Biophys. 273: 375 (1989). The enzyme was diluted into HBSA prior to the assay in which the final concentration was 0.5 nM). Following a 30 minute incubation at ambient temperature, 50 microliters of the substrate S2765 (N-alpha-benzyloxycarbonyl-D-argininyl -L-glycyl-L-arginine-p-nitroanilide dihydrochloride, obtained from Kabi Diagnostica (or Kabi Pharmacia Hepar Inc., Franklin, Ohio) and made up in deionized water followed by dilution in HBSA prior to the assay) was added to the wells yielding a final total volume of 200 microliters and a final concentration of 250 micromolar (about 5-times Km). The initial velocity of chromogenic substrate hydrolysis was measured by the change in absorbance at 405 nm using a Thermo Max® Kinetic Microplate Reader (Molecular Devices, Palo alto, Calif.) over a 5 minute period in which less than 5% of the added substrate was utilized.

Ratios of inhibited pre-equilibrium, steady-state velocities containing NAP (Vi) to the uninhibited velocity of free fXa alone ($V_o$) were plotted against the corresponding concentrations of NAP. These data were then directly fit to an equation for tight-binding inhibitors [Morrison, J. F., and Walsh, C. T., Adv. Enzymol. 61:201–300 (1988)], from which the apparent equilibrium dissociation inhibitory constant $K_i^*$ was calculated.

Table 1 below gives the Ki* values for the test compounds AcaNAP5 [SEQ. ID. NO. 4], AcaNAP6 [SEQ. ID. NO. 6], and AcaNAPc2 [SEQ, ID. NO. 59], prepared as described in Examples 3, 4, and 15, respectively. The data show the utility of AcaNAP5 and AcaNAP6 as potent in vitro inhibitors of human FXa. In contrast, AcaNAPc2 did not effectively inhibit FXa amidolytic activity.

TABLE 1

| Compound | Ki* (pM) |
| --- | --- |
| AcaNAP5 | 43 ± 5 |
| AcaNAP6 | 996 ± 65 |
| AcaNAPc2 | NI[a] |

[a]NI = no inhibition; a maximum of 15% inhibition was observed up to 1 μM.

Example B

Prothrombin Time (PT) and Activated Partial Thromboplastin Time (aPTT) Assays

The ex vivo anticoagulant effects of NAPs of the present invention in human plasma were evaluated by measuring the prolongation of the activated partial thromboplastin time (aPTT) and prothrombin time (PT) over a broad concentration range of each inhibitor.

Fresh frozen pooled normal citrated human plasma was obtained from George King Biomedical, Overland Park, Kans. Respective measurements of aPTT and PT were made using the Coag-A-Mate RA4 automated coagulometer (General Diagnostics, Organon Technica, Oklahoma City, Okla.) using the Automated aPTT PlatelinO L reagent (Organon Technica, Durham, N.C.) and Simplastin® Excel (Organon Technica, Durham, N.C.) respectively, as initiators of clotting according to the manufacturers instructions.

The assay was conducted by making a series of dilutions of each tested NAP in rapidly thawed plasma followed by adding 200 microliters or 100 microliters to the wells of the assay carousel for the aPTT or PT measurements, respectively. Alternatively, the NAPs were serially diluted into HBSA and 10 μl of each dilution were added to 100 μl of normal human plasma in the wells of the Coag-A-Mate assay carosel.

Concentrations of NAP were plotted against clotting time, and a doubling time concentration was calculated, i.e., a specified concentration of NAP that doubled the control clotting time of either the PT or the aPTT. The control clotting times of NHP in the PT and APTT were 12.1 sec and 28.5 sec, respectively.

Table 2 below shows the ex vivo anticoagulant effects of AcaNAPS [SEQ. ID. NO. 4], AcaNAP6 [SEQ. ID. NO. 6], AcaNAPc2 [SEQ. ID. NO. 59], and AceNAP4 [SEQ. ID. NO. 62] and Pro-AcaNAP5 [SEQ. ID. NO. 7] represented by the concentration of each that doubled (doubling concentration) the control clotting time of normal human plasma in the respective PT and APTT clotting assays relative to a control assay where no such NAP was present. The data show the utility of these compounds as potent anticoagulants of clotting human plasma. The data also demonstrate the equivalency of native NAP and recombinant NAP.

TABLE 2

| Compound | Doubling Concentration (nM) in the PT | Doubling Concentration (nM) in the aPTT |
| --- | --- | --- |
| AcaNAP5[a] | 43 ± 8 | 87 ± 4 |
| AcaNAP6[a] | 37 ± 3 | 62 ± 0 |
| AcaNApc2[a] | 15 ± 1 | 105 ± 11 |
| AceNAP4[a] | 40 ± 4 | 115 ± 12 |
| AcaNAP5[b] | 26.9 | 76.2 |
| AcaNAP5[c] | 39.2 | 60.0 |
| Pro-AcaNAP5[d] | 21.9 | 31.0 |

[a]Made in Pichia pastoris.
[b]Native protein.
[c]Made in Pichia pastoris (different recombinant batch than (a)).
[d]Made in COS cells.

Figure 10B:
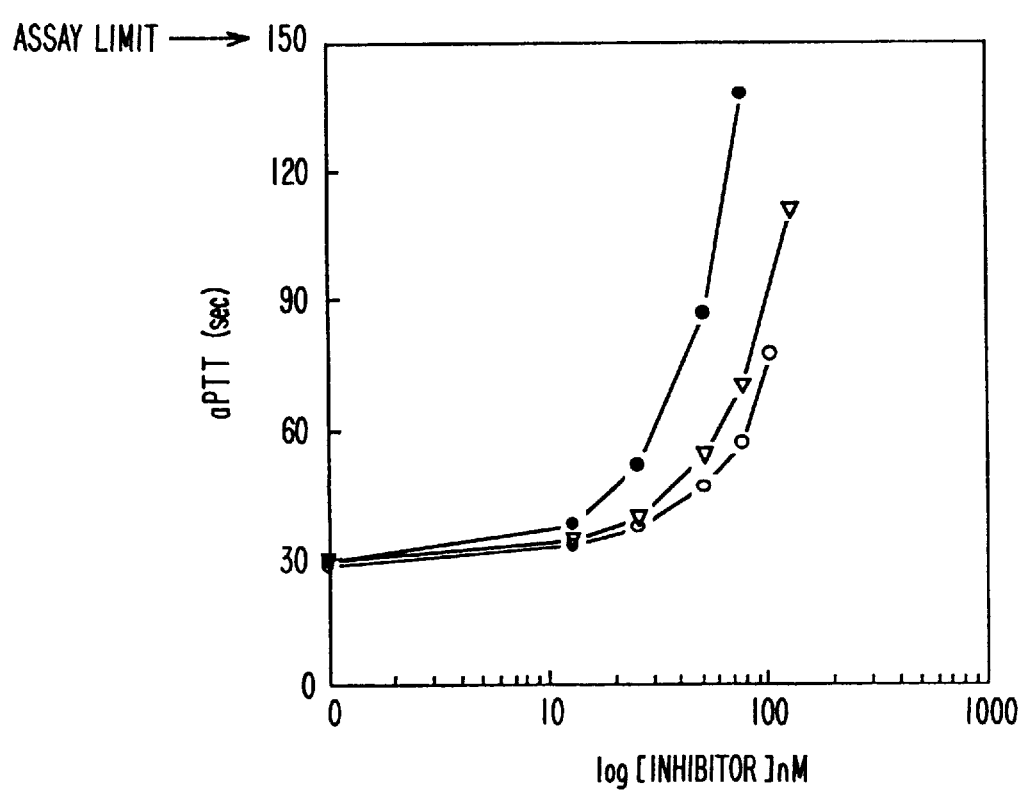

FIGS. 10A and 10B also show NAP-induced prolongation of the PT (FIG. 10A) and aPTT (FIG. 10B) in a dose-dependent manner.

Example C

Prothrombinase inhibition assay

The ability of NAP of the present invention to act as an inhibitor of the activation of prothrombin by Factor Xa that has been assembled into a physiologic prothrombinase complex was assessed by determining the respective inhibition constant, Ki*.

Prothrombinase activity was measured using a coupled amidolytic assay, where a preformed complex of human FXa, human Factor Va (FVa), and phospholipid vesicles first activates human prothrombin to thrombin. The amidolytic activity of the generated thrombin is measured simultaneously using a chromogenic substrate. Purified human FVa was obtained from Haematologic Technologies, Inc. (Essex Junction, Vt.). Purified human prothrombin was purchased from Celsus Laboratories, Inc. (Cincinnati, Ohio). The chromogenic substrate Pefachrome t-PA ($CH_3SO_2$-D-hexahydrotyrosine-glycyl-L-arginine-p-nitroanilide) from Pentapharm Ltd (Basel, Switzerland) was purchased from Centerchem, Inc. (Tarrytown, N.Y.). The substrate was reconstituted in deionized water prior to use. Phospholipid vesicles were made, consisting of phosphotidyl choline (67%, w/v), phosphatidyl glycerol (16%, w/v), phosphatidyl ethanolamine (10%, w/v), and phosphatidyl serine (7%, w/v) in the presence of detergent, as described by Ruf et al [Ruf, W., Miles, D. J., Rehemtulla, A., and Edgington, T. S. Methods in Enzymology 222: 209–224 (1993)]. The phospholipids were purchased from Avanti Polar Lipids, (Alabaster, Ala.).

The prothrombinase complex was formed in a polypropylene test tube by combining FVa, FXa, and phospholipid vesicles (PLV) in HBSA containing 3 mM $CaCl_2$ for 10 min. In appropriate wells of a microtiter plate, 50 µl of the complex were combined with 50 µl of NAP diluted in HBSA, or HBSA alone (for $V_o$ (uninhibited velocity) measurement). Following an incubation of 30 min at room temperature, the triplicate reactions were initiated by the addition of a substrate solution, containing human prothrombin and the chromogenic substrate for thrombin, Pefachrome tPA. The final concentration of reactants in a total volume of 150 µL of HBSA was: NAP (0.025–25 nM), FXa (250 µM), PLV (5 µM), prothrombin (250 nM), Pefachrome tPA (250 µM, 5× Km), and $CaCl_2$ (3 mM).

The prothrombinase activity of fXa was measured as an increase in the absorbance at 405 nm over 10 min (velocity), exactly as described in Example A, under steady-state conditions. The absorbance increase was sigmoidal over time, reflecting the coupled reactions of the activation of prothrombin by the FXa-containing prothrombinase complex, and the subsequent hydrolysis of Pefachrome tPA by the generated thrombin. The data from each well of a triplicate were combined and fit by reiterative, linear least squares regression analysis, as a function of absorbance versus time$^2$, as described [Carson, S. D. Comput. Prog. Biomed. 19: 151–157 (1985)] to determine the initial velocity ($V_i$) of prothrombin activation. Ratios of inhibited steady-state initial velocities containing NAP (Vi) to the uninhibited velocity of prothrombinase fXa alone ($V_o$) were plotted against the corresponding concentrations of NAP. These data were directly fit to the equation for tight-binding inhibitors, as in Example A above, and the apparent equilibrium dissociation inhibitory constant $K_i^*$ was calculated.

Table 3 below gives the dissociation inhibitor constant (Ki*) of recombinant AcaNAP5 [SEQ. ID. NO. 4], AcaNAP6 [SEQ. ID. NO. 6] and AcaNAPc2 [SEQ. ID. NO. 59] (all made in *Pichia pastoris* as described) against the activation of prothrombin by human fXa incorporated into a prothrombinase complex. These data show the utility of these compounds as inhibitors of human FXa incorporated into the prothrombinase complex.

TABLE 3

| Compound | Ki* (pM) |
|---|---|
| AcaNAP5 | 144 ± 15 |
| AcaNAP6 | 207 ± 40 |
| AcaNAPc2 | 2385 ± 283 |

The data presented in Examples A, B, and C suggest that AcaNAP5 and AcaNAP6 may be interacting with FXa in a similar manner that involves directly restricting access of both the peptidyl and macromoleular substrate (prothrombin) to the catalytic center of the enzyme. In contrast, AcaNAPc2 appears to be interacting with FXa in a way that only perturbs the macromolecular interactions of this enzyme with either the substrate and/or cofactor (Factor Va), while not directly inhibiting the catalytic turnover of the peptidyl substrate.

Example D

In vitro Enzyme Assays for Activity Specificity Determination

The ability of NAP of the present invention to act as a selective inhibitor of FXa catalytic activity or TF/VIIa activity was assessed by determining whether the test NAP would inhibit other enzymes in an assay at a concentration that was 100-fold higher than the concentration of the following related serine proteases: thrombin, Factor Xa, Factor XIa, Factor XIIa, kallikrein, activated protein C, plasmin, recombinant tissue plasminogen activator (rt-PA), urokinase, chymotrypsin, and trypsin.

1. General protocol for enzyme inhibition assays

The buffer used for all assays was HBSA (Example A). All substrates were reconstituted in deionized water, followed by dilution into HBSA prior to the assay. The amidolytic assay for determining the specificity of inhibition of serine proteases was conducted by combining in appropriate wells of a Corning microtiter plate, 50 µl of HBSA, 50 µl of NAP at a specified concentration diluted in HBSA, or HBSA alone (uninhibited control velocity, Vo), and 50 µl of a specified enzyme (see specific enzymes below). Following a 30 minute incubation at ambient temperature, 50 µl of substrate were added to triplicate wells. The final concentration of reactants in a total volume of 200 µl of HBSA was: NAP (75 nM), enzyme (750 pM), and chromogenic substrate (as indicated below). The initial velocity of chromogenic substrate hydrolysis was measured as a change in absorbance at 405 nm over a 5 minute period, in which less than 5% of the added substrate was hydrolyzed. The velocities of test samples, containing NAP (Vi) were then expressed as a percent of the uninhibited control velocity (Vo) by the following formula: Vi/Vo×100, for each of the enzymes.

2. Specific enzyme assays a. Thrombin Assay

Thrombin catalytic activity was determined using the chromogenic substrate Pefachrome t-PA ($CH_3SO_2$-D-hexahydrotyrosine-glycyl-L-arginine-p-nitroaniline, obtained from Pentapharm Ltd., Basel, Switzerland). The final concentration of Pefachrome t-PA was 250 µM (about 5-times Km). Purified human alpha-thrombin was obtained from Enzyme Research Laboratories, Inc.(South Bend, Ind.).

b. Factor Xa Assay

Factor Xa catalytic activity was determined using the chromogenic substrate S-2765 (N-benzyloxycarbonyl-D-arginine-L-glycine-L-arginine-p-nitroaniline), obtained from Kabi Pharmacia Hepar, Inc. (Franklin, Ohio). All substrates were reconstituted in deionized water prior to use. The final concentration of S-2765 was 250 µM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. Arch. Biochem. Biophys. 273:375–388 (1989)].

c. Factor XIa Assay

Factor FXIa catalytic activity was determined using the chromogenic substrate S-2366 (L-Pyroglutamyl-L-prolyl-L-arginine-p-nitroaniline, obtained from Kabi Pharmacia Hepar, Franklin, Ohio). The final concentration of S-2366 was 750 µM. Purified human FXIa was obtained from Enzyme Research Laboratories, Inc.(South Bend, Ind.).

d. Factor XIIa Assay

Factor FXIIa catalytic activity was determined using the chromogenic substrate Spectrozyme FXIIa (H-D-CHT-L- glycyl-L-arginine-p-nitroaniline), obtained from American Diagnostica, Greenwich, Conn.). The final concentration of Spectrozyme FXIIa was 100 μM. Purified human FXIIa was obtained from Enzyme Research Laboratories, Inc. (South Bend, Ind.).

e. Kallikrein Assay

Kallikrein catalytic activity was determined using the chromogenic substrate S-2302 (H-D-prolyl-L-phenylalanyl-L-arginine-p-nitroaniline, obtained from Kabi Pharmacia Hepar, Franklin, Ohio). The final concentration of S-2302 was 400 μM. Purified human kallikrein was obtained from Enzyme Research Laboratories, Inc. (South Bend, Ind.).

f. Activated Protein C (aPC)

Activated Protein C catalytic activity was determined using the chromogenic substrate Spectrozyme PCa (H-D-lysyl-(-Cbo)-L-prolyl-L-arginine-p-nitroaniline) were obtained from American Diagnostica Inc. (Greenwich, Conn.). The final concentration was 400 μM (about 4-times Km). Purified human aPC was obtained from Hematologic Technologies, Inc.(Exxex Junction, Vt.)

g. Plasmin Assay

Plasmin catalytic activity was determined using the chromogenic substrate S-2366 (L-Pyroglutamyl-L-prolyl-L-arginine-p-nitroaniline, obtained from Kabi Pharmacia Hepar, Franklin, Ohio). The final concentration of S-2366 was 300 μM. (about 4-times Km). Purified human plasmin was obtained from Enzyme Research Laboratories, Inc. (South Bend, Ind.).

h. Recombinant tissue plasminogen activator (rt-PA)

rt-PA catalytic activity was determined using the substrate, Pefachrome t-PA (CH$_3$SO$_2$-D-hexahydrotyrosine-glycyl-L-arginine-p-nitroaniline, obtained from Pentapharm Ltd., Basel, Switzerland). The final concentration was 500 μM (about 3-times Km). Human rt-PA (Activase®) was obtained from Genentech, Inc. (So. San Fransisco, Calif.).

i. Urokinase

Urokinase catalytic activity was determined using the substrate S-2444 (L-Pyroglutamyl-L-glycyl-L-arginine-p-nitroaniline, obtained from Kabi Pharmacia Hepar, Franklin, Ohio). The final concentration of S-2444 was 150 μM. (about 7-times Km). Human urokinase (Abbokinase®), purified from cultured human kidney cells, was obtained from Abbott Laboratories (North Chicago, Ill.).

j. Chymotrypsin

Chymotrypsin catalytic activity was determined using the chromogenic substrate, S-2586 (Methoxy-succinyl-L-argininyl-L-prolyl-L-tyrosine-p-nitroaniline, which was obtained from Kabi Pharmacia Hepar, Franklin, Ohio). The final concentration of S-2586 was 100 μM. (about 8-times Km). Purified (3x-crystallized;CDI) bovine pancreatic-chymotrypsin was obtained from Worthington Biochemical Corp. (Freehold, N.J.).

k. Trypsin

Trypsin catalytic activity was determined using the chromogenic substrate S-2222 (N-benzoyl-L-isoleucyl-L-glutamyl [-methyl ester]-L-arginine-p-nitroaniline, which was obtained from Kabi Pharmacia Hepar, Franklin, Ohio). The final concentration of S-2222 was 300 μM. (about 5-times Km). Purified human pancreatic trypsin was obtained from Scripps Laboratories (San Diego, Calif.).

Table 4 lists the inhibition of the amidolytic acativity of FXa and 10 additional serine proteases by either recombinant AcaNAP-5 [SEQ. ID. NO. 4] or recombinant AcaNAP-6 [SEQ. ID. NO. 6] (both expressed in *Pichia pastoris*, as described), expressed as percent of control velocity. These NAPs demonstrate a high degree of specificity for the inhibition of FXa compared to the other, related serine proteases.

TABLE 4

| Enzyme | % Control Velocity +AcaNAP5 | % Control Velocity +AcaNAP6 |
|---|---|---|
| FXa | 1 ± 1 | 14 ± 1 |
| FIIa | 104 ± 5 | 98 ± 3 |
| FXIa | 34 ± 12 | 98 ± 3 |
| FXIIa | 103 ± 6 | 100 ± 4 |
| kallikrein | 102 ± 4 | 101 ± 3 |
| aPC | 95 ± 2 | 98 ± 1 |
| plasmin | 111 ± 6 | 113 ± 12 |
| r-tPA | 96 ± 9 | 96 ± 7 |
| urokinase | 101 ± 14 | 96 ± 2 |
| chymotrypsin | 105 ± 0 | 100 ± 11 |
| trypsin | 98 ± 6 | 93 ± 4 |

Table 5 lists the inhibitory effect of recombinant AcaNAPc2 [SEQ. ID. NO. 59] and recombinant AceNAP4 [SEQ. ID. NO. 62] (both expressed in *Pichia pastoris*, as described) on the amidolytic activity of 11 selected serine proteases. Inhibition is expressed as percent of control velocity. These data demonstrate that these NAPs possess a high degree of specificity, and are not specific inhibitors of FXa.

TABLE 5

| Enzyme | % Control Velocity +AcaNAPc2 | % Control Velocity +AcaNAP4 |
|---|---|---|
| FXa | 84 ± 3 | 76 ± 3 |
| FIIa | 99 ± 3 | 93 ± 3 |
| FXIa | 103 ± 4 | 96 ± 1 |
| FXIIa | 97 ± 1 | 102 ± 2 |
| kallikrein | 101 ± 1 | 32 ± 1 |
| aPC | 97 ± 3 | 103 ± 1 |
| plasmin | 107 ± 9 | 100 ± 1 |
| r-tPA | 96 ± 2 | 108 ± 3 |
| urokinase | 97 ± 1 | 103 ± 4 |
| chymotrypsin | 99 ± 0 | 96 ± 4 |
| trypsin | 93 ± 4 | 98 ± 4 |

Example E

Assays for measuring the inhibition of the fVIIa/TF complex by NAP

A. fVIIa/TF fIX activation assay

This Example measures the ability of NAPs of the present invention to act as an inhibitor of the catalytic complex of fVIIa/TF, which has a primary role in initiation of the coagulation response in the ex vivo prothrombin time assay (Example B). Activation of tritiated Factor IX by the rFVIIa/rTF/PLV complex was assessed by determining the respective intrinsic inhibition constant, Ki*.

Lyophilized, purified, recombinant human factor VIIa was obtained from BiosPacific, Inc (Emeryville, Calif.), and reconstituted in HBS (10 mM HEPES, pH 7.5, 150 mM sodium chloride) prior to use. Purified human Factor X was obtained from Enzyme Research Laboratories, Inc. (South Bend, Ind.) and Factor Xa ( free FXa) was activated and prepared from it as described (Bock, P. E., Craig, P. A., Olson, S. T., and Singh, P. Arch. Biochem. Biophys. 273:375–388 (1989)). Active site-blocked human Factor Xa (EGR-FXa), which had been irreversibly inactivated with L-Glutamyl-L-glycyl-L-arginyl chloromethylketone, was obtained from Haematologic Technologies, Inc. (Essex Junction, Vt.). Recombinant human tissue factor (rTF) was produced by a baculovirus-expression system, and purified to homogeneity by monoclonal antibody affinity chromatography (Corvas International, Inc., San Diego, Calif.).

The purified rTF apoprotein was incorporated into phospholipid vesicles (rTF/PLV), consisting of phosphotidyl choline (75%, w/v) and phosphotidyl serine (25%, w/v) in the presence of detergent, as described by Ruf et al. (Ruf, W., Miles, D. J., Rehemtulla, A., and Edgington, T. S. Methods in Enzymology 222: 209–224 (1993)). The phospholipids were purchased from Avanti Polar Lipids, (Alabaster, Ala.). The buffer used for all assays was HBSA, HBS containing 0.1% (w/v) bovine serum albumin. All reagents were obtained from Sigma Chemical Co. (St. Louis, Mo.), unless otherwise indicated.

The activation of human $^3$H-Factor IX (FIX) by the rFVIIa/rTF complex was monitored by measuring the release of the radiolabelled activation peptide. Purified human fIX was obtained from Haematologic Technologies, Inc. (Essex Junction, Vt.), and radioactively labelled by reductive tritiation as described (Van Lenten & Ashwell, 1971, JBC 246, 1889–1894). The resulting tritiated preparation of FIX had a specific activity of 194 clotting units/mg as measured in immuno-depleted FIX deficient plasma (Ortho), and retained 97% of its activity. The radiospecific activity was $2.7 \times 10^8$ dpm/mg. The Km for the activation of $^3$H-FIX by rFVIIa/rTF/PLV was 25 nM, which was equivalent to the Km obtained for untreated (unlabelled) FIX.

The assay for Ki* determinations was conducted as follows: rFVIIa and rTF/PLV were combined in a polypropylene test tube, and allowed to form a complex for 10 min in HBSA, containing 5 mM CaCl$_2$. Aliquots of rFVIIa/rTF/PLV complex were combined in the appropriate polypropylene microcentrifuge tubes with EGR-FXa or free FXa, when included, and either the NAP test compound at various concentrations, after dilution into HBSA, or HBSA alone (as V$_o$ (uninhibited velocity) control). Following an incubation of 60 min at ambient temperature, reactions were initiated by the addition of $^3$H-FIX. The final concentration of the reactants in 420 μl of HBSA was: rFVIIa [50 pM], rTF [2.7 nM], PLV [6.4 micromolar], either EGR-FXa or free FXa [300 pM], recombinant NAP [5–1,500 pM], $^3$H-FIX [200 nM], and CaCl$_2$ [5 mM]. In addition, a background control reaction was run that included all of the above reactants, except rFVIIa.

At specific time points (8, 16, 24, 32, and 40 min), 80 μl of the reaction mixture was added to an eppendorf tube that contained an equal volume of 50 mM EDTA in HBS with 0.5% BSA to stop the reaction; this was followed by the addition of 160 μL of 6% (w/v) trichloroacetic acid. The protein was precipitated, and separated from the supernatant by centrifugation at 16,000× g for 6 min at 4° C. The radioactivity contained in the resulting supernatant was measured by removing triplicate aliquots that were added to Scintiverse BD (Fisher Scientific, Fairlawn, N.J.), and quantitated by liquid scintillation counting. The control rate of activation was determined by linear regression analysis of the soluble counts released over time under steady-state conditions, where less than 5% of the tritiated FIX was consumed. The background control (<1.0% of control velocity) was subtracted from all samples. Ratios of inhibited pre-equilibrium, steady-state velocities (Vi), containing either NAP to the uninhibited control velocity of rFVIIa/TF alone (V$_o$) were plotted against the corresponding concentrations of NAP. These data were then directly fit to an equation for tight-binding inhibitors [Morrison, J. F., and Walsh, C. T., Adv. Enzymol. 61:201–300 (1988)], from which the apparent equilibrium dissociation inhibitory constant K$_i$* was calculated.

The data for recombinant AcaNAP5, AcaNAP6, AcaNAPc2, and AceNAP4 (prepared as described) is presented in Table 6 following Section B, below.

B. Factor VIIa/Tissue factor amidolytic assay

The ability of NAPs of the present invention to act as an inhibitor of the amidolytic activity of the fVIIa/TF complex was assessed by determining the respective inhibition constant, Ki*, in the presence and absence of active site-blocked human Factor Xa (EGR-fXa).

rFVIIa/rTF amidolytic activity was determined using the chromogenic substrate S-2288 (H-D-isoleucyl-L-prolyl-L-arginine-p-nitroaniline), obtained from Kabi Pharmacia Hepar, Inc. (Franklin, Ohio). The substrate was reconstituted in deionized water prior to use. rFVIIa and rTF/PLV were combined in a polypropylene test tube, and allowed to form a complex for 10 min in HBSA, containing 3 mM CaCl$_2$. The assay for Ki* determinations was conducted by combining in appropriate wells of a Corning microtiter plate 50 μL of the rFVIIa/rTF/PLV complex, 50 μL of EGR-FXa, and 50 μL of either the NAP test compound at various concentrations, after dilution into HBSA, or HBSA alone (for V$_o$ (uninhibited velocity) measurement). Following an incubation of 30 min at ambient temperature, the triplicate reactions were initiated by adding 50 μL of S-2288. The final concentration of reactants in a total volume of 200 μL of HBSA was: recombinant NAP (0.025–25 nM), rFVIIa (750 pM), rTF (3.0 nM), PLV (6.4 micromolar), EGR-FXa (2.5 nM), and S-2288 (3.0 mM, 3× Km).

The amidolytic activity of rFVIIa/rTF/PLV was measured as a linear increase in the absorbance at 405 nm over 10 min (velocity), using a Thermo Max® Kinetic Microplate Reader (Molecular Devices, Palo Alto, Calif.), under steady-state conditions, where less than 5% of the substrate was consumed. Ratios of inhibited pre-equilibrium, steady-state velocities (Vi), containing NAP to the uninhibited velocity of free fXa alone (V$_o$) were plotted against the corresponding concentrations of NAP. These data were then directly fit to the same equation for tight-binding inhibitors, used in Example E.1., from which the apparent equilibrium dissociation inhibitory constant K$_i$* was calculated.

Table 6 below gives the Ki* values of recombinant AcaNAPc2 [SEQ. ID. NO. 59], AceNAP4 [SEQ. ID. NO. 62], AcaNAP5 [SEQ. ID. NO. 4], and AcaNAP6 [SEQ. ID. NO. 6] (prepared in *Pichia pastoris*, as described) in inhibitory assays of rFVIIa/rTF activity. The data shows the utility of AcaNAPc2 and AceNAP4 as potent inhibitors of the human rFVIIa/rTF/PLV complex in the absence and presence of either free FXa or active site-blocked FXa.

TABLE 6

| | Ki* (pM) | | | | |
|---|---|---|---|---|---|
| | Amidolytic Assay | | $^3$H-FIX Activation | | |
| NAP Compound | No Addition | Plus EGR-FXa | No Addition | + free FXa | +EGR-FXa |
| AcaNAPc2 | NI | 36 ± 20 | NI | 35 ± 5 | 8.4 ± 1.5 |
| AceNAP4 | 59,230 ± 8,600 | 378 ± 37 | ND | ND | ND |
| AcaNAP5 | NI | NI | NI | NI | NI |
| AcaNAP6 | NI | NI | NI | NI | NI |

NI = no inhibition
ND = not determined

Example F

In vivo Models of NAP activity

A. Evaluation of the antithrombotic activity of NAP in the rat model of $FeCl_3$-induced platelet-dependent arterial thrombosis The antithrombotic (prevention of thrombus formation) properties of NAP were evaluated using the established experimental rat model of acute vascular thrombosis.

The rat $FeCl_3$ model is a well characterized model of platelet dependent, arterial thrombosis which has been used to evaluate potential antithrombotic compounds. Kurz, K. D., Main, B. W., and Sandusky, G. E., *Thromb. Res.*, 60:269–280 (1990). In this model a platelet-rich, occlusive thrombus is formed in a segment of the rat carotid artery treated locally with a fresh solution of $FeCl_3$ absorbed to a piece of filter paper. The $FeCl_3$ is thought to diffuse into the treated segment of artery and cause de-endothelialization of the affected vessel surface. This results in the exposure of blood to subendothelial structures which in turn cause platelet adherence, thrombin formation and platelet aggregation. The net result is occlusive thrombus formation. The effect of a test compound on the incidence of occlusive thrombus formation following application of $FeCl_3$ is monitored by ultrasonic flowtometry and is used as the primary end point. The use of flowtometry to measure carotid artery blood flow, is a modification of the original procedure in which thermal detection of clot formation was employed. Kurz, K. D., Main, B. W., and Sandusky, G. E., *Thromb. Res.*, 60: 269–280 (1990).

1. Intravenous administration

Male Harlan Sprague Dawley rats (420–450 g) were acclimated at least 72 hours prior to use and fasted for 12 hours prior to surgery with free access to water. The animals were prepared, anesthetized with Nembutal followed by the insertion of catheters for blood pressure monitoring, drug and anesthesia delivery. The left carotid artery was isolated by making a midline cervical incision followed by blunt dissection and spreading techniques to separate a 2 cm segment of the vessel from the carotid sheath. A silk suture is inserted under the proximal and distal ends of the isolated vessel to provide clearance for the placement of a ultrasonic flow probe (Transonic) around the proximal end of the vessel. The probe is then secured with a stationary arm.

Following surgery the animals were randomized in either a control (saline) or treatment (recombinant AcaNAP5) group. The test compound (prepared in *P. pastoris* according to Example 3) was administered as a single intravenous bolus at the doses outlined in Table 8 after placement of the flow probe and 5 min prior to the thrombogenic stimulus. At t=0, a 3 mm diameter piece of filter paper (Whatman #3) soaked with 10 μL of a 35% solution of fresh $FeCl_3$ (made up in water) was applied to the segment of isolated carotid artery distal to the flow probe. Blood pressure, blood flow, heart rate, and respiration were monitored for 60 minutes. The incidence of occlusion (defined as the attainment of zero blood flow) was recorded as the primary end point.

The efficacy of AcaNAP5 [SEQ. ID. NO. 4] as an antithrombotic agent in preventing thrombus formation in this in vivo model was demonstrated by the dose-dependent reduction in the incidence of thrombotic occlusion, as shown in Table 7 below.

TABLE 7

| Treatment Group | Dose (mg/kg) | n | Incidence of Occlusion |
|---|---|---|---|
| Saline | — | 8 | 8/8 |
| AcaNAP5 | 0.001 | 8 | 7/8 |
| AcaNAP5 | 0.003 | 8 | 5/8 |
| AcaNAP5 | 0.01 | 8 | 3/8* |
| AcaNAP5 | 0.03 | 8 | 1/8* |
| AcaNAP5 | 0.1 | 8 | 0/8* |
| AcaNAP5 | 0.3 | 4 | 0/4* |
| AcaNAP5 | 1.0 | 2 | 0/2* |

*-$p \leq 0.05$ from saline control by Fishers test

The effective dose which prevents 50% of thrombotic occlusions in this model ($ED_{50}$) can be determined from the above data by plotting the incidence of occlusion versus the dose administered. This allows a direct comparison of the antithrombotic efficacy of AcaNAP5 with other antithrombotic agents which have also been evaluated in this model as described above. Table 8 below lists the $ED_{50}$ values for several well known anticoagulant agents in this model compared to AcaNAP5.

TABLE 8

| Compound | $ED_{50}$[a] |
|---|---|
| Standard Heparin | 300 U/kg |
| Argatroban | 3.8 mg/kg |
| Hirulog ™ | 3.0 mg/kg |
| rTAP[b] | 0.6 mg/kg |
| AcaNAP5 | 0.0055 mg/kg |

[a]$ED_{50}$ is defined as the dose that prevents the incidence of complete thrombotic occlusion in 50% of animals tested [b]-recombinant Tick Anticoagulant Peptide, Vlasuk et al. Thromb. Haemostas. 70: 212–216 (1993)

2. Subcutaneous administration

The antithrombotic effect of AcaNAP5 compared to Low Molecular Weight heparin (Enoxaparin; Lovenox, Rhone-Poulenc Rorer) after subcutaneous administration was evaluated in rats using the $FeCl_3$ model. The model was performed in an identical manner to that described above with the exception that the compound was administered subcutaneously and efficacy was determined at two different times: 30 and 150 minutes after administration. To accomplish this, both carotid arteries were employed in a sequential manner. The results of these experiments indicate that AcaNAP5 [SEQ. ID. NO. 4] is an effective antithrombotic agent in vivo after subcutaneous administration. The results are shown below in Table 9.

TABLE 9

| Compound | 30" $ED_{50}$[a] (mg/kg) | 150" $ED_{50}$[a] (mg/kg) |
|---|---|---|
| Low Molecular Weight Heparin | 30.0 | 15.0 |
| AcaNAP5 | 0.07 | 0.015 |

[a]$ED_{50}$ is defined as the dose that prevents the incidence of complete thrombotic occlusion in 50% of animals tested.

B. Deep Wound Bleeding Measurement

A model of deep wound bleeding was used to measure the effect of NAP on bleeding and compare the effect with that of Low Molecular Weight Heparin.

Male rats were anesthetized and instrumented in an identical manner to those undergoing the $FeCl_3$ model. However, $FeCl_3$ was not applied to the carotid artery. The deep surgical wound in the neck that exposes the carotid artery was employed to quantify blood loss over time. Blood loss was measured over a period of 3.5 hours following subcutaneous administration of either AcaNAP5 or LMWH. The wound was packed with surgical sponges which were removed every 30 minutes. The sponges were subsequently immersed in Drabkin's reagent (sigma Chemical Co., St. Louis, Mo.) which lyses the red blood cells and reacts with hemoglobin in a colorimetric fashion. The colorimetric samples were then quantified by measuring absorbance at 550 nM, which provides a determination of the amount of blood in the sponge.

The dose response characteristics for both test compounds are shown in FIG. 15 along with efficacy data for both compounds. AcaNAP5 [SEQ. ID. NO. 4] was much more potent than Low Molecular Weight heparin in preventing occlusive arterial thrombus formation in this model. Furthermore, animals treated with NAP bled less than those treated with Low Molecular Weight heparin.

The data presented in Tables 7 and 9 and FIG. 15 clearly demonstrate the effectiveness of NAP in preventing occlusive thrombus formation in this experimental model. The relevance of this data to preventing human thrombosis is clear when compared to the other anticoagulant agents, listed in Table 8. These agents have been evaluated in an identical manner in this experimental model and have demonstrated antithrombotic efficacy in preventing thrombus formation clinically as described in the following literature citations: Heparin-Hirsh, J. N. Engl. J. Med 324:1565–1574 1992, Cairns, J. A. et. al. Chest 102: 456S–481S (1992); Argatroban-Gold, H. K. et. al. J. Am. Coll. Cardiol. 21: 1039–1047 (1993); and Hirulog™-Sharma, G. V. R. K. et. al. Am. J. Cardiol. 72: 1357–1360 (1993) and Lidón, R. M. et. al. Circulation 88: 1495–1501 (1993).

We claim:

1. An isolated protein having Factor VIIa/TF inhibitory activity and having one or more Nematode-extracted Anticoagulant Protein domains ("NAP domains"), wherein each NAP domain includes the sequence; Cys-A1-Cys-A2-Cys-A3-Cys-A4-Cys-A5-Cys-A6-Cys-A7-Cys-A8-Cys-A9-Cys-A10, wherein (a) A1 is an amino acid sequence of 7 to 8 amino acid residues (b) A2 is an amino acid sequence;

(c) A3 is an amino acid sequence of 3 amino acid residues;

(d) A4 is an amino acid sequence;

(e) A5 is an amino acid sequence of 3 to 4 amino acid residues;

(f) A6 is an amino acid sequence;

(g) A7 is an amino acid residue;

(h) A8 is an amino acid sequence of 11 to 12 amino acid residues;

(i) A9 is an amino acid sequence of 5 to 7 amino acid residues; and (j) A10 is an amino acid sequence;

wherein each of A2, A4, A6 and A10 has an independently selected number of independently selected amino acid residues and each sequence is selected such that each NAP domain has in total less than about 120 amino acid residues and wherein said isolated protein is derived from a hematophagous nematode species.

2. The protein of claim 1, wherein A3 has the sequence Asp-A3$_a$-A3$_b$, wherein A3$_a$ and A3$_b$ are independently selected amino acid residues.

3. The protein of claim 1, wherein A3 is Asp-Lys-Lys.

4. The protein of claim 1, wherein A4 is an amino acid sequence having a net anionic charge.

5. The protein of claim 1, wherein A5 has the sequence A5$_a$-A5$_b$-A5$_c$-A5$_d$ [SEQ. ID. NO. 85], wherein A5$_a$ through A5$_d$ are independently selected amino acid residues.

6. The protein of claim 5, wherein A5$_a$ is Leu and A5$_c$ is Arg.

7. The protein of claim 1, wherein A7 is selected from the group consisting of Val and Ile.

8. The protein of claim 1, wherein A7 is Val.

9. The protein of claim 1, wherein A8 includes an amino acid sequence A8$_a$-A8$_b$-A8$_c$-A8$_d$-A8$_e$-A8$_f$-A8$_g$- [SEQ. ID. NO. 68], wherein
    (a) A8$_a$ is the first amino acid residue in A8,
    (b) at least one of A8$_a$ and A8$_b$ is selected from the group consisting of Glu or Asp, and
    (c) A8$_c$ through A8$_g$ are independently selected amino acid residues.

10. The protein of claim 9, wherein
    (a) A8$_a$ is Glu or Asp,
    (b) A8$_b$ is an independently selected amino acid residue,
    (c) A8$_c$ is Gly,
    (d) A8$_d$ is selected from the group consisting of Phe, Tyr, and Leu,
    (e) A8$_e$ is Tyr,
    (f) A8$_f$ is Arg, and
    (g) A8$_g$ is selected from Asp and Asn.

11. The protein of claim 10, wherein -A8$_c$-A8$_d$-A8$_e$-A8$_f$-A8$_g$- is Gly-Phe-Tyr-Arg-Asn [SEQ. ID. NO. 70].

12. The protein of claim 9, wherein
    (a) A8$_a$ is an independently selected amino acid residue,
    (b) A8$_b$ is Glu or Asp,
    (c) A8$_c$ is Gly,
    (d) A8$_d$ is selected from the group consisting of Phe, Tyr, and Leu,
    (e) A8$_e$ is Tyr,
    (f) A8$_f$ is Arg, and
    (g) A8$_g$ is selected from Asp and Asn.

13. The protein of claim 12, wherein -A8$_c$-A8$_d$-A8$_e$-A8$_f$-A8$_g$- is -Gly-Phe-Tyr-Arg-Asn [SEQ. ID. NO. 70].

14. The protein of claim 1, wherein said nematode species is selected from the group consisting of *Ancylostoma caninum, Ancylostoma ceylanicum, Ancylostoma duodenale, Necator americanus,* and *Heligomosomoides polygyrus.*

15. The protein of claim 1, wherein
    (a) A3 is has the sequence Asp-A3$_a$-A3$_b$, wherein A3$_a$ and A3$_b$ are independently selected amino acid residues;
    (b) A4 is an amino acid sequence having a net anionic charge;
    (c) A5 has the sequence A5$_a$-A5$_b$-A5$_c$-A5$_d$ [SEQ. ID. NO. 85], wherein A5$_a$ through A5$_d$ are independently selected amino acid residues, and
    (d) A7 is selected from the group consisting of Val and Ile.

16. The protein of claim 15 having a NAP domain of AcaNAPc2 (SEQ. ID. NO. 59).

17. The protein of claim 15, wherein said nematode species is selected from the group consisting of *Ancylostoma caninum, Ancylostoma ceylanicum, Ancylostoma duodenale, Necator americanus,* and *Heligomosomoides polygyrus.*

18. The protein of claim 1, wherein
    (a) A3 is Asp-Lys-Lys;
    (b) A4 is an amino acid sequence having a net anionic charge;
    (c) A5 has the sequence A5$_a$-A5$_b$-A5$_c$-A5$_d$, wherein A5$_a$ is Leu, A5$_c$ is Arg, and A5$_b$ and A5$_d$ are independently selected amino acid residues [SEQ. ID. NO. 357],
    (d) A7 is Val; and
    (e) A8 includes an amino acid sequence A8$_a$-A8$_b$-Gly-Phe-Tyr-Arg-Asn [SEQ. ID. NO. 79], wherein at least one of A8$_a$ and A8$_b$ is Glu or Asp.

19. The protein of claim 18 having a NAP domain of AcaNAPc2 (SEQ. ID. NO. 59).

20. The protein of claim 18, wherein said nematode species is selected from the group consisting of *Ancylostoma caninum, Ancylostoma ceylanicum, Ancylostoma duodenale, Necator americanus,* and *Heligomosomoides polygyrus.*

21. An isolated protein having Factor VIIa/TF inhibitory activity having a NAP domain with an amino acid sequence of AcaNAPc2 (SEQ. ID. NO. 59).

22. A pharmaceutical composition comprising the protein of claim 1.

23. A pharmaceutical composition comprising the protein of claim 15.

24. A pharmaceutical composition comprising the protein of claim 18.

25. A pharmaceutical composition comprising an AcaNAPc2 protein [SEQ. ID. NO. 59].

26. A method of inhibiting blood coagulation comprising administering a protein of claim 1 with a pharmaceutically acceptable carrier.

27. A method of inhibiting blood coagulation comprising administering a protein of claim 15 with a pharmaceutically acceptable carrier.

28. A method of inhibiting blood coagulation comprising administering a protein of claim 18 with a pharmaceutically acceptable carrier.

29. A method of inhibiting blood coagulation comprising administering an AcaNAPc2 protein [SEQ. ID. NO. 59].

30. A protein of claim 1, wherein said protein has two NAP domains.

31. A protein of claim 15, wherein said protein has two NAP domains.

32. A protein of claim 18, wherein said protein has two NAP domains.

33. An isolated protein having anticoagulant activity, wherein said protein specifically inhibits the catalytic activity of the fVIIa/TF complex in the presence of fXa or catalytically inactive fXa derivative and not in the absence of fXa or catalytically inactive fXa derivative and does not specifically inhibit the activity of fVIIa in the absence of TF and does not specifically inhibit prothrombinase and wherein said protein is derived from a hematophagous nematode species.

34. An isolated protein having an amino acid sequence of AcaNAPc2 (SEQ, ID. NO. 59), wherein said protein specifically inhibits the catalytic activity of the fVIIa/TF complex in the presence of fXa or catalytically inactive fXa derivative, and does not specifically inhibit the activity of FVIIA in the absence of TF and does not specifically inhibit prothrombinase.

35. An isolated protein having an amino acid sequence of AcaNAPc2 (SEQ. ID. NO. 59).

36. A protein having an amino acid sequence of AcaNAPc2/proline.

37. A method of treating a pathologic condition characterized by abnormal thrombosis by preventing or decreasing said abnormal thrombosis, which comprises administering a protein of claim 1.

38. A method according to claim 37 wherein said pathologic condition is disseminated intravascular coagulopathy.

39. A method of treating a pathologic condition characterized by abnormal thrombosis by preventing or decreasing said abnormal thrombosis, which comprises administering a protein of claim 15.

40. A method according to claim 39 wherein said pathologic condition is disseminated intravascular coagulopathy.

41. A method of treating a pathologic condition characterized by abnormal thrombosis by preventing or decreasing said abnormal thrombosis, which comprises administering a protein of claim 18.

42. A method according to claim 41 wherein said pathologic condition is disseminated intravascular coagulopathy.

43. A method of treating a pathologic condition characterized by abnormal thrombosis by preventing or decreasing said abnormal thrombosis, which comprises administering a protein of claim 21.

44. A method according to claim 43 wherein said pathologic condition is disseminated intravascular coagulopathy.

45. A method of treating a pathologic condition characterized by abnormal thrombosis by preventing or decreasing said abnormal thrombosis, which comprises administering a protein of claim 33.

46. A method according to claim 45 wherein said pathologic condition is disseminated intravascular coagulopathy.

47. A method of treating a pathologic condition characterized by abnormal thrombosis by preventing or decreasing said abnormal thrombosis, which comprises administering a protein of claim 35.

48. A method according to claim 47 wherein said pathologic condition is disseminated intravascular coagulopathy.

49. A method of treating a pathologic condition characterized by abnormal thrombosis by preventing or decreasing said abnormal thrombosis, which comprises administering a protein of claim 36.

50. A method according to claim 49 wherein said pathologic condition is disseminated intravascular coagulopathy.

* * * * *